(12) United States Patent
Falkner et al.

(10) Patent No.: US 10,189,888 B2
(45) Date of Patent: Jan. 29, 2019

(54) VIRAL VECTORS ENCODING RECOMBINANT FVIII VARIANTS WITH INCREASED EXPRESSION FOR GENE THERAPY OF HEMOPHILIA A

(71) Applicants: Baxalta Incorporated, Bannockburn, IL (US); Baxalta GmbH, Zug (CH)

(72) Inventors: Falko-Günter Falkner, Orth/Donau (AT); Franziska Horling, Gaenserndorf (AT); Johannes Lengler, Vienna (AT); Hanspeter Rottensteiner, Vienna (AT); Friedrich Scheiflinger, Vienna (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 0 days.

(21) Appl. No.: 15/349,930

(22) Filed: Nov. 11, 2016

(65) Prior Publication Data

US 2017/0233455 A1 Aug. 17, 2017

Related U.S. Application Data

(60) Provisional application No. 62/255,317, filed on Nov. 13, 2015.

(51) Int. Cl.
| | |
|---|---|
| *C07K 14/755* | (2006.01) |
| *A61K 48/00* | (2006.01) |
| *C12N 15/86* | (2006.01) |

(52) U.S. Cl.
CPC ........ *C07K 14/755* (2013.01); *A61K 48/0008* (2013.01); *A61K 48/0058* (2013.01); *A61K 48/0066* (2013.01); *C12N 15/86* (2013.01); *C12N 2750/14143* (2013.01); *C12N 2800/22* (2013.01); *C12N 2840/007* (2013.01)

(58) Field of Classification Search
None
See application file for complete search history.

(56) References Cited

U.S. PATENT DOCUMENTS

| | | |
|---|---|---|
| 4,797,368 A | 1/1989 | Carter et al. |
| 4,868,112 A | 9/1989 | Toole, Jr. |
| 5,112,950 A | 5/1992 | Meulien et al. |
| 5,139,941 A | 8/1992 | Muzyczka et al. |
| 5,171,844 A | 12/1992 | Van Ooyen et al. |
| 5,543,502 A | 8/1996 | Nordfang et al. |
| 5,595,886 A | 1/1997 | Chapman et al. |
| 5,610,278 A | 3/1997 | Nordfang et al. |
| 5,789,203 A | 4/1998 | Chapman et al. |
| 5,935,935 A | 8/1999 | Connelly et al. |
| 5,972,885 A | 10/1999 | Spira et al. |
| 5,994,136 A | 11/1999 | Naldini et al. |
| 6,013,516 A | 1/2000 | Verma et al. |
| 6,048,720 A | 4/2000 | Dalborg et al. |
| 6,060,447 A | 5/2000 | Chapman et al. |
| 6,114,148 A | 9/2000 | Seed et al. |
| 6,200,560 B1 | 3/2001 | Couto et al. |
| 6,228,620 B1 | 5/2001 | Chapman et al. |
| 6,316,226 B1 | 11/2001 | Van Ooyen et al. |
| 6,346,513 B1 | 2/2002 | Van Ooyen et al. |
| 6,458,563 B1 | 10/2002 | Lollar |
| 6,649,375 B2 | 11/2003 | Connelly et al. |
| 6,924,365 B1 | 8/2005 | Miller et al. |
| 7,041,635 B2 | 5/2006 | Kim et al. |
| 7,635,763 B2 | 12/2009 | Lollar |
| 7,943,374 B2 | 5/2011 | Hildinger |
| 7,973,374 B2 | 7/2011 | Jeong |
| 8,188,246 B2 | 5/2012 | Lollar |
| 8,519,111 B2 | 8/2013 | Lollar |
| 8,986,991 B2 | 3/2015 | Denning et al. |
| 9,393,323 B2 | 7/2016 | Nathwani et al. |
| 9,447,168 B2 | 9/2016 | Nathwani et al. |
| 9,504,762 B2 | 11/2016 | Colosi et al. |
| 2013/0017997 A1 | 1/2013 | Schellenberger et al. |
| 2013/0024960 A1 | 1/2013 | Nathwani et al. |
| 2015/0071883 A1* | 3/2015 | Colosi ................ A61K 48/0058 424/93.2 |
| 2015/0158930 A1 | 6/2015 | Nathwani et al. |
| 2015/0283267 A1 | 10/2015 | Vandendriessche et al. |
| 2015/0361158 A1 | 12/2015 | Tan et al. |
| 2016/0229904 A1* | 8/2016 | Xiao .................... C12N 15/63 |
| 2017/0233455 A1 | 8/2017 | Falkner et al. |

FOREIGN PATENT DOCUMENTS

| | | |
|---|---|---|
| WO | WO 2003/052051 A2 | 6/2003 |
| WO | WO 2013/123503 A1 | 8/2013 |
| WO | WO 2013/151666 A2 | 10/2013 |
| WO | WO 2013/186563 A2 | 12/2013 |
| WO | WO 2014/064277 A1 | 5/2014 |
| WO | WO 2014/127215 A1 | 8/2014 |
| WO | WO 2016/025764 A2 | 2/2016 |
| WO | WO 2016/146757 A1 | 9/2016 |

OTHER PUBLICATIONS

Ward et al., Blood 2011, 117(3)798-807 (Year: 2011).*
Cao et al. ("Cao"; Mol. Ther. 2014, 22, Supplement 1, S176 (Year: 2014).*
Selvaraj et al., J Thromb Haemost. 2012, 10(1)107-115 (Year: 2012).*
Asokan et al. "The AAV Vector Toolkit: Poised at the Clinical Crossroads" Molecular Therapy, vol. 20, No. 4, pp. 699-708 (2012).
Bancel. S. et al., EBII Accession No. GSN:BAW43417.
Blomer et al. "Highly Efficient and Sustained Gene Transfer in Adult Neurons with a Lentivirus Vector" Journal of Virology, vol. 71, No. 9, pp. 6641-6649 (1997).
Cao et al. "ASGCT abstract #460; details of mutations disclosed in oral presentation" (2014).
Cotten et al. "High-efficiency receptor-mediated delivery of small and large (48 kilobase gene constructs using the endosome-disruption activity of defective or chemically inactivated adenovirus particles" Proc. Natl. Acad. Sci. USA, vol. 89, pp. 6094-6098 (1992).

(Continued)

*Primary Examiner* — James D Schultz
(74) *Attorney, Agent, or Firm* — Morgan, Lewis & Bockius LLP

(57) ABSTRACT

The present disclosure provides, among other aspects, codon-altered polynucleotides encoding Factor VIII variants for expression in mammalian cells. In some embodiments, the disclosure also provides mammalian gene therapy vectors and methods for treating hemophilia A.

38 Claims, 89 Drawing Sheets

Specification includes a Sequence Listing.

(56) References Cited

OTHER PUBLICATIONS

Curiel "High-efficiency gene transfer employing adenovirus-polylysine-DNA complexes." Natural Immunity, vol. 13, pp. 141-164 (1994).
Daya and Berns "Gene Therapy Using Adeno-Associated Virus Vectors" Clinical Microbiology Reviews, vol. 21, No. 4, pp. 583-593 (2008).
Donath et al. "Characterization of des-(741-1668)-factor VIII, a single-chain factor VIII variant with a fusion site susceptible to proteolysis by thrombin and factor Xa" Biochem Journal, vol. 312, pp. 49-55 (1995).
Fath et al. "Multiparameter RNA and Codon Optimization: A Standardized Tool to Assess and Enhance Autologous Mammalian Gene Expression" PLoS ONE, vol. 6, Issue 3, pp. 1-14 (2011).
Gardinier-Garden et al. "CpG Islands in vertebrate genomes" Journal of Molecular Biology, vol. 196, Issue 2, pp. 261-282 (1987).
Gray et al. "Optimizing Promoters for Recombinant Adeno-Associated Virus-Mediated Gene Expression in the Peripheral and Central Nervous System Using Self-Complementary Vectors" Human Gene Therapy, vol. 22, pp. 1143-1153 (2011).
Grieger et al. "Production of Recombinant Adeno-associated Virus Vectors Using Suspension HEK293 Cells and Continuous Harvest of Vector From the Culture Media for GMP FIX and FLT1 Clinical Vector" Molecular Therapy, vol. 24, No. 2, pp. 287-297 (2015).
Grote et al. "JCat: a novel tool to adapt codon usage of a target gene to its potential expression host" Nucleic Acid Research, vol. 33, pp. W526-W531 (2005).
Gupta, R. et al., "NetNGlyc 1.0 Server," located at: http://www.cbs.dtu.dk/services/NetNGlyc/, 2004, last accessed, May 30, 2018.
Haas et al. "Codon usage limitation in the expression of HIV-1 envelope glycoprotein" Current Biology, vol. 6, No. 3, pp. 315-324 (1996).
International Search Report for International Application No. PCT/US2016/061684, dated Feb. 15, 2017, 16 pages.
International Search Report for International Application No. PCT/US2016/061688, dated Feb. 6, 2017, 16 pages.
Kelleher and Vos, "Long-term episomal gene delivery in human lymphoid cells using human and avian adenoviral-assisted transfection" Biotechniques, vol. 17, pp. 1110-1117 (1994).
Kriegler "Gene Transfer and Expression, A Laboratory Manual" (1990).
Krinner et al. "CpG domains downstream of TSSs promote high levels of gene expression" Nucleic Acid Research, vol. 42, No. 6, pp. 3551-3564 (2014).
Kudla et al. "High Guanine and Cytosine Content Increases mRNA Levels in Mammalian Cells" PLoS Biology, vol. 4, Issue 6, pp. 0933-0942 (2006).
Mann et al. "Construction of a retrovirus packaging mutant and its use to produce helper-free defective retrovirus" Cell, vol. 33, Issue 1, pp. 153-159 (1983).
Manno et al. "Successful transduction of liver in hemophilia by AAV-Factor IX and limitations imposed by the host immune response." Nature Medicine, vol. 12 pp. 342-347 (2006).
McIntosh et al. "Therapeutic levels of FVIII following a single peripheral vein administration of rAAV vector encoding a novel human factor VIII variant" Blood Journal, vol. 121, No. 17, pp. 3335-3344 (2013).
Miao et al. "Bioengineering of coagulation factor VIII for improved secretion" Blood Journal, vol. 103, No. 9, pp. 3412-3419 (2004).
Mirsafian et al. "A Comparative Analysis of Synonymous Codon Usage Bias Pattern in Human Albumin Superfamily" Scientific World Journal, vol. 2014, Article 639682, pp. 1-7 (2014).
Murray, E.J., "Gene Transfer and Expression Protocols" Methods in Molecular Biology, vol. 7, Humana Press, Inc. (1991).
Muzyczka "Use of adeno-associated virus as a general transduction vector for mammalian cells." Current Topics Microbiology and Immunology, vol. 158, pp. 97-129 (1992).
Naldini et al. "In Vivo Gene Delivery and Stable Transduction of Nondividing Cells by a Lentiviral Vector" Science, Vol. 272, Issue 5259, pp. 263-267 (1996).
Nicolas and Rubenstein, "Retroviral vectors," In: Vectors. A survey of molecular cloning vectors and their uses, Rodriguez and Denhardt (eds.), Stoneham: Butterworth, pp. 494-513 (1988).
Oh et al. "Purification of Recombinant Human B-Domain-Deleted Factor VIII Using Anti-Factor VIII Monoclonal Antibody Selected by the Surface Plasmon Resonance Biosensor" Biotechnol. Prog., vol. 17, pp. 1119-1127 (2001).
Radcliff et al. "Analysis of factor VIII mediated suppression of lentiviral vector titres" Gene Therapy, vol. 15, pp. 289-297 (2008).
Sandberg et al. "Structural and functional characteristics of the B-domain-deleted recombinant factor VIII, r-VIII SQ", Journal of Thrombosis and Haemostasis, vol. 85, pp. 93-100 (2001).
Selvaraj et al. "Bioengineering of coagulation factor VIII for efficient expression through elimination of a dispensable disulfide loop" Journal of Thrombosis and Haemostasis, vol. 10, pp. 107-115 (2012).
Swaaroop et al. "Mutagenesis of a Potential Immunoglobulin-binding Protein-binding Site Enhances Secretion of Coagulation Factor VIII" Journal of Biological Chemistry, vol. 272, No. 39, pp. 24121-24124 (1997).
Tats et al. "Preferred and avoided codon pairs in three domains of life" BMC Genomics, vol. 9, Issue 463, pp. 1-15 (2008).
Temin, H.M. "Retrovirus Vectors for Gene Transfer: Efficient Integration into and Expression of Exogenous DNA in Vertebrate Cell Genomes" In: Kucherlapati R. (eds) Gene Transfer (1986).
Thim et al., "Purification and characterization of a new recombinant factor VIII (N8)" Haemophilia, vol. 16, Issue 2, pp. 349-359 (2010).
Toschi et al. OBI-1, porcine recombinant Factor VIII for the potential treatment of patients with congenital hemophilia A and alloantibodies against human Factor VIII, Current Opinion in Molecular Therapy, vol. 12, No. 5, pp. 617-625 (2010).
Varfaj et al. "Residues Surrounding Arg336 and Arg562 Contribute to the Disparate Rates of Proteolysis of Factor VIIIa Catalyzed by Activated Protein C" Journal of Biological Chemistry, vol. 282, No. 28, pp. 20264-20272 (2007).
Wakabayashi et al. "A Glu113Ala mutation within a factor VIII Ca2+ binding site enhances cofactor interactions in factor Xase" Biochemistry, vol. 44, pp. 10298-10304 (2005).
Wakabayashi et al. "Ca(2+) binding to both the heavy and light chains of factor VIII is required for cofactor activity" Biochemistry, vol. 41, pp. 8485-8492 (2002).
Wakabayashi et al. "Combining mutations of charged residues at the A2 domain interface enhances factor VIII stability over single point mutations" Journal of Thrombosis and Haemostasis, vol. 7, pp. 438-444 (2009).
Wakabayashi et al. "Enhancing factor VIII and VIIIa stability by combining mutations at the A2 domain interface and A1-C2 domain interface" Journal of Thrombosis and Haemostasis., vol. 10, pp. 492-495 (2012).
Wakabayashi et al. "Generation of enhanced stability factor VIII variants by replacement of charged residues at the A2 domain interface" Blood, vol. 12, No. 7, pp. 2761-2769 (2008).
Wakabayashi et al. "Increasing Hydrophobicity or Disulfide Bridging at the Factor VIII A1 and C2 Domain Interface Enhances Procofactor Stability" Journal of Biological Chemistry, vol. 286, No. 29 pp. 25748-25755 (2011).
Wakabayashi et al. "Residues 110-126 in the A1 Domain of Factor VIII Contain a Ca2+ Binding Site Required for Cofactor Activity" Journal of Biochemistry, vol. 279, No. 13, pp. 12677-12684 (2004).
Ward et al. "Codon optimization of human factor VIII cDNAs leads to high-level expression" Blood Journal, vol. 117, No. 3, pp. 798-807 (2011).
Zollner et al. "Non-clinical pharmacokinetics and pharmacodynamics of rVIII-SingleChain, a novel recombinant single-chain factor VIII", Thrombosis Research, vol. 134, pp. 125-131 (2014).
Zufferey et al. "Multiply attenuated lentiviral vector achieves efficient gene delivery in vivo" Nature Biotechnology, vol. 15, pp. 871-875 (1997).

* cited by examiner

CS04-FL-NA

```
atgcagattgagctgagcacctgcttcttcctgtgcctgctgaggttctgcttctctgccaccagga
gatactacctgggggctgtggagctttcttgggactacatgcagtctgacctgggggagctgcctgt
ggatgccaggttcccacccagagtgcccaaatccttcccattcaacacctctgtggtctacaagaag
accctctttgtggagttcactgaccacctgttcaacattgccaaacccaggccaccctggatgggac
tcctgggacccaccattcaggctgaggtgtatgacactgtggtcatcaccctcaagaacatggcctc
ccaccctgtgagcctgcatgctgtgggggtcagctactggaaggcctctgaggggctgagtatgat
gaccagacctcccagagggagaaggaggatgacaaagtgttccctgggggcagccacacctatgtgt
ggcaggtcctcaaggagaatggcccatggcctctgacccactctgcctgacctactcctacctttc
tcatgtggacctggtcaaggacctcaactctggactgattgggccctgctggtgtgcagggaggc
tccctggccaaagagaagacccagaccctgcacaagttcattctcctgtttgctgtctttgatgagg
gcaagagctggcactctgaaaccaagaactccctgatgcaggacagggatgctgcctctgccaggc
ctggcccaagatgcacactgtgaatggctatgtgaacaggagcctgcctggactcattggctgccac
aggaaatctgtctactggcatgtgattggcatggggacaaccctgaggtgcactccattttcctgg
agggccacaccttcctggtcaggaaccacagacaggccagcctggagatcagccccatcaccttcct
cactgcccagacctgctgatggacctcggacagttcctgctgttctgccacatcagctcccaccag
catgatggcatggaggcctatgtcaaggtggacagctgccctgaggagccacagctcaggatgaaga
acaatgaggaggctgaggactatgatgatgacctgactgactctgagatggatgtggtccgctttga
tgatgacaacagccatccttcattcagatcaggtctgtggccaagaaacaccccaagacctgggtg
cactacattgctgctgaggaggaggactgggactatgcccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtggggacaccctgctcatcatcttcaagaaccaggcctccaggcct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgaccccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattgggcccagactgacttccttttctgtc
ttcttctctggctacaccttcaaacacaagatggtgtatgaggacacccctgaccctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatccacctgtcctgaaacgccaccagaggggagatcaccaggaccaccctccagtc
tgaccaggaggagattgactatgatgacaccatttctgtggagatgaagaaagaggactttgacatc
tatgacgaggacgagaaccagagcccaaggagcttccagaagaagaccaggcactacttcattgctg
ctgtggagcgcctgtgggactatggcatgagctccagccccatgtcctcaggaacagggcccagtc
tggctctgtgccacagttcaagaaagtggtcttccaagagttcactgatggcagcttcacccagccc
ctgtacagagggagctgaatgagcacctgggactcctgggcccatacatcagggctgaggtggagg
acaacatcatggtgaccttccgcaaccaggcctccaggccctacagcttctacagctccctcatcag
ctatgagGaggaccagaggcaggggctgagccacgcaagaactttgtgaaacccaatgaaaccaag
acctacttctggaaagtccagcaccacatggcccccaccaaggatgagtttgactgcaaggcctggg
```

```
cctacttctctgatgtggacctggagaaggatgtgcactctggcctgattggcccactcctggtctg
ccacaccaacaccctgaaccctgcccatggaaggcaagtgactgtgcaggagtttgccctcttcttc
accatctttgatgaaaccaagagctggtacttcactgagaacatggagcgcaactgcagggccccat
gcaacattcagatggaggaccccaccttcaaagagaactaccgcttccatgccatcaatggctacat
catggacaccctgcctgggcttgtcatggccaggaccagaggatcaggtggtacctgctttctatg
ggctccaatgagaacattcactccatccacttctctgggcatgtcttcactgtgcgcaagaaggagg
agtacaagatggccctgtacaacctctaccctggggtcttttgagactgtggagatgctgccctccaa
agctggcatctggagggtggagtgcctcattggggagcacctgcatgctggcatgagcaccctgttc
ctggtctacagcaacaagtgccagaccccctgggaatggcctctggccacatcagggacttccaga
tcactgcctctggccagtatggccagtgggcccccaagctggccaggctccactactctggatccat
caatgcctggagcaccaaggagccattcagctggatcaaagtggacctgctggcccccatgatcatc
catggcatcaagacccagggggccaggcagaagttctccagcctgtacatcagccagttcatcatca
tgtacagcctggatggcaagaaatggcagacctacagaggcaactccactggaacactcatggtctt
ctttggcaatgtggacagctctggcatcaagcacaacatcttcaaccccccaatcatcgccagatac
atcaggctgcaccccacccactacagcatccgcagcaccctcaggatggagctgatgggctgtgacc
tgaactcctgcagcatgcccctgggcatggagagcaaggccattctgatgccagatcactgcctc
cagctacttcaccaacatgtttgccacctggagcccaagcaaggccaggctgcacctccagggaagg
agcaatgcctggaggccccaggtcaacaacccaaaggagtggctgcaggtggacttccagaagacca
tgaaggtcactggggtgaccacccaggggggtcaagagcctgctcaccagcatgtatgtgaaggagtt
cctgatcagctccagccaggatggccaccagtggaccctcttcttccagaatggcaaggtcaaggtg
ttccagggcaaccaggacagcttcacCcctgtggtgaacagcctggaccccccctcctgaccagat
acctgaggattcaccccagagctgggtccaccagattgccctgaggatggaggtcctgggatgtga
ggcccaggacctgtactga (SEQ ID NO:1)
```

MQIELSTCFFLCLLRFCFSATRRYYLGAVELSWDYMQSDLGELPVDAR'FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY    (SEQ ID NO:2)

```
                                                                     gcc
accaggagat actacctggg ggctgtggag ctttcttggg actacatgca gtctgacctg
ggggagctgc ctgtggatgc caggttccca cccagagtgc ccaaatcctt cccattcaac
acctctgtgg tctacaagaa gaccctcttt gtggagttca ctgaccacct gttcaacatt
gccaaaccca ggccaccctg gatgggactc ctgggaccca ccattcaggc tgaggtgtat
gacactgtgg tcatcaccct caagaacatg gcctcccacc ctgtgagcct gcatgctgtg
ggggtcagct actggaaggc ctctgagggg gctgagtatg atgaccagac ctcccagagg
gagaaggagg atgacaaagt gttccctggg ggcagccaca cctatgtgtg gcaggtcctc
aaggagaatg gcccatggc ctctgaccca ctctgcctga cctactccta cctttctcat
gtggacctgg tcaaggacct caactctgga ctgattgggg ccctgctggt gtgcagggag
ggctccctgg ccaaagagaa gacccagacc ctgcacaagt tcattctcct gtttgctgtc
tttgatgagg gcaagagctg gcactctgaa accaagaact ccctgatgca ggacagggat
gctgcctctg ccagggcctg gcccaagatg cacactgtga atggctatgt gaacaggagc
ctgcctggac tcattggctg ccacaggaaa tctgtctact ggcatgtgat tggcatgggg
acaacccctg aggtgcactc cattttcctg gagggccaca ccttcctggt caggaaccac
agacaggcca gcctggagat cagcccatc accttcctca ctgcccagac cctgctgatg
gacctcggac agttcctgct gttctgccac atcagctccc accagcatga tggcatggag
gcctatgtca aggtggacag ctgcctgag gagccacagc tcaggatgaa gaacaatgag
gaggctgagg actatgatga tgacctgact gactctgaga tggatgtggt ccgctttgat
gatgacaaca gcccatcctt cattcagatc aggtctgtgg ccaagaaaca ccccaagacc
tgggtgcact acattgctgc tgaggaggag gactgggact atgccccact ggtcctggcc
cctgatgaca ggagctacaa gagccagtac ctcaacaatg gcccacagag gattggacgc
aagtacaaga agtcaggtt catggcctac actgatgaaa ccttcaagac cagggaggcc
attcagcatg agtctggcat cctgggccca ctcctgtatg gggaggtggg ggacaccctg
ctcatcatct tcaagaacca ggcctccagg ccctacaaca tctacccaca tggcatcact
gatgtcaggc ccctgtacag ccgcaggctg ccaaagggg tgaaacacct caaggacttc
cccattctgc ctggggagat cttcaagtac aagtggactg tcactgtgga ggatggacca
accaaatctg accccaggtg cctcaccaga tactactcca gctttgtgaa catggagagg
gacctggcct ctggcctgat tggcccactg tcatctgct acaaggagtc tgtggaccag
aggggaaacc agatcatgtc tgacaagagg aatgtgattc tgttctctgt ctttgatgag
aacaggagct ggtacctgac tgagaacatt cagcgcttcc tgcccaaccc tgctggggtg
cagctggagg acctgagtt ccaggccagc aacatcatgc actccatcaa tggctatgtg
tttgacagcc tccagctttc tgtctgcctg catgaggtgg cctactggta cattctttct
attggggccc agactgactt cctttctgtc ttcttctctg gctacacctt caaacacaag
atggtgtatg aggacaccct gacctcttc ccattctctg gggagactgt gttcatgagc
atggagaacc ctggcctgtg gattctggga tgccacaact ctgacttccg caacaggggc
atgactgccc tgctcaaagt ctcctcctgt gacaagaaca ctggggacta ctatgaggac
agctatgagg acatctctgc ctacctgctc agcaagaaca atgccattga gcccagg
(SEQ ID NO:3)
```

```
                                        g agatcaccag gaccaccctc
cagtctgacc aggaggagat tgactatgat gacaccattt ctgtggagat gaagaaagag
gactttgaca tctatgacga ggacgagaac cagagcccaa ggagcttcca gaagaagacc
aggcactact tcattgctgc tgtggagcgc ctgtgggact atggcatgag ctccagcccc
catgtcctca ggaacagggc ccagtctggc tctgtgccac agttcaagaa agtggtcttc
caagagttca ctgatggcag cttcacccag ccctgtaca gagggggagct gaatgagcac
ctgggactcc tgggcccata catcagggct gaggtggagg acaacatcat ggtgaccttc
cgcaaccagg cctccaggcc ctacagcttc tacagctccc tcatcagcta tgaggaggac
cagaggcagg gggctgagcc acgcaagaac tttgtgaaac ccaatgaaac caagacctac
ttctggaaag tccagcacca catggcccccc accaaggatg agtttgactg caaggcctgg
gcctacttct ctgatgtgga cctggagaag gatgtgcact ctggcctgat tggcccactc
ctggtctgcc acaccaacac cctgaaccct gccatggaa ggcaagtgac tgtgcaggag
tttgccctct tcttcaccat ctttgatgaa accaagagct ggtacttcac tgagaacatg
gagcgcaact gcaggcccc atgcaacatt cagatggagg accccacctt caaagagaac
taccgcttcc atgccatcaa tggctacatc atggacaccc tgcctgggct tgtcatggcc
caggaccaga ggatcagtg gtacctgctt tctatgggct ccaatgagaa cattcactcc
atccacttct ctgggcatgt cttcactgtg cgcaagaagg aggagtacaa gatggccctg
tacaacctct accctgggt cttgagact gtggagatgc tgccctccaa agctggcatc
tggagggtgg agtgcctcat tggggagcac ctgcatgctg catgagcac cctgttcctg
gtctacagca acaagtgcca gacccctg ggaatggcct ctggccacat cagggacttc
cagatcactg cctctggcca gtatggccag tgggcccca agctggccag gctccactac
tctggatcca tcaatgcctg gagcaccaag gagccattca gctggatcaa agtggacctg
ctggcccca tgatcatcca tggcatcaag cccagggg ccaggcagaa gttctccagc
ctgtacatca gccagtcat catcatgtac agcctggatg gcaagaaatg gcagacctac
agaggcaact ccactggaac actcatggtc ttctttggca atgtggacag ctctggcatc
aagcacaaca tcttcaaccc cccaatcatc gccagataca tcaggctgca ccccaccac
tacagcatcc gcagcacct caggatggag ctgatgggct gtgacctgaa ctcctgcagc
atgcccctgg gcatggagag caaggccatt tctgatgccc agatcactgc ctccagctac
ttcaccaaca tgtttgccac ctggagccca agcaaggcca ggctgcacct ccagggaagg
agcaatgcct ggaggcccca ggtcaacaac ccaaaggagt ggctgcaggt ggacttccag
aagaccatga aggtcactgg ggtgaccacc agggggtca agagcctgct caccagcatg
tatgtgaagg agttcctgat cagctccagc caggatggcc accagtggac cctcttcttc
cagaatggca aggtcaaggt gttccagggc aaccaggaca gcttcacccc tgtggtgaac
agcctggacc ccccctcct gaccagatac ctgaggattc accccagag ctgggtccac
cagattgccc tgaggatgga ggtcctggga tgtgaggccc aggacctgta c
(SEQ ID NO:4)
```

Figure 5

BDLO01 - agc ttctctcaga atccacctgt cctgaagaga caccagaga (SEQ ID NO:5)
BDLO04 - agc ttcagccaga atccacctgt cctgaaacgc caccagagg (SEQ ID NO:6)
BDLO23 - agc ttcagccaga accccccgt gctgaagagg caccagagg (SEQ ID NO:7)
BDLNG1 - agcttcagccagaatGTGAGCAACAATGTGAGCAACAATAATGTACCAACccacctgtcctgaaacgccaccagagg (SEQ ID NO:36)
BDLNG4 - agcttcagccagaatGTGAGCAACAATGTGAGCAACAATGTGAGCAACccacctgtcctgaaacgccaccagagg (SEQ ID NO:37)
BDLNG5 - agcttcagccagaatGTGAGCAACAATGTGAGCAACAATAATGCCACCAACccacctgtcctgaaacgccaccagagg (SEQ ID NO:38)
BDLNG6 - agcttcagccagaatGTGAGCAACAATGTGAGCAATAAHccacctgtcctgaaacgccaccagagg (SEQ ID NO:39)
BDLNG9 - agcttcagccagaatAGGAGCCTGccacctgtcctgaaacgccaccagagg (SEQ ID NO:40)
BDLNG10 - agcttcagccagaatGCCACTAATGTGTCTAACAACTCTGCTACCCTCTGCTGCTGTGAGCCcacctgtcctgaaacgccaccagagg (SEQ ID NO:41)
BDLNG16 - agcttcagccagaatGCCACCAACTATGTGAACAGAGCCTGccacctgtcctgaaacgccaccagagg (SEQ ID NO:42)
BDLNG17 - agcttcagccagaatGCCACCAATAHGTGAACAACAATGTGAACAGAGCCHGTCTGCCACCCTGCHGACTCHGCTGTGAGCCAGAAHccacctgtcctgaaacgccaccagagg (SEQ ID NO:43)
BDLNG18 - agcttcagccagaatGTGAGCAACAATGTGAGCAACAATGTGTCTGCCCTTCTGCTGTGHCTGCTccacctgtcctgaaacgccaccagagg (SEQ ID NO:44)
BDLNG19 - agcttcagccagaatATCACTGTGACCAACATCACTGTGGCCTTCTGCCACCTCTAACATCACTGTGGCCTTCTGCTGACccacctgtcctgaaacgccaccagagg (SEQ ID NO:45)
BDLNG20 - agcttcagccagaatATCACTGTGACCAACATCACTGTGACTGCCccacctgtcctgaaacgccaccagagg (SEQ ID NO:46)
BDLNG21 - agcttcagccagaatCAGACTGTGACCAACATCACTGTGACTGCCccacctgtcctgaaacgccaccagagg (SEQ ID NO:47)
BDLNGV - agcttcagccagaatGCCACTAATGTGTCTAACAACAGCAACAATGACAGCAATGTGTCTccacctgtcctgaaacgccaccagagg (SEQ ID NO:48)

```
   1    tcgcgcgttt cggtgatgac ggtgaaaacc tctgacacat gcagctcccg gagacggtca
  61    cagcttgtct gtaagcggat gccgggagca gacaagcccg tcagggcgcg tcagcgggtg
 121    ttggcgggtg tcgggctgg  cttaactatg cggcatcaga gcagattgta ctgagagtgc
 181    accatatgcg gtgtgaaata ccgcacagat gcgtaaggag aaaatacccg atcaggcgcc
 241    attcgccatt caggctcgc  aactgttggg aagggcgatc ggtgcgggcc tcttcgctat
 301    tacgccagct ggcgaaaggg ggatgtgctg caaggcgatt aagttgggta acgccagggt
 361    tttcccagtc acgacgttgt aaaacgacgg ccagtgaatt cctcgagatt taaatgacgt
 421    tggccactcc ctctctgcgc gctcgctcgc tcactgaggc cgggcgacca aggtcgccc
 481    gacgcccggg ctttgcccgg gcggcctcag tgagcgagcg agcgcgcaga gagggagtgg
 541    ccaactccat cactagggt  tcctgagttt aaacttcgtc gacgattcga gcttgggctg
 601    caggtcgagg gcactggag  gatgttgagt aagatggaaa actactgatg acccttgcag
 661    agacagagta ttaggacatg tttgaacagg gccgggcga  tcagcaggta gtctagagg
 721    atccccgtct gtctgcacat tcgtagagc  gagtgttccg atactctaat ctccctaggc
 781    aaggttcata tttgtgtagg ttacttattc tccttttgtt gactaagtca ataatcagaa
 841    tcagcaggtt tggagtcagc ttggcaggga tcagcagcct gggttggaag gagggggtat
 901    aaaagcccct tcaccaggag aagccgtcac acagactagg cgcgccaccg ccaccatgca
 961    gattgagctg agcacctgct tcttcctgtg cctgctgagg ttctgcttct ctgccaccag
1021    gagatactac ctggggctg  tggagctttc ttgggactac atgcagtctg acctggggga
1081    gctgctgtg  gatgccaggt tcccacccag agtgcccaaa tccttcccat tcaacacctc
1141    tgtggtctac aagaagaccc tctttgtgga gttcactgac cacctgttca acattgccaa
1201    acccaggcca ccctggatgg gactcctggg acccaccatt caggctgagg tgtatgacac
1261    tgtggtcatc acccotcaaga acatggcctc ccacctgtg  agcctgcatg ctgtggggt
1321    cagctactgg aaggcctctg aggggctga  gtatgatgac cagacctccc agagggagaa
1381    ggaggatgac aaagtgttcc ctggggcag  ccacacctat gtgtgcagg  tcctcaagga
1441    gaatggcccc atggcctctg accactctg  cctgacctac tcctaccttt ctcatgtgga
1501    cctggtcaag gacctcaact ctggactgat tggggccctg ctggtgtgca gggagggctc
1561    cctgccaaa  gagaagaccc agaccctgca caagttcatt ctcctgtttg ctgtctttga
1621    tgagggcaag agctggcact ctgaaaccaa gaactccctg atgcaggaca gggatgctgc
1681    ctctgccagg gcctggccca agatgcacac tgtgaatggc tatgtgaaca ggagcctgcc
1741    tggactcatt ggctgccaca ggaaatctgt ctactggcat gtgattggca tgggacaac
1801    ccctgaggtg cactccattt tcctggaggg ccacaccttc ctggtcagga ccacagaca
1861    ggccagcctg gagatcagcc ccatcacctt cctcactgcc cagaccctgc tgatggacct
1921    cggacagttc ctgctgttct gccacatcag ctcccaccag catgatggca tggaggccta
1981    tgtcaaggtg gacagctgcc ctgaggagcc acagctcagg atgaagaaca atgaggaggc
2041    tgaggactat gatgatgacc tgactgactc tgagatggat gtggtccgct tgatgatga
2101    caacagccca tccttcattc agatcaggtc tgtggccaag aaacaccccc agacctgggt
2161    gcactacatt gctgctgagg aggaggactg ggactatgcc ccactggtcc tggcccctga
2221    tgacaggagc tacaagagcc agtacctcaa caatggccca cagaggattg gacgcaagta
2281    caagaaagtc aggttcatgg cctacactga tgaaaccttc aagaccaggg aggccattca
2341    gcatgagtct ggcatcctgg gccactcct  gtatgggag  gtggggaca ccctgctcat
2401    catcttcaag aaccaggcct ccaggcccta caacatctac ccacatggca tcactgatgt
2461    caggcccctg tacagccgca ggctgccaaa gggggtgaaa cacctcaagg acttccccat
```

Figure 7A

```
2521 tctgcctggg gagatcttca agtacaagtg gactgtcact gtggaggatg gaccaaccaa
2581 atctgacccc aggtgcctca ccagatacta ctccagcttt gtgaacatgg agagggacct
2641 ggcctctggc ctgattggcc cactgctcat ctgctacaag gagtctgtgg accagagggg
2701 aaaccagatc atgtctgaca agaggaatgt gattctgttc tctgtctttg atgagaacag
2761 gagctggtac ctgactgaga acattcagcg cttcctgccc aaccctgctg gggtgcagct
2821 ggaggaccct gagttccagg ccagcaacat catgcactcc atcaatggct atgtgtttga
2881 cagcctccag ctttctgtct gcctgcatga ggtggcctac tggtacattc tttctattgg
2941 ggcccagact gacttccttt ctgtcttctt ctctggctac accttcaaac acaagatggt
3001 gtatgaggac accctgaccc tcttcccatt ctctggggag actgtgttca tgagcatgga
3061 gaaccctggc ctgtggattc tgggatgcca caatctgac ttccgcaaca ggggcatgac
3121 tgccctgctc aaagtctcct cctgtgacaa gaacactggg gactactatg aggacagcta
3181 tgaggacatc tctgcctacc tgctcagcaa gaacaatgcc attgagccca ggagcttcag
3241 ccagaatcca cctgtcctga acgccacca gagggagatc accaggacca ccctccagtc
3301 tgaccaggag gagattgact atgatgacac catttctgtg gagatgaaga agagggactt
3361 tgacatctat gacgaggacg agaaccagag cccaaggagc ttccagaaga agaccaggca
3421 ctacttcatt gctgctgtgg agcgcctgtg ggactatggc atgagctcca gccccatgt
3481 cctcaggaac agggcccagt ctggctctgt gccacagttc aagaaagtgg tcttccaaga
3541 gttcactgat ggcagcttca cccagccct gtacagaggg gagctgaatg agcacctggg
3601 actcctgggc ccatacatca gggctgaggt ggaggacaac atcatggtga ccttccgcaa
3661 ccaggcctcc aggccctaca gcttctacag ctccctcatc agctatgagg aggaccagag
3721 gcaggggct gagccacgca agaactttgt gaaacccaat gaaaccaaga ctacttctg
3781 gaaagtccag caccacatgg cccccaccaa ggatgagttt gactgcaagg cctgggccta
3841 cttctctgat gtggacctgg agaaggatgt gcactctggc ctgattggcc cactcctggt
3901 ctgccacacc aacacctga ccctgccca tggaaggcaa gtgactgtgc aggagtttgc
3961 cctcttcttc accatctttg atgaaaccaa gagctggtac ttcactgaga catggagcg
4021 caactgcagg gccccatgca acattcagat ggaggacccc accttcaaag agaactaccg
4081 cttccatgcc atcaatggct acatcatgga cacctgcct gggcttgtca tggcccagga
4141 ccagaggatc aggtggtacc tgctttctat gggctccaat gagaacattc actccatcca
4201 cttctctggg catgtcttca ctgtgcgcaa gaaggaggag tacaagatgg ccctgtacaa
4261 cctctaccct gggtctttg agactgtgga gatgctgcc tccaaagctg catctggag
4321 ggtggagtgc ctcattgggg agcacctgca tgctggcatg agcacctgt tctggtcta
4381 cagcaacaag tgccagaccc cctgggaat ggcctctggc cacatcaggg acttccagat
4441 cactgcctct ggccagtatg ccagtgggc cccaagctg gccaggctcc actactctgg
4501 atccatcaat gctggagca ccaaggagcc attcagctgg atcaaagtgg acctgctggc
4561 ccccatgatc atccatggca tcaagaccca gggggccagg cagaagttct ccagcctgta
4621 catcagccag ttcatcatca tgtacagcct ggatggcaag aaatggcaga cctacagagg
4681 caactccact ggaacactca tggtcttctt tggcaatgtg gacagctctg gcatcaagca
4741 caacatcttc aaccccccaa tcatcgccag atacatcagg ctgcacccca cccactacag
4801 catccgcagc accctcagga tggagctgat gggctgtgac ctgaactcct gcagcatgcc
4861 cctgggcatg gagagcaagg ccattctga tgcccagatc actgcctcca gtacttcac
4921 caacatgttt gccacctgga gcccaagcaa ggccaggctc acctccagg aaggagcaa
4981 tgcctggagg ccccaggtca acaacccaaa ggagtggctg caggtggact ccagaagac
```

Figure 7B

```
5041 catgaaggtc actggggtga ccacccaggg ggtcaagagc ctgctcacca gcatgtatgt
5101 gaaggagttc ctgatcagct ccagccagga tggccaccag tggaccctct tcttccagaa
5161 tggcaaggtc aaggtgttcc agggcaacca ggacagcttc accoctgtgg tgaacagcct
5221 ggacccccc ctcctgacca gatacctgag gattcaccc cagagctggg tccaccagat
5281 tgccctgagg atggaggtcc tgggatgtga ggcccaggac ctgtactgat gacgagcggc
5341 cgctcttagt agcagtatcg ataataaaag atctttattt tcattagatc tgtgtgttgg
5401 ttttttgtgt gttaattaag ctcgcgaagg aaccctagt gatggagttg gccactccct
5461 ctctgcgcgc tcgctcgctc actgaggccg ggcaccaaa ggtcgcccga cgcccgggct
5521 ttgcccgggc ggcctcagtg agcgagcgag cgcgcagaga gggagtggcc aagacgattt
5581 aaatgacaag cttggcgtaa tcatggtcat agctgtttcc tgtgtgaaat tgttatccgc
5641 tcacaattcc acacaacata cgagccggaa gcataaagtg taaagcctgg ggtgcctaat
5701 gagtgagcta actcacatta attgcgttgc gctcactgcc cgctttccag tcgggaaacc
5761 tgtcgtgcca gctgcattaa tgaatcggcc aacgcgcggg gagaggcggt ttgcgtattg
5821 ggcgctcttc cgcttcctcg ctcactgact cgctgcgctc ggtcgttcgg ctgcggcgag
5881 cggtatcagc tcactcaaag gcggtaatac ggttatccac agaatcaggg gataacgcag
5941 gaaagaacat gtgagcaaaa ggccagcaaa aggccaggaa ccgtaaaaag gccgcgttgc
6001 tggcgttttt ccataggctc cgcccccctg acgagcatca caaaaatcga cgctcaagtc
6061 agaggtggcg aaacccgaca ggactataaa gataccaggc gtttccccct ggaagctccc
6121 tcgtgcgctc tcctgttccg accctgccgc ttaccggata cctgtccgcc tttctccctt
6181 cgggaagcgt ggcgctttct catagctcac gctgtaggta tctcagttcg gtgtaggtcg
6241 ttcgctccaa gctgggctgt gtgcacgaac cccccgttca gcccgaccgc tgcgccttat
6301 ccggtaacta tcgtcttgag tccaacccgg taagacacga cttatcgcca ctggcagcag
6361 ccactggtaa caggattagc agagcgaggt atgtaggcgg tgctacagag ttcttgaagt
6421 ggtggcctaa ctacggctac actagaagaa cagtatttgg tatctgcgct ctgctgaagc
6481 cagttacctt cggaaaaaga gttggtagct cttgatccgg caaacaaacc accgctggta
6541 gcggtggttt ttttgtttgc aagcagcaga ttacgcgcag aaaaaagga tctcaagaag
6601 atcctttgat cttttctacg gggtctgacg ctcagtggaa cgaaaactca cgttaaggga
6661 ttttggtcat gagattatca aaaaggatct tcacctagat ccttttaaat taaaaatgaa
6721 gttttaaatc aatctaaagt atatatgagt aaacttggtc tgacagttac caatgcttaa
6781 tcagtgaggc acctatctca gcgatctgtc tatttcgttc atccatagtt gcctgactcc
6841 ccgtcgtgta gataactacg atacgggagg gcttaccatc tggccccagt gctgcaatga
6901 taccgcgaga cccacgctca ccggctccag atttatcagc aataaaccag ccagccggaa
6961 gggccgagcg cagaagtggt cctgcaactt tatccgcctc catccagtct attaattgtt
7021 gccgggaagc tagagtaagt agttcgccag ttaatagttt gcgcaacgtt gttgccattg
7081 ctacaggcat cgtggtgtca cgctcgtcgt ttggtatggc ttcattcagc tccggttccc
7141 aacgatcaag gcgagttaca tgatccccca tgttgtgcaa aaaagcggtt agctccttcg
7201 gtcctccgat cgttgtcaga agtaagttgg ccgcagtgtt atcactcatg gttatggcag
7261 cactgcataa ttctcttact gtcatgccat ccgtaagatg cttttctgtg actggtgagt
7321 actcaaccaa gtcattctga gaatagtgta tgcggcgacc gagttgctct tgcccggcgt
7381 caatacggga taataccgcg ccacatagca gaactttaaa agtgctcatc attggaaaac
7441 gttcttcggg gcgaaaactc tcaaggatct taccgctgtt gagatccagt tcgatgtaac
7501 ccactcgtgc acccaactga tcttcagcat cttttacttt caccagcgtt tctgggtgag
7561 caaaaacagg aaggcaaaat gccgcaaaaa agggaataag ggcgacacgg aaatgttgaa
7621 tactcatact cttcctttt caatattatt gaagcattta tcagggttat tgtctcatga
7681 gcggatacat atttgaatgt atttagaaaa ataaacaaat aggggttccg cgcacatttc
7741 cccgaaaagt gccacctgac gtctaagaaa ccattattat catgacatta acctataaaa
7801 ataggcgtat cacgaggccc tttcgtc  (SEQ ID NO:8)
```

ATGCAGATTGAGCTGTCCACCTGCTTCTTTCTGTGCCTGCTGAGATTCTGCTTCTCTGCCACCAGGA
GATACTACCTGGGGGCTGTGGAACTTTCTTGGGACTACATGCAGTCTGACCTGGGAGAGCTGCCTGT
GGATGCCAGGTTCCCACCCAGAGTGCCCAAGTCCTTCCCATTCAACACCTCTGTGGTCTACAAGAAG
ACACTCTTTGTGGAATTCACTGACCACCTGTTCAACATTGCAAAACCCAGACCACCCTGGATGGGAC
TCCTGGGACCCACCATTCAGGCTGAGGTGTATGACACTGTGGTCATCACCCTCAAGAACATGGCATC
CCACCCTGTGTCTCTGCATGCTGTGGGAGTCTCATACTGGAAAGCCTCTGAAGGGGCTGAGTATGAT
GACCAGACATCCCAGAGAGAGAAAGAGGATGACAAGGTGTTCCCTGGGGATCTCACACCTATGTGT
GGCAAGTCCTCAAGGAGAATGGACCCATGGCATCTGACCCACTCTGCCTGACATACTCCTACCTTTC
TCATGTGGACCTGGTCAAGGACCTCAACTCTGGACTGATTGGGGCACTGCTGGTGTGCAGGGAAGGA
TCCCTGGCCAAGGAGAAAACCCAGACACTGCACAAGTTCATTCTCCTGTTTGCTGTCTTTGATGAGG
GCAAGTCTTGGCACTCTGAAACAAAGAACTCCCTGATGCAAGACAGGGATGCTGCCTCTGCCAGGGC
ATGGCCCAAGATGCACACTGTGAATGGCTATGTGAACAGATCACTGCCTGGACTCATTGGCTGCCAC
AGGAAATCTGTCTACTGGCATGTGATTGGCATGGGGACAACCCCTGAAGTGCACTCCATTTTCCTGG
AGGGACACACCTTCCTGGTCAGGAACCACAGACAAGCCTCTCTGGAGATCTCTCCCATCACCTTCCT
CACTGCACAGACACTGCTGATGGACCTTGGACAGTTCCTGCTGTCCTGCCACATCTCTTCCCACCAG
CATGATGGCATGGAAGCCTATGTCAAGGTGGACTCATGCCCTGAGGAACCACAGCTCAGGATGAAGA
ACAATGAGGAGGCTGAGGACTATGATGATGACCTGACTGACTCTGAGATGGATGTGGTCAGATTTGA
TGATGACAACTCTCCATCCTTCATTCAGATCAGGTCTGTGGCAAAGAAACACCCCAAGACATGGGTG
CACTACATTGCTGCTGAGGAAGAGGACTGGGACTATGCACCACTGGTCCTGGCCCCTGATGACAGGA
GCTACAAGTCTCAGTACCTCAACAATGGCCCACAAAGAATTGGAAGAAAGTACAAGAAAGTCAGATT
CATGGCCTACACTGATGAAACCTTCAAGACAAGAGAAGCCATTCAGCATGAGTCTGGCATTCTGGGA
CCACTCCTGTATGGGGAAGTGGGAGACACCCTGCTCATCATCTTCAAGAACCAGGCCTCCAGGCCCT
ACAACATCTACCCACATGGCATCACTGATGTCAGGCCCCTGTACAGCAGGAGACTGCCAAAAGGGGT
GAAACACCTCAAGGACTTCCCCATTCTGCCTGGAGAGATCTTCAAGTACAAGTGGACTGTCACTGTG
GAGGATGGACCAACAAAGTCTGACCCCAGGTGCCTCACCAGATACTACTCCTCTTTTGTGAACATGG
AGAGAGACCTGGCATCTGGACTGATTGGACCACTGCTCATCTGCTACAAGGAGTCTGTGGACCAGAG
AGGCAACCAGATCATGTCTGACAAGAGAAATGTGATTCTGTTCTCTGTCTTTGATGAGAACAGATCA
TGGTACCTGACTGAGAACATTCAGAGATTCCTGCCCAACCCTGCTGGGGTGCAACTGGAAGACCCTG
AGTTCCAGGCAAGCAACATCATGCACTCCATCAATGGCTATGTGTTTGACTCTCTCCAGCTTTCTGT
CTGCCTGCATGAGGTGGCCTACTGGTACATTCTTTCTATTGGGGCACAAACTGACTTCCTTTCTGTC
TTCTTCTCTGGATACACCTTCAAGCACAAGATGGTGTATGAGGACACCCTGACACTCTTCCCATTCT
CTGGGGAAACTGTGTTCATGAGCATGGAGAACCCTGGACTGTGGATTCTGGGATGCCACAACTCTGA
CTTCAGAAACAGGGGAATGACTGCACTGCTCAAAGTCTCCTCCTGTGACAAGAACACTGGGGACTAC
TATGAGGACTCTTATGAGGACATCTCTGCCTACCTGCTCAGCAAGAACAATGCCATTGAGCCCAGAA
GCTTCTCTCAGAATCCACCTGTCCTGAAGAGACACCAGAGAGAGATCACCAGGACAACCCTCCAGTC
TGACCAGGAAGAGATTGACTATGATGACACCATTTCTGTGGAGATGAAGAAGGAGGACTTTGACATC
TATGATGAGGACGAGAACCAGTCTCCAAGATCATTCCAGAAGAAGACAAGACACTACTTCATTGCTG
CTGTGGAAAGACTGTGGGACTATGGCATGTCTTCCTCTCCCCATGTCCTCAGGAACAGGGCACAGTC
TGGCTCTGTGCCACAGTTCAAGAAAGTGGTCTTCCAGGAGTTCACTGATGGCTCATTCACCCAGCCC
CTGTACAGAGGGGAACTGAATGAGCACCTGGGACTCCTGGGACCATACATCAGGGCTGAGGTGGAAG
ACAACATCATGGTGACATTCAGAAACCAGGCCTCCAGGCCCTACAGCTTCTACTCTTCCCTCATCAG
CTATGAGGAAGACCAGAGACAAGGGGCTGAGCCAAGAAAGAACTTTGTGAAACCCAATGAAACCAAG
ACCTACTTCTGGAAAGTCCAGCACCACATGGCACCCACCAAGGATGAGTTTGACTGCAAGGCCTGGG (Continued)

Figure 8A

```
CATACTTCTCTGATGTGGACCTGGAGAAAGATGTGCACTCTGGCCTGATTGGCCCACTCCTGGTCTG
CCACACCAACACCCTGAACCCTGCACATGGAAGGCAAGTGACTGTGCAGGAGTTTGCCCTCTTCTTC
ACCATCTTTGATGAAACCAAGTCATGGTACTTCACTGAGAACATGGAGAGAAACTGCAGAGCACCAT
GCAACATTCAGATGGAAGACCCCACCTTCAAGGAGAACTACAGGTTCCATGCCATCAATGGCTACAT
CATGGACACCCTGCCTGGGCTTGTCATGGCACAGGACCAGAGAATCAGATGGTACCTGCTTTCTATG
GGATCCAATGAGAACATTCACTCCATCCACTTCTCTGGGCATGTCTTCACTGTGAGAAAGAAGGAGG
AATACAAGATGGCCCTGTACAACCTCTACCCTGGGGTCTTTGAGACTGTGGAGATGCTGCCCTCCAA
AGCTGGCATCTGGAGGGTGGAATGCCTCATTGGGGAGCACCTGCATGCTGGCATGTCAACCCTGTTC
CTGGTCTACAGCAACAAGTGCCAGACACCCCTGGGAATGGCCTCTGGCCACATCAGGGACTTCCAGA
TCACTGCCTCTGGCCAGTATGGCCAGTGGGCACCCAAACTGGCCAGGCTCCACTACTCTGGCTCCAT
CAATGCATGGTCAACCAAGGAGCCATTCTCTTGGATCAAGGTGGACCTGCTGGCACCCATGATCATT
CATGGCATCAAGACACAGGGGGCAAGACAGAAATTCTCCTCTCTGTACATCTCACAGTTCATCATCA
TGTACTCTCTGGATGGCAAGAAGTGGCAGACATACAGAGGCAACTCCACTGGCACCCTCATGGTCTT
CTTTGGCAATGTGGACAGCTCTGGCATCAAGCACAACATCTTCAACCCTCCCATCATTGCCAGATAC
ATCAGGCTGCACCCCACCCACTACTCAATCAGATCAACCCTCAGGATGGAACTGATGGGATGTGACC
TGAACTCCTGCTCAATGCCCCTGGGAATGGAGAGCAAGGCCATTTCTGATGCCCAGATCACTGCATC
CTCTTACTTCACCAACATGTTTGCCACCTGGTCACCATCAAAAGCCAGGCTGCACCTCCAGGGAAGA
AGCAATGCCTGGAGACCCCAGGTCAACAACCCAAAGGAATGGCTGCAAGTGGACTTCCAGAAGACAA
TGAAAGTCACTGGGGTGACAACCCAGGGGGTCAAGTCTCTGCTCACCTCAATGTATGTGAAGGAGTT
CCTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCTCCTGACAAGAT
ACCTGAGAATTCACCCCCAGTCTTGGGTCCACCAGATTGCCCTGAGAATGGAAGTCCTGGGATGTGA
GGCACAAGACCTGTACTGA (SEQ ID NO:49)
```

ATGCAGATTGAGCTGAGCACCTGCTTCTTCCTGTGCCTGCTGAGGTTCTGCTTCTCTGCCACCAGGAGATAC
TACCTGGGGGCTGTGGAGCTTTCTTGGGACTACATGCAGTCTGACCTGGGGGAGCTGCCTGTGGATGCCAGG
TTCCCACCCAGAGTGCCCAAATCCTTCCCATTCAACACCTCTGTGGTCTACAAGAAGACCCTCTTTGTGGAG
TTCACTGACCACCTGTTCAACATTGCCAAACCCAGGCCACCCTGGATGGGACTCCTGGGACCCACCATTCAG
GCTGAGGTGTATGACACTGTGGTCATCACCCTCAAGAACATGGCCTCCCACCCTGTGAGCCTGCATGCTGTG
GGGGTCAGCTACTGGAAGGCCTCTGAGGGGGCTGAGTATGATGACCAGACCTCCCAGAGGGAGAAGGAGGAT
GACAAAGTGTTCCCTGGGGGCAGCCACACCTATGTGTGGCAGGTCCTCAAGGAGAATGGCCCCATGGCCTCT
GACCCACTCTGCCTGACCTACTCCTACCTTTCTCATGTGGACCTGGTCAAGGACCTCAACTCTGGACTGATT
GGGGCCCTGCTGGTGTGCAGGGAGGGCTCCCTGGCCAAAGAGAAGACCCAGACCCTGCACAAGTTCATTCTC
CTGTTTGCTGTCTTTGATGAGGGCAAGAGCTGGCACTCTGAAACCAAGAACTCCCTGATGCAGGACAGGGAT
GCTGCCTCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGACAACCCCTGAGGTGCACTCCATT
TTCCTGGAGGGCCACACCTTCCTGGTCAGGAACCACAGACAGGCCAGCCTGGAGATCAGCCCCATCACCTTC
CTCACTGCCCAGACCCTGCTGATGGACCTCGGACAGTTCCTGCTGTTCTGCCACATCAGCTCCACCAGCAT
GATGGCATGGAGGCCTATGTCAAGGTGGACAGCTGCCCTGAGGAGCCACAGCTCAGGATGAAGAACAATGAG
GAGGCTGAGGACTATGATGATGACCTGACTGACTCTGAGATGGATGTGGTCCGCTTTGATGATGACAACAGC
CCATCCTTCATTCAGATCAGGTCTGTGGCCAAGAAACACCCCAAGACCTGGGTGCACTACATTGCTGCTGAG
GAGGAGGACTGGGACTATGCCCCACTGGTCCTGGCCCCTGATGACAGGAGCTACAAGAGCCAGTACCTCAAC
AATGGCCCACAGAGGATTGGACGCAAGTACAAGAAAGTCAGGTTCATGGCCTACACTGATGAAACCTTCAAG
ACCAGGGAGGCCATTCAGCATGAGTCTGGCATCCTGGGCCCACTCCTGTATGGGGAGGTGGGGGACACCCTG
CTCATCATCTTCAAGAACCAGGCCTCCAGGCCCTACAACATCTACCCACATGGCATCACTGATGTCAGGCCC
CTGTACAGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGATACTAC
TCCAGCTTTGTGAACATGGAGAGGGACCTGGCCTCTGGCCTGATTGGCCCACTGCTCATCTGCTACAAGGAG
TCTGTGGACCAGAGGGGAAACCAGATCATGTCTGACAAGAGGAATGTGATTCTGTTCTCTGTCTTTGATGAG
AACAGGAGCTGGTACCTGACTGAGAACATTCAGCGCTTCCTGCCCAACCCTGCTGGGGTGCAGCTGGAGGAC
CCTGAGTTCCAGGCCAGCAACATCATGCACTCCATCAATGGCTATGTGTTTGACAGCCTCCAGCTTTCTGTC
TGCCTGCATGAGGTGGCCTACTGGTACATTCTTTCTATTGGGGCCCAGACTGACTTCCTTTCTGTCTTCTTC
TCTGGCTACACCTTCAAACACAAGATGGTGTATGAGGACACCCTGACCCTCTTCCCATTCTCTGGGGAGACT
GTGTTCATGAGCATGGAGAACCCTGGCCTGTGGATTCTGGGATGCCACAACTCTGACTTCCGCAACAGGGGC
ATGACTGCCCTGCTCAAAGTCTCCTCCTGTGACAAGAACACTGGGGACTACTATGAGGACAGCTATGAGGAC
ATCTCTGCCTACCTGCTCAGCAAGAACAATGCCATTGAGCCCAGGGAGATCACCAGGACCACCCTCCAGTCT
GACCAGGAGGAGATTGACTATGATGACACCATTTCTGTGGAGATGAAGAAAGAGGACTTTGACATCTATGAC
GAGGACGAGAACCAGAGCCCAAGGAGCTTCCAGAAGAAGACCAGGCACTACTTCATTGCTGCTGTGGAGCGC
CTGTGGGACTATGGCATGAGCTCCAGCCCCCATGTCCTCAGGAACAGGGCCCAGTCTGGCTCTGTGCCACAG
TTCAAGAAAGTGGTCTTCCAAGAGTTCACTGATGGCAGCTTCACCCAGCCCCTGTACAGAGGGGAGCTGAAT
GAGCACCTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGGGCTGAG
CCACGCAAGAACTTTGTGAAACCCAATGAAACCAAGACCTACTTCTGGAAAGTCCAGCACCACATGGCCCCC (Continued)

Figure 9A

```
ACCAAGGATGAGTTTGACTGCAAGGCCTGGGCCTACTTCTCTGATGTGGACCTGGAGAAGGATGTGCACTCT
GGCCTGATTGGCCCACTCCTGGTCTGCCACACCAACACCCTGAACCCTGCCCATGGAAGGCAAGTGACTGTG
CAGGAGTTTGCCCTCTTCTTCACCATCTTTGATGAAACCAAGAGCTGGTACTTCACTGAGAACATGGAGCGC
AACTGCAGGGCCCCATGCAACATTCAGATGGAGGACCCCACCTTCAAAGAGAACTACCGCTTCCATGCCATC
AATGGCTACATCATGGACACCCTGCCTGGGCTTGTCATGGCCCAGGACCAGAGGATCAGGTGGTACCTGCTT
TCTATGGGCTCAATGAGAACATTCACTCCATCCACTTCTCTGGGCATGTCTTCACTGTGCGCAAGAAGGAG
GAGTACAAGATGGCCCTGTACAACCTCTACCCTGGGGTCTTTGAGACTGTGGAGATGCTGCCCTCCAAAGCT
GGCATCTGGAGGGTGGAGTGCCTCATTGGGGAGCACCTGCATGCTGGCATGAGCACCCTGTTCCTGGTCTAC
AGCAACAAGTGCCAGACCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCCATGATCATCCATGGCATCAAGACCCAGGGGGCC
AGGCAGAAGTTCTCCAGCCTGTACATCAGCCAGTTCATCATCATGTACAGCCTGGATGGCAAGAAATGGCAG
ACCTACAGAGGCAACTCCACTGGAACACTCATGGTCTTCTTTGGCAATGTGGACAGCTCTGGCATCAAGCAC
AACATCTTCAACCCCCCAATCATCGCCAGATACATCAGGCTGCACCCCACCCACTACAGCATCCGCAGCACC
CTCAGGATGGAGCTGATGGGCTGTGACCTGAACTCCTGCAGCATGCCCCTGGGCATGGAGAGCAAGGCCATT
TCTGATGCCCAGATCACTGCCTCCAGCTACTTCACCAACATGTTTGCCACCTGGAGCCCAAGCAAGGCCAGG
CTGCACCTCCAGGGAAGGAGCAATGCCTGGAGGCCCCAGGTCAACAACCCAAAGGAGTGGCTGCAGGTGGAC
TTCCAGAAGACCATGAAGGTCACTGGGGTGACCACCCAGGGGGTCAAGAGCCTGCTCACCAGCATGTATGTG
AAGGAGTTCCTGATCAGCTCCAGCCAGGATGGCCACCAGTGGACCCTCTTCTTCCAGAATGGCAAGGTCAAG
GTGTTCCAGGGCAACCAGGACAGCTTCACCCCTGTGGTGAACAGCCTGGACCCCCCCTCCTGACCAGATAC
CTGAGGATTCACCCCAGAGCTGGGTCCACCAGATTGCCCTGAGGATGGAGGTCCTGGGATGTGAGGCCCAG
GACCTGTACTGA    (SEQ ID NO:9)
```

MQIELSTCFFLCLLRFCFSATRRYYLGAVELSWDYMQSDLGELPVDARFPPRVPKSFPFNTSVVYKK
TLFVEFTDHLFNIAKPRPPWMGLLGPTIQAEVYDTVVITLKNMASHPVSLHAVGVSYWKASEGAEYD
DQTSQREKEDDKVFPGGSHTYVWQVLKENGPMASDPLCLTYSLSHVDLVKDLNSGLIGALLVCREG
SLAKEKTQTLHKFILLFAVFDEGKSWHSETKNSLMQDRDAASARAWPKMHTVNGYVNRSLPGLIGCH
RKSVYWHVIGMGTTPEVHSIFLEGHTFLVRNHRQASLEISPITFLTAQTLLMDLGQFLLFCHISSHQ
HDGMEAYVKVDSCPEEPQLRMKNNEEAEDYDDDLTDSEMDVVRFDDDNSPSFIQIRSVAKKHPKTWV
HYIAAEEEDWDYAPLVLAPDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKDFPILPGEIFKYKWTVTV
EDGPTKSDPRCLTRYYSSFVNMERDLASGLIGPLLICYKESVDQRGNQIMSDKRNVILFSVFDENRS
WYLTENIQRFLPNPAGVQLEDPEFQASNIMHSINGYVFDSLQLSVCLHEVAYWYILSIGAQTDFLSV
FFSGYTFKHKMVYEDTLTLFPFSGETVFMSMENPGLWILGCHNSDFRNRGMTALLKVSSCDKNTGDY
YEDSYEDISAYLLSKNNAIEPREITRTTLQSDQEEIDYDDTISVEMKKEDFDIYDEDENQSPRSFQK
KTRHYFIAAVERLWDYGMSSSPHVLRNRAQSGSVPQFKKVVFQEFTDGSFTQPLYRGELNEHLGLLG
PYIRAEVEDNIMVTFRNQASRPYSFYSSLISYEEDQRQGAEPRKNFVKPNETKTYFWKVQHHMAPTK
DEFDCKAWAYFSDVDLEKDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYLLSMGSNENIHSIHFSGH
VFTVRKKEEYKMALYNLYPGVFETVEMLPSKAGIWRVECLIGEHLHAGMSTLFLVYSNKCQTPLGMA
SGHIRDFQITASGQYGQWAPKLARLHYSGSINAWSTKEPFSWIKVDLLAPMIIHGIKTQGARQKFSS
LYISQFIIMYSLDGKKWQTYRGNSTGTLMVFFGNVDSSGIKHNIFNPPIIARYIRLHPTHYSIRSTL
RMELMGCDLNSCSMPLGMESKAISDAQITASSYFTNMFATWSPSKARLHLQGRSNAWRPQVNNPKEW
LQVDFQKTMKVTGVTTQGVKSLLTSMYVKEFLISSSQDGHQWTLFFQNGKVKVFQGNQDSFTPVVNS
LDPPLLTRYLRIHPQSWVHQIALRMEVLGCEAQDLY   (SEQ ID NO:10)

```
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGTCAGCTACTGGAAGGCCTCTGAGGGGCTGAG
TATGATGACCAGACCTCCCAGAGGGAGAAGGAGGATGACAAAGTGTTCCCTGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCAAGATGCACACTGTGAATGGCTATGTGAACAGGAGCCTGCCTGGACTC
ATTGGCTGCCACAGGAAATCTGTCTACTGGCATGTGATTGGCATGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATTCCAGACACCCCAGCACC
AGGGAGATCACCAGGACCACCCTCCAGTCTGACCAGGAGGAGATTGACTATGATGACACCATTTCT
GTGGAGATGAAGAAGAGGACTTTGACATCTATGACGAGGACGAGAACCAGAGCCCAAGGAGCTTC
```

```
CAGAAGAAGACCAGGCACTACTTCATTGCTGCTGTGGAGCGCCTGTGGGACTATGGCATGAGCTCC
AGCCCCATGTCCTCAGGAACAGGGCCCAGTCTGGCTCTGTGCCACAGTTCAAGAAAGTGGTCTTC
CAAGAGTTCACTGATGGCAGCTTCACCCAGCCCCTGTACAGAGGGGAGCTGAATGAGCACCTGGGA
CTCCTGGGCCCATACATCAGGGCTGAGGTGGAGGACAACATCATGGTGACCTTCCGCAACCAGGCC
TCCAGGCCCTACAGCTTCTACAGCTCCCTCATCAGCTATGAGGAGGACCAGAGGCAGGGGCTGAG
CCACGCAAGAACTTTGTGAAACCCAATGAAACCAAGACCTACTTCTGGAAAGTCCAGCACCACATG
GCCCCACCAAGGATGAGTTTGACTGCAAGGCCTGGGCCTACTTCTCTGATGTGGACCTGGAGAAG
GATGTGCACTCTGGCCTGATTGGCCCACTCCTGGTCTGCCACACCAACACCCTGAACCCTGCCCAT
GGAAGGCAAGTGACTGTGCAGGAGTTTGCCCTCTTCTTCACCATCTTTGATGAAACCAAGAGCTGG
TACTTCACTGAGAACATGGAGCGCAACTGCAGGGCCCCATGCAACATTCAGATGGAGGACCCCACC
TTCAAAGAGAACTACCGCTTCCATGCCATCAATGGCTACATCATGGACACCCTGCCTGGGCTTGTC
ATGGCCCAGGACCAGAGGATCAGGTGGTACCTGCTTTCTATGGGCTCCAATGAGAACATTCACTCC
ATCCACTTCTCTGGGCATGTCTTCACTGTGCGCAAGAAGGAGGAGTACAAGATGGCCCTGTACAAC
CTCTACCCTGGGGTCTTTGAGACTGTGGAGATGCTGCCCTCCAAAGCTGGCATCTGGAGGGTGGAG
TGCCTCATTGGGGAGCACCTGCATGCTGGCATGAGCACCCTGTTCCTGGTCTACAGCAACAAGTGC
CAGACCCCCCTGGGAATGGCCTCTGGCCACATCAGGGACTTCCAGATCACTGCCTCTGGCCAGTAT
GGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCATGATCATCCATGGCATCAAGACCCAG
GGGGCCAGGCAGAAGTTCTCCAGCCTGTACATCAGCCAGTTCATCATCATGTACAGCCTGGATGGC
AAGAAATGGCAGACCTACAGAGGCAACTCCACTGGAACACTCATGGTCTTCTTTGGCAATGTGGAC
AGCTCTGGCATCAAGCACAACATCTTCAACCCCCCAATCATCGCCAGATACATCAGGCTGCACCCC
ACCCACTACAGCATCCGCAGCACCCTCAGGATGGAGCTGATGGGCTGTGACCTGAACTCCTGCAGC
ATGCCCCTGGGCATGGAGAGCAAGGCCATTTCTGATGCCCAGATCACTGCCTCCAGCTACTTCACC
AACATGTTTGCCACCTGGAGCCCAAGCAAGGCCAGGCTGCACCTCCAGGGAAGGAGCAATGCCTGG
AGGCCCCAGGTCAACAACCCAAAGGAGTGGCTGCAGGTGGACTTCCAGAAGACCATGAAGGTCACT
GGGGTGACCACCCAGGGGGTCAAGAGCCTGCTCACCAGCATGTATGTGAAGGAGTTCCTGATCAGC
TCCAGCCAGGATGGCCACCAGTGGACCCTCTTCTTCCAGAATGGCAAGGTCAAGGTGTTCCAGGGC
AACCAGGACAGCTTCACCCCTGTGGTGAACAGCCTGGACCCCCCCTCCTGACCAGATACCTGAGG
ATTCACCCCAGAGCTGGGTCCACCAGATTGCCCTGAGGATGGAGGTCCTGGGATGTGAGGCCCAG
GACCTGTACTGA    (SEQ ID NO:11)
```

MQIELSTCFFLCLLRFCFSATRRYYLGAVELSWDYMQSDLGELPVDARFPPRVPKSFPFNTSVVYKKTLFVEF
TDHLFNIAKPRPPWMGLLGPTIQAEVYDTVVITLKNMASHPVSLHAVGVSYWKASEGAEYDDQTSQREKEDDK
VFPGGSHTYVWQVLKENGPMASDPLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHRKSVYWHVIGMGTTPEVHSIFLEG
HTFLVRNHRQASLEISPITFLTAQTLLMDLGQFLLFCHISSHQHDGMEAYVKVDSCPEEPQLRMKNNEEAEDY
DDDLTDSEMDVVRFDDDNSPSFIQIRSVAKKHPKTWVHYIAAEEEDWDYAPLVLAPDDRSYKSQYLNNGPQRI
GRKYKKVRFMAYTDETFKTREAIQHESGILGPLLYGEVGDTLLIIFKNQASRPYNIYPHGITDVRPLYSRRLP
KGVKHLKDFPILPGEIFKYKWTVTVEDGPTKSDPRCLTRYYSSFVNMERDLASGLIGPLLICYKESVDQRGNQ
IMSDKRNVILFSVFDENRSWYLTENIQRFLPNPAGVQLEDPEFQASNIMHSINGYVFDSLQLSVCLHEVAYWY
ILSIGAQTDFLSVFFSGYTFKHKMVYEDTLTLFPFSGETVFMSMENPGLWILGCHNSDFRNRGMTALLKVSSC
DKNTGDYYEDSYEDISAYLLSKNNAIEPRSFSQNSRHPSTREITRTTLQSDQEEIDYDDTISVEMKKEDFDIY
DEDENQSPRSFQKKTRHYFIAAVERLWDYGMSSSPHVLRNRAQSGSVPQFKKVVFQEFTDGSFTQPLYRGELN
EHLGLLGPYIRAEVEDNIMVTFRNQASRPYSFYSSLISYEEDQRQGAEPRKNFVKPNETKTYFWKVQHHMAPT
KDEFDCKAWAYFSDVDLEKDVHSGLIGPLLVCHTNTLNPAHGRQVTVQEFALFFTIFDETKSWYFTENMERNC
RAPCNIQMEDPTFKENYRFHAINGYIMDTLPGLVMAQDQRIRWYLLSMGSNENIHSIHFSGHVFTVRKKEEYK
MALYNLYPGVFETVEMLPSKAGIWRVECLIGEHLHAGMSTLFLVYSNKCQTPLGMASGHIRDFQITASGQYGQ
WAPKLARLHYSGSINAWSTKEPFSWIKVDLLAPMIIHGIKTQGARQKFSSLYISQFIIMYSLDGKKWQTYRGN
STGTLMVFFGNVDSSGIKHNIFNPPIIARYIRLHPTHYSIRSTLRMELMGCDLNSCSMPLGMESKAISDAQIT
ASSYFTNMFATWSPSKARLHLQGRSNAWRPQVNNPKEWLQVDFQKTMKVTGVTTQGVKSLLTSMYVKEFLISS
SQDGHQWTLFFQNGKVKVFQGNQDSFTPVVNSLDPPLLTRYLRIHPQSWVHQIALRMEVLGCEAQDLY
(SEQ ID NO:12)

Figure 12

```
NG1:   V   S   N   N   V   S   N   N   A   T   N   N   A   T   N   (SEQ ID NO:51)
       GTG AGC AAT AAC GTG AGC AAC AAT GCC ACC AAT AAT GCT ACC AAC (SEQ ID NO:50)

NG4:   V   S   N   N   A   T   N   N   V   S   N   (SEQ ID NO:53)
       GTG AGC AAC AAT GCC ACC AAC AAT GTG AGC AAC (SEQ ID NO:52)

NG5:   V   S   N   N   A   T   N   (SEQ ID NO:55)
       GTG AGC AAT AAT GCC ACC AAC (SEQ ID NO:54)

NG6:   V   S   N   N   (SEQ ID NO:57)
       GTG AGC AAT AAT (SEQ ID NO:56)

NG9:   R   S   L   (SEQ ID NO:59)
       AGG AGC CTG (SEQ ID NO:58)

NG10:  A   T   N   V   S   N   N   S   A   T   S   A   D   S   A   V   S   (SEQ ID NO:61)
       GCC ACT AAT GTG TCT AAC AAC TCT GCT ACC TCT GCT GAC TCT GCT GTG AGC (SEQ ID NO:60)

NG16:  A   T   N   Y   V   N   R   S   L   (SEQ ID NO:63)
       GCC ACC AAC TAT GTG AAC AGG AGC CTG (SEQ ID NO:62)
```

Figure 13A

```
NG17: A   T   N   Y   V   N   R   S   L   S   A   T   S   A   D   S   A   V   S   Q   N    (SEQ ID NO:65)
      GCC ACC AAC TAT GTG AAC AGG AGC CTG TCT GCC ACC TCT GCT GAC TCT GCT GTG AGC CAG AAT  (SEQ ID NO:64)

NG18: V   S   N   V   S   A   N   A   V   S   A   T   S   A   D   S   A    (SEQ ID NO:67)
      GTG AGC AAC GTG AGC GCT AAT GCT GTG TCT GCT ACC TCT GCT GAC TCT GCT  (SEQ ID NO:66)

NG19: I   T   V   A   S   A   T   S   N   I   T   V   A   S   A   D    (SEQ ID NO:69)
      ATC ACT GTG GCC TCT GCC ACC TCT AAC ATC ACT GTG GCC TCT GCT GAC  (SEQ ID NO:68)

NG20: I   T   V   T   N   I   T   V   T   A    (SEQ ID NO:71)
      ATC ACT GTG ACC AAC ATC ACT GTG ACT GCC  (SEQ ID NO:70)

NG21: Q   T   V   T   N   I   T   V   T   A    (SEQ ID NO:73)
      CAG ACT GTG ACC AAC ATC ACT GTG ACT GCC  (SEQ ID NO:72)

NGV:  A   T   N   V   S   V   N   S   N   T   S   N   D   S   N   V   S    (SEQ ID NO:75)
      GCC ACT AAT GTG TCT GTG AAC AGC AAT ACC AGC AAC GAC AGC AAT GTG TCT  (SEQ ID NO:74)
```

```
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCATGTCCTCAGGAACAGGGCACAGTCTGGCTCTGTGCCACAGTTCAAGAAAGTG
GTCTTCCAGGAGTTCACTGATGGCTCATTCACCCAGCCCCTGTACAGAGGGAACTGAATGAGCAC
```

```
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCTCCTGACAAGATAC
CTGAGAATTCACCCCAGTCTTGGGTCCACCAGATTGCCCTGAGAATGGAAGTCCTGGGATGTGAG
GCACAAGACCTGTACTGA   (SEQ ID NO:13)
```

```
ATGCAGATCGAACTGAGCACTTGCTTCTTCCTGTGTCTCCTGCGCTTTTGCTTCTCCGCCACAAGG
AGATACTATCTCGGTGCCGTGGAGCTCAGCTGGGACTACATGCAGAGCGACTTGGGTGAACTGCCT
GTGGACGCCAGGTTTCCACCCCGCGTGCCCAAGAGTTTCCCGTTCAACACCAGTGTCGTGTACAAG
AAAACCCTCTTCGTGGAATTCACCGACCACCTGTTCAACATCGCCAAACCGCGCCCTCCCTGGATG
GGGCTGCTCGGCCCGACGATCCAGGCTGAGGTCTATGACACGGTGGTGATTACCCTCAAGAACATG
GCTAGCCACCGGTGAGCCTGCACGCCGTGGGCGTGTCCTATTGGAAAGCGTCCGAGGGTGCGGAG
TACGATGACCAGACTTCACAGCGGGAGAAGGAAGACGACAAAGTGTTCCCGGGGGTTCCCACACC
TATGTCTGGCAGGTCCTGAAGGAGAATGGTCCTATGGCCTCCGACCCATTGTGCCTCACCTACTCT
TACCTAAGCCATGTGGATCTCGTCAAGGACCTGAACTCGGGGCTGATCGGCGCCCTGCTCGTGTGC
CGGGAGGGCTCACTGGCCAAGGAGAAGACCCAAACTCTGCACAAGTTCATCCTGCTGTTCGCGGTA
TTCGACGAGGGGAAGTCCTGGCACTCCGAGACCAAGAACAGCCTGATGCAGGACCGCGACGCAGCC
TCGGCCCGTGCGTGGCCAAAGATGCACACCGTGAACGGCTACGTTAACAGGAGCCTACCCGGCCTG
ATCGGCTGCCACCGCAAATCGGTCTACTGGCATGTGATCGGAATGGGCACAACGCCCGAGGTCCAC
AGTATCTTCCTCGAGGGCCACACTTTCCTGGTCCGGAATCACCGCCAGGCCAGCCTGGAGATCAGC
CCCATAACCTTTCTGACGGCGCAGACCTTACTCATGGATCTCGGCCAGTTCCTCCTGTTCTGCCAC
ATTTCGTCCCACCAGCACGATGGGATGGAAGCATATGTGAAAGTGGACTCCTGCCCCGAGGAACCC
CAGCTTAGGATGAAGAACAATGAGGAGGCCGAGGACTACGACGATGACCTTACCGATTCAGAAATG
GACGTAGTACGCTTTGACGACGACAACTCTCCATCCTTCATACAGATTCGCTCCGTCGCCAAGAAG
CACCCTAAGACTTGGGTGCACTACATCGCGGCCGAGGAGGAGGACTGGGATTATGCTCCCCTGGTG
CTGGCCCCGACGACCGCAGCTACAAGAGCCAGTACCTGAATAACGGGCCCCAGCGCATCGGCCGG
AAGTACAAGAAAGTGCGGTTCATGGCTTACACGGACGAGACCTTCAAGACCCGGGAGGCTATCCAG
CATGAGAGCGGCATCTTGGGGCCCCTCCTGTACGGCGAAGTTGGAGACACACTGCTGATCATCTTC
AAGAACCAGGCGAGCAGGCCCTACAACATCTACCCCCACGGCATTACCGATGTCCGGCCGTTGTAC
AGCCGACGGCTGCCCAAGGGCGTGAAGCACCTGAAGGACTTTCCGATCCTGCCGGGCGAGATCTTC
AAGTACAAGTGGACTGTGACCGTGGAGGATGGGCCGACCAAGAGCGATCCGCGCTGCCTGACCCGT
TACTACTCCAGCTTTGTCAATATGGAGCGCGACCTCGCTAGCGGCTTGATTGGCCCTCTGCTGATC
TGCTACAAGGAGTCCGTGGACCAGAGGGGGAATCAGATCATGAGTGACAAGAGGAACGTGATCCTG
TTCTCCGTGTTCGACGAAAACCGCAGCTGGTATCTCACCGAGAATATCCAGCGCTTCCTGCCCAAC
CCGGCCGGTGTGCAGCTGGAGGACCCCGAGTTTCAGGCCAGCAACATCATGCATTCTATCAACGGA
TATGTGTTTGATTCCCTGCAGCTCTCAGTGTGTCTGCACGAGGTCGCCTACTGGTATATCCTCAGC
ATTGGGGCACAGACCGACTTCCTGAGCGTGTTCTTCTCCGGGTATACCTTCAAGCACAAGATGGTG
TACGAGGATACCCTGACCCTGTTCCCCTTTAGCGGCGAAACCGTGTTTATGTCTATGGAGAACCCC
GGGCTCTGGATCCTTGGCTGCCATAACTCCGACTTCCGCAACCGCGGAATGACCGCGCTCCTGAAA
GTGTCGAGTTGTGACAAGAACACCGGCGACTATTACGAGGACAGTTACGAGGACATCTCTGCGTAC
CTCCTTAGCAAGAATAACGCCATCGAGCCAAGATCCTTCAGCCAGAACCCCCCAGTGCTGAAGAGG
CATCAGCGGGAGATCACCCGCACGACCCTGCAGTCGGATCAGGAGGAGATTGATTACGACGACACG
ATCAGTGTGGAGATGAAGAAGGAGGACTTCGACATCTACGACGAAGATGAAAACCAGTCCCCTCGG
TCCTTCCAAAAGAAGACCCGGCACTACTTCATCGCCGCTGTGGAACGCCTGTGGGACTATGGAATG
```

```
TCTTCTAGCCCTCACGTTTTGAGGAACCGCGCCCAGTCGGGCAGCGTGCCCCAGTTCAAGAAAGTG
GTGTTCCAGGAGTTCACCGACGGCTCCTTCACCCAGCCACTTTACCGGGGCGAGCTCAATGAACAT
CTGGGCCTGCTGGGACCCTACATCAGGGCTGAGGTGGAGGACAACATCATGGTGACATTCCGGAAT
CAGGCCAGCAGACCATACAGTTTCTACAGTTCACTCATCTCCTACGAGGAGGACCAGCGCCAGGGG
GCTGAACCCCGTAAGAACTTCGTGAAGCCAAACGAAACAAAGACCTACTTCTGGAAGGTCCAGCAC
CACATGGCACCTACCAAGGACGAGTTCGATTGCAAGGCCTGGGCCTACTTCTCCGACGTGGACCTG
GAGAAAGATGTGCACAGCGGCCTGATTGGCCCTCTGCTGGTGTGTCACACGAACACACTCAACCCT
GCACACGGGCGGCAGGTCACTGTGCAGGAATTCGCCCTGTTCTTTACCATCTTTGATGAGACGAAG
TCCTGGTATTTCACCGAAAACATGGAGAGGAACTGCCGCGCACCCTGCAACATCCAGATGGAAGAT
CCGACATTCAAGGAGAACTACCGGTTCCATGCCATCAATGGCTACATCATGGACACCCTGCCTGGC
CTCGTGATGGCCCAAGACCAGCGTATCCGCTGGTATCTGCTGTCGATGGGCTCCAACGAGAACATC
CATAGTATCCACTTCAGCGGGCATGTCTTCACGGTGAGGAAAAAGGAGGAGTACAAGATGGCACTG
TACAACCTCTATCCCGGCGTGTTCGAGACCGTGGAGATGCTGCCCTCCAAGGCCGGCATCTGGAGA
GTGGAATGCCTGATCGGCGAGCACCTCCACGCTGGGATGTCCACGCTGTTCCTCGTTTACAGCAAT
AAGTGCCAGACCCCTCTGGGCATGGCGAGCGGCCACATCCGCGACTTCCAGATTACAGCCAGCGGC
CAGTACGGTCAGTGGGCTCCAAAGCTGGCCCGTCTGCACTACTCCGGATCCATCAACGCCTGGTCC
ACCAAGGAACCGTTCTCCTGGATCAAAGTAGACCTGCTAGCCCCCATGATCATTCACGGCATCAAG
ACACAAGGCGCCCGACAGAAGTTCTCGAGCCTCTATATCTCCCAGTTCATCATCATGTATAGCCTG
GACGGAAAGAAGTGGCAGACTTACCGCGGAAACTCGACAGGGACCCTGATGGTATTCTTCGGTAAC
GTGGACAGCTCCGGAATCAAGCACAACATCTTCAACCCACCCATTATCGCCCGCTACATCCGCCTG
CACCCCACTCACTATAGCATTAGGTCCACCCTGCGAATGGAGCTCATGGGCTGTGACCTGAACAGC
TGTAGCATGCCCCTCGGCATGGAGTCTAAGGCGATCTCCGACGCACAGATAACGGCATCATCCTAC
TTTACCAACATGTTCGCTACCTGGTCCCCCTCCAAGGCCCGACTCCACCTGCAAGGGAGATCCAAC
GCCTGGCGGCCACAGGTCAACAATCCCAAGGAGTGGCTGCAAGTGGACTTTCAGAAAACTATGAAA
GTCACCGGAGTGACCACACAGGGAGTGAAGTCTCTGCTGACCAGCATGTACGTGAAGGAGTTCCTC
ATCTCCAGTTCGCAGGATGGCCACCAGTGGACGTTGTTCTTCCAAAACGGTAAAGTCAAAGTCTTC
CAAGGGAACCAGGACAGCTTTACACCCGTCGTGAACTCCCTGGACCCCCGCTTCTCACTAGATAC
CTCCGCATCCACCCTCAGAGCTGGGTGCACCAGATTGCCCTGCGCATGGAGGTTCTGGGGTGTGAA
GCCCAGGACCTGTACTAA (SEQ ID NO:14)
```

```
ATGCAGATTGAGCTCTCCACCTGCTTCTTTCTCTGCCTTCTTCGCTTCTGCTTTTCTGCCACACGC
AGGTACTATTTGGGAGCAGTGGAACTGAGCTGGGATTACATGCAGAGTGACCTTGGTGAACTTCCT
GTGGACGCTCGTTTTCCACCTAGAGTTCCCAAGTCCTTCCCCTTCAACACCTCAGTGGTCTACAAG
AAAACGCTGTTTGTGGAGTTCACTGACCACCTCTTCAACATTGCCAAACCAAGACCCCCTTGGATG
GGATTGCTGGGACCCACAATACAAGCAGAAGTCTACGACACGGTGGTGATTACCCTGAAGAACATG
GCGTCACACCCTGTTTCACTTCACGCTGTTGGGGTCAGTTATTGGAAAGCCTCAGAGGGTGCGGAA
TACGATGATCAAACCAGCCAGAGGGAGAAGGAAGATGACAAGGTCTTTCCTGGGGGTAGCCATACC
TATGTTTGGCAGGTGCTGAAAGAGAATGGGCCTATGGCCTCTGATCCCTTGTGCCTCACATACTCT
TACCTGAGTCACGTCGACCTGGTGAAAGACCTGAATAGCGGTCTGATTGGTGCACTGCTTGTTTGT
AGAGAGGGGAGTTTGGCCAAGGAGAAAACTCAGACTCTCCACAAGTTTATCCTCCTGTTTGCTGTG
TTCGACGAGGGCAAGTCTTGGCACTCTGAAACAAAGAACTCCCTGATGCAGGACAGAGATGCTGCA
TCTGCAAGGGCTTGGCCAAAAATGCACACAGTGAACGGCTATGTGAATCGATCACTGCCAGGACTG
ATAGGCTGTCATCGCAAGTCAGTGTATTGGCACGTTATCGGGATGGGAACAACTCCAGAAGTGCAC
AGCATCTTCCTTGAGGGCCACACTTTCCTGGTTCGGAATCATAGACAGGCCAGCCTTGAGATCAGC
CCAATCACCTTTCTGACTGCCCAAACCTTGCTGATGGATCTGGGACAGTTCCTCCTGTTTTGTCAC
ATCTCCTCCCACCAACATGACGGGATGGAGGCTTATGTGAAGGTCGATAGCTGTCCGGAGGAACCA
CAACTGAGGATGAAGAACAACGAAGAGGCAGAGGACTATGACGACGATCTGACTGACAGTGAAATG
GACGTGGTTCGGTTCGACGATGACAATTCTCCTTCATTTATCCAGATCCGTTCCGTGGCCAAGAAG
CACCCCAAGACTTGGGTTCATTACATCGCTGCTGAGGAGGAGGATTGGGACTACGCGCCCTTGGTG
TTGGCCCCAGACGATCGCTCATACAAGAGCCAGTACCTTAACAATGGTCCACAAAGGATCGGCCGG
AAGTACAAGAAGGTTAGATTTATGGCTTATACCGACGAGACTTTTAAAACTAGGGAAGCAATTCAG
CATGAAAGTGGCATTCTTGGACCCCTGCTGTATGGCGAGGTTGGCGACACCCTGCTGATTATCTTT
AAGAACCAGGCAAGCCGGCCCTACAACATCTACCCGCACGGCATAACCGATGTACGACCCCTGTAC
AGTCGCAGACTTCCTAAAGGGGTGAAACACCTGAAGGACTTCCCAATTCTGCCCGGGGAGATCTTC
AAGTATAAATGGACCGTGACGGTTGAGGATGGTCCCACAAAGTCCGATCCGAGATGCCTTACCCGA
TATTATTCCAGCTTCGTGAACATGGAAAGGGACCTGGCCAGCGGGCTGATTGGCCCACTGCTGATT
TGTTACAAGGAGTCTGTCGATCAAAGAGGAAACCAAATAATGAGCGACAAACGTAACGTCATCCTG
TTCAGCGTCTTTGATGAGAATAGAAGCTGGTACCTCACAGAAAATATTCAGCGGTTTCTGCCTAAC
CCCGCAGGCGTCCAGCTGGAAGATCCCGAGTTCCAAGCCTCAAACATCATGCATAGCATCAACGGA
TACGTATTCGATAGCCTGCAGCTGTCCGTCTGTCTCCATGAAGTGGCATATTGGTACATCCTGAGT
ATCGGGGCGCAGACCGACTTCCTGAGCGTGTTCTTTTCTGGATACACGTTCAAACACAAAATGGTC
TATGAAGATACCCTGACTCTGTTTCCATTCTCAGGAGAGACAGTCTTTATGAGTATGGAAAATCCT
GGACTGTGGATCCTGGGCTGTCACAATTCTGATTTCGGAACAGAGGCATGACAGCCCTGCTTAAA
GTGAGCTCATGCGACAAGAACACCGGTGATTACTACGAAGATAGCTATGAGGACATCAGTGCGTAT
TTGCTCTCCAAGAACAACGCTATCGAGCCACGGTCTTTCAGTCAGAATCCTCCGTTCTGAAGCGG
CATCAGCGCGAAATAACACGCACAACCCTTCAGTCAGACCAAGAGGAAATCGACTACGATGATACT
ATCTCTGTGGAGATGAAGAAGGAGGATTTCGACATTTACGACGAGGACGAGAATCAGTCCCCAAGG
AGCTTTCAGAAGAAAACAAGACACTATTTCATTGCCGCCGTGGAGCGACTGTGGGACTACGGCATG
```

```
TCTAGCTCTCCGCATGTACTTAGAAATAGGGCACAAAGCGGATCCGTGCCTCAGTTTAAGAAAGTT
GTCTTTCAGGAGTTTACAGATGGCTCCTTCACCCAGCCCTTGTATCGCGGGAACTCAATGAACAC
CTGGGCCTCCTGGGTCCTTATATTAGGGCCGAAGTCGAGGACAATATCATGGTGACCTTTAGGAAC
CAGGCATCTAGACCTTACTCTTTCTACTCCTCCCTGATATCCTATGAGGAGGACCAGCGGCAAGGC
GCTGAGCCTCGGAAGAACTTTGTGAAGCCAAATGAAACCAAAACATACTTTTGGAAAGTTCAGCAC
CACATGGCTCCCACGAAGGACGAATTTGACTGTAAAGCCTGGGCCTACTTCTCAGATGTAGATCTC
GAGAAAGACGTGCACTCAGGGCTCATTGGTCCCCTCCTGGTCTGTCATACTAATACCCTCAATCCA
GCACACGGACGTCAGGTAACCGTCCAGGAATTTGCCCTGTTCTTTACCATTTTCGATGAGACTAAA
TCCTGGTACTTTACCGAAAACATGGAGAGGAATTGCAGAGCCCCATGCAACATCCAGATGGAGGAC
CCTACCTTCAAAGAGAACTATCGCTTCCATGCCATTAACGGTTACATTATGGATACTCTCCCAGGA
CTTGTGATGGCACAGGATCAGCGGATAAGATGGTATCTGTTGAGCATGGGCTCCAACGAGAATATT
CACAGCATCCATTTCTCCGGTCACGTGTTTACAGTGAGAAAGAAAGAAGAGTACAAGATGGCTCTG
TATAATCTCTATCCAGGCGTATTCGAAACGGTGGAGATGTTGCCTAGCAAGGCCGGCATTTGGCGA
GTAGAATGCCTTATCGGGGAACATCTGCATGCCGGAATGAGCACGCTCTTCCTGGTGTATAGTAAC
AAGTGCCAGACTCCGCTGGGCATGGCATCTGGCCATATACGGGACTTTCAGATTACGGCTAGCGGG
CAGTATGGGCAGTGGGCACCCAAACTTGCGCGACTGCACTATTCAGGCTCTATCAATGCATGGTCC
ACCAAGGAACCCTTCTCTTGGATTAAGGTGGACCTTTTGGCGCCCATGATAATCCATGGGATCAAA
ACCCAGGGCGCTCGTCAGAAATTCTCATCACTCTACATCTCTCAGTTCATAATAATGTATTCACTG
GATGGGAAGAAATGGCAGACTTACAGAGGAAACAGCACCGGGACGCTGATGGTGTTCTTTGGCAAC
GTGGACAGCAGCGGCATCAAACACAACATCTTCAATCCTCCCATTATTGCCCGTTATATTAGACTG
CATCCCACTCACTACTCTATACGCAGCACACTTAGGATGGAGCTCATGGGATGCGACCTGAACAGT
TGTAGTATGCCCTTGGGGATGGAGTCCAAAGCTATAAGCGACGCACAAATTACAGCTAGCTCTTAC
TTTACGAATATGTTCGCCACGTGGAGCCCAAGCAAAGCCCGGCTGCATTTGCAGGGTCGGAGTAAT
GCTTGGCGCCCACAGGTGAATAACCCTAAGGAATGGTTGCAAGTAGATTTCCAGAAAACTATGAAG
GTAACCGGCGTCACTACACAGGGAGTCAAGTCCCTCTTGACCTCTATGTACGTCAAGGAGTTCCTG
ATTAGCAGCAGTCAGGATGGGCACCAATGGACACTGTTCTTCCAGAATGGGAAAGTTAAAGTATTT
CAGGGTAACCAGGACTCCTTTACACCTGTGGTGAATAGCCTCGACCCACCCCTGCTGACACGATAC
CTCCGCATCCACCCTCAGTCTTGGGTGCATCAAATTGCCCTGCGAATGGAGGTGTTGGGATGCGAA
GCTCAGGACCTCTACTGA (SEQ ID NO:15)
```

```
ATGCAGATCGAACTCTCTACTTGCTTCTTCCTGTGCCTTCTGAGGTTCTGCTTCTCTGCCACTCGC
CGATATTACCTCGGGGCCGTGGAGTTGAGTTGGGACTACATGCAATCAGATCTGGGCGAACTCCCT
GTGGATGCCCGATTCCCACCGCGCGTGCCCAAGTCTTTCCCATTTAATACTTCTGTGGTGTACAAG
AAGACATTGTTTGTGGAGTTTACCGATCACCTGTTCAACATCGCCAAACCGCGGCCCCCATGGATG
GGTCTGCTTGGGCCCACCATTCAAGCGGAGGTCTATGATACAGTGGTGATAACGCTTAAGAACATG
GCGAGCCACCCAGTGTCTCTGCATGCCGTTGGTGTATCATATTGGAAGGCCAGCGAAGGAGCGGAG
TACGATGACCAGACCTCTCAGAGAGAGAAGGAAGACGATAAGGTTTTTCCTGGCGGAAGTCATACA
TATGTATGGCAGGTCCTGAAAGAGAATGGGCCGATGGCTTCTGACCCCCTTTGTCTTACCTATAGT
TATCTGAGCCACGTGGACCTGGTCAAGGACCTCAACAGTGGTCTGATTGGGGCTCTGCTTGTTTGT
AGAGAGGGTAGCTTGGCTAAGGAGAAAACCCAAACACTCCATAAGTTCATTTTGCTGTTCGCGGTG
TTCGACGAGGGAAAGAGTTGGCACAGCGAAACAAAGAATTCACTGATGCAAGACAGGGACGCCGCT
TCCGCAAGGGCTTGGCCTAAGATGCATACGGTGAATGGGTATGTGAACCGGAGCCTCCCGGGGCTG
ATCGGGTGCCATCGCAAGTCTGTTTACTGGCACGTCATTGGAATGGGGACAACGCCAGAGGTACAT
AGTATATTTCTTGAAGGCCACACGTTCCTCGTACGGAACCACCGACAGGCTTCCCTGGAGATAAGC
CCCATTACCTTTCTGACCGCTCAGACTCTGCTGATGGACCTTGGCCAGTTTCTCCTGTTCTGCCAT
ATTAGCAGCCACCAGCACGACGGTATGGAAGCATACGTGAAAGTCGATAGCTGTCCTGAGGAGCCT
CAGCTCAGAATGAAGAACAACGAGGAGGCCGAAGACTATGACGATGACCTTACAGATTCCGAGATG
GACGTGGTGCGCTTTGACGACGATAACAGTCCTAGTTTCATTCAAATCAGATCCGTAGCCAAAAAG
CATCCAAAGACATGGGTGCATTACATTGCAGCCGAAGAGGAGGATTGGGATTATGCGCCCCTTGTT
CTGGCTCCAGATGACAGGAGCTATAAGTCCCAGTACTTGAACAACGGGCCACAGCGAATCGGTAGA
AAATATAAGAAGGTAAGATTCATGGCCTACACTGACGAAACATTTAAAACCAGGGAAGCTATCCAA
CACGAATCTGGAATTCTCGGCCCTCTGCTCTACGGTGAGGTGGGGGACACCTTGCTGATCATTTTC
AAAAATCAGGCATCCAGGCCTTACAACATATACCCCCATGGCATCACCGATGTCCGCCCGCTGTAT
TCCAGAAGACTCCCCAAGGGAGTGAAACATCTGAAAGATTTTCCCATCCTGCCGGGCGAGATCTTT
AAATACAAATGGACTGTGACTGTAGAGGACGGGCCTACAAAATCAGACCCACGGTGCCTGACAAGG
TATTACAGTAGCTTCGTCAACATGGAACGCGACCTCGCCAGCGGACTCATTGGCCCACTGTTGATC
TGTTACAAAGAGTCAGTGGATCAGAGGGGAAATCAGATCATGAGCGATAAGAGAAACGTTATCCTG
TTTAGTGTCTTCGACGAGAACCGGTCTTGGTACCTTACTGAGAACATCCAGAGGTTCCTGCCGAAT
CCGGCTGGCGTTCAGCTCGAGGACCCAGAGTTCCAGGCCAGTAATATAATGCACTCAATCAACGGT
TATGTGTTCGATAGCCTGCAGCTGAGCGTCTGCCTCCACGAGGTAGCCTATTGGTACATATTGTCC
ATCGGGGCTCAGACCGATTTTCTGTCCGTGTTCTTTAGCGGGTATACCTTTAAACATAAAATGGTC
TATGAAGACACCCTGACCCTGTTCCCATTCTCCGGTGAGACTGTGTTCATGTCCATGGAGAACCCA
GGGCTGTGGATCCTGGGGTGTCACAATAGTGACTTTAGGAATCGGGAATGACGGCACTGCTGAAG
GTGAGTTCTTGCGATAAAAATACAGGAGATTACTATGAGGATAGTTACGAGGATATCAGTGCCTAT
CTGCTTTCAAAAAACAACGCAATTGAGCCCCGGTCTTTCTCACAAAACCCCCGGTGCTGAAGCGC
CACCAGCGCGAAATTACCCGGACAACCTTGCAGTCCGACCAGGAGGAAATCGATTATGACGATACT
ATCAGTGTAGAAATGAAAAAGGAGGATTTTGATATTTACGACGAAGACGAGAACCAGTCTCCGCGA
```

```
AGTTTTCAGAAGAAAACGCGACACTACTTTATAGCTGCCGTGGAACGACTCTGGGATTATGGCATG
TCCTCCAGCCCTCATGTCCTTAGGAATCGAGCGCAGAGTGGCTCTGTGCCTCAGTTCAAAAAGGTT
GTGTTCCAGGAATTCACCGACGGCTCATTTACCCAGCCGCTGTACAGAGGCGAACTCAACGAACAC
CTTGGGCTGCTTGGGCCATATATTCGAGCAGAGGTGGAAGATAATATCATGGTAACCTTTAGAAAC
CAGGCGTCAAGACCCTATTCCTTCTACAGTTCTCTGATCAGCTACGAGGAGGACCAAAGACAGGGA
GCTGAACCCAGGAAGAACTTTGTGAAACCTAATGAGACCAAGACCTACTTCTGGAAGGTCCAGCAC
CATATGGCCCCAACTAAAGATGAATTCGATTGCAAGGCCTGGGCTTATTTCAGCGACGTGGATCTC
GAAAAGGATGTGCACAGCGGGTTGATCGGACCGCTTTTGGTGTGCCACACAAATACCCTCAATCCT
GCCCACGGGCGGCAGGTCACAGTTCAAGAGTTTGCACTCTTCTTTACAATATTTGACGAGACAAAG
TCATGGTATTTTACAGAGAATATGGAGAGAAATTGTCGCGCACCTTGCAACATTCAGATGGAGGAC
CCCACATTTAAGGAGAATTACAGATTTCATGCTATCAATGGGTACATTATGGATACTCTGCCTGGT
CTGGTCATGGCCCAGGATCAGCGCATAAGGTGGTACTTGCTGAGCATGGGATCTAATGAGAATATA
CACAGCATTCACTTCAGTGGCCACGTTTTTACTGTTAGAAAGAAGGAGGAGTACAAAATGGCGCTC
TACAACCTTTACCCGGGTGTGTTTGAGACAGTGGAGATGCTGCCAAGCAAGGCAGGCATCTGGAGG
GTTGAGTGTCTTATTGGGGAGCATCTGCATGCTGGAATGTCCACCCTCTTTCTTGTGTACAGCAAT
AAGTGCCAGACACCGCTTGGCATGGCCAGCGGCCACATTAGGGACTTTCAGATAACTGCCAGTGGA
CAGTACGGCCAGTGGGCTCCCAAGCTTGCAAGACTCCACTACTCCGGAAGCATAAACGCATGGAGC
ACCAAGGAACCCTTCTCTTGGATTAAGGTGGACCTGCTGGCGCCAATGATCATTCACGGCATAAAA
ACCCAAGGGGCACGACAGAAATTTTCATCTTTGTATATTAGTCAGTTTATCATCATGTACAGCTTG
GATGGAAAGAAGTGGCAGACGTACAGGGGCAATTCTACAGGAACACTTATGGTGTTTTTGGGAAT
GTCGATTCCAGCGGGATCAAACATAACATCTTCAATCCTCCTATTATCGCCCGATATATCCGCCTG
CACCCTACGCATTACTCCATCAGGTCCACATTGAGAATGGAACTGATGGGGTGCGACCTGAATAGT
TGTAGTATGCCACTGGGCATGGAGTCTAAAGCCATCAGCGATGCACAGATCACTGCCAGCTCTTAC
TTCACCAACATGTTTGCAACTTGGTCCCCTCTAAAGCTCGCCTGCATCTGCAGGGACGCTCAAAT
GCATGGCGACCACAGGTGAACAATCCAAAAGAGTGGCTCCAGGTCGACTTTCAGAAGACAATGAAG
GTAACAGGAGTGACAACCCAGGGTGTAAAAAGCCTCCTTACGAGTATGTACGTTAAGGAGTTTCTG
ATTTCTAGCTCCCAGGACGGACACCAGTGGACTCTGTTCTTCCAGAACGGCAAAGTGAAGGTATTT
CAGGGAAACCAGGATTCTTTTACCCCGGTAGTGAATAGCCTGGATCCACCGTTGCTGACCCGCTAT
CTGAGAATTCATCCACAATCCTGGGTGCATCAGATTGCCCTCCGGATGGAAGTGCTCGGCTGTGAA
GCTCAGGATCTGTATTAG (SEQ ID NO:16)
```

```
ATGCAAATAGAGCTCTCCACCTGCTTCTTTCTGTGCCTTTTGCGATTCTGCTTTAGTGCCACCAGA
AGATACTACCTGGGTGCAGTGGAACTGTCATGGGACTATATGCAAAGTGATCTCGGTGAGCTGCCT
GTGGACGCAAGATTTCCTCCTAGAGTGCCAAAATCTTTTCCATTCAACACCTCAGTCGTGTACAAA
AAGACTCTGTTTGTAGAATTCACGGATCACCTTTTCAACATCGCTAAGCCAAGGCCACCCTGGATG
GGTCTGCTAGGTCCTACCATCCAGGCTGAGGTTTATGATACAGTGGTCATTACACTTAAGAACATG
GCTTCCCATCCTGTCAGTCTTCATGCTGTTGGTGTATCCTACTGGAAAGCTTCTGAGGGAGCTGAA
TATGATGATCAGACCAGTCAAAGGGAGAAAGAAGATGATAAAGTCTTCCCTGGTGGAAGCCATACA
TATGTCTGGCAGGTCCTGAAAGAGAATGGTCCAATGGCCTCTGACCCACTGTGCCTTACCTACTCA
TATCTTTCTCATGTGGACCTGGTAAAAGACTTGAATTCAGGCCTCATTGGAGCCCTACTAGTATGT
AGAGAAGGGAGTCTGGCCAAGGAAAAGACACAGACCTTGCACAAATTTATACTACTTTTTGCTGTA
TTTGATGAAGGGAAAAGTTGGCACTCAGAAACAAAGAACTCCTTGATGCAGGATAGGGATGCTGCA
TCTGCTCGGGCCTGGCCTAAAATGCACACAGTCAATGGTTATGTAAACAGGTCTCTGCCAGGTCTG
ATTGGATGCCACAGGAAATCAGTCTATTGGCATGTGATTGGAATGGGCACCACTCCTGAAGTGCAC
TCAATATTCCTCGAAGGTCACACATTTCTTGTGAGGAACCATCGCCAGGCGTCCTTGGAAATCTCG
CCAATAACTTTCCTTACTGCTCAAACACTCTTGATGGACCTTGGACAGTTTCTACTGTTTTGTCAT
ATCTCTTCCCACCAACATGATGGCATGGAAGCTTATGTCAAAGTAGACAGCTGTCCAGAGGAACCC
CAACTACGAATGAAAAATAATGAAGAAGCGGAAGACTATGATGATGATCTTACTGATTCTGAAATG
GATGTGGTCAGGTTTGATGATGACAACTCTCCTTCCTTTATCCAAATTCGCTCAGTTGCCAAGAAG
CATCCTAAAACTTGGGTACATTACATTGCTGCTGAAGAGGAGGACTGGGACTATGCTCCCTTAGTC
CTCGCCCCCGATGACAGAAGTTATAAAAGTCAATATTTGAACAATGGCCCTCAGCGGATTGGTAGG
AAGTACAAAAAAGTCCGATTTATGGCATACACAGATGAAACCTTTAAGACTCGTGAAGCTATTCAG
CATGAATCAGGAATCTTGGGACCTTTACTTTATGGGGAAGTTGGAGACACACTGTTGATTATATTT
AAGAATCAAGCAAGCAGACCATATAACATCTACCCTCACGGAATCACTGATGTCCGTCCTTTGTAT
TCAAGGAGATTACCAAAAGGTGTAAAACATTTGAAGGATTTTCCAATTCTGCCAGGAGAAATATTC
AAATATAAATGGACAGTGACTGTAGAAGATGGGCCAACTAAATCAGATCCTCGGTGCCTGACCCGC
TATTACTCTAGTTTCGTTAATATGGAGAGAGATCTAGCTTCAGGACTCATTGGCCCTCCTCATC
TGCTACAAAGAATCTGTAGATCAAAGAGGAAACCAGATAATGTCAGACAAGAGGAATGTCATCCTG
TTTTCTGTATTTGATGAGAACCGAAGCTGGTACCTCACAGAGAATATACAACGCTTTCTCCCCAAT
CCAGCTGGAGTGCAGCTTGAGGATCCAGAGTTCCAAGCCTCCAACATCATGCACAGCATCAATGGC
TATGTTTTTGATAGTTTGCAGTTGTCAGTTTGTTGCATGAGGTGGCATACTGGTACATTCTAAGC
ATTGGAGCACAGACTGACTTCCTTTCTGTCTTCTTCTCTGGATATACCTTCAAACACAAAATGGTC
TATGAAGACACACTCACCCTATTCCATTCTCAGGAGAAACTGTCTTCATGTCGATGGAAAACCCA
GGTCTATGGATTCTGGGGTGCCACAACTCAGACTTTCGGAACAGAGGCATGACCGCCTTACTGAAG
GTTTCTAGTTGTGACAAGAACACTGGTGATTATTACGAGGACAGTTATGAAGATATTTCAGCATAC
TTGCTGAGTAAAAACAATGCCATTGAACCAAGAAGCTTCTCCCAGAATCCACCAGTCTTGAAACGC
CATCAACGGGAAATAACTCGTACTACTCTTCAGTCAGATCAAGAGGAAATTGACTATGATGATACC
ATATCAGTTGAAATGAAGAAGGAAGATTTTGACATTTATGATGAGGATGAAAATCAGAGCCCCCGC
AGCTTTCAAAAGAAAACACGACACTATTTTATTGCTGCAGTGGAGAGGCTCTGGGATTATGGGATG
```

```
AGTAGCTCCCCACATGTTCTAAGAAACAGGGCTCAGAGTGGCAGTGTCCCTCAGTTCAAGAAAGTT
GTTTTCCAGGAATTTACTGATGGCTCCTTTACTCAGCCCTTATACCGTGGAGAACTAAATGAACAT
TTGGGACTCCTGGGGCCATATATAAGAGCAGAAGTTGAAGATAATATCATGGTAACTTTCAGAAAT
CAGGCCTCTCGTCCCTATTCCTTCTATTCTAGCCTTATTTCTTATGAGGAAGATCAGAGGCAAGGA
GCAGAACCTAGAAAAAACTTTGTCAAGCCTAATGAAACCAAAACTTACTTTTGGAAAGTGCAACAT
CATATGGCACCCACTAAAGATGAGTTTGACTGCAAAGCCTGGGCTTATTTCTCTGATGTTGACCTG
GAAAAGATGTGCACTCAGGCCTGATTGGACCCCTTCTGGTCTGCCACACTAACACACTGAACCCT
GCTCATGGGAGACAAGTGACAGTACAGGAATTTGCTCTGTTTTTCACCATCTTTGATGAGACCAAA
AGCTGGTACTTCACTGAAAATATGGAAAGAAACTGCAGGGCTCCCTGCAATATCCAGATGGAAGAT
CCCACTTTTAAAGAGAATTATCGCTTCCATGCAATCAATGGCTACATAATGGATACACTACCTGGC
TTAGTAATGGCTCAGGATCAAAGGATTCGATGGTATCTGCTCAGCATGGGCAGCAATGAAAACATC
CATTCTATTCATTTCAGTGGACATGTGTTCACTGTACGAAAAAAAGAGGAGTATAAAATGGCACTG
TACAATCTCTATCCAGGTGTTTTTGAGACAGTGGAAATGTTACCATCCAAAGCTGGAATTTGGCGG
GTGGAATGCCTTATTGGCGAGCATCTACATGCTGGGATGAGCACACTTTTTCTGGTGTACAGCAAT
AAGTGTCAGACTCCCCTGGGAATGGCTTCTGGACACATTAGAGATTTTCAGATTACAGCTTCAGGA
CAATATGGACAGTGGGCCCCAAAGCTGGCCAGACTTCATTATTCCGGATCAATCAATGCCTGGAGC
ACCAAGGAGCCCTTTCTTGGATCAAGGTGGATCTGTTGGCACCAATGATTATTCACGGCATCAAG
ACCCAGGGTGCCCGTCAGAAGTTCTCCAGCCTCTACATCTCTCAGTTTATCATCATGTATAGTCTT
GATGGGAAGAAGTGGCAGACTTATCGAGGAAATTCCACTGGAACCTTAATGGTCTTCTTTGGCAAT
GTGGATTCATCTGGGATAAAACACAATATTTTTAACCCTCCAATTATTGCTCGATACATCCGTTTG
CACCCAACTCATTATAGCATTCGCAGCACTCTTCGCATGGAGTTGATGGGCTGTGATTTAAATAGT
TGCAGCATGCCATTGGGAATGGAGAGTAAAGCAATATCAGATGCACAGATTACTGCTTCATCCTAC
TTTACCAATATGTTTGCCACCTGGTCTCCTTCAAAAGCTCGACTTCACCTCCAAGGGAGGAGTAAT
GCCTGGAGACCTCAGGTGAATAATCCAAAAGAGTGGCTGCAAGTGGACTTCCAGAAGACAATGAAA
GTCACAGGAGTAACTACTCAGGGAGTAAAATCTCTGCTTACCAGCATGTATGTGAAGGAGTTCCTC
ATCTCCAGCAGTCAAGATGGCCATCAGTGGACTCTCTTTTTCAGAATGGCAAAGTAAAGGTTTTT
CAGGGAAATCAAGACTCCTTCACACCTGTGGTGAACTCTCTAGACCCACCGTTACTGACTCGCTAC
CTTCGAATTCACCCCCAGAGTTGGGTGCACCAGATTGCCCTGAGGATGGAGGTTCTGGGCTGCGAG
GCACAGGACCTCTACTGA (SEQ ID NO:17)
```

```
ATGCAGATCGAGCTGTCCACATGCTTTTTTCTGTGCCTGCTGCGGTTCTGCTTCAGCGCCACCCGG
CGGTACTACCTGGGCGCCGTGGAGCTGTCCTGGGACTACATGCAGAGCGACCTGGGCGAGCTGCCC
GTGGACGCCCGGTTCCCCCCCAGAGTGCCCAAGAGCTTCCCCTTCAACACCAGCGTGGTGTACAAG
AAAACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCCGAGGGCGCCGAG
TACGACGACCAGACCAGCCAGCGGGAGAAGAGGACGACAAAGTCTTTCCTGGCGGCAGCCACACC
TACGTGTGGCAGGTCCTGAAAGAAAACGGCCCCATGGCCTCCGACCCCCTGTGCCTGACCTACAGC
TACCTGAGCCACGTGGACCTGGTGAAGGACCTGAACAGCGGGCTGATTGGGGCCCTGCTGGTCTGC
CGGGAGGGCAGCCTGGCCAAAGAGAAAACCCAGACCCTGCACAAGTTCATCCTGCTGTTCGCCGTG
TTCGACGAGGGCAAGAGCTGGCACAGCGAGACCAAGAACAGCCTGATGCAGGACCGGGACGCCGCC
TCTGCCAGAGCCTGGCCCAAGATGCACACCGTGAACGGCTACGTGAACAGAAGCCTGCCCGGCCTG
ATTGGCTGCCACCGGAAGAGCGTGTACTGGCACGTGATCGGCATGGGCACCACACCCGAGGTGCAC
AGCATCTTTCTGGAAGGGCACACCTTTCTGGTGCGGAACCACCGGCAGGCCAGCCTGGAAATCAGC
CCTATCACCTTCCTGACCGCCCAGACACTGCTGATGGACCTGGGCCAGTTCCTGCTGTTTTGCCAC
ATCAGCTCTCACCAGCACGACGGCATGGAAGCCTACGTGAAGGTGGACTCCTGCCCCGAGGAACCC
CAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAG
CACCCCAAGACCTGGGTGCACTACATCGCCGCCGAGGAAGAGGACTGGGACTACGCCCCCCTGGTG
CTGGCCCCCGACGACAGAAGCTACAAGAGCCAGTACCTGAACAATGGCCCCCAGCGGATCGGCCGG
AAGTACAAGAAAGTGCGGTTCATGGCCTACACCGACGAGACCTTCAAGACCCGGGAGGCCATCCAG
CACGAGAGCGGCATCCTGGGCCCCCTGCTGTACGGCGAAGTGGGCGACACACTGCTGATCATCTTC
AAGAACCAGGCCAGCCGGCCCTACAACATCTACCCCCACGGCATCACCGACGTGCGGCCCCTGTAC
AGCAGGCGGCTGCCCAAGGGCGTGAAGCACCTGAAGGACTTCCCCATCCTGCCCGGCGAGATCTTC
AAGTACAAGTGGACCGTGACCGTGGAGGACGGCCCCACCAAGAGCGACCCCAGATGCCTGACCCGG
TACTACAGCAGCTTCGTGAACATGGAACGGGACCTGGCCTCCGGGCTGATCGGACCTCTGCTGATC
TGCTACAAAGAAAGCGTGGACCAGCGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAAC
CCTGCCGGGGTGCAGCTGGAAGATCCCGAGTTCCAGGCCAGCAACATCATGCACTCCATCAATGGC
TACGTGTTCGACAGCCTGCAGCTGTCCGTGTGTCTGCACGAGGTGGCCTACTGGTACATCCTGAGC
ATCGGCGCCCAGACCGACTTCCTGAGCGTGTTCTTCAGCGGCTACACCTTCAAGCACAAGATGGTG
TACGAGGACACCCTGACCCTGTTCCCTTTCAGCGGCGAGACCGTGTTCATGAGCATGGAAAACCCC
GGCCTGTGGATCCTGGGCTGCCACAACAGCGACTTCCGGAACCGGGGCATGACCGCCCTGCTGAAG
GTGTCCAGCTGCGACAAGAACACCGGCGACTACTACGAGGACAGCTACGAGGATATCAGCGCCTAC
CTGCTGTCCAAGAACAACGCCATCGAGCCCAGAAGCTTCAGCCAGAACCCCCTGTGCTGAAGCGG
CACCAGAGAGAGATCACCCGGACCACCCTGCAGTCCGACCAGGAAGAGATCGATTACGACGACACC
```

```
ATCAGCGTGGAGATGAAAAAAGAAGATTTCGACATCTACGACGAGGACGAGAACCAGAGCCCCCGG
TCCTTCCAGAAGAAAACCCGGCACTACTTTATCGCCGCCGTGGAGCGGCTGTGGGACTACGGCATG
AGCAGCAGCCCCACGTGCTGCGGAACCGGGCCCAGAGCGGCAGCGTGCCCCAGTTCAAGAAAGTG
GTGTTCCAGGAATTCACCGACGGCAGCTTCACCCAGCCCTGTACCGGGGCGAGCTGAACGAGCAC
CTGGGGCTGCTGGGGCCCTACATCAGGGCCGAAGTGGAGGACAACATCATGGTGACCTTCCGGAAT
CAGGCCAGCAGACCCTACTCCTTCTACAGCAGCCTGATCAGCTACGAAGAGGACCAGCGGCAGGGC
GCTGAACCCCGGAAGAACTTCGTGAAGCCCAATGAGACCAAGACCTACTTCTGGAAAGTGCAGCAC
CACATGGCCCCCACCAAGGACGAGTTCGACTGCAAGGCCTGGGCCTACTTCAGCGACGTGGATCTG
GAAAAGGACGTGCACTCTGGACTGATTGGCCCTCTGCTGGTGTGCCACACCAACACCCTGAACCCC
GCCCACGGCCGGCAGGTGACCGTGCAGGAATTCGCCCTGTTCTTCACCATCTTCGACGAGACCAAG
TCCTGGTACTTCACCGAGAATATGGAACGGAACTGCAGAGCCCCCTGCAACATCCAGATGGAAGAT
CCTACCTTCAAAGAGAACTACCGGTTCCACGCCATCAACGGCTACATCATGGACACCCTGCCTGGC
CTGGTGATGGCCCAGGACCAGAGGATCCGGTGGTATCTGCTGTCCATGGGCAGCAACGAGAATATC
CACAGCATCCACTTCAGCGGCCACGTGTTCACCGTGAGGAAGAAAGAAGAGTACAAGATGGCCCTG
TACAACCTGTACCCCGGCGTGTTCGAGACCGTGGAGATGCTGCCCAGCAAGGCCGGCATCTGGCGG
GTGGAGTGTCTGATCGGCGAGCACCTGCATGCCGGGATGAGCACCCTGTTTCTGGTGTACAGCAAC
AAGTGCCAGACCCCCCTGGGCATGGCCAGCGGCCACATCCGGGACTTCCAGATCACCGCCTCCGGC
CAGTACGGCCAGTGGGCCCCCAAGCTGGCCCGGCTGCACTACAGCGGCAGCATCAACGCCTGGTCC
ACCAAAGAGCCCTTCAGCTGGATCAAGGTGGACCTGCTGGCCCCTATGATCATCCACGGCATTAAG
ACCCAGGGCGCCAGGCAGAAGTTCAGCAGCCTGTACATCAGCCAGTTCATCATCATGTACAGCCTG
GACGGCAAGAAGTGGCAGACCTACCGGGGCAACAGCACCGGCACCCTGATGGTGTTCTTCGGCAAC
GTGGACAGCAGCGGCATCAAGCACAACATCTTCAACCCCCCCATCATCGCCCGGTACATCCGGCTG
CACCCCACCCACTACAGCATCAGATCCACCCTGCGGATGGAACTGATGGGCTGCGACCTGAACTCC
TGCAGCATGCCTCTGGGCATGGAAAGCAAGGCCATCAGCGACGCCCAGATCACAGCCAGCAGCTAC
TTCACCAACATGTTCGCCACCTGGTCCCCCTCCAAGGCCAGGCTGCACCTGCAGGGCCGGTCCAAC
GCCTGGCGGCCTCAGGTGAACAACCCCAAAGAATGGCTGCAGGTGGACTTTCAGAAAACCATGAAG
GTGACCGGCGTGACCACCCAGGGCGTGAAAAGCCTGCTGACCAGCATGTACGTGAAAGAGTTTCTG
ATCAGCAGCAGCCAGGACGGCCACCAGTGGACCCTGTTCTTTCAGAACGGCAAGGTGAAAGTGTTC
CAGGGCAACCAGGACTCCTTCACCCCCGTGGTGAACTCCCTGGACCCCCCCCTGCTGACCCGCTAC
CTGCGGATCCACCCCCAGTCTTGGGTGCACCAGATCGCCCTGAGGATGGAAGTGCTGGGATGTGAG
GCCCAGGATCTGTACTGA (SEQ ID NO:18)
```

Figure 21B

FVIII-FL-AA

```
mqielstcff lcllrfcfsa trryylgave lswdymqsdl gelpvdarfp prvpksfpfn
tsvvykktlf veftdhlfni akprppwmgl lgptiqaevy dtvvitlknm ashpvslhav
gvsywkaseg aeyddqtsqr ekeddkvfpg gshtyvwqvl kenqpmasdp lcltysylsh
vdlvkdlnsg ligallvcre gslakektqt lhkfillfav fdegkswhse tknslmqdrd
aasarawpkm htvngyvnrs lpgligchrk svywhvigmg ttpevhsifl eghtflvrnh
rqasleispi tfltaqtllm dlgqfllfch isshqhdgme ayvkvdscpe epqlrmknne
eaedydddlt dsemdvvrfd ddnspsfiqi rsvakkhpkt wvhyiaaeee dwdyaplvla
pddrsyksqy lnngpqrigr kykkvrfmay tdetfktrea iqhesgilgp llygevgdtl
liifknqasr pyniyphgit dvrplysrrl pkgvkhlkdf pilpgeifky kwtvtvedgp
tksdprcltr yyssfvnmer dlasgligpl licykesvdq rgnqimsdkr nvilfsvfde
nrswylteni qrflpnpagv qledpefqas nimhsingyv fdslqlsvcl hevaywyils
igaqtdflsv ffsgytfkhk mvyedtltlf pfsgetvfms menpglwilg chnsdfrnrg
mtallkvssc dkntgdyyed syedisayll sknnaieprs fsqnsrhpst rqkqfnatti
pendiektdp wfahrtpmpk iqnvsssdll mllrqsptph glslsdlqea kyetfsddps
pgaidsnnsl semthfrpql hhsgdmvftp esglqlrlne klgttaatel kkldfkvsst
sonlistips dnlaagtdnt sslgppsmpv hydsqldttl fgkksspite sggplslsee
nndskllesg lmnsqesswg knvsstesgr lfkgkrahgp alltkdnalf kvsisllktn
ktsnnsatnr kthidgpsll ienspsvwqn ilesdtefkk vtplihdrml mdknatalrl
nhmsnkttss knmemvqqkk egpippdaqn pdmsffkmlf lpesarwiqr thgknslnsg
qgpspkqlvs lgpeksvegq nflseknkvv vgkgeftkdv glkemvfpss rnlfltnldn
lhennthnqe kkiqeeiekk etliqenvvl pqihtvtgtk nfmknlflls trqnvegsyd
gayapvlqdf rslndstnrt kkhtahfskk qeeenleglg nqtkqiveky acttrispnt
sqqnfvtqrs kralkqfrlp leetelekri ivddtstqws knmkhltpst ltqidyneke
kgaitqspls dcltrshsip qanrsplpia kvssfpsirp iyltrvlfqd nsshlpaasy
rkkdsgvqes shflqgakkn nlslailtle mtgdqrevgs lgtsatnsvt ykkventvlp
kpdlpktsgk vellpkvhiy qkdlfptets ngspghldlv egsllqgteg aikwneanrp
gkvpflrvat essaktpskl ldplawdnhy gtqipkeewk sqekspekta fkkkdtiisl
nacesnhaia ainegqnkpe ievtwakqgr terlcsqnpp vlkrhqreit rttlqsdqee
idyddtisve mkkedfdiyd edenqsprsf qkktrhyfia averlwdygm ssphvlrnr
aqsqsvpqfk kvvfqeftdg sftqplyrge lnehlgllgp yiraevedni mvtfrnqasr
pysfysslis yeedqrqgae prknfvkpne tktyfwkvqh hmaptkdefd ckawayfsdv
dlekdvhsgl igpllvchtn tlnpahgrqv tvqefalfft ifdetkswyf tenmerncra
pcniqmedpt fkenyrfhai ngyimdtlpg lvmaqdqrir wyllsmgsne nihsihfsgh
vftvrkkeey kmalynlypg vfetvemlps kagiwrvecl igehlhagms tlflvysnkc
qtplgmasgh irdfqitasg qygqwapkla rlhysgsina wstkepfswi kvdllapmii
hgiktqgarq kfsslyisqf iimysldgkk wqtyrgnstg tlmvffgnvd ssgikhnifn
ppiiaryirl hpthysirst lrmelmgcdl nscsmplgme skaisdaqit assyftnmfa
twspskarlh lqgrsnawrp qvnnpkewlq vdfqktmkvt gvttqgvksl ltsmyvkefl
isssqdghqw tlffqngkvk vfqgnqdsft pvvnsldppl ltrylrihpq swvhqialrm
evlgceaqdl y (SEQ ID NO:19)
```

```
atgcagattgagctgagcacctgcttcttcctgtgcctgctgaggttctgcttctctgccaccagg
agatactacctgggcgccgtggagctgagctgggactacatgcagtctgacctgggcgagctgcct
gtggacgccaggttcccccccagagtgcccaagagcttccccttcaacacctcagtggtgtacaag
aagaccctgttcgtggagttcaccgaccacctgttcaacatcgccaagcccaggccccccggatg
ggcctgctgggccccaccatccaggccgaggtgtacgacaccgtggtgatcaccctgaagaacatg
gccagccacccgtgagcctgcacgccgtgggcgtgagctactggaaggcctctgagggcgccgag
tatgacgaccagaccagccagagggagaaggaggacgacaaggtgttccccggcggcagccacacc
tacgtgtggcaggtgctgaaggagaacgccccatggccagcgacccctgtgcctgacctacagc
tacctgagccacgtggacctggtgaaggacctgaactctggcctgatcggcgccctgctggtgtgc
agggagggcagcctggccaaggagaagacccagaccctgcacaagttcatcctgctgttcgccgtg
ttcgatgagggcaagagctggcacagcgagaccaagaacagcctgatgcaggacagggatgccgcc
tctgccagggcctggcccaagatgcacaccgtgaacggctacgtgaacaggagcctgcccggcctg
atcggctgccacaggaagtctgtgtactggcacgtgatcggcatgggcaccaccccgaggtgcac
agcatcttcctggagggccacaccttcctggtgaggaaccacaggcaggccagcctggagatcagc
cccatcaccttcctgaccgcccagaccctgctgatggacctgggccagttcctgctgttctgccac
atcagcagccaccagcacgacggcatggaggcctacgtgaaggtggacagctgccccgaggagccc
cagctgaggatgaagaacaacgaggaggccgaggactatgatgatgacctgaccgactctgagatg
gacgtggtgaggtttgatgatgacaacagcccagcttcatccagatcaggtctgtggccaagaag
caccccaagacctgggtgcactacatcgccgcgaggaggaggactgggactacgccccctggtg
ctggccccgacgacaggagctacaagagccagtacctgaacaacggccccagaggatcggcagg
aagtacaagaaggtcagattcatggcctacaccgacgagaccttcaagaccagggaggccatccag
cacgagtctggcatcctgggcccctgctgtacggcgaggtgggcgacaccctgctgatcatcttc
aagaaccaggccagcaggccctacaacatctaccccacggcatcaccgatgtgaggccctgtac
agcaggaggctgcccaagggcgtgaagcacctgaaggacttccccatcctgcccggcgagatcttc
aagtacaagtggaccgtgaccgtggaggatggcccccaccaagtctgaccccaggtgcctgaccagg
tactacagcagcttcgtgaacatggagagggacctggctctggcctgatcggcccctgctgatc
tgctacaaggagagcgtggaccagaggggcaaccagatcatgtctgacaagaggaacgtgatcctg
ttctctgtgttcgatgagaacaggagctggtatctgaccgagaacatccagaggttcctgcccaac
ccgccggcgtgcagctggaggaccccgagttccaggccagcaacatcatgcacagcatcaacggc
tacgtgttcgacagcctgcagctgtctgtgtgcctgcacgaggtggcctactggtacatcctgagc
atcggcgcccagaccgacttcctgtctgtgttcttctctggctacaccttcaagcacaagatggtg
tacgaggacaccctgaccctgttcccttcagcggcgagaccgtgttcatgagcatggagaacccc
ggcctgtggatcctgggctgccacaacagcgacttcaggaacaggggcatgaccgccctgctgaaa
gtcagcagctgcgacaagaacaccggcgactactacgaggacagctacgaggacatcagcgcctac
ctgctgagcaagaacaacgccatcgagcccaggagcttcagccagaacccccgtgctgaagagg
caccagagggagatcaccaggaccacctgcagagcgaccaggaggagatcgactatgatgacacc
```

```
atcagcgtggagatgaagaaggaggacttcgacatctacgacgaggacgagaaccagagccccagg
agcttccagaagaagaccaggcactacttcatcgccgccgtggagaggctgtgggactatggcatg
agcagcagccccacgtgctgaggaacagggcccagagcggcagcgtgccccagttcaagaaggtg
gtgttccaggagttcaccgacggcagcttcaccagcccctgtacagaggcgagctgaacgagcac
ctgggcctgctgggccctacatcagggccgaggtggaggacaacatcatggtgaccttcaggaac
caggccagcaggccctacagcttctacagcagcctgatcagctacgaggaggaccagaggcaggc
gccgagcccaggaagaacttcgtgaagcccaacgagaccaagacctacttctggaaggtgcagcac
cacatggccccaccaaggacgagttcgactgcaaggcctgggcctacttctctgatgtggacctg
gagaaggacgtgcacagcggcctgatcggcccctgctggtgtgccacaccaacaccctgaacccc
gcccacggcaggcaggtgaccgtgcaggagttcgccctgttcttcaccatcttcgacgagaccaag
agctggtacttcaccgagaacatggagaggaactgcagggccccctgcaacatccagatggaggac
cccaccttcaaggagaactacaggttccacgccatcaacggctacatcatggacaccctgccggc
ctggtgatggcccaggaccagaggatcaggtggtatctgctgagcatgggcagcaacgagaacatc
cacagcatccacttcagcggccacgtgttcaccgtgaggaagaaggaggagtacaagatggccctg
tacaacctgtaccccggcgtgttcgagaccgtggagatgctgcccagcaaggccggcatctggagg
gtggagtgcctgatcggcgagcacctgcacgccggcatgagcacctgttcctggtgtacagcaac
aagtgccagaccccctgggcatggccagcggccacatcagggacttccagatcaccgcctctggc
cagtacggccagtgggccccaagctggccaggctgcactacagcggcagcatcaacgcctggagc
accaaggagcccttcagctggatcaaggtggacctgctggccccatgatcatccacggcatcaag
acccagggcgccaggcagaagttcagcagcctgtacatcagccagttcatcatcatgtacagcctg
gacggcaagaagtggcagacctacaggggcaacagcaccggcacctgatggtgttcttcggcaac
gtggacagcagcggcatcaagcacaacatcttcaaccccccatcatcgccaggtacatcaggctg
cacccccactacagcatcaggagcacctgcggatggaactgatgggctgcgacctgaacagc
tgcagcatgccctgggcatggagagcaaggccatctctgacgcccagatcaccgccagcagctac
ttcaccaacatgttcgccacctggagcccagcaaggccaggctgcacctgcagggcaggagcaac
gcctggaggccccaggtgaacaaccccaaggagtggctgcaggtggacttccagaagaccatgaag
gtgaccggcgtgaccacccagggcgtgaagagcctgctgaccagcatgtacgtgaaggagttcctg
atcagcagcagccaggacggccaccagtggaccctgttcttccagaacggcaaagtgaaggtgttc
cagggcaaccaggacagcttcacCcccgtggtgaacagcctggaccccccctgctgaccaggtat
ctgaggatccaccccagagctgggtgcaccagatcgccctgagaatggaagtgctgggatgcgag
gcccaggacctgtactga  (SEQ ID NO:20)
```

MQIELSTCFFLCLLRFCFSATRRYYLGAVELSWDYMQSDLGELPVDAR'FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY    (SEQ ID NO:21)

```
                                                                gcc
accaggagat actacctggg cgccgtggag ctgagctggg actacatgca gtctgacctg
ggcgagctgc ctgtggacgc caggttcccc cccagagtgc ccaagagctt ccccttcaac
acctcagtgg tgtacaagaa gaccctgttc gtggagttca ccgaccacct gttcaacatc
gccaagccca ggccccctg gatgggcctg ctgggcccca ccatccaggc cgaggtgtac
gacaccgtgg tgatcaccct gaagaacatg ccagccacc ccgtgagcct gcacgccgtg
ggcgtgagct actggaaggc ctctgaggc gccgagtatg acaccagac cagccagagg
gagaaggagg acgacaaggt gttccccggc ggcagccaca cctacgtgtg gcaggtgctg
aaggagaacg gccccatggc cagcgacccc ctgtgcctga cctacagcta cctgagccac
gtggacctgg tgaaggacct gaactctggc ctgatcggcg ccctgctggt gtgcagggag
ggcagcctgg ccaaggagaa gacccagacc ctgcacaagt tcatcctgct gttcgccgtg
ttcgatgagg gcaagagctg gcacagcgag accaagaaca gcctgatgca ggacagggat
gccgcctctg ccagggcctg gccaagatg cacaccgtga acggctacgt gaacaggagc
ctgccggcc tgatcggctg ccacaggaag tctgtgtact ggcacgtgat cggcatgggc
accaccccg aggtgcacag catcttcctg gagggccaca ccttcctggt gaggaaccac
aggcaggcca gctggagat cagccccatc accttcctga ccgcccagac cctgctgatg
gacctggcc agttcctgct gttctgccac atcagcagcc accagcacga cggcatggag
gcctacgtga aggtggacag ctgccccgag gagccccagc tgaggatgaa gaacaacgag
gaggccgagg actatgatga tgacctgacc gactctgaga tggacgtggt gaggtttgat
gatgacaaca gcccagctt catccagatc aggtctgtgg ccaagaagca ccccaagacc
tgggtgcact acatcgccgc cgaggaggag gactgggact acgccccct ggtgctggcc
cccgacgaca ggagctacaa gagccagtac ctgaacaacg gccccagag gatcggcagg
aagtacaaga aggtcagatt catggcctac accgacgaga ccttcaagac cagggaggcc
atccagcacg agtctggcat cctgggcccc ctgctgtacg gcgaggtggg cgacaccctg
ctgatcatct tcaagaacca ggccagcagg ccctacaaca tctaccccca cggcatcacc
gatgtgaggc cctgtacag caggagctg cccaagggcg tgaagcacct gaaggacttc
cccatcctgc cggcgagat cttcaagtac aagtggaccg tgaccgtgga ggatggcccc
accaagtctg accccaggtg cctgaccagg tactacagca gcttcgtgaa catggagagg
gacctggcct ctggctgat cgcccctg ctgatctgct acaaggagag cgtggaccag
aggggcaacc agatcatgtc tgacaagagg aacgtgatcc tgttctctgt gttcgatgag
aacaggagct ggtatctgac cgagaacatc cagaggttcc tgcccaaccc cgccggcgtg
cagctggagg accccgagtt ccaggccagc aacatcatgc acagcatcaa cggctacgtg
ttcgacagcc tgcagctgtc tgtgtgcctg cacgaggtgg cctactggta catcctgagc
atcggcgccc agaccgactt cctgtctgtg ttcttctctg gctacacctt caagcacaag
atggtgtacg aggacacct gaccctgttc cccttcagcg gcgagaccgt gttcatgagc
atggagaacc ccggcctgtg gatcctgggc tgccacaaca gcgacttcag gaacagggc
atgaccgccc tgctgaaagt cagcagctgc gacaagaaca ccggcgacta ctacgaggac
agctacgagg acatcagcgc ctacctgctg agcaagaaca ccgccatcga gcccagg
(SEQ ID NO:22)
```

```
                                                        g agatcaccag gaccaccctg
cagagcgacc aggaggagat cgactatgat gacaccatca gcgtggagat gaagaaggag
gacttcgaca tctacgacga ggacgagaac cagagcccca ggagcttcca gaagaagacc
aggcactact tcatcgccgc cgtggagagg ctgtgggact atggcatgag cagcagcccc
cacgtgctga ggaacagggc ccagagcggc agcgtgcccc agttcaagaa ggtggtgttc
caggagttca ccgacggcag cttcacccag cccctgtaca gaggcgagct gaacgagcac
ctgggcctgc tgggccccta catcagggcc gaggtggagg acaacatcat ggtgaccttc
aggaaccagg ccagcaggcc ctacagcttc tacagcagcc tgatcagcta cgaggaggac
cagaggcagg gcgccgagcc caggaagaac ttcgtgaagc ccaacgagac caagacctac
ttctgaaggg tgcagcacca catggccccc accaaggacg agttcgactg caaggcctgg
gcctacttct ctgatgtgga cctggagaag gacgtgcaca gcggcctgat cggccccctg
ctggtgtgcc acaccaacac cctgaacccc gcccacggca ggcaggtgac cgtgcaggag
ttcgccctgt tcttcaccat cttcgacgag accaagagct ggtacttcac cgagaacatg
gagaggaact gcagggcccc ctgcaacatc agatggagg acccccactt caaggagaac
tacaggttcc acgccatcaa cggctacatc atggacaccc tgcccggcct ggtgatggcc
caggaccaga ggatcaggtg gtatctgctg agcatgggca gcaacgagaa catccacagc
atccacttca gcggccacgt gttcaccgtg aggaagaagg aggagtacaa gatggccctg
tacaacctgt acccggcgt gttcgagacc gtggagatgc tgcccagcaa ggccggcatc
tggagggtgg agtgcctgat cggcgagcac ctgcacgccg gcatgagcac cctgttcctg
gtgtacagca acaagtgcca gaccccctg ggcatggcca gcgccacat caggacttc
cagatcaccg cctctggcca gtacgccag tgggcccca agctggccag gctgcactac
agcggcagca tcaacgcctg gagcaccaag gagcccttca gctggatcaa ggtggacctg
ctggccccca tgatcatcca cggcatcaag acccagggcg ccaggcagaa gttcagcagc
ctgtacatca gccagttcat catcatgtac agcctggacg caagaagtg gcagacctac
agggcaaca gcaccggcac cctgatggtg ttcttcggca acgtggacag cagcggcatc
aagcacaaca tcttcaaccc ccccatcatc gccaggtaca tcaggctgca cccaccccac
tacagcatca ggagcaccct gcggatggaa ctgatgggct gcgacctgaa cagctgcagc
atgcccctgg gcatggagag caaggccatc tctgacgccc agatcaccgc cagcagctac
ttcaccaaca tgttcgccac ctggagcccc agcaaggcca ggctgcacct gcagggcagg
agcaacgcct ggaggcccca ggtgaacaac cccaaggagt ggctgcaggt ggacttccag
aagaccatga aggtgaccgg cgtgaccacc agggcgtga gagcctgct gaccagcatg
tacgtgaagg agttcctgat cagcagcagc caggacggcc accagtggac cctgttcttc
cagaacggca agtgaaggt gttccagggc aaccaggaca gcttcacccc cgtggtgaac
agcctggacc cccccctgct gaccaggtat ctgaggatcc accccagag ctgggtgcac
cagatcgccc tgagaatgga agtgctggga tgcgaggccc aggacctgta c
(SEQ ID NO:23)
```

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTCCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA (Continued)

Figure 30A

```
GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCCATCATTGCCAGATACATCAGG
CTGCACCCCACCCACTACTCAATCAGATCAACCCTCAGGATGGAACTGATGGGATGTGACCTGAAC
TCCTGCTCAATGCCCCTGGGAATGGAGAGCAAGGCCATTTCTGATGCCCAGATCACTGCATCCTCT
TACTTCACCAACATGTTTGCCACCTGGTCACCATCAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCCTCCTGACAAGA
TACCTGAGAATTCACCCCAGTCTTGGGTCCACCAGATTGCCCTGAGAATGGAAGTCCTGGGATGT
GAGGCACAAGACCTGTACTGA (SEQ ID NO:90)
```

```
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA
```

```
GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCATCATTGCCAGATACATCAGG
CTGCACCCCACCCACTACTCAATCAGATCAACCCTCAGGATGGAACTGATGGGATGTGACCTGAAC
TCCTGCTCAATGCCCTGGGAATGGAGAGCAAGGCCATTTCTGATGCCCAGATCACTGCATCCTCT
TACTTCACCAACATGTTTGCCACCTGGTCACCATCAAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCTCCTGACAAGA
TACCTGAGAATTCACCCCAGTCTTGGGTCCACCAGATTGCCCTGAGAATGGAAGTCCTGGGATGT
GAGGCACAAGACCTGTACTGA (SEQ ID NO:91)
```

```
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATACCACCTACGTGAACCGCTCCCTGTCTCAGAATCCACCTGTCCTGAAG
AGACACCAGAGAGAGATCACCAGGACAACCCTCCAGTCTGACCAGGAAGAGATTGACTATGATGAC
ACCATTTCTGTGGAGATGAAGAAGGAGGACTTTGACATCTATGATGAGGACGAGAACCAGTCTCCA
AGATCATTCCAGAAGAAGACAAGACACTACTTCATTGCTGCTGTGGAAAGACTGTGGGACTATGGC
ATGTCTTCCTCTCCCCATGTCCTCAGGAACAGGGCACAGTCTGGCTCTGTGCCACAGTTCAAGAAA
```

```
GTGGTCTTCCAGGAGTTCACTGATGGCTCATTCACCCAGCCCCTGTACAGAGGGGAACTGAATGAG
CACCTGGGACTCCTGGGACCATACATCAGGGCTGAGGTGGAAGACAACATCATGGTGACATTCAGA
AACCAGGCCTCCAGGCCCTACAGCTTCTACTCTTCCCTCATCAGCTATGAGGAAGACCAGAGACAA
GGGGCTGAGCCAAGAAAGAACTTTGTGAAACCCAATGAAACCAAGACCTACTTCTGGAAAGTCCAG
CACCACATGGCACCCACCAAGGATGAGTTTGACTGCAAGGCCTGGGCATACTTCTCTGATGTGGAC
CTGGAGAAAGATGTGCACTCTGGCCTGATTGGCCCACTCCTGGTCTGCCACACCAACACCCTGAAC
CCTGCACATGGAAGGCAAGTGACTGTGCAGGAGTTTGCCCTCTTCTTCACCATCTTTGATGAAACC
AAGTCATGGTACTTCACTGAGAACATGGAGAGAAACTGCAGAGCACCATGCAACATTCAGATGGAA
GACCCCACCTTCAAGGAGAACTACAGGTTCCATGCCATCAATGGCTACATCATGGACACCCTGCCT
GGGCTTGTCATGGCACAGGACCAGAGAATCAGATGGTACCTGCTTTCTATGGGATCCAATGAGAAC
ATTCACTCCATCCACTTCTCTGGGCATGTCTTCACTGTGAGAAAGAAGGAGGAATACAAGATGGCC
CTGTACAACCTCTACCCTGGGGTCTTTGAGACTGTGGAGATGCTGCCCTCCAAAGCTGGCATCTGG
AGGGTGGAATGCCTCATTGGGGAGCACCTGCATGCTGGCATGTCAACCCTGTTCCTGGTCTACAGC
AACAAGTGCCAGACACCCCTGGGAATGGCCTCTGGCCACATCAGGGACTTCCAGATCACTGCCTCT
GGCCAGTATGGCCAGTGGGCACCCAAACTGGCCAGGCTCCACTACTCTGGCTCCATCAATGCATGG
TCAACCAAGGAGCCATTCTCTTGGATCAAGGTGGACCTGCTGGCACCCATGATCATTCATGGCATC
AAGACACAGGGGGCAAGACAGAAATTCTCCTCTCTGTACATCTCACAGTTCATCATCATGTACTCT
CTGGATGGCAAGAAGTGGCAGACATACAGAGGCAACTCCACTGGCACCCTCATGGTCTTCTTTGGC
AATGTGGACAGCTCTGGCATCAAGCACAACATCTTCAACCCTCCCATCATTGCCAGATACATCAGG
CTGCACCCCACCCACTACTCAATCAGATCAACCCTCAGGATGGAACTGATGGGATGTGACCTGAAC
TCCTGCTCAATGCCCCTGGGAATGGAGAGCAAGGCCATTTCTGATGCCCAGATCACTGCATCCTCT
TACTTCACCAACATGTTTGCCACCTGGTCACCATCAAAAGCCAGGCTGCACCTCCAGGGAAGAAGC
AATGCCTGGAGACCCCAGGTCAACAACCCAAAGGAATGGCTGCAAGTGGACTTCCAGAAGACAATG
AAAGTCACTGGGGTGACAACCCAGGGGGTCAAGTCTCTGCTCACCTCAATGTATGTGAAGGAGTTC
CTGATCTCTTCCTCACAGGATGGCCACCAGTGGACACTCTTCTTCCAGAATGGCAAAGTCAAGGTG
TTCCAGGGCAACCAGGACTCTTTCACACCTGTGGTGAACTCACTGGACCCCCCCTCCTGACAAGA
TACCTGAGAATTCACCCCCAGTCTTGGGTCCACCAGATTGCCCTGAGAATGGAAGTCCTGGGATGT
GAGGCACAAGACCTGTACTGA    (SEQ ID NO:92)
```

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG (Continued)

Figure 33A

```
GTCTTCCAGGAGTTCACTGATGGCTCATTCACCCAGCCCTGTACAGAGGGGAACTGAATGAGCAC
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCTCCTGACAAGATAC
CTGAGAATTCACCCCCAGTCTTGGGTCCACCAGATTGCCCTGAGAATGGAAGTCCTGGGATGTGAG
GCACAAGACCTGTACTGA   (SEQ ID NO:93)
```

```
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCATGTCCTCAGGAACAGGGCCCAGTCTGGCTCTGTGCCACAGTTCAAGAAAGTG
```

```
GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAG
GCCCAGGACCTGTACTGA    (SEQ ID NO:94)
```

```
ATGCAGATTGAGCTGAGCACCTGCTTCTTCCTGTGCCTGCTGAGGTTCTGCTTCTCTGCCACCAGG
AGATACTACCCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGCTGAG
TATGATGACCAGACCTCCCAGAGGGAGAAGGAGGATGACAAAGTGTTCCCTGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCCATGTCCTCAGGAACAGGGCCCAGTCTGGCTCTGTGCCACAGTTCAAGAAA
```

```
GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCTGGGAATGGCCTCTGGCCACATCAGGGACTTCCAGATCACTGCCTCT
GGCCAGTATGGCCAGTGGGCCCCAAGCTGGCCAGGCTCCACTACTCTGGATCCATCAATGCCTGG
AGCACCAAGGAGCCATTCAGCTGGATCAAAGTGGACCTGCTGGCCCCATGATCATCCATGGCATC
AAGACCCAGGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCTTCCAGAATGGCAAGGTCAAGGTG
TTCCAGGGCAACCAGGACAGCTTCACCCCTGTGGTGAACAGCCTGGACCCCCCCCTCCTGACCAGA
TACCTGAGGATTCACCCCCAGAGCTGGGTCCACCAGATTGCCCTGAGGATGGAGGTCCTGGGATGT
GAGGCCCAGGACCTGTACTGA  (SEQ ID NO:95)
```

```
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCCATGTCCTCAGGAACAGGGCCAGTCTGGCTCTGTGCCACAGTTCAAGAAA
```

```
GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCTGGGAATGGCCTCTGGCCACATCAGGGACTTCCAGATCACTGCCTCT
GGCCAGTATGGCCAGTGGGCCCCCAAGCTGGCCAGGCTCCACTACTCTGGATCCATCAATGCCTGG
AGCACCAAGGAGCCATTCAGCTGGATCAAAGTGGACCTGCTGGCCCCCATGATCATCCATGGCATC
AAGACCCAGGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCTTCCAGAATGGCAAGGTCAAGGTG
TTCCAGGGCAACCAGGACAGCTTCACCCCTGTGGTGAACAGCCTGGACCCCCCCTCCTGACCAGA
TACCTGAGGATTCACCCCCAGAGCTGGGTCCACCAGATTGCCCTGAGGATGGAGGTCCTGGGATGT
GAGGCCCAGGACCTGTACTGA    (SEQ ID NO:96)
```

```
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGTCAGCTACTGGAAGGCCTCTGAGGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCCATGTCCTCAGGAACAGGGCCCAGTCTGGCTCTGTGCCACAGTTCAAGAAAGTG
```

```
GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCCTCCTGACCAGATAC
CTGAGGATTCACCCCCAGAGCTGGGTCCACCAGATTGCCCTGAGGATGGAGGTCCTGGGATGTGAG
GCCCAGGACCTGTACTGA    (SEQ ID NO:97)
```

```
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGTCAGCTACTGGAAGGCCTCTGAGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATACCACCTACGTGAACCGCTCCCTGAGCCAGAATCCACCTGTCCTGAAA
CGCCACCAGAGGGAGATCACCAGGACCACCCTCCAGTCTGACCAGGAGGAGATTGACTATGATGAC
ACCATTTCTGTGGAGATGAAGAAAGAGGACTTTGACATCTATGACGAGGACGAGAACCAGAGCCCA
AGGAGCTTCCAGAAGAAGACCAGGCACTACTTCATTGCTGCTGTGGAGCGCCTGTGGGACTATGGC
ATGAGCTCCAGCCCCATGTCCTCAGGAACAGGGCCCAGTCTGGCTCTGTGCCACAGTTCAAGAAA
```

```
GTGGTCTTCCAAGAGTTCACTGATGGCAGCTTCACCCAGCCCCTGTACAGAGGGGAGCTGAATGAG
CACCTGGGACTCCTGGGCCCATACATCAGGGCTGAGGTGGAGGACAACATCATGGTGACCTTCCGC
AACCAGGCCTCCAGGCCCTACAGCTTCTACAGCTCCCTCATCAGCTATGAGGAGGACCAGAGGCAG
GGGGCTGAGCCACGCAAGAACTTTGTGAAACCCAATGAAACCAAGACCTACTTCTGGAAAGTCCAG
CACCACATGGCCCCCACCAAGGATGAGTTTGACTGCAAGGCCTGGGCCTACTTCTCTGATGTGGAC
CTGGAGAAGGATGTGCACTCTGGCCTGATTGGCCCACTCCTGGTCTGCCACACCAACACCCTGAAC
CCTGCCCATGGAAGGCAAGTGACTGTGCAGGAGTTTGCCCTCTTCTTCACCATCTTTGATGAAACC
AAGAGCTGGTACTTCACTGAGAACATGGAGCGCAACTGCAGGGCCCCATGCAACATTCAGATGGAG
GACCCCACCTTCAAAGAGAACTACCGCTTCCATGCCATCAATGGCTACATCATGGACACCCTGCCT
GGGCTTGTCATGGCCCAGGACCAGAGGATCAGGTGGTACCTGCTTTCTATGGGCTCCAATGAGAAC
ATTCACTCCATCCACTTCTCTGGGCATGTCTTCACTGTGCGCAAGAAGGAGGAGTACAAGATGGCC
CTGTACAACCTCTACCCTGGGGTCTTTGAGACTGTGGAGATGCTGCCCTCCAAAGCTGGCATCTGG
AGGGTGGAGTGCCTCATTGGGGAGCACCTGCATGCTGGCATGAGCACCCTGTTCCTGGTCTACAGC
AACAAGTGCCAGACCCCCCTGGGAATGGCCTCTGGCCACATCAGGGACTTCCAGATCACTGCCTCT
GGCCAGTATGGCCAGTGGGCCCCCAAGCTGGCCAGGCTCCACTACTCTGGATCCATCAATGCCTGG
AGCACCAAGGAGCCATTCAGCTGGATCAAAGTGGACCTGCTGGCCCCCATGATCATCCATGGCATC
AAGACCCAGGGGCCAGGCAGAAGTTCTCCAGCCTGTACATCAGCCAGTTCATCATCATGTACAGC
CTGGATGGCAAGAAATGGCAGACCTACAGAGGCAACTCCACTGGAACACTCATGGTCTTCTTTGGC
AATGTGGACAGCTCTGGCATCAAGCACAACATCTTCAACCCCCCAATCATCGCCAGATACATCAGG
CTGCACCCCACCCACTACAGCATCCGCAGCACCCTCAGGATGGAGCTGATGGGCTGTGACCTGAAC
TCCTGCAGCATGCCCCTGGGCATGGAGAGCAAGGCCATTTCTGATGCCCAGATCACTGCCTCCAGC
TACTTCACCAACATGTTTGCCACCTGGAGCCCAAGCAAGGCCAGGCTGCACCTCCAGGGAAGGAGC
AATGCCTGGAGGCCCCAGGTCAACAACCCAAAGGAGTGGCTGCAGGTGGACTTCCAGAAGACCATG
AAGGTCACTGGGGTGACCACCCAGGGGGTCAAGAGCCTGCTCACCAGCATGTATGTGAAGGAGTTC
CTGATCAGCTCCAGCCAGGATGGCCACCAGTGGACCCTCTTCCAGAATGGCAAGGTCAAGGTG
TTCCAGGGCAACCAGGACAGCTTCACCCCTGTGGTGAACAGCCTGGACCCCCCCTCCTGACCAGA
TACCTGAGGATTCACCCCAGAGCTGGGTCCACCAGATTGCCCTGAGGATGGAGGTCCTGGGATGT
GAGGCCCAGGACCTGTACTGA    (SEQ ID NO:98)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTCCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG
```

```
GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCTGCTGACCAGG
TATCTGAGGATCCACCCCAGAGCTGGGTGCACCAGATCGCCCTGAGAATGGAAGTGCTGGGATGC
GAGGCCCAGGACCTGTACTGA   (SEQ ID NO:99)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG
```

```
GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCCTGCTGACCAGG
TATCTGAGGATCCACCCCCAGAGCTGGGTGCACCAGATCGCCCTGAGAATGGAAGTGCTGGGATGC
GAGGCCCAGGACCTGTACTGA   (SEQ ID NO:100)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGGTCACCCTGAAGAACATG
GCCAGCCACCCCGTGAGCCTGCACGCCGTGGGCGTGAGCTACTGGAAGTCCTCTGAGGGCGCCGAG
TATGACGACCAGACCAGCCAGAGGGAGAAGGAGGACGACAAGGTGTTCCCCGGCAAGAGCCACACC
TACGTGTGGCAGGTGCTGAAGGAGAACGGCCCCACTGCCAGCGACCCCCCCTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACCCCCCGTGCTGAAGAGG
CACCAGAGGGAGATCACCAGGACCACCCTGCAGAGCGACCAGGAGGAGATCGACTATGATGACACC
ATCAGCGTGGAGATGAAGAAGGAGGACTTCGACATCTACGACGAGGACGAGAACCAGAGCCCCAGG
AGCTTCCAGAAGAAGACCAGGCACTACTTCATCGCCGCCGTGGAGAGGCTGTGGGACTATGGCATG
AGCAGCAGCCCCCACGTGCTGAGGAACAGGGCCCAGAGCGGCAGCGTGCCCCAGTTCAAGAAGGTG
```

```
GTGTTCCAGGAGTTCACCGACGGCAGCTTCACCCAGCCCCTGTACAGAGGCGAGCTGAACGAGCAC
CTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGC
GCCGAGCCCAGGAAGAACTTCGTGAAGCCCAACGAGACCAAGACCTACTTCTGGAAGGTGCAGCAC
CACATGGCCCCCACCAAGGACGAGTTCGACTGCAAGGCCTGGGCCTACTTCTCTGATGTGGACCTG
GAGAAGGACGTGCACAGCGGCCTGATCGGCCCCTGCTGGTGTGCCACACCAACACCCTGAACCCC
GCCCACGGCAGGCAGGTGACCGTGCAGGAGTTCGCCCTGTTCTTCACCATCTTCGACGAGACCAAG
AGCTGGTACTTCACCGAGAACATGGAGAGGAACTGCAGGGCCCCCTGCAACATCCAGATGGAGGAC
CCCACCTTCAAGGAGAACTACAGGTTCCACGCCATCAACGGCTACATCATGGACACCCTGCCCGGC
CTGGTGATGGCCCAGGACCAGAGGATCAGGTGGTATCTGCTGAGCATGGGCAGCAACGAGAACATC
CACAGCATCCACTTCAGCGGCCACGTGTTCACCGTGAGGAAGAAGGAGGAGTACAAGATGGCCCTG
TACAACCTGTACCCCGGCGTGTTCGAGACCGTGGAGATGCTGCCCAGCAAGGCCGGCATCTGGAGG
GTGGAGTGCCTGATCGGCGAGCACCTGCACGCCGGCATGAGCACCCTGTTCCTGGTGTACAGCAAC
AAGTGCCAGACCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGC
ACCAAGGAGCCCTTCAGCTGGATCAAGGTGGACCTGCTGGCCCCCATGATCATCCACGGCATCAAG
ACCCAGGGCGCCAGGCAGAAGTTCAGCAGCCTGTACATCAGCCAGTTCATCATCATGTACAGCCTG
GACGGCAAGAAGTGGCAGACCTACAGGGGCAACAGCACCGGCACCCTGATGGTGTTCTTCGGCAAC
GTGGACAGCAGCGGCATCAAGCACAACATCTTCAACCCCCCCATCATCGCCAGGTACATCAGGCTG
CACCCCACCCACTACAGCATCAGGAGCACCCTGCGGATGGAACTGATGGGCTGCGACCTGAACAGC
TGCAGCATGCCCCTGGGCATGGAGAGCAAGGCCATCTCTGACGCCCAGATCACCGCCAGCAGCTAC
TTCACCAACATGTTCGCCACCTGGAGCCCCAGCAAGGCCAGGCTGCACCTGCAGGGCAGGAGCAAC
GCCTGGAGGCCCCAGGTGAACAACCCCAAGGAGTGGCTGCAGGTGGACTTCCAGAAGACCATGAAG
GTGACCGGCGTGACCACCCAGGGCGTGAAGAGCCTGCTGACCAGCATGTACGTGAAGGAGTTCCTG
ATCAGCAGCAGCCAGGACGGCCACCAGTGGACCCTGTTCTTCCAGAACGGCAAAGTGAAGGTGTTC
CAGGGCAACCAGGACAGCTTCACCCCCGTGGTGAACAGCCTGGACCCCCCCTGCTGACCAGGTAT
CTGAGGATCCACCCCCAGAGCTGGGTGCACCAGATCGCCCTGAGAATGGAAGTGCTGGGATGCGAG
GCCCAGGACCTGTACTGA   (SEQ ID NO:101)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTCCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACCCCCCCGTGCTGAAGAGG
CACCAGAGGGAGATCACCAGGACCACCCTGCAGAGCGACCAGGAGGAGATCGACTATGATGACACC
ATCAGCGTGGAGATGAAGAAGGAGGACTTCGACATCTACGACGAGGACGAGAACCAGAGCCCCAGG
AGCTTCCAGAAGAAGACCAGGCACTACTTCATCGCCGCCGTGGAGAGGCTGTGGGACTATGGCATG
AGCAGCAGCCCCCACGTGCTGAGGAACAGGGCCCAGAGCGGCAGCGTGCCCCAGTTCAAGAAGGTG
```

```
GTGTTCCAGGAGTTCACCGACGGCAGCTTCACCCAGCCCCTGTACAGAGGCGAGCTGAACGAGCAC
CTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGC
GCCGAGCCCAGGAAGAACTTCGTGAAGCCCAACGAGACCAAGACCTACTTCTGGAAGGTGCAGCAC
CACATGGCCCCCACCAAGGACGAGTTCGACTGCAAGGCCTGGGCCTACTTCTCTGATGTGGACCTG
GAGAAGGACGTGCACAGCGGCCTGATCGGCCCCTGCTGGTGTGCCACACCAACACCCTGAACCCC
GCCCACGGCAGGCAGGTGACCGTGCAGGAGTTCGCCCTGTTCTTCACCATCTTCGACGAGACCAAG
AGCTGGTACTTCACCGAGAACATGGAGAGGAACTGCAGGGCCCCCTGCAACATCCAGATGGAGGAC
CCCACCTTCAAGGAGAACTACAGGTTCCACGCCATCAACGGCTACATCATGGACACCCTGCCCGGC
CTGGTGATGGCCCAGGACCAGAGGATCAGGTGGTATCTGCTGAGCATGGGCAGCAACGAGAACATC
CACAGCATCCACTTCAGCGGCCACGTGTTCACCGTGAGGAAGAAGGAGGAGTACAAGATGGCCCTG
TACAACCTGTACCCCGGCGTGTTCGAGACCGTGGAGATGCTGCCCAGCAAGGCCGGCATCTGGAGG
GTGGAGTGCCTGATCGGCGAGCACCTGCACGCCGGCATGAGCACCCTGTTCCTGGTGTACAGCAAC
AAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGC
ACCAAGGAGCCCTTCAGCTGGATCAAGGTGGACCTGCTGGCCCCCATGATCATCCACGGCATCAAG
ACCCAGGGCGCCAGGCAGAAGTTCAGCAGCCTGTACATCAGCCAGTTCATCATCATGTACAGCCTG
GACGGCAAGAAGTGGCAGACCTACAGGGGCAACAGCACCGGCACCCTGATGGTGTTCTTCGGCAAC
GTGGACAGCAGCGGCATCAAGCACAACATCTTCAACCCCCCCATCATCGCCAGGTACATCAGGCTG
CACCCCACCCACTACAGCATCAGGAGCACCCTGCGGATGGAACTGATGGGCTGCGACCTGAACAGC
TGCAGCATGCCCCTGGGCATGGAGAGCAAGGCCATCTCTGACGCCCAGATCACCGCCAGCAGCTAC
TTCACCAACATGTTCGCCACCTGGAGCCCCAGCAAGGCCAGGCTGCACCTGCAGGGCAGGAGCAAC
GCCTGGAGGCCCCAGGTGAACAACCCCAAGGAGTGGCTGCAGGTGGACTTCCAGAAGACCATGAAG
GTGACCGGCGTGACCACCCAGGGCGTGAAGAGCCTGCTGACCAGCATGTACGTGAAGGAGTTCCTG
ATCAGCAGCAGCCAGGACGGCCACCAGTGGACCCTGTTCTTCCAGAACGGCAAAGTGAAGGTGTTC
CAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAG
GCCCAGGACCTGTACTGA   (SEQ ID NO:102)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGGTCACCCTGAAGAACATG
GCCAGCCACCCCGTGAGCCTGCACGCCGTGGGCGTGAGCTACTGGAAGTCCTCTGAGGGCGCCGAG
TATGACGACCAGACCAGCCAGAGGGAGAAGGAGGACGACAAGGTGTTCCCCGGCAAGAGCCACACC
TACGTGTGGCAGGTGCTGAAGGAGAACGGCCCCACTGCCAGCGACCCCCCTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACACCACCTACGTGAACCGCTCCCTGAGCCAGAACCCCCCCGTGCTGAAG
AGGCACCAGAGGGAGATCACCAGGACCACCCTGCAGAGCGACCAGGAGGAGATCGACTATGATGAC
ACCATCAGCGTGGAGATGAAGAAGGAGGACTTCGACATCTACGACGAGGACGAGAACCAGAGCCCC
AGGAGCTTCCAGAAGAAGACCAGGCACTACTTCATCGCCGCCGTGGAGAGGCTGTGGGACTATGGC
ATGAGCAGCAGCCCCCACGTGCTGAGGAACAGGGCCCAGAGCGGCAGCGTGCCCCAGTTCAAGAAG
```

```
GTGGTGTTCCAGGAGTTCACCGACGGCAGCTTCACCCAGCCCCTGTACAGAGGCGAGCTGAACGAG
CACCTGGGCCTGCTGGGCCCCTACATCAGGGCCGAGGTGGAGGACAACATCATGGTGACCTTCAGG
AACCAGGCCAGCAGGCCCTACAGCTTCTACAGCAGCCTGATCAGCTACGAGGAGGACCAGAGGCAG
GGCGCCGAGCCCAGGAAGAACTTCGTGAAGCCCAACGAGACCAAGACCTACTTCTGGAAGGTGCAG
CACCACATGGCCCCCACCAAGGACGAGTTCGACTGCAAGGCCTGGGCCTACTTCTCTGATGTGGAC
CTGGAGAAGGACGTGCACAGCGGCCTGATCGGCCCCCTGCTGGTGTGCCACACCAACACCCTGAAC
CCCGCCCACGGCAGGCAGGTGACCGTGCAGGAGTTCGCCCTGTTCTTCACCATCTTCGACGAGACC
AAGAGCTGGTACTTCACCGAGAACATGGAGAGGAACTGCAGGGCCCCCTGCAACATCCAGATGGAG
GACCCCACCTTCAAGGAGAACTACAGGTTCCACGCCATCAACGGCTACATCATGGACACCCTGCCC
GGCCTGGTGATGGCCCAGGACCAGAGGATCAGGTGGTATCTGCTGAGCATGGGCAGCAACGAGAAC
ATCCACAGCATCCACTTCAGCGGCCACGTGTTCACCGTGAGGAAGAAGGAGGAGTACAAGATGGCC
CTGTACAACCTGTACCCCGGCGTGTTCGAGACCGTGGAGATGCTGCCCAGCAAGGCCGGCATCTGG
AGGGTGGAGTGCCTGATCGGCGAGCACCTGCACGCCGGCATGAGCACCCTGTTCCTGGTGTACAGC
AACAAGTGCCAGACCCCCCTGGGCATGGCCAGCGGCCACATCAGGGACTTCCAGATCACCGCCTCT
GGCCAGTACGGCCAGTGGGCCCCCAAGCTGGCCAGGCTGCACTACAGCGGCAGCATCAACGCCTGG
AGCACCAAGGAGCCCTTCAGCTGGATCAAGGTGGACCTGCTGGCCCCCATGATCATCCACGGCATC
AAGACCCAGGGCGCCAGGCAGAAGTTCAGCAGCCTGTACATCAGCCAGTTCATCATCATGTACAGC
CTGGACGGCAAGAAGTGGCAGACCTACAGGGGCAACAGCACCGGCACCCTGATGGTGTTCTTCGGC
AACGTGGACAGCAGCGGCATCAAGCACAACATCTTCAACCCCCCCATCATCGCCAGGTACATCAGG
CTGCACCCCACCCACTACAGCATCAGGAGCACCCTGCGGATGGAACTGATGGGCTGCGACCTGAAC
AGCTGCAGCATGCCCCTGGGCATGGAGAGCAAGGCCATCTCTGACGCCCAGATCACCGCCAGCAGC
TACTTCACCAACATGTTCGCCACCTGGAGCCCCAGCAAGGCCAGGCTGCACCTGCAGGGCAGGAGC
AACGCCTGGAGGCCCCAGGTGAACAACCCCAAGGAGTGGCTGCAGGTGGACTTCCAGAAGACCATG
AAGGTGACCGGCGTGACCACCCAGGGCGTGAAGAGCCTGCTGACCAGCATGTACGTGAAGGAGTTC
CTGATCAGCAGCAGCCAGGACGGCCACCAGTGGACCCTGTTCTTCCAGAACGGCAAAGTGAAGGTG
TTCCAGGGCAACCAGGACAGCTTCACCCCCGTGGTGAACAGCCTGGACCCCCCCCTGCTGACCAGG
TATCTGAGGATCCACCCCCAGAGCTGGGTGCACCAGATCGCCCTGAGAATGGAAGTGCTGGGATGC
GAGGCCCAGGACCTGTACTGA    (SEQ ID NO:103)
```

```
                                                                     gcc
accaggagat actacctggg ggctgtggaa cttcttgggg actacatgca gtctgacctg
ggagagctgc ctgtggatgc caggttccca cccagagtgc ccaagtcctt cccattcaac
acctctgtgg tctacaagaa gacactcttt gtggaattca ctgaccacct gttcaacatt
gcaaaaccca gaccaccctg gatgggactc ctgggaccca ccattcaggc tgaggtgtat
gacactgtgg tcatcaccct caagaacatg gcatcccacc ctgtgtctct gcatgctgtg
ggagtctcat actggaaagc ctctgaaggg gctgagtatg atgaccagac atcccagaga
gagaaagagg atgacaaggt gttccctggg ggatctcaca cctatgtgtg gcaagtcctc
aaggagaatg gacccatggc atctgaccca ctctgcctga catactccta cctttctcat
gtggacctgg tcaaggacct caactctgga ctgattgggg cactgctggt gtgcagggaa
ggatccctgg ccaaggagaa aacccagaca ctgcacaagt tcattctcct gtttgctgtc
tttgatgagg gcaagtcttg gcactctgaa acaaagaact ccctgatgca agacagggat
gctgcctctg ccagggcatg gccaagatg cacactgtga atggctatgt gaacagatca
ctgcctggac tcattggctg ccacaggaaa tctgtctact ggcatgtgat tggcatgggg
acaaccctg aagtgcactc cattttcctg gagggacaca cctcctggt caggaaccac
agacaagcct ctctggagat ctctcccatc accttcctca ctgcacagac actgctgatg
gaccttggac agttcctgct gttctgccac atctcttccc accagcatga tggcatggaa
gcctatgtca aggtggactc atgccctgag gaaccacagc tcaggatgaa gaacaatgag
gaggctgagg actatgatga tgacctgact gactctgaga tggatgtggt cagatttgat
gatgacaact ctccatcctt cattcagatc aggtctgtgg caaagaaaca ccccaagaca
tgggtgcact acattgctgc tgaggaagag gactgggact atgcaccact ggtcctggcc
cctgatgaca ggagctacaa gtctcagtac ctcaacaatg gcccacaaag aattggaaga
aagtacaaga aagtcagatt catggcctac actgatgaaa ccttcaagac aagagaagcc
attcagcatg agtctggcat tctgggacca ctcctgtatg ggaagtggg agacaccctg
ctcatcatct tcaagaacca ggcctccagg ccctacaaca tctacccaca tggcatcact
gatgtcagc cctgtacag caggagactg ccaaaagggg tgaaacacct caaggacttc
cccattctgc ctggagagat cttcaagtac aagtggactg tcactgtgga ggatggacca
acaaagtctg accccaggtg cctcaccaga tactactcct ttttgtgaa catggagaga
gacctggcat ctggactgat ggaccactg ctcatctgct acaaggagtc tgtggaccag
agaggcaacc agatcatgtc tgacaagaga aatgtgattc tgttctctgt ctttgatgag
aacagatcat ggtacctgac tgagaacatt cagagattcc tgcccaaccc tgctggggtg
caactggaag accctgagtt ccaggcaagc aacatcatgc actccatcaa tggctatgtg
tttgactctc tccagctttc tgtctgcctg catgaggtgg cctactggta cattctttct
attgggcac aaactgactt cctttctgtc ttcttctctg gatacacctt caagcacaag
atggtgtatg aggacaccct gacactcttc ccattctctg gggaaactgt gttcatgagc
atggagaacc ctggactgtg gattctggga tgccacaact ctgacttcag aaacagggga
atgactgcac tgctcaaagt ctcctcctgt gacaagaaca ctggggacta ctatgaggac
tcttatgagg acatctctgc ctacctgctc agcaagaaca atgccattga gcccaga
(SEQ ID NO:24X)
```

```
                                                   g agatcaccag gacaaccctc
cagtctgacc aggaagagat tgactatgat gacaccattt ctgtggagat gaagaaggag
gactttgaca tctatgatga ggacgagaac cagtctccaa gatcattcca gaagaagaca
agacactact tcattgctgc tgtggaaaga ctgtgggact atggcatgtc ttcctctccc
catgtcctca ggaacagggc acagtctgcc tctgtgccac agttcaagaa agtggtcttc
caggagttca ctgatggctc attcacccag ccctgtaca gaggggaact gaatgagcac
ctgggactcc tgggaccata catcagggct gaggtggaag acaacatcat ggtgacattc
agaaaccagg cctccaggcc ctacagcttc tactcttccc tcatcagcta tgaggaagac
cagagacaag gggctgagcc aagaaagaac tttgtgaaac ccaatgaaac caagacctac
ttctggaaag tccagcacca catggcaccc accaaggatg agtttgactg caaggcctgg
gcatacttct ctgatgtgga cctggagaaa gatgtgcact ctggcctgat tggcccactc
ctggtctgcc acaccaacac cctgaaccct gcacatggaa ggcaagtgac tgtgcaggag
tttgccctct tcttccacat ctttgatgaa accaagtcat ggtacttcac tgagaacatg
gagagaaact gcagagcacc atgcaacatt cagatggaag acccccactt caaggagaac
tacaggttcc atgccatcaa tggctacatc atggacaccc tgcctgggct tgtcatggca
caggaccaga gaatcagatg gtacctgctt tctatgggat ccaatgagaa cattcactcc
atccacttct ctggcatgt cttcactgtg agaaagaagg aggaatacaa gatggccctg
tacaacctct accctgggt ctttgagact gtggagatgc tgccctccaa agctggcatc
tggagggtgg aatgcctcat tggggagcac ctgcatgctg catgtcaac cctgttcctg
gtctacagca acaagtgcca gacaccctg ggaatggcct ctggccacat cagggacttc
cagatcactg cctctggcca gtatggccag tgggcaccca actggccag gctccactac
tctggctcca tcaatgcatg gtcaaccaag gagccattct cttggatcaa ggtggacctg
ctggcaccca tgatcattca tggcatcaag acacagggg caagacagaa attctcctct
ctgtacatct cacagttcat catcatgtac tctctggatg gcaagaagtg gcagacatac
agaggcaact ccactggcac cctcatggtc ttctttggca atgtggacag ctctggcatc
aagcacaaca tcttcaaccc tccatcatt gccagataca tcaggctgca cccacccac
tactcaatca gatcaaccct caggatggaa ctgatgggat gtgacctgaa ctcctgctca
atgcccctgg gaatggagag caaggccatt tctgatgccc agatcactgc atcctcttac
ttcaccaaca tgtttgccac ctggtcacca tcaaaagcca ggctgcacct ccagggaaga
agcaatgcct ggagacccca ggtcaacaac ccaaaggaat ggctgcaagt ggacttccag
aagacaatga aagtcactgg ggtgacaacc caggggtca agtctctgct cacctcaatg
tatgtgaagg agttcctgat ctcttcctca caggatggcc accagtggac actcttcttc
cagaatggca aagtcaaggt gttccaggc aaccaggact ctttcacacc tgtggtgaac
tcactggacc ccccctcct gacaagatac ctgagaattc accccagtc ttgggtccac
cagattgccc tgagaatgga agtcctggga tgtgaggcac aagacctgta c
(SEQ ID NO:25)
```

ATGCAGATTGAGCTGTCCACCTGCTTCTTTCTGTGCCTGCTGAGATTCTGCTTCTCTGCCACCAGGAGATAC
TACCTGGGGGCTGTGGAACTTTCTTGGGACTACATGCAGTCTGACCTGGGAGAGCTGCCTGTGGATGCCAGG
TTCCCACCCAGAGTGCCCAAGTCCTTCCCATTCAACACCTCTGTGGTCTACAAGAAGACACTCTTTGTGGAA
TTCACTGACCACCTGTTCAACATTGCAAAACCCAGACCACCCTGGATGGGACTCCTGGGACCCACCATTCAG
GCTGAGGTGTATGACACTGTGGTCATCACCCTCAAGAACATGGCATCCCACCCTGTGTCTCTGCATGCTGTG
GGAGTCTCATACTGGAAAGCCTCTGAAGGGGCTGAGTATGATGACCAGACATCCCAGAGAGAGAAAGAGGAT
GACAAGGTGTTCCCTGGGGGATCTCACACCTATGTGTGGCAAGTCCTCAAGGAGAATGGACCCATGGCATCT
GACCCACTCTGCCTGACATACTCCTACCTTTCTCATGTGGACCTGGTCAAGGACCTCAACTCTGGACTGATT
GGGGCACTGCTGGTGTGCAGGGAAGGATCCCTGGCCAAGGAGAAAACCCAGACACTGCACAAGTTCATTCTC
CTGTTTGCTGTCTTTGATGAGGGCAAGTCTTGGCACTCTGAAACAAAGAACTCCCTGATGCAAGACAGGGAT
GCTGCCTCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGACAACCCCTGAAGTGCACTCCATT
TTCCTGGAGGGACACACCTTCCTGGTCAGGAACCACAGACAAGCCTCTCTGGAGATCTCTCCCATCACCTTC
CTCACTGCACAGACACTGCTGATGGACCTTGGACAGTTCCTGCTGTTCTGCCACATCTCTTCCCACCAGCAT
GATGGCATGGAAGCCTATGTCAAGGTGGACTCATGCCCTGAGGAACCACAGCTCAGGATGAAGAACAATGAG
GAGGCTGAGGACTATGATGATGACCTGACTGACTCTGAGATGGATGTGGTCAGATTTGATGATGACAACTCT
CCATCCTTCATTCAGATCAGGTCTGTGGCAAGAAACACCCCAAGACATGGGTGCACTACATTGCTGCTGAG
GAAGAGGACTGGGACTATGCACCACTGGTCCTGGCCCCTGATGACAGGAGCTACAAGTCTCAGTACCTCAAC
AATGGCCCACAAAGAATTGGAAGAAAGTACAAGAAAGTCAGATTCATGGCCTACACTGATGAAACCTTCAAG
ACAAGAGAAGCCATTCAGCATGAGTCTGGCATTCTGGGACCACTCCTGTATGGGGAAGTGGGAGACACCCTG
CTCATCATCTTCAAGAACCAGGCCTCCAGGCCCTACAACATCTACCCACATGGCATCACTGATGTCAGGCCC
CTGTACAGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGATACTAC
TCCTCTTTTGTGAACATGGAGAGAGACCTGGCATCTGGACTGATTGGACCACTGCTCATCTGCTACAAGGAG
TCTGTGGACCAGAGAGGCAACCAGATCATGTCTGACAAGAGAAATGTGATTCTGTTCTCTGTCTTTGATGAG
AACAGATCATGGTACCTGACTGAGAACATTCAGAGATTCCTGCCCAACCCTGCTGGGGTGCAACTGGAAGAC
CCTGAGTTCCAGGCAAGCAACATCATGCACTCCATCAATGGCTATGTGTTTGACTCTCTCCAGCTTTCTGTC
TGCCTGCATGAGGTGGCCTACTGGTACATTCTTTCTATTGGGGCACAAACTGACTTCCTTTCTGTCTTCTTC
TCTGGATACACCTTCAAGCACAAGATGGTGTATGAGGACACCCTGACACTCTTCCCATTCTCTGGGGAAACT
GTGTTCATGAGCATGGAGAACCCTGGACTGTGGATTCTGGGATGCCACAACTCTGACTTCAGAAACAGGGGA
ATGACTGCACTGCTCAAAGTCTCCTCCTGTGACAAGAACACTGGGGACTACTATGAGGACTCTTATGAGGAC
ATCTCTGCCTACCTGCTCAGCAAGAACAATGCCATTGAGCCCAGAGAGATCACCAGGACAACCCTCCAGTCT
GACCAGGAAGAGATTGACTATGATGACACCATTTCTGTGGAGATGAAGAAGGAGGACTTTGACATCTATGAT
GAGGACGAGAACCAGTCTCCAAGATCATTCCAGAAGAAGACAAGACACTACTTCATTGCTGCTGTGGAAAGA
CTGTGGGACTATGGCATGTCTTCCTCTCCCCATGTCCTCAGGAACAGGGCACAGTCTGGCTCTGTGCCACAG
TTCAAGAAAGTGGTCTTCCAGGAGTTCACTGATGGCTCATTCACCCAGCCCCTGTACAGAGGGGAACTGAAT
GAGCACCTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATGGCACCC (Continued)

Figure 49A

```
ACCAAGGATGAGTTTGACTGCAAGGCCTGGGCATACTTCTCTGATGTGGACCTGGAGAAAGATGTGCACTCT
GGCCTGATTGGCCCACTCCTGGTCTGCCACACCAACACCCTGAACCCTGCACATGGAAGGCAAGTGACTGTG
CAGGAGTTTGCCCTCTTCTTCACCATCTTTGATGAAACCAAGTCATGGTACTTCACTGAGAACATGGAGAGA
AACTGCAGAGCACCATGCAACATTCAGATGGAAGACCCCACCTTCAAGGAGAACTACAGGTTCCATGCCATC
AATGGCTACATCATGGACACCCTGCCTGGGCTTGTCATGGCACAGGACCAGAGAATCAGATGGTACCTGCTT
TCTATGGGATCCAATGAGAACATTCACTCCATCCACTTCTCTGGGCATGTCTTCACTGTGAGAAAGAAGGAG
GAATACAAGATGGCCCTGTACAACCTCTACCCTGGGGTCTTTGAGACTGTGGAGATGCTGCCCTCCAAAGCT
GGCATCTGGAGGGTGGAATGCCTCATTGGGGAGCACCTGCATGCTGGCATGTCAACCCTGTTCCTGGTCTAC
AGCAACAAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAGGGGGCA
AGACAGAAATTCTCCTCTCTGTACATCTCACAGTTCATCATCATGTACTCTCTGGATGGCAAGAAGTGGCAG
ACATACAGAGGCAACTCCACTGGCACCCTCATGGTCTTCTTTGGCAATGTGGACAGCTCTGGCATCAAGCAC
AACATCTTCAACCCTCCCATCATTGCCAGATACATCAGGCTGCACCCCACCCACTACTCAATCAGATCAACC
CTCAGGATGGAACTGATGGGATGTGACCTGAACTCCTGCTCAATGCCCCTGGGAATGGAGAGCAAGGCCATT
TCTGATGCCCAGATCACTGCATCCTCTTACTTCACCAACATGTTTGCCACCTGGTCACCATCAAAAGCCAGG
CTGCACCTCCAGGGAAGAAGCAATGCCTGGAGACCCCAGGTCAACAACCCAAAGGAATGGCTGCAAGTGGAC
TTCCAGAAGACAATGAAAGTCACTGGGGTGACAACCCAGGGGGTCAAGTCTCTGCTCACCTCAATGTATGTG
AAGGAGTTCCTGATCTCTTCCTCACAGGATGGCCACCAGTGGACACTCTTCTTCCAGAATGGCAAAGTCAAG
GTGTTCCAGGGCAACCAGGACTCTTTCACACCTGTGGTGAACTCACTGGACCCCCCCCTCCTGACAAGATAC
CTGAGAATTCACCCCAGTCTTGGGTCCACCAGATTGCCCTGAGAATGGAAGTCCTGGGATGTGAGGCACAA
GACCTGTACTGA  (SEQ ID NO:26)
```

```
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCTGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATTCCAGACACCCCAGCACC
AGGGAGATCACCAGGACAACCCTCCAGTCTGACCAGGAAGAGATTGACTATGATGACACCATTTCT
GTGGAGATGAAGAAGGAGGACTTTGACATCTATGATGAGGACGAGAACCAGTCTCCAAGATCATTC
```

CAGAAGAAGACAAGACACTACTTCATTGCTGCTGTGGAAAGACTGTGGGACTATGGCATGTCTTCC
TCTCCCCATGTCCTCAGGAACAGGGCACAGTCTGGCTCTGTGCCACAGTTCAAGAAAGTGGTCTTC
CAGGAGTTCACTGATGGCTCATTCACCCAGCCCCTGTACAGAGGGGAACTGAATGAGCACCTGGGA
CTCCTGGGACCATACATCAGGGCTGAGGTGGAAGACAACATCATGGTGACATTCAGAAACCAGGCC
TCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATG
GCACCCACCAAGGATGAGTTTGACTGCAAGGCCTGGGCATACTTCTCTGATGTGGACCTGGAGAAA
GATGTGCACTCTGGCCTGATTGGCCCACTCCTGGTCTGCCACACCAACACCCTGAACCCTGCACAT
GGAAGGCAAGTGACTGTGCAGGAGTTTGCCCTCTTCTTCACCATCTTTGATGAAACCAAGTCATGG
TACTTCACTGAGAACATGGAGAGAAACTGCAGAGCACCATGCAACATTCAGATGGAAGACCCCACC
TTCAAGGAGAACTACAGGTTCCATGCCATCAATGGCTACATCATGGACACCCTGCCTGGGCTTGTC
ATGGCACAGGACCAGAGAATCAGATGGTACCTGCTTTCTATGGGATCCAATGAGAACATTCACTCC
ATCCACTTCTCTGGGCATGTCTTCACTGTGAGAAAGAAGGAGGAATACAAGATGGCCCTGTACAAC
CTCTACCCTGGGGTCTTTGAGACTGTGGAGATGCTGCCCTCCAAAGCTGGCATCTGGAGGGTGGAA
TGCCTCATTGGGGAGCACCTGCATGCTGGCATGTCAACCCTGTTCCTGGTCTACAGCAACAAGTGC
CAGACACCCCTGGGAATGGCCTCTGGCCACATCAGGGACTTCCAGATCACTGCCTCTGGCCAGTAT
GGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAG
GGGGCAAGACAGAAATTCTCCTCTCTGTACATCTCACAGTTCATCATCATGTACTCTCTGGATGGC
AAGAAGTGGCAGACATACAGAGGCAACTCCACTGGCACCCTCATGGTCTTCTTTGGCAATGTGGAC
AGCTCTGGCATCAAGCACAACATCTTCAACCCTCCATCATTGCCAGATACATCAGGCTGCACCCC
ACCCACTACTCAATCAGATCAACCCTCAGGATGGAACTGATGGGATGTGACCTGAACTCCTGCTCA
ATGCCCCTGGGAATGGAGAGCAAGGCCATTTCTGATGCCCAGATCACTGCATCCTCTTACTTCACC
AACATGTTTGCCACCTGGTCACCATCAAAAGCCAGGCTGCACCTCCAGGGAAGAAGCAATGCCTGG
AGACCCCAGGTCAACAACCCAAAGGAATGGCTGCAAGTGGACTTCCAGAAGACAATGAAAGTCACT
GGGGTGACAACCCAGGGGGTCAAGTCTCTGCTCACCTCAATGTATGTGAAGGAGTTCCTGATCTCT
TCCTCACAGGATGGCCACCAGTGGACACTCTTCTTCCAGAATGGCAAAGTCAAGGTGTTCCAGGGC
AACCAGGACTCTTTCACACCTGTGGTGAACTCACTGGACCCCCCCTCCTGACAAGATACCTGAGA
ATTCACCCCAGTCTTGGGTCCACCAGATTGCCCTGAGAATGGAAGTCCTGGGATGTGAGGCACAA
GACCTGTACTGA     (SEQ ID NO:27)

```
ATGCAGATTGAGCTGAGCACCTGCTTCTTCCTGTGCCTGCTGAGGTTCTGCTTCTCTGCCACCAGGAGATAC
TACCTGGGCGCCGTGGAGCTGAGCTGGGACTACATGCAGTCTGACCTGGGCGAGCTGCCTGTGGACGCCAGG
TTCCCCCCAGAGTGCCCAAGAGCTTCCCCTTCAACACCTCAGTGGTGTACAAGAAGACCCTGTTCGTGGAG
TTCACCGACCACCTGTTCAACATCGCCAAGCCCAGGCCCCCTGGATGGGCCTGCTGGGCCCCACCATCCAG
GCCGAGGTGTACGACACCGTGGTGATCACCCTGAAGAACATGGCCAGCCACCCCGTGAGCCTGCACGCCGTG
GGCGTGAGCTACTGGAAGGCCTCTGAGGGCGCCGAGTATGACGACCAGACCAGCCAGAGGGAGAAGGAGGAC
GACAAGGTGTTCCCCGGCGGCAGCCACACCTACGTGTGGCAGGTGCTGAAGGAGAACGGCCCCATGGCCAGC
GACCCCCTGTGCCTGACCTACAGCTACCTGAGCCACGTGGACCTGGTGAAGGACCTGAACTCTGGCCTGATC
GGCGCCCTGCTGGTGTGCAGGGAGGGCAGCCTGGCCAAGGAGAAGACCCAGACCCTGCACAAGTTCATCCTG
CTGTTCGCCGTGTTCGATGAGGGCAAGAGCTGGCACAGCGAGACCAAGAACAGCCTGATGCAGGACAGGGAT
GCCGCCTCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCACAGCATC
TTCCTGGAGGGCCACACCTTCCTGGTGAGGAACCACAGGCAGGCCAGCCTGGAGATCAGCCCCATCACCTTC
CTGACCGCCAGACCCTGCTGATGGACCTGGGCCAGTTCCTGCTGTTCTGCCACATCAGCAGCCACCAGCAC
GACGGCATGGAGGCCTACGTGAAGGTGGACAGCTGCCCCGAGGAGCCCCAGCTGAGGATGAAGAACAACGAG
GAGGCCGAGGACTATGATGATGACCTGACCGACTCTGAGATGGACGTGGTGAGGTTTGATGATGACAACAGC
CCCAGCTTCATCCAGATCAGGTCTGTGGCCAAGAAGCACCCCAAGACCTGGGTGCACTACATCGCCGCCGAG
GAGGAGGACTGGGACTACGCCCCCTGGTGCTGGCCCCCGACGACAGGAGCTACAAGAGCCAGTACCTGAAC
AACGGCCCCCAGAGGATCGGCAGGAAGTACAAGAAGGTCAGATTCATGGCCTACACCGACGAGACCTTCAAG
ACCAGGGAGGCCATCCAGCACGAGTCTGGCATCCTGGGCCCCCTGCTGTACGGCGAGGTGGGCGACACCCTG
CTGATCATCTTCAAGAACCAGGCCAGCAGGCCCTACAACATCTACCCCACGGCATCACCGATGTGAGGCCC
CTGTACAGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGGTACTAC
AGCAGCTTCGTGAACATGGAGAGGGACCTGGCCTCTGGCCTGATCGGCCCCCTGCTGATCTGCTACAAGGAG
AGCGTGGACCAGAGGGGCAACCAGATCATGTCTGACAAGAGGAACGTGATCCTGTTCTCTGTGTTCGATGAG
AACAGGAGCTGGTATCTGACCGAGAACATCCAGAGGTTCCTGCCCAACCCCGCCGGCGTGCAGCTGGAGGAC
CCCGAGTTCCAGGCCAGCAACATCATGCACAGCATCAACGGCTACGTGTTCGACAGCCTGCAGCTGTCTGTG
TGCCTGCACGAGGTGGCCTACTGGTACATCCTGAGCATCGGCGCCCAGACCGACTTCCTGTCTGTGTTCTTC
TCTGGCTACACCTTCAAGCACAAGATGGTGTACGAGGACACCCTGACCCTGTTCCCCTTCAGCGGCGAGACC
GTGTTCATGAGCATGGAGAACCCCGGCCTGTGGATCCTGGGCTGCCACAACAGCGACTTCAGGAACAGGGGC
ATGACCGCCCTGCTGAAAGTCAGCAGCTGCGACAAGAACACCGGCGACTACTACGAGGACAGCTACGAGGAC
ATCAGCGCCTACCTGCTGAGCAAGAACAACGCCATCGAGCCCAGGGAGATCACCAGGACCACCCTGCAGAGC
GACCAGGAGGAGATCGACTATGATGACACCATCAGCGTGGAGATGAAGAAGGAGGACTTCGACATCTACGAC
GAGGACGAGAACCAGAGCCCCAGGAGCTTCCAGAAGAAGACCAGGCACTACTTCATCGCCGCCGTGGAGAGG
CTGTGGGACTATGGCATGAGCAGCAGCCCCCACGTGCTGAGGAACAGGGCCCAGAGCGGCAGCGTGCCCCAG
TTCAAGAAGGTGGTGTTCCAGGAGTTCACCGACGGCAGCTTCACCCAGCCCCTGTACAGAGGCGAGCTGAAC
GAGCACCTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGCGCCGAG
```

```
CCCAGGAAGAACTTCGTGAAGCCCAACGAGACCAAGACCTACTTCTGGAAGGTGCAGCACCACATGGCCCCC
ACCAAGGACGAGTTCGACTGCAAGGCCTGGGCCTACTTCTCTGATGTGGACCTGGAGAAGGACGTGCACAGC
GGCCTGATCGGCCCCCTGCTGGTGTGCCACACCAACACCCTGAACCCCGCCCACGGCAGGCAGGTGACCGTG
CAGGAGTTCGCCCTGTTCTTCACCATCTTCGACGAGACCAAGAGCTGGTACTTCACCGAGAACATGGAGAGG
AACTGCAGGGCCCCCTGCAACATCCAGATGGAGGACCCCACCTTCAAGGAGAACTACAGGTTCCACGCCATC
AACGGCTACATCATGGACACCCTGCCCGGCCTGGTGATGGCCCAGGACCAGAGGATCAGGTGGTATCTGCTG
AGCATGGGCAGCAACGAGAACATCCACAGCATCCACTTCAGCGGCCACGTGTTCACCGTGAGGAAGAAGGAG
GAGTACAAGATGGCCCTGTACAACCTGTACCCCGGCGTGTTCGAGACCGTGGAGATGCTGCCCAGCAAGGCC
GGCATCTGGAGGGTGGAGTGCCTGATCGGCGAGCACCTGCACGCCGGCATGAGCACCCTGTTCCTGGTGTAC
AGCAACAAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAGGGCGCC
AGGCAGAAGTTCAGCAGCCTGTACATCAGCCAGTTCATCATCATGTACAGCCTGGACGGCAAGAAGTGGCAG
ACCTACAGGGGCAACAGCACCGGCACCCTGATGGTGTTCTTCGGCAACGTGGACAGCAGCGGCATCAAGCAC
AACATCTTCAACCCCCCCATCATCGCCAGGTACATCAGGCTGCACCCCACCCACTACAGCATCAGGAGCACC
CTGCGGATGGAACTGATGGGCTGCGACCTGAACAGCTGCAGCATGCCCCTGGGCATGGAGAGCAAGGCCATC
TCTGACGCCCAGATCACCGCCAGCAGCTACTTCACCAACATGTTCGCCACCTGGAGCCCCAGCAAGGCCAGG
CTGCACCTGCAGGGCAGGAGCAACGCCTGGAGGCCCCAGGTGAACAACCCCAAGGAGTGGCTGCAGGTGGAC
TTCCAGAAGACCATGAAGGTGACCGGCGTGACCACCCAGGGCGTGAAGAGCCTGCTGACCAGCATGTACGTG
AAGGAGTTCCTGATCAGCAGCAGCCAGGACGGCCACCAGTGGACCCTGTTCTTCCAGAACGGCAAAGTGAAG
GTGTTCCAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAGGCCCAG
GACCTGTACTGA  (SEQ ID NO:28)
```

ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACTCCAGACACCCCAGCACC (Continued)

Figure 52A

```
AGGGAGATCACCAGGACCACCCTGCAGAGCGACCAGGAGGAGATCGACTATGATGACACCATCAGC
GTGGAGATGAAGAAGGAGGACTTCGACATCTACGACGAGGACGAGAACCAGAGCCCCAGGAGCTTC
CAGAAGAAGACCAGGCACTACTTCATCGCCGCCGTGGAGAGGCTGTGGGACTATGGCATGAGCAGC
AGCCCCACGTGCTGAGGAACAGGGCCCAGAGCGGCAGCGTGCCCCAGTTCAAGAAGGTGGTGTTC
CAGGAGTTCACCGACGGCAGCTTCACCCAGCCCCTGTACAGAGGCGAGCTGAACGAGCACCTGGGC
CTGCTGGGCCCCTACATCAGGGCCGAGGTGGAGGACAACATCATGGTGACCTTCAGGAACCAGGCC
AGCAGGCCCTACAGCTTCTACAGCAGCCTGATCAGCTACGAGGAGGACCAGAGGCAGGGCGCCGAG
CCCAGGAAGAACTTCGTGAAGCCCAACGAGACCAAGACCTACTTCTGGAAGGTGCAGCACCACATG
GCCCCCACCAAGGACGAGTTCGACTGCAAGGCCTGGGCCTACTTCTCTGATGTGGACCTGGAGAAG
GACGTGCACAGCGGCCTGATCGGCCCCCTGCTGGTGTGCCACACCAACACCCTGAACCCCGCCCAC
GGCAGGCAGGTGACCGTGCAGGAGTTCGCCCTGTTCTTCACCATCTTCGACGAGACCAAGAGCTGG
TACTTCACCGAGAACATGGAGAGGAACTGCAGGGCCCCCTGCAACATCCAGATGGAGGACCCCACC
TTCAAGGAGAACTACAGGTTCCACGCCATCAACGGCTACATCATGGACACCCTGCCCGGCCTGGTG
ATGGCCCAGGACCAGAGGATCAGGTGGTATCTGCTGAGCATGGGCAGCAACGAGAACATCCACAGC
ATCCACTTCAGCGGCCACGTGTTCACCGTGAGGAAGAAGGAGGAGTACAAGATGGCCCTGTACAAC
CTGTACCCCGGCGTGTTCGAGACCGTGGAGATGCTGCCCAGCAAGGCCGGCATCTGGAGGGTGGAG
TGCCTGATCGGCGAGCACCTGCACGCCGGCATGAGCACCCTGTTCCTGGTGTACAGCAACAAGTGC
CAGACCCCCCTGGGCATGGCCAGCGGCCACATCAGGGACTTCCAGATCACCGCCTCTGGCCAGTAC
GGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAG
GGCGCCAGGCAGAAGTTCAGCAGCCTGTACATCAGCCAGTTCATCATCATGTACAGCCTGGACGGC
AAGAAGTGGCAGACCTACAGGGGCAACAGCACCGGCACCCTGATGGTGTTCTTCGGCAACGTGGAC
AGCAGCGGCATCAAGCACAACATCTTCAACCCCCCCATCATCGCCAGGTACATCAGGCTGCACCCC
ACCCACTACAGCATCAGGAGCACCCTGCGGATGGAACTGATGGGCTGCGACCTGAACAGCTGCAGC
ATGCCCCTGGGCATGGAGAGCAAGGCCATCTCTGACGCCCAGATCACCGCCAGCAGCTACTTCACC
AACATGTTCGCCACCTGGAGCCCCAGCAAGGCCAGGCTGCACCTGCAGGGCAGGAGCAACGCCTGG
AGGCCCCAGGTGAACAACCCCAAGGAGTGGCTGCAGGTGGACTTCCAGAAGACCATGAAGGTGACC
GGCGTGACCACCCAGGGCGTGAAGAGCCTGCTGACCAGCATGTACGTGAAGGAGTTCCTGATCAGC
AGCAGCCAGGACGGCCACCAGTGGACCCTGTTCTTCCAGAACGGCAAAGTGAAGGTGTTCCAGGGC
AACCAGGACAGCTTCACCCCCGTGGTGAACAGCCTGGACCCCCCCCTGCTGACCAGGTATCTGAGG
ATCCACCCCCAGAGCTGGGTGCACCAGATCGCCCTGAGAATGGAAGTGCTGGGATGCGAGGCCCAG
GACCTGTACTGA    (SEQ ID NO:29)
```

Figure 52B

CS01m23-FL-AA (SEQ ID NO: 104)

MQIELSTCFFLCLLRFCFSATRRYYLGAVELSWDYMQSDLGELPVDARFPPRVPKSFPFN
TSVVYKKTLFVEFTDHLFNIAKPRPPWMGLLGPTIQAEVYDTVVVTLKNMASHPVSLHAV
GVSYWKSSEGAEYDDQTSQREKEDDKVFPGKSHTYVWQVLKENGPTASDPPCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNTTYVNRSLSQNPPVLKRHQREITRTT
LQSDQEEIDYDDTISVEMKKEDFDIYDEDENQSPRSFQKKTRHYFIAAVERLWDYGMSSS
PHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKA
WAYFSDVDLEKDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYLLSMGSNENIH
SIHFSGHVFTVRKKEEYKMALYNLYPGVFETVEMLPSKAGIWRVECLIGEHLHAGMSTLF
LVYSNKCQTPLGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLMVFFGNVDSSG
IKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTS
MYVKEFLISSSQDGHQWTLFFQNGKVKVFQGNQDSFTPVVNSLDPPLLTRYLRIHPQSWV
HQIALRMEVLGCEAQDLY

Figure 53

CS04m3-FL-AA (SEQ ID NO: 105)

MQIELSTCFFLCLLRFCFSATRRYYLGAVELSWDYMQSDLGELPVDARFPPRVPKSFPFN
TSVVYKKTLFVEFTDHLFNIAKPRPPWMGLLGPTIQAEVYDTVVITLKNMASHPVSLHAV
GVSYWKASEGAEYDDQTSQREKEDDKVFPGGSHTYVWQVLKENGPMASDPLCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNTTYVNRSLSQNPPVLKRHQREITRTT
LQSDQEEIDYDDTISVEMKKEDFDIYDEDENQSPRSFQKKTRHYFIAAVERLWDYGMSSS
PHVLRNRAQSGSVPQFKKVVFQEFTDGSFTQPLYRGELNEHLGLLGPYIRAEVEDNIMVT
FRNQASRPYSFYSSLISYEEDQRQGAEPRKNFVKPNETKTYFWKVQHHMAPTKDEFDCKA
WAYFSDVDLEKDVHSGLIGPLLVCHTNTLNPAHGRQVTQEFALFFTIFDETKSWYFTEN
MERNCRAPCNIQMEDPTFKENYRFHAINGYIMDTLPGLVMAQDQRIRWYLLSMGSNENIH
SIHFSGHVFTVRKKEEYKMALYNLYPGVFETVEMLPSKAGIWRVECLIGEHLHAGMSTLF
LVYSNKCQTPLGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLMVFFGNVDSSG
IKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVGVTTQGVKSLLTS
MYVKEFLISSSQDGHQWTLFFQNGKVKVFQGNQDSFTPVVNSLDPPLLTRYLRIHPQSWV
HQIALRMEVLGCEAQDLY

Figure 54

CS01-FL-AAm12 (SEQ ID NO: 106)

MQIELSTCFFLCLLRFCFSATRRYYLGAVELSWDYMQSDLGELPVDARFPPRVPKSFPFNTSVVYK
KTLFVEFTDHLFNIAKPRPPWMGLLGPTIQAEVYDTVVVTLKNMASHPVSLHAVGVSYWKSSEGAE
YDDQTSQREKEDDKVFPGKSHTYVWQVLKENGPTASDPPCLTYSYLSHVDLVKDLNSGLIGALLVC
REGSLAKEKTQTLHKFILLFAVFDEGKSWHSETKNSLMQDRDAASARAWPKMHTVNGYVNRSLPGL
IGCHRKSVYWHVIGMGTTPEVHSIFLEGHTFLVRNHRQASLEISPITFLTAQTLLMDLGQFLLSCH
ISSHQHDGMEAYVKVDSCPEEPQLRMKNNEEAEDYDDDLTDSEMDVVRFDDDNSPSFIQIRSVAKK
HPKTWVHYIAAEEEDWDYAPLVLAPDDRSYKSQYLNNGPQRIGRKYKKVRFMAYTDETFKTREAIQ
HESGILGPLLYGEVGDTLLIIFKNQASRPYNIYPHGITDVRPLYSRRLPKGVKHLKDFPILPGEIF
KYKWTVTEDGPTKSDPRCLTRYYSSFVNMERDLASGLIGPLLICYKESVDQRGNQIMSDKRNVIL
FSVFDENRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRGMTALLK
VSSCDKNTGDYYEDSYEDISAYLLSKNNAIEPRSFSQNPPVLKRHQREITRTTLQSDQEEIDYDDT
ISVEMKKEDFDIYDEDENQSPRSFQKKTRHYFIAAVERLWDYGMSSSPHVLRNRAQSGSVPQFKKV
VFQEFTDGSFTQPLYRGELNEHLGLLGPYIRAEVEDNIMVTFRNQASRPYSFYSSLISYEEDQRQG
AEPRKNFVKPNETKTYFWKVQHHMAPTKDEFDCKAWAYFSDVDLEKDVHSGLIGPLLVCHTNTLNP
AHGRQVTVQEFALFFTIFDETKSWYFTENMERNCRAPCNIQMEDPTFKENYRFHAINGYIMDTLPG
LVMAQDQRIRWYLLSMGSNENIHSIHFSGHVFTVRKKEEYKMALYNLYPGVFETVEMLPSKAGIWR
VECLIGEHLHAGMSTLFLVYSNKCQTPLGMASGHIRDFQITASGQYGQWAPKLARLHYSGSINAWS
TKEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSMYVKEFL
ISSSQDGHQWTLFFQNGKVKVFQGNQDSFTPVVNSLDPPLLTRYLRIHPQSWVHQIALRMEVLGCE
AQDLY

Figure 55

CS04-FL-AAm12 (SEQ ID NO: 107)

MQIELSTCFFLCLLRFCFSATRRYYLGAVELSWDYMQSDLGELPVDARFPPRVPKSFPFNTSVVYK
KTLFVEFTDHLFNIAKPRPPWMGLLGPTIQAEVYDTVVVTLKNMASHPVSLHAVGVSYWKSSEGAE
YDDQTSQREKEDDKVFPGKSHTYVWQVLKENGPTASDPPCLTYSYLSHVDLVKDLNSGLIGALLVC
REGSLAKEKTQTLHKFILLFAVFDEGKSWHSETKNSLMQDRDAASARAWPKMHTVNGYVNRSLPGL
IGCHRKSVYWHVIGMGTTPEVHSIFLEGHTFLVRNHRQASLEISPITFLTAQTLLMDLGQFLLSCH
ISSHQHDGMEAYVKVDSCPEEPQLRMKNNEEAEDYDDDLTDSEMDVVRFDDDNSPSFIQIRSVAKK
HPKTWVHYIAAEEEDWDYAPLVLAPDDRSYKSQYLNNGPQRIGRKYKKVRFMAYTDETFKTREAIQ
HESGILGPLLYGEVGDTLLIIFKNQASRPYNIYPHGITDVRPLYSRRLPKGVKHLKDFPILPGEIF
KYKWTVTVEDGPTKSDPRCLTRYYSSFVNMERDLASGLIGPLLICYKESVDQRGNQIMSDKRNVIL
FSVFDENRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRGMTALLK
VSSCDKNTGDYYEDSYEDISAYLLSKNNAIEPRSFSQNPPVLKRHQREITRTTLQSDQEEIDYDDT
ISVEMKKEDFDIYDEDENQSPRSFQKKTRHYFIAAVERLWDYGMSSSPHVLRNRAQSGSVPQFKKV
VFQEFTDGSFTQPLYRGELNEHLGLLGPYIRAEVEDNIMVTFRNQASRPYSFYSSLISYEEDQRQG
AEPRKNFVKPNETKTYFWKVQHHMAPTKDEFDCKAWAYFSDVDLEKDVHSGLIGPLLVCHTNTLNP
AHGRQVTVQEFALFFTIFDETKSWYFTENMERNCRAPCNIQMEDPTFKENYRFHAINGYIMDTLPG
LVMAQDQRIRWYLLSMGSNENIHSIHFSGHVFTVRKKEEYKMALYNLYPGVFETVEMLPSKAGIWR
VECLIGEHLAGMSTLFLVYSNKCQTPLGMASGHIRDFQITASGQYGQWAPKLARLHYSGSINAWS
TKEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSMYVKEFL
ISSSQDGHQWTLFFQNGKVKVFQGNQDSFTPVVNSLDPPLLTRYLRIHPQSWVHQIALRMEVLGCE
AQDLY

Figure 56

CS01-FL-NAm12 (SEQ ID NO: 108)
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCGTCACCCTCAAGAACATG
GCATCCCACCCTGTGTCTCTGCATGCTGTGGGAGTCTCATACTGGAAATCCTCTGAAGGGGCTGAG
TATGATGACCAGACATCCCAGAGAGAGAAAGAGGATGACAAGGTGTTCCCTGGGAAGTCTCACACC
TATGTGTGGCAAGTCCTCAAGGAGAATGGACCCACTGCATCTGACCCACCCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTCCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG (Continued)

Figure 57A

```
GTCTTCCAGGAGTTCACTGATGGCTCATTCACCCAGCCCCTGTACAGAGGGGAACTGAATGAGCAC
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCTCCTGACAAGATAC
CTGAGAATTCACCCCAGTCTTGGGTCCACCAGATTGCCCTGAGAATGGAAGTCCTGGGATGTGAG
GCACAAGACCTGTACTGA
```

Figure 57B

CS04-FL-NAm12 (SEQ ID NO: 109)
ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCGTCACCCTCAAGAACATG
GCCTCCCACCCTGTGAGCCTGCATGCTGTGGGGGTCAGCTACTGGAAGTCCTCTGAGGGGCTGAG
TATGATGACCAGACCTCCCAGAGGGAGAAGGAGGATGACAAAGTGTTCCCTGGGAAGAGCCACACC
TATGTGTGGCAGGTCCTCAAGGAGAATGGCCCCACTGCCTCTGACCCACCCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTCCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATCCACCTGTCCTGAAACGC
CACCAGAGGGAGATCACCAGGACCACCCTCCAGTCTGACCAGGAGGAGATTGACTATGATGACACC
ATTTCTGTGGAGATGAAGAAAGAGGACTTTGACATCTATGACGAGGACGAGAACCAGAGCCCAAGG
AGCTTCCAGAAGAAGACCAGGCACTACTTCATTGCTGCTGTGGAGCGCCTGTGGGACTATGGCATG
AGCTCCAGCCCCATGTCCTCAGGAACAGGGCCCAGTCTGGCTCTGTGCCACAGTTCAAGAAAGTG
GTCTTCCAAGAGTTCACTGATGGCAGCTTCACCCAGCCCCTGTACAGAGGGGAGCTGAATGAGCAC
CTGGGACTCCTGGGCCCATACATCAGGGCTGAGGTGGAGGACAACATCATGGTGACCTTCCGCAAC (Continued)

Figure 58A

```
CAGGCCTCCAGGCCCTACAGCTTCTACAGCTCCCTCATCAGCTATGAGGAGGACCAGAGGCAGGGG
GCTGAGCCACGCAAGAACTTTGTGAAACCCAATGAAACCAAGACCTACTTCTGGAAAGTCCAGCAC
CACATGGCCCCCACCAAGGATGAGTTTGACTGCAAGGCCTGGGCCTACTTCTCTGATGTGGACCTG
GAGAAGGATGTGCACTCTGGCCTGATTGGCCCACTCCTGGTCTGCCACACCAACACCCTGAACCCT
GCCCATGGAAGGCAAGTGACTGTGCAGGAGTTTGCCCTCTTCTTCACCATCTTTGATGAAACCAAG
AGCTGGTACTTCACTGAGAACATGGAGCGCAACTGCAGGGCCCCATGCAACATTCAGATGGAGGAC
CCCACCTTCAAAGAGAACTACCGCTTCCATGCCATCAATGGCTACATCATGGACACCCTGCCTGGG
CTTGTCATGGCCCAGGACCAGAGGATCAGGTGGTACCTGCTTTCTATGGGCTCCAATGAGAACATT
CACTCCATCCACTTCTCTGGGCATGTCTTCACTGTGCGCAAGAAGGAGGAGTACAAGATGGCCCTG
TACAACCTCTACCCTGGGGTCTTTGAGACTGTGGAGATGCTGCCCTCCAAAGCTGGCATCTGGAGG
GTGGAGTGCCTCATTGGGGAGCACCTGCATGCTGGCATGAGCACCCTGTTCCTGGTCTACAGCAAC
AAGTGCCAGACCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGC
ACCAAGGAGCCATTCAGCTGGATCAAAGTGGACCTGCTGGCCCCATGATCATCCATGGCATCAAG
ACCCAGGGGGCCAGGCAGAAGTTCTCCAGCCTGTACATCAGCCAGTTCATCATCATGTACAGCCTG
GATGGCAAGAAATGGCAGACCTACAGAGGCAACTCCACTGGAACACTCATGGTCTTCTTTGGCAAT
GTGGACAGCTCTGGCATCAAGCACAACATCTTCAACCCCCCAATCATCGCCAGATACATCAGGCTG
CACCCCACCCACTACAGCATCCGCAGCACCCTCAGGATGGAGCTGATGGGCTGTGACCTGAACTCC
TGCAGCATGCCCCTGGGCATGGAGAGCAAGGCCATTTCTGATGCCCAGATCACTGCCTCCAGCTAC
TTCACCAACATGTTTGCCACCTGGAGCCCAAGCAAGGCCAGGCTGCACCTCCAGGGAAGGAGCAAT
GCCTGGAGGCCCCAGGTCAACAACCCAAAGGAGTGGCTGCAGGTGGACTTCCAGAAGACCATGAAG
GTCACTGGGGTGACCACCCAGGGGGTCAAGAGCCTGCTCACCAGCATGTATGTGAAGGAGTTCCTG
ATCAGCTCCAGCCAGGATGGCCACCAGTGGACCCTCTTCTTCCAGAATGGCAAGGTCAAGGTGTTC
CAGGGCAACCAGGACAGCTTCACCCCTGTGGTGAACAGCCTGGACCCCCCCTCCTGACCAGATAC
CTGAGGATTCACCCCAGAGCTGGGTCCACCAGATTGCCCTGAGGATGGAGGTCCTGGGATGTGAG
GCCCAGGACCTGTACTGA
```

Figure 58B

SEQUENCE LISTING

<160> NUMBER OF SEQ ID NOS: 109

<210> SEQ ID NO 1
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
atgcagattg agctgagcac ctgcttcttc ctgtgcctgc tgaggttctg cttctctgcc    60
accaggagat actacctggg ggctgtggag ctttcttggg actacatgca gtctgacctg   120
ggggagctgc ctgtggatgc caggttccca cccagagtgc ccaaatcctt cccattcaac   180

```
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
gacactgtgg tcatcaccct caagaacatg gcctcccacc ctgtgagcct gcatgctgtg    360
ggggtcagct actggaaggc ctctgagggg gctgagtatg atgaccagac ctcccagagg    420
gagaaggagg atgacaaagt gttccctggg ggcagccaca cctatgtgtg gcaggtcctc    480
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc catttttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga agtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaagggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tgcccactg ctcatctgct acaaggagtc tgtggaccag   1740
agggaaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980 attgggccc agactgactt cctttctgtc ttcttctctg ctacaccctt caaacacaag   2040
atggtgtatg aggacaccct gaccctcttc ccattctctg gggagactgt gttcatgagc   2100
atggagaacc ctggcctgtg gattctggga tgccacaact ctgacttccg caacaggggc   2160
atgactgccc tgctcaaagt ctcctcctgt gacaagaaca ctgggggacta ctatgaggac   2220 agctatgagg acatctctgc ctacctgctc agcaagaaca atgccattga gcccaggagc   2280
ttcagccaga atccacctgt cctgaaacgc accagagggg agatcaccag gaccaccctc   2340
cagtctgacc aggaggagat tgactatgat gacaccattt ctgtggagat gaagaaagag   2400
gactttgaca tctatgacga ggacgagaac cagagcccaa ggagcttcca agaagaagacc   2460 aggcactact tcattgctgc tgtggagcgc ctgtgggact atggcatgag ctccagcccc   2520
catgtcctca ggaacagggc ccagtctggc tctgtgccac agttcaagaa agtggtcttc   2580
```

```
caagagttca ctgatggcag cttcacccag ccctgtaca gagggagct gaatgagcac    2640 ctgggactcc tgggcccata catcagggct gaggtggagg acaacatcat ggtgaccttc    2700
cgcaaccagg cctccaggcc ctacagcttc tacagctccc tcatcagcta tgaggaggac    2760
cagaggcagg gggctgagcc acgcaagaac tttgtgaaac ccaatgaaac caagacctac    2820
ttctggaaag tccagcacca catggccccc accaaggatg agtttgactg caaggcctgg    2880
gcctacttct ctgatgtgga cctggagaag gatgtgcact ctggcctgat tggcccactc    2940
ctggtctgcc acaccaacac cctgaaccct gcccatggaa ggcaagtgac tgtgcaggag    3000
tttgccctct tcttcaccat ctttgatgaa accaagagct ggtacttcac tgagaacatg    3060
gagcgcaact gcagggcccc atgcaacatt cagatggagg accccacctt caaagagaac    3120
taccgcttcc atgccatcaa tggctacatc atggacaccc tgcctgggct tgtcatggcc    3180
caggaccaga ggatcaggtg gtacctgctt tctatgggct ccaatgagaa cattcactcc    3240
atccacttct ctgggcatgt cttcactgtg cgcaagaagg aggagtacaa gatggccctg    3300
tacaacctct accctgggt ctttgagact gtggagatgc tgccctccaa agctggcatc    3360
tggagggtgg agtgcctcat tggggagcac ctgcatgctg gcatgagcac cctgttcctg    3420
gtctacagca acaagtgcca gaccccctg gaatggcct ctggccacat cagggacttc    3480
cagatcactg cctctggcca gtatggccag tgggccccca gctggccag gctccactac    3540 tctggatcca tcaatgcctg gagcaccaag gagccattca gctggatcaa agtggacctg    3600
ctggccccca tgatcatcca tggcatcaag acccagggg ccaggcagaa gttctccagc    3660
ctgtacatca gccagttcat catcatgtac agcctggatg gcaagaaatg gcagacctac    3720
agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcaccct caggatggag ctgatgggct gtgacctgaa ctcctgcagc    3900 atgccctgg gcatggagag caaggccatt tctgatgccc agatcactgc ctccagctac    3960
ttcaccaaca tgtttgccac ctggagccca agcaaggcca ggctgcacct ccagggaagg    4020
agcaatgcct ggaggcccca ggtcaacaac ccaaaggagt ggctgcaggt ggacttccag    4080
aagaccatga aggtcactgg ggtgaccacc cagggggtca agagcctgct caccagcatg    4140
tatgtgaagg agttcctgat cagctccagc caggatggcc accagtggac cctcttcttc    4200
cagaatggca aggtcaaggt gttccagggc aaccaggaca gcttcacccc tgtggtgaac    4260
agcctggacc cccccctcct gaccagatac ctgaggattc accccagag ctgggtccaa    4320 cagattgccc tgaggatgga ggtcctggga tgtgaggccc aggacctgta ctga         4374
```

<210> SEQ ID NO 2
<211> LENGTH: 1457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
```

```
                35                  40                  45
Phe Pro Pro Arg Val Pro Lys Ser Phe Pro Phe Asn Thr Ser Val Val
 50                  55                  60
Tyr Lys Lys Thr Leu Phe Val Glu Phe Thr Asp His Leu Phe Asn Ile
 65                  70                  75                  80
Ala Lys Pro Arg Pro Trp Met Gly Leu Gly Pro Thr Ile Gln
                     85                  90                  95
Ala Glu Val Tyr Asp Thr Val Val Ile Thr Leu Lys Asn Met Ala Ser
             100                 105                 110
His Pro Val Ser Leu His Ala Val Gly Val Ser Tyr Trp Lys Ala Ser
             115                 120                 125
Glu Gly Ala Glu Tyr Asp Asp Gln Thr Ser Gln Arg Glu Lys Glu Asp
130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                 165                 170                 175
Tyr Leu Ser His Val Asp Leu Val Lys Asp Leu Asn Ser Gly Leu Ile
             180                 185                 190
Gly Ala Leu Leu Val Cys Arg Glu Gly Ser Leu Ala Lys Glu Lys Thr
             195                 200                 205
Gln Thr Leu His Lys Phe Ile Leu Leu Phe Ala Val Phe Asp Glu Gly
210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                 245                 250                 255
Val Asn Arg Ser Leu Pro Gly Leu Ile Gly Cys His Arg Lys Ser Val
             260                 265                 270
Tyr Trp His Val Ile Gly Met Gly Thr Thr Pro Glu Val His Ser Ile
             275                 280                 285
Phe Leu Glu Gly His Thr Phe Leu Val Arg Asn His Arg Gln Ala Ser
290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                 325                 330                 335
Asp Gly Met Glu Ala Tyr Val Lys Val Asp Ser Cys Pro Glu Glu Pro
             340                 345                 350
Gln Leu Arg Met Lys Asn Asn Glu Glu Ala Glu Asp Tyr Asp Asp Asp
             355                 360                 365
Leu Thr Asp Ser Glu Met Asp Val Val Arg Phe Asp Asp Asp Asn Ser
             370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                 405                 410                 415
Leu Val Leu Ala Pro Asp Asp Arg Ser Tyr Lys Ser Gln Tyr Leu Asn
             420                 425                 430
Asn Gly Pro Gln Arg Ile Gly Arg Lys Tyr Lys Lys Val Arg Phe Met
             435                 440                 445
Ala Tyr Thr Asp Glu Thr Phe Lys Thr Arg Glu Ala Ile Gln His Glu
450                 455                 460
```

-continued

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

-continued

Leu Gly Leu Leu Gly Pro Tyr Ile Arg Ala Glu Val Glu Asp Asn Ile
            885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Glu Pro Phe Ser Trp Ile Lys Val Asp Leu Leu Ala Pro
        1190                1195                1200

Met Ile Ile His Gly Ile Lys Thr Gln Gly Ala Arg Gln Lys Phe
        1205                1210                1215

Ser Ser Leu Tyr Ile Ser Gln Phe Ile Ile Met Tyr Ser Leu Asp
        1220                1225                1230

Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn
        1250                1255                1260

Ile Phe Asn Pro Pro Ile Ile Ala Arg Tyr Ile Arg Leu His Pro
        1265                1270                1275

Thr His Tyr Ser Ile Arg Ser Thr Leu Arg Met Glu Leu Met Gly

```
                 1280              1285              1290
Cys Asp Leu Asn Ser Cys Ser Met Pro Leu Gly Met Glu Ser Lys
            1295              1300              1305
Ala Ile Ser Asp Ala Gln Ile Thr Ala Ser Ser Tyr Phe Thr Asn
            1310              1315              1320
Met Phe Ala Thr Trp Ser Pro Ser Lys Ala Arg Leu His Leu Gln
            1325              1330              1335
Gly Arg Ser Asn Ala Trp Arg Pro Gln Val Asn Asn Pro Lys Glu
            1340              1345              1350
Trp Leu Gln Val Asp Phe Gln Lys Thr Met Lys Val Thr Gly Val
            1355              1360              1365
Thr Thr Gln Gly Val Lys Ser Leu Leu Thr Ser Met Tyr Val Lys
            1370              1375              1380
Glu Phe Leu Ile Ser Ser Ser Gln Asp Gly His Gln Trp Thr Leu
            1385              1390              1395
Phe Phe Gln Asn Gly Lys Val Lys Val Phe Gln Gly Asn Gln Asp
            1400              1405              1410
Ser Phe Thr Pro Val Val Asn Ser Leu Asp Pro Pro Leu Leu Thr
            1415              1420              1425
Arg Tyr Leu Arg Ile His Pro Gln Ser Trp Val His Gln Ile Ala
            1430              1435              1440
Leu Arg Met Glu Val Leu Gly Cys Glu Ala Gln Asp Leu Tyr
            1445              1450              1455
```

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gccaccagga gatactacct gggggctgtg gagctttctt ggactacat gcagtctgac      60
ctgggggagc tgcctgtgga tgccaggttc ccacccagag tgcccaaatc cttcccattc     120
aacacctctg tggtctacaa gaagaccctc tttgtggagt tcactgacca cctgttcaac     180
attgccaaac caggccacc ctggatggga ctccctggga ccaccattca ggctgaggtg     240
tatgacactg tggtcatcac cctcaagaac atggcctccc accctgtgag cctgcatgct     300
gtggggtca gctactggaa ggcctctgag ggggctgagt atgatgacca gacctcccag     360
agggagaagg aggatgacaa agtgttccct gggggcagcc acacctatgt gtggcaggtc     420
ctcaaggaga atggccccat ggcctctgac ccactctgcc tgaccactc ctacctttct     480
catgtggacc tggtcaagga cctcaactct ggactgattg gggccctgct ggtgtgcagg     540
gagggctccc tggccaaaga gaagacccag accctgcaca gttcattct cctgtttgct     600
gtctttgatg agggcaagag ctggcactct gaaaccaaga ctccctgat gcaggacagg     660
gatgctgcct ctgccagggc ctggccaag atgcacactg tgaatggcta tgtgaacagg     720
agcctgcctg gactcattgg ctgccacagg aaatctgtct actggcatgt gattggcatg     780
gggacaaccc ctgaggtgca ctccattttc ctggagggcc acaccttcct ggtcaggaac     840
cacagacagg ccagcctgga gatcagcccc atcaccttcc tcactgccca gacctgctg     900
atggacctcg gacagttcct gctgttctgc cacatcagct cccaccagca tgatggcatg     960
gaggcctatg tcaaggtgga cagctgccct gaggagccac agctcaggat gaagaacaat   1020
```

-continued

```
gaggaggctg aggactatga tgatgacctg actgactctg agatggatgt ggtccgcttt    1080
gatgatgaca acagcccatc cttcattcag atcaggtctg tggccaagaa acaccccaag    1140
acctgggtgc actacattgc tgctgaggag gaggactggg actatgcccc actggtcctg    1200
gcccctgatg acaggagcta caagagccag tacctcaaca atgggcccaca gaggattgga    1260 cgcaagtaca agaaagtcag gttcatggcc tacactgatg aaaccttcaa gaccagggag    1320
gccattcagc atgagtctgg catcctgggc ccactcctgt atggggaggt ggggacacc     1380 ctgctcatca tcttcaagaa ccaggcctcc aggccctaca acatctaccc acatggcatc    1440
actgatgtca ggcccctgta cagccgcagg ctgccaaagg gggtgaaaca cctcaaggac    1500
ttccccattc tgcctgggga gatcttcaag tacaagtgga ctgtcactgt ggaggatgga    1560
ccaaccaaat ctgaccccag gtgcctcacc agatactact ccagctttgt gaacatggag    1620
agggacctgg cctctggcct gattggccca ctgctcatct gctacaagga gtctgtggac    1680
cagaggggaa accagatcat gtctgacaag aggaatgtga ttctgttctc tgtctttgat    1740
gagaacagga gctggtacct gactgagaac attcagcgct tcctgcccaa ccctgctggg    1800
gtgcagctgg aggaccctga gttccaggcc agcaacatca tgcactccat caatggctat    1860
gtgtttgaca gcctccagct ttctgtctgc ctgcatgagg tggcctactg gtacattctt    1920
tctattgggg cccagactga cttcctttct gtcttcttct ctggctacac cttcaaacac    1980
aagatggtgt atgaggacac cctgaccctc ttcccattct ctggggagac tgtgttcatg    2040
agcatggaga accctggcct gtggattctg ggatgccaca actctgactt ccgcaacagg    2100
ggcatgactg ccctgctcaa agtctcctcc tgtgacaaga acactgggga ctactatgag    2160
gacagctatg aggacatctc tgcctacctg ctcagcaaga acaatgccat tgagcccagg    2220
```

```
<210> SEQ ID NO 4
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

```
gagatcacca ggaccaccct ccagtctgac caggaggaga ttgactatga tgacaccatt      60
tctgtggaga tgaagaaaga ggactttgac atctatgacg aggacgagaa ccagagccca    120
aggagcttcc agaagaagac caggcactac ttcattgctg ctgtggagcg cctgtgggac    180
tatggcatga gctccagccc ccatgtcctc aggaacaggg cccagtctgg ctctgtgcca    240
cagttcaaga aagtggtctt ccaagagttc actgatggca gcttcaccca gcccctgtac    300
agaggggagc tgaatgagca cctgggactc ctgggcccat acatcagggc tgaggtggag    360
gacaacatca tggtgacctt ccgcaaccag gcctccaggc cctacagctt ctacagctcc    420
ctcatcagct atgaggagga ccagaggcag ggggctgagc acgcaagaa ctttgtgaaa    480 cccaatgaaa ccaagaccta cttctggaaa gtccagcacc acatggcccc caccaaggat    540
gagtttgact gcaaggcctg gcctacttc tctgatgtgg acctgagaa ggatgtgcac    600 tctggcctga ttggcccact cctggtctgc cacaccaaca ccctgaaccc tgcccatgga    660
aggcaagtga ctgtgcagga gtttgcccte ttcttcacca tctttgatga aaccaagagc    720
tggtacttca ctgagaacat ggagcgcaac tgcagggccc catgcaacat tcagatggag    780
gaccccacct tcaaagagaa ctaccgcttc catgccatca atggctacat catggacacc    840
```

```
ctgcctgggc ttgtcatggc ccaggaccag aggatcaggt ggtacctgct ttctatgggc      900
tccaatgaga acattcactc catccacttc tctgggcatg tcttcactgt gcgcaagaag      960
gaggagtaca agatggccct gtacaacctc taccctgggg tctttgagac tgtggagatg     1020
ctgccctcca agctggcat ctggagggtg gagtgcctca ttggggagca cctgcatgct      1080
ggcatgagca ccctgttcct ggtctacagc aacaagtgcc agaccccct gggaatggcc      1140 tctggccaca tcagggactt ccagatcact gcctctggcc agtatggcca gtgggccccc     1200
aagctggcca ggctccacta ctctggatcc atcaatgcct ggagcaccaa ggagccattc     1260
agctggatca aagtggacct gctggccccc atgatcatcc atggcatcaa gacccagggg     1320
gccaggcaga agttctccag cctgtacatc agccagttca tcatcatgta cagcctggat     1380
ggcaagaaat ggcagaccta cagaggcaac tccactggaa cactcatggt cttctttggc     1440
aatgtggaca gctctggcat caagcacaac atcttcaacc ccccaatcat cgccagatac     1500
atcaggctgc acccccaccca ctacagcatc cgcagcaccc tcaggatgga gctgatgggc     1560
tgtgacctga actcctgcag catgccctg gcatggaga gcaaggccat ttctgatgcc      1620
cagatcactg cctccagcta cttccacaac atgtttgcca cctggagccc aagcaaggcc     1680
aggctgcacc tccagggaag gagcaatgcc tggaggcccc aggtcaacaa cccaaaggag     1740
tggctgcagg tggacttcca gaagaccatg aaggtcactg gggtgaccac ccaggggggtc     1800 aagagcctgc tcaccagcat gtatgtgaag gagttcctga tcagctccag ccaggatggc     1860
caccagtgga ccctcttctt ccagaatggc aaggtcaagg tgttccaggg caaccaggac     1920
agcttcaccc ctgtggtgaa cagcctggac ccccccctcc tgaccagata cctgaggatt     1980
cacccccaga gctgggtcca ccagattgcc ctgaggatgg aggtcctggg atgtgaggcc     2040
caggacctgt ac                                                        2052

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agcttctctc agaatccacc tgtcctgaag agacaccaga ga                          42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agcttcagcc agaatccacc tgtcctgaaa cgccaccaga gg                          42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```
agcttcagcc agaacccccc cgtgctgaag aggcaccaga gg                42

<210> SEQ ID NO 8
<211> LENGTH: 7827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cctcgagatt taaatgacgt   420
tggccactcc ctctctgcgc gctcgctcgc tcactgaggc cgggcgacca aggtcgccc    480
gacgcccggg cttcgcccgg gcggcctcag tgagcgagcg agcgcgcaga gagggagtgg   540
ccaactccat cactagggggt tcctgagttt aaacttcgtc gacgattcga gcttgggctg   600
caggtcgagg gcactgggag gatgttgagt aagatggaaa actactgatg acccttgcag   660
agacagagta ttaggacatg tttgaacagg ggccgggcga tcagcaggta gctctagagg   720
atccccgtct gtctgcacat ttcgtagagc gagtgttccg atactctaat ctccctaggc   780
aaggttcata tttgtgtagg ttacttattc tccttttgtt gactaagtca ataatcagaa   840
tcagcaggtt tggagtcagc ttggcaggga tcagcagcct gggttggaag gaggggggtat   900
aaaagcccct tcaccaggag aagccgtcac acagactagg cgcgccaccg ccaccatgca   960
gattgagctg agcacctgct tcttcctgtg cctgctgagg ttctgcttct ctgccaccag  1020
gagatactac ctgggggctg tggagctttc ttgggactac atgcagtctg acctggggga  1080
gctgcctgtg gatgccaggt tcccacccag agtgcccaaa tccttcccat tcaacaccct  1140
tgtggtctac aagaagaccc tctttgtgga gttcactgac cacctgttca acattgccaa  1200
acccaggcca ccctggatgg gactcctggg acccaccatt caggctgagg tgtatgacac  1260
tgtggtcatc accctcaaga acatggcctc ccaccctgtg agcctgcatg ctgtggggggt  1320
cagctactgg aaggcctctg aggggggctga gtatgatgac cagacctccc agagggagaa  1380
ggaggatgac aaagtgttcc ctgggggcag ccacacctat gtgtggcagg tcctcaagga  1440
gaatggcccc atggcctctg acccactctg cctgacctac tcctaccttt ctcatgtgga  1500
cctggtcaag gacctcaact ctggactgat tggggccctg ctggtgtgca ggagggggctc  1560
cctggccaaa gagaagaccc agaccctgca caagttcatt ctcctgtttg ctgtctttga  1620
tgagggcaag agctggcact ctgaaaccaa gaactccctg atgcaggaca gggatgctgc  1680
ctctgccagg gcctggccca gatgcacac tgtgaatggc tatgtgaaca ggagcctgcc  1740
tggactcatt ggctgccaca ggaaatctgt ctactggcat gtgattggca tggggacaac  1800
ccctgaggtg cactccattt cctggagggg ccacacccttc ctggtcagga accacagaca  1860
ggccagcctg gagatcagcc ccatcacctt cctcactgcc agaccctgc tgatggacct  1920
cggacagttc ctgctgtttc gccacatcag ctcccaccag catgatggca tggaggccta  1980
```

```
tgtcaaggtg gacagctgcc ctgaggagcc acagctcagg atgaagaaca atgaggaggc    2040
tgaggactat gatgatgacc tgactgactc tgagatggat gtggtccgct ttgatgatga    2100
caacagccca tccttcattc agatcaggtc tgtggccaag aaacacccca agacctgggt    2160
gcactacatt gctgctgagg aggaggactg ggactatgcc ccactggtcc tggcccctga    2220
tgacaggagc tacaagagcc agtacctcaa caatgccca cagaggattg acgcaagta     2280 caagaaagtc aggttcatgg cctacactga tgaaaccttc aagaccaggg aggccattca    2340
gcatgagtct ggcatcctgg cccactcct gtatgggag gtgggggaca ccctgctcat     2400
catcttcaag aaccaggcct ccaggcccta acacatctac ccacatggca tcactgatgt    2460
caggcccctg tacagccgca ggctgccaaa gggggtgaaa cacctcaagg acttccccat    2520
tctgcctggg gagatcttca gtacaagtg actgtcact gtggaggatg accaaccaa      2580 atctgacccc aggtgcctca ccagatacta ctccagcttt gtgaacatgg agagggacct    2640
ggcctctggc ctgattggcc cactgctcat ctgctacaag gagtctgtgg accagagggg    2700
aaaccagatc atgtctgaca gaggaatgt gattctgttc tctgtctttg atgagaacag     2760
gagctggtac ctgactgaga acattcagcg cttcctgccc aaccctgctg gggtgcagct    2820
ggaggaccct gagttccagg ccagcaacat catgcactcc atcaatggct atgtgtttga    2880
cagcctccag ctttctgtct gcctgcatga ggtggcctac tggtacattc tttctattgg    2940
ggcccagact gacttccttt ctgtcttctt ctctggctac accttcaaac acaagatggt    3000
gtatgaggac accctgaccc tcttcccatt ctctgggag actgtgttca tgagcatgga     3060
gaaccctggc ctgtggattc tgggatgcca caactctgac ttccgcaaca ggggcatgac    3120
tgccctgctc aaagtctcct cctgtgacaa gaacactggg gactactatg aggacagcta    3180
tgaggacatc tctgcctacc tgctcagcaa gaacaatgcc attgagccca ggagcttcag    3240
ccagaatcca cctgtcctga aacgccacca gagggagatc accaggacca ccctccagtc    3300
tgaccaggag gagattgact atgatgacac catttctgtg gagatgaaga agaggacttt   3360
tgacatctat gacgaggacg agaaccagag cccaaggagc ttccagaaga agaccaggca    3420
ctacttcatt gctgctgtgg agcgcctgtg ggactatggc atgagctcca gccccatgt     3480 cctcaggaac agggcccagt ctggctctgt gccacagttc aagaaagtgg tcttccaaga    3540
gttcactgat ggcagcttca cccagccct gtacagaggg gagctgaatg agcacctggg     3600
actcctgggc ccatacatca gggctgaggt ggaggacaac atcatggtga ccttccgcaa    3660
ccaggcctcc aggccctaca gcttctacag ctccctcatc agctatgagg aggaccagag    3720 gcaggggct gagccacgca agaactttgt gaaacccaat gaaaccaaga cctacttctg    3780
gaaagtccag caccacatgg cccccaccaa ggatgagttt gactgcaagg cctgggccta    3840
cttctctgat gtggacctgg agaaggatgt gcactctggc ctgattggcc cactcctggt    3900
ctgccacacc aacaccctga ccctgcccca tggaaggcaa gtgactgtgc aggagtttgc    3960
cctcttcttc accatctttg atgaaaccaa gagctggtac ttcactgaga acatggagcg    4020
caactgcagg gccccatgca acattcagat ggaggacccc accttcaaag agaactaccg    4080
cttccatgcc atcaatggct acatcatgga caccctgcct gggcttgtca tggcccagga    4140
ccagaggatc aggtggtacc tgctttctat gggctccaat gagaacattc actccatcca    4200
cttctctggg catgtcttca ctgtgcgcaa gaaggaggag tacaagatgg ccctgtacaa    4260
cctctaccct gggggtcttg agactgtgga gatgctgccc tccaaagctg gcatctggag    4320
```

```
ggtggagtgc ctcattgggg agcacctgca tgctggcatg agcaccctgt tcctggtcta      4380
cagcaacaag tgccagaccc ccctgggaat ggcctctggc cacatcaggg acttccagat      4440
cactgcctct ggccagtatg ccagtgggc ccccaagctg gccaggctcc actactctgg       4500
atccatcaat gcctggagca ccaaggagcc attcagctgg atcaaagtgg acctgctggc      4560
ccccatgatc atccatggca tcaagaccca gggggccagg cagaagttct ccagcctgta      4620
catcagccag ttcatcatca tgtacagcct ggatggcaag aaatggcaga cctacagagg      4680
caactccact ggaacactca tggtcttctt tggcaatgtg acagctctg gcatcaagca       4740 caacatcttc aacccccaa tcatcgccag atacatcagg ctgcacccca cccactacag       4800
catccgcagc accctcagga tggagctgat gggctgtgac ctgaactcct gcagcatgcc      4860
cctgggcatg gagagcaagg ccatttctga tgcccagatc actgcctcca gctacttcac      4920
caacatgttt gccacctgga gcccaagcaa ggccaggctg cacctccagg aaggagcaa      4980 tgcctggagg ccccaggtca caacccaaa ggagtggctg caggtggact tccagaagac       5040
catgaaggtc actggggtga ccacccaggg ggtcaagagc ctgctcacca gcatgtatgt      5100
gaaggagttc ctgatcagct ccagccagga tggccaccag tggaccctct tcttccagaa      5160
tggcaaggtc aaggtgttcc agggcaacca ggacagcttc acccctgtgg tgaacagcct      5220 ggacccccc ctcctgacca gatacctgag gattcacccc cagagctggg tccaccagat      5280
tgccctgagg atggaggtcc tgggatgtga ggcccaggac ctgtactgat gacgagcggc      5340
cgctcttagt agcagtatcg ataataaaag atctttattt tcattagatc tgtgtgttgg     5400
ttttttgtgt gttaattaag ctcgcgaagg aaccctagt gatggagttg ccactccct       5460 ctctgcgcgc tcgctcgctc actgaggccg ggcgaccaaa ggtcgcccga cgcccgggct      5520
ttgcccgggc ggcctcagtg agcgagcgag cgcgcagaga gggagtggcc aagacgattt      5580
aaatgacaag cttggcgtaa tcatggtcat agctgtttcc tgtgtgaaat tgttatccgc      5640
tcacaattcc acacaacata cgagccggaa gcataaagtg taaagcctgg ggtgcctaat      5700
gagtgagcta actcacatta attgcgttgc gctcactgcc cgctttccag tcgggaaacc      5760
tgtcgtgcca gctgcattaa tgaatcggcc aacgcgcggg gagaggcggt ttgcgtattg      5820
ggcgctcttc cgcttcctcg ctcactgact cgctgcgctc ggtcgttcgg ctgcggcgag      5880
cggtatcagc tcactcaaag gcggtaatac ggttatccac agaatcaggg gataacgcag      5940
gaaagaacat gtgagcaaaa ggccagcaaa aggccaggaa ccgtaaaaag gccgcgttgc      6000
tggcgttttt ccataggctc cgcccccctg acgagcatca caaaaatcga cgctcaagtc      6060
agaggtggcg aaacccgaca ggactataaa gataccaggc gtttccccct ggaagctccc      6120
tcgtgcgctc tcctgttccg accctgccgc ttaccggata cctgtccgcc tttctccctt      6180
cgggaagcgt ggcgctttct catagctcac gctgtaggta tctcagttcg gtgtaggtcg      6240
ttcgctccaa gctgggctgt gtgcacgaac cccccgttca gcccgaccgc tgcgccttat      6300
ccggtaacta tcgtcttgag tccaacccgg taagacacga cttatcgcca ctggcagcag      6360
ccactggtaa caggattagc agagcgaggt atgtaggcgg tgctacagag ttcttgaagt      6420
ggtggcctaa ctacggctac actagaagaa cagtatttgg tatctgcgct ctgctgaagc      6480
cagttacctt cggaaaaaga gttggtagct cttgatccgg caaacaaacc accgctggta      6540
gcggtggttt ttttgtttgc aagcagcaga ttacgcgcag aaaaaagga tctcaagaag       6600 atcctttgat cttttctacg gggtctgacg ctcagtggaa cgaaaactca cgttaaggga      6660
ttttggtcat gagattatca aaaaggatct tcacctagat cctttaaat taaaaatgaa      6720
```

```
gttttaaatc aatctaaagt atatatgagt aaacttggtc tgacagttac caatgcttaa      6780
tcagtgaggc acctatctca gcgatctgtc tatttcgttc atccatagtt gcctgactcc      6840
ccgtcgtgta gataactacg atacgggagg gcttaccatc tggccccagt gctgcaatga      6900
taccgcgaga cccacgctca ccggctccag atttatcagc aataaaccag ccagccggaa      6960
gggccgagcg cagaagtggt cctgcaactt tatccgcctc catccagtct attaattgtt      7020
gccgggaagc tagagtaagt agttcgccag ttaatagttt gcgcaacgtt gttgccattg      7080
ctacaggcat cgtggtgtca cgctcgtcgt ttggtatggc ttcattcagc tccggttccc      7140
aacgatcaag gcgagttaca tgatccccca tgttgtgcaa aaaagcggtt agctccttcg      7200
gtcctccgat cgttgtcaga agtaagttgg ccgcagtgtt atcactcatg gttatggcag      7260
cactgcataa ttctcttact gtcatgccat ccgtaagatg cttttctgtg actggtgagt      7320
actcaaccaa gtcattctga aatagtgta tgcggcgacc gagttgctct tgcccggcgt       7380
caatacggga taataccgcg ccacatagca gaactttaaa agtgctcatc attggaaaac      7440
gttcttcggg gcgaaaactc tcaaggatct taccgctgtt gagatccagt tcgatgtaac      7500
ccactcgtgc acccaactga tcttcagcat cttttacttt caccagcgtt tctgggtgag      7560
caaaaacagg aaggcaaaat gccgcaaaaa agggaataag ggcgacacgg aaatgttgaa      7620
tactcatact cttcctttt caatattatt gaagcattta tcagggttat tgtctcatga      7680
gcggatacat atttgaatgt atttagaaaa ataaacaaat aggggttccg cgcacatttc      7740
cccgaaaagt gccacctgac gtctaagaaa ccattattat catgacatta acctataaaa      7800
ataggcgtat cacgaggccc tttcgtc                                          7827

<210> SEQ ID NO 9
<211> LENGTH: 4332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgcagattg agctgagcac ctgcttcttc ctgtgcctgc tgaggttctg cttctctgcc        60
accaggagat actacctggg ggctgtggag ctttcttggg actacatgca gtctgacctg       120
ggggagctgc ctgtggatgc caggttccca cccagagtgc ccaaatcctt cccattcaac       180
acctctgtgg tctacaagaa gaccctcttt gtggagttca ctgaccacct gttcaacatt       240
gccaaaccca ggccaccctg gatgggactc ctgggaccca ccattcaggc tgaggtgtat       300
gacactgtgg tcatcacccc tcaagaacatg gcctcccacc ctgtgagcct gcatgctgtg       360
ggggtcagct actggaaggc ctctgagggg gctgagtatg atgaccagac ctcccagagg       420
gagaaggagg atgacaaagt gttccctggg ggcagccaca cctatgtgtg gcaggtcctc       480
aaggagaatg gccccatggc ctctgaccca ctctgcctga cctactccta cctttctcat       540
gtggacctgg tcaaggacct caactctgga ctgattgggg ccctgctggt gtgcagggag       600
ggctccctgg ccaaagagaa gacccagacc ctgcacaagt tcattctcct gtttgctgtc       660
tttgatgagg gcaagagctg gcactctgaa accaagaact ccctgatgca ggacagggat       720
gctgcctctg ccagggcctg gcccaagatg cacactgtga atggctatgt gaacaggagc       780
ctgcctggac tcattggctg ccacaggaaa tctgtctact ggcatgtgat tggcatgggg       840
acaacccctg aggtgcactc catttttctg gagggccaca ccttcctggt caggaaccac       900
```

```
agacaggcca gcctggagat cagccccatc accttcctca ctgcccagac cctgctgatg      960
gacctcggac agttcctgct gttctgccac atcagctccc accagcatga tggcatggag     1020
gcctatgtca aggtggacag ctgccctgag gagccacagc tcaggatgaa gaacaatgag     1080
gaggctgagg actatgatga tgacctgact gactctgaga tggatgtggt ccgctttgat     1140
gatgacaaca gcccatcctt cattcagatc aggtctgtgg ccaagaaaca ccccaagacc     1200
tgggtgcact acattgctgc tgaggaggag gactgggact atgccccact ggtcctggcc     1260
cctgatgaca ggagctacaa gagccagtac ctcaacaatg gcccacagag gattggacgc     1320
aagtacaaga agtcaggtt catggcctac actgatgaaa ccttcaagac cagggaggcc      1380
attcagcatg agtctggcat cctgggccca ctcctgtatg ggaggtgggg ggacaccctg     1440
ctcatcatct tcaagaacca ggcctccagg ccctacaaca tctacccaca tggcatcact     1500
gatgtcaggc ccctgtacag ccgcaggctg ccaaaggggg tgaaacacct caaggacttc     1560
cccattctgc ctggggagat cttcaagtac aagtggactg tcactgtgga ggatggacca     1620
accaaatctg accccaggtg cctcaccaga tactactcca gctttgtgaa catggagagg     1680
gacctggcct ctggcctgat ggcccactgc tcatctgct acaaggagtc tgtgaccag       1740
aggggaaacc agatcatgtc tgacaagagg aatgtgattc tgttctctgt ctttgatgag     1800
aacaggagct ggtacctgac tgagaacatt cagcgcttcc tgcccaaccc tgctggggtg     1860
cagctggagg accctgagtt ccaggccagc aacatcatgc actccatcaa tggctatgtg     1920
tttgacagcc tccagctttc tgtctgcctg catgaggtgg cctactggta cattctttct     1980
attgggccc agactgactt cctttctgtc ttcttctctg gctacaccctt caaacacaag    2040
atggtgtatg aggacaccct gaccctcttc ccattctctg gggagactgt gttcatgagc     2100
atggagaacc ctggcctgtg gattctggga tgccacaact ctgacttccg caacaggggc     2160
atgactgccc tgctcaaagt ctcctcctgt gacaagaaca ctgggactaa ctatgaggac     2220
agctatgagg acatctctgc ctacctgctc agcaagaaca atgccattga gcccagggag     2280
atcaccagga ccaccctcca gtctgaccag gaggagattg actatgatga caccatttct     2340
gtggagatga agaaagagga ctttgacatc tatgacgagg acgagaacca gagcccaagg     2400
agcttccaga gaagaccag gcactacttc attgctgctg tggagcgcct gtgggactat      2460
ggcatgagct ccagccccca tgtcctcagg aacagggccc agtctggctc tgtgccacag     2520
ttcaagaaag tggtcttcca agagttcact gatggcagct tcacccagcc cctgtacaga    2580
ggggagctga atgagcacct gggactcctg gcccatacat cagggctga ggtggaggac      2640
aacatcatgg tgaccttccg caaccaggcc tccaggccct acagcttcta cagctccctc     2700
atcagctatg aggaggacca gaggcagggg gctgagccac gcaagaactt tgtgaaaccc     2760
aatgaaacca gacctacttt ctggaaagtc cagcaccaca tggccccac caaggatgag      2820
tttgactgca aggcctgggc ctacttctct gatgtggacc tggagaagga tgtgcactct    2880
ggcctgattg cccactcct ggtctgccac accaacaccc tgaaccctgc ccatggaagg      2940
caagtgactg tgcaggagtt tgcccttcttc ttcaccatct ttgatgaaac caagagctgg    3000
tacttcactg agaacatgga gcgcaactgc agggcccat gcaacattca gatggaggac     3060
cccaccttca agagaactaa ccgcttccat gccatcaatg gctacatcat ggacaccctg     3120
cctgggcttg tcatggccca ggaccagagg atcaggtggt acctgctttc tatgggctcc     3180
aatgagaaca ttcactccat ccacttctct gggcatgtct tcactgtgcg caagaaggag     3240
```

```
gagtacaaga tggccctgta caacctctac cctggggtct ttgagactgt ggagatgctg   3300
ccctccaaag ctggcatctg gagggtggag tgcctcattg gggagcacct gcatgctggc   3360
atgagcaccc tgttcctggt ctacagcaac aagtgccaga ccccctggg aatggcctct    3420 ggccacatca gggacttcca gatcactgcc tctggccagt atggccagtg ggccccaag    3480 ctggccaggc tccactactc tggatccatc aatgcctgga gcaccaagga gccattcagc   3540
tggatcaaag tggacctgct ggcccccatg atcatccatg catcaagac ccagggggcc    3600 aggcagaagt tctccagcct gtacatcagc cagttcatca tcatgtacag cctggatggc   3660
aagaaatggc agacctacag aggcaactcc actggaacac tcatggtctt ctttggcaat   3720
gtggacagct ctggcatcaa gcacaacatc ttcaaccccc aatcatcgc cagatacatc    3780 aggctgcacc ccaccactac agcatccgc agcaccctca ggatggagct gatgggctgt    3840
gacctgaact cctgcagcat gccctgggc atggagagca aggccatttc tgatgcccag   3900
atcactgcct ccagctactt caccaacatg tttgccacct ggagcccaag caaggccagg   3960
ctgcacctcc agggaaggag caatgcctgg aggcccagg tcaacaaccc aaaggagtgg    4020
ctgcaggtgg acttccagaa gaccatgaag gtcactgggg tgaccaccca ggggtcaag    4080 agcctgctca ccagcatgta tgtgaaggag ttcctgatca gctccagcca ggatggccac   4140
cagtggaccc tcttcttcca gaatggcaag gtcaaggtgt ccagggcaa ccaggacagc   4200 ttcaccctg tggtgaacag cctggacccc ccctcctga ccagatacct gaggattcac     4260
ccccagagct gggtccacca gattgccctg aggatggagg tcctgggatg tgaggcccag   4320
gacctgtact ga                                                       4332
```

<210> SEQ ID NO 10
<211> LENGTH: 1443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160
```

```
Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
```

-continued

```
              580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                        645                 650                 655
Tyr Ile Leu Ser Ile Gly Ala Gln Thr Asp Phe Leu Ser Val Phe Phe
                        660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                        725                 730                 735
Tyr Tyr Glu Asp Ser Tyr Glu Asp Ile Ser Ala Tyr Leu Leu Ser Lys
                        740                 745                 750
Asn Asn Ala Ile Glu Pro Arg Glu Ile Thr Arg Thr Thr Leu Gln Ser
            755                 760                 765
Asp Gln Glu Glu Ile Asp Tyr Asp Asp Thr Ile Ser Val Glu Met Lys
            770                 775                 780
Lys Glu Asp Phe Asp Ile Tyr Asp Glu Asp Glu Asn Gln Ser Pro Arg
785                 790                 795                 800
Ser Phe Gln Lys Lys Thr Arg His Tyr Phe Ile Ala Ala Val Glu Arg
                        805                 810                 815
Leu Trp Asp Tyr Gly Met Ser Ser Ser Pro His Val Leu Arg Asn Arg
                        820                 825                 830
Ala Gln Ser Gly Ser Val Pro Gln Phe Lys Lys Val Val Phe Gln Glu
            835                 840                 845
Phe Thr Asp Gly Ser Phe Thr Gln Pro Leu Tyr Arg Gly Glu Leu Asn
            850                 855                 860
Glu His Leu Gly Leu Leu Gly Pro Tyr Ile Arg Ala Glu Val Glu Asp
865                 870                 875                 880
Asn Ile Met Val Thr Phe Arg Asn Gln Ala Ser Arg Pro Tyr Ser Phe
                        885                 890                 895
Tyr Ser Ser Leu Ile Ser Tyr Glu Glu Asp Gln Arg Gln Gly Ala Glu
                        900                 905                 910
Pro Arg Lys Asn Phe Val Lys Pro Asn Glu Thr Lys Thr Tyr Phe Trp
            915                 920                 925
Lys Val Gln His His Met Ala Pro Thr Lys Asp Glu Phe Asp Cys Lys
            930                 935                 940
Ala Trp Ala Tyr Phe Ser Asp Val Asp Leu Glu Lys Asp Val His Ser
945                 950                 955                 960
Gly Leu Ile Gly Pro Leu Leu Val Cys His Thr Asn Thr Leu Asn Pro
                        965                 970                 975
Ala His Gly Arg Gln Val Thr Val Gln Glu Phe Ala Leu Phe Phe Thr
                        980                 985                 990
Ile Phe Asp Glu Thr Lys Ser Trp Tyr Phe Thr Glu Asn Met Glu Arg
            995                 1000                1005
```

-continued

```
Asn Cys Arg Ala Pro Cys Asn Ile Gln Met Glu Asp Pro Thr Phe
1010                1015                1020

Lys Glu Asn Tyr Arg Phe His Ala Ile Asn Gly Tyr Ile Met Asp
1025                1030                1035

Thr Leu Pro Gly Leu Val Met Ala Gln Asp Gln Arg Ile Arg Trp
1040                1045                1050

Tyr Leu Leu Ser Met Gly Ser Asn Glu Asn Ile His Ser Ile His
1055                1060                1065

Phe Ser Gly His Val Phe Thr Val Arg Lys Lys Glu Glu Tyr Lys
1070                1075                1080

Met Ala Leu Tyr Asn Leu Tyr Pro Gly Val Phe Glu Thr Val Glu
1085                1090                1095

Met Leu Pro Ser Lys Ala Gly Ile Trp Arg Val Glu Cys Leu Ile
1100                1105                1110

Gly Glu His Leu His Ala Gly Met Ser Thr Leu Phe Leu Val Tyr
1115                1120                1125

Ser Asn Lys Cys Gln Thr Pro Leu Gly Met Ala Ser Gly His Ile
1130                1135                1140

Arg Asp Phe Gln Ile Thr Ala Ser Gly Gln Tyr Gly Gln Trp Ala
1145                1150                1155

Pro Lys Leu Ala Arg Leu His Tyr Ser Gly Ser Ile Asn Ala Trp
1160                1165                1170

Ser Thr Lys Glu Pro Phe Ser Trp Ile Lys Val Asp Leu Leu Ala
1175                1180                1185

Pro Met Ile Ile His Gly Ile Lys Thr Gln Gly Ala Arg Gln Lys
1190                1195                1200

Phe Ser Ser Leu Tyr Ile Ser Gln Phe Ile Ile Met Tyr Ser Leu
1205                1210                1215

Asp Gly Lys Lys Trp Gln Thr Tyr Arg Gly Asn Ser Thr Gly Thr
1220                1225                1230

Leu Met Val Phe Phe Gly Asn Val Asp Ser Ser Gly Ile Lys His
1235                1240                1245

Asn Ile Phe Asn Pro Pro Ile Ile Ala Arg Tyr Ile Arg Leu His
1250                1255                1260

Pro Thr His Tyr Ser Ile Arg Ser Thr Leu Arg Met Glu Leu Met
1265                1270                1275

Gly Cys Asp Leu Asn Ser Cys Ser Met Pro Leu Gly Met Glu Ser
1280                1285                1290

Lys Ala Ile Ser Asp Ala Gln Ile Thr Ala Ser Ser Tyr Phe Thr
1295                1300                1305

Asn Met Phe Ala Thr Trp Ser Pro Ser Lys Ala Arg Leu His Leu
1310                1315                1320

Gln Gly Arg Ser Asn Ala Trp Arg Pro Gln Val Asn Asn Pro Lys
1325                1330                1335

Glu Trp Leu Gln Val Asp Phe Gln Lys Thr Met Lys Val Thr Gly
1340                1345                1350

Val Thr Thr Gln Gly Val Lys Ser Leu Leu Thr Ser Met Tyr Val
1355                1360                1365

Lys Glu Phe Leu Ile Ser Ser Ser Gln Asp Gly His Gln Trp Thr
1370                1375                1380

Leu Phe Phe Gln Asn Gly Lys Val Lys Val Phe Gln Gly Asn Gln
1385                1390                1395
```

| | | |
|---|---|---|
| Asp Ser Phe Thr Pro Val Val Asn Ser Leu Asp Pro Pro Leu Leu | | |
| 1400 1405 1410 | | |
| Thr Arg Tyr Leu Arg Ile His Pro Gln Ser Trp Val His Gln Ile | | |
| 1415 1420 1425 | | |
| Ala Leu Arg Met Glu Val Leu Gly Cys Glu Ala Gln Asp Leu Tyr | | |
| 1430 1435 1440 | | |

<210> SEQ ID NO 11
<211> LENGTH: 4368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

| | |
|---|---|
| atgcagattg agctgagcac ctgcttcttc ctgtgcctgc tgaggttctg cttctctgcc | 60 |
| accaggagat actacctggg ggctgtggag ctttcttggg actacatgca gtctgacctg | 120 |
| ggggagctgc ctgtggatgc caggttccca cccagagtgc caaatccttc ccattcaac | 180 |
| acctctgtgg tctacaagaa gaccctcttt gtggagttca ctgaccacct gttcaacatt | 240 |
| gccaaaccca ggccaccctg gatgggactc tgggaccca ccattcaggc tgaggtgtat | 300 |
| gacactgtgg tcatcaccct caagaacatg gcctcccacc ctgtgagcct gcatgctgtg | 360 |
| ggggtcagct actggaaggc ctctgagggg gctgagtatg atgaccagac ctcccagagg | 420 |
| gagaaggagg atgacaaagt gttccctggg ggcagccaca cctatgtgtg gcaggtcctc | 480 |
| aaggagaatg cccccatggc ctctgaccca ctctgcctga cctactccta cctttctcat | 540 |
| gtggacctgg tcaaggacct caactctgga ctgattgggg ccctgctggt gtgcagggag | 600 |
| ggctccctgg ccaaagagaa gacccagacc ctgcacaagt tcattctcct gtttgctgtc | 660 |
| tttgatgagg gcaagagctg gcactctgaa accaagaact ccctgatgca ggacagggat | 720 |
| gctgcctctg ccagggcctg gcccaagatg cacactgtga atggctatgt gaacaggagc | 780 |
| ctgcctggac tcattggctg ccacaggaaa tctgtctact ggcatgtgat tggcatgggg | 840 |
| acaaccctg aggtgcactc catttttctg gagggccaca ccttcctggt caggaaccac | 900 |
| agacaggcca gcctggagat cagccccatc accttcctca ctgcccagac cctgctgatg | 960 |
| gacctcggac agttcctgct gttctgccac atcagctccc accagcatga tggcatggag | 1020 |
| gcctatgtca aggtggacag ctgccctgag gagccacagc tcaggatgaa gaacaatgag | 1080 |
| gaggctgagg actatgatga tgacctgact gactctgaga tggatgtggt ccgctttgat | 1140 |
| gatgacaaca gccatcctt cattcagatc aggtctgtgg ccaagaaaca ccccaagacc | 1200 |
| tgggtgcact acattgctgc tgaggaggag gactgggact atgccccact ggtcctggcc | 1260 |
| cctgatgaca ggagctacaa gagccagtac ctcaacaatg gcccacagag gattggacgc | 1320 |
| aagtacaaga agtcaggtt catggcctac actgatgaaa ccttcaagac cagggaggcc | 1380 |
| attcagcatg agtctggcat cctgggccca ctcctgtatg gggaggtggg ggacaccctg | 1440 |
| ctcatcatct tcaagaacca ggcctccagg ccctacaaca tctacccaca tggcatcact | 1500 |
| gatgtcaggc cctgtacag ccgcaggctg ccaaaggggg tgaaacacct caaggacttc | 1560 |
| cccattctgc tggggagat cttcaagtac aagtggactg tcactgtgga ggatggacca | 1620 |
| accaaatctg accccaggtg cctcaccaga tactactcca gctttgtgaa catggagagg | 1680 |
| gacctggcct ctgcctgat ggccccactg ctcatctgct acaaggagtc gtggaccag | 1740 |
| aggggaaacc agatcatgtc tgacaagagg aatgtgattc tgttctctgt ctttgatgag | 1800 |

```
aacaggagct ggtacctgac tgagaacatt cagcgcttcc tgcccaaccc tgctggggtg    1860
cagctggagg accctgagtt ccaggccagc aacatcatgc actccatcaa tggctatgtg    1920
tttgacagcc tccagctttc tgtctgcctg catgaggtgg cctactggta cattctttct    1980
attgggccca agactgactt cctttctgtc ttcttctctg gctacacctt caaacacaag    2040
atggtgtatg aggacaccct gaccctcttc ccattctctg gggagactgt gttcatgagc    2100
atggagaacc ctggcctgtg gattctggga tgccacaact ctgacttccg caacaggggc    2160
atgactgccc tgctcaaagt ctcctcctgt gacaagaaca ctggggacta ctatgaggac    2220
agctatgagg acatctctgc ctacctgctc agcaagaaca atgccattga gcccaggagc    2280
ttcagccaga attccagaca ccccagcacc agggagatca ccaggaccac cctccagtct    2340
gaccaggagg agattgacta tgatgacacc atttctgtgg agatgaagaa agaggacttt    2400
gacatctatg acgaggacga gaaccagagc ccaaggagct tccagaagaa gaccaggcac    2460
tacttcattg ctgctgtgga gcgcctgtgg gactatggca tgagctccag cccccatgtc    2520
ctcaggaaca gggcccagtc tggctctgtg ccacagttca gaaagtggt cttccaagag    2580 ttcactgatg gcagcttcac ccagcccctg tacagagggg agctgaatga gcacctggga    2640
ctcctgggcc catacatcag ggctgaggtg gaggacaaca tcatggtgac cttccgcaac    2700
caggcctcca ggccctacag cttctacagc tccctcatca gctatgagga ggaccagagg    2760 caggggctg agccacgcaa gaactttgtg aaacccaatg aaaccaagac ctacttctgg    2820
aaagtccagc accacatggc ccccaccaag gatgagtttg actgcaaggc ctgggcctac    2880
ttctctgatg tggacctgga aaggatgtg cactctggcc tgattggccc actcctggtc    2940
tgccacacca cacccctgaa ccctgcccat ggaaggcaag tgactgtgca ggagtttgcc    3000
ctcttcttca ccatctttga tgaaaccaag agctggtact tcactgagaa catggagcgc    3060
aactgcaggg ccccatgcaa cattcagatg gaggacccca ccttcaaaga gaactaccgc    3120
ttccatgcca tcaatggcta catcatggac accctgcctg ggcttgtcat ggcccaggac    3180
cagaggatca ggtggtacct gctttctatg ggctccaatg agaacattca ctccatccac    3240
ttctctgggc atgtcttcac tgtgcgcaag aaggaggagt acaagatggc cctgtacaac    3300
ctctaccctg gggtctttga ctgtggag atgctgccct ccaaagctgg catctggagg    3360
gtggagtgcc tcattgggga gcacctgcat gctggcatga gcaccctgtt cctggtctac    3420
agcaacaagt gccagacccc cctgggaatg gcctctggcc acatcaggga cttccagatc    3480
actgcctctg gccagtatgg ccagtgggcc cccaagctgg ccaggctcca ctactctgga    3540
tccatcaatg cctggagcac caaggagcca ttcagctgga tcaaagtgga cctgctggcc    3600
cccatgatca tccatggcat caagacccag ggggccaggc agaagttctc cagcctgtac    3660
atcagccagt tcatcatcat gtacagcctg gatggcaaga atggcagac ctacagaggc    3720 aactccactg gaacactcat ggtcttcttt ggcaatgtgg acagctctgg catcaagcac    3780
aacatcttca ccccccaat catcgccaga tacatcaggc tgcaccccac ccactacagc    3840
atccgcagca ccctcaggat ggagctgatg ggctgtgacc tgaactcctg cagcatgccc    3900
ctgggcatgg agagcaaggc catttctgat gcccagatca ctgcctccag ctacttcacc    3960
aacatgtttg ccacctggag cccaagcaag gccaggctgc acctccaggg aaggagcaat    4020
gcctggaggc cccaggtcaa caacccaaag gagtggctgc aggtggactt ccagaagacc    4080
atgaaggtca ctggggtgac cacccagggg gtcaagagcc tgctcaccag catgtatgtg    4140
```

-continued

```
aaggagttcc tgatcagctc cagccaggat ggccaccagt ggaccctctt cttccagaat    4200
ggcaaggtca aggtgttcca gggcaaccag gacagcttca cccctgtggt gaacagcctg    4260 gaccccccccc tcctgaccag atacctgagg attcacccccc agagctgggt ccaccagatt   4320
gccctgagga tggaggtcct gggatgtgag gcccaggacc tgtactga                 4368
```

<210> SEQ ID NO 12
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

-continued

```
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Pro
        340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
```

-continued

```
                740                 745                 750
Asn Asn Ala Ile Glu Pro Arg Ser Phe Ser Gln Asn Ser Arg His Pro
            755                 760                 765

Ser Thr Arg Glu Ile Thr Arg Thr Leu Gln Ser Asp Gln Glu Glu
770                 775                 780

Ile Asp Tyr Asp Asp Thr Ile Ser Val Glu Met Lys Lys Glu Asp Phe
785                 790                 795                 800

Asp Ile Tyr Asp Glu Asp Glu Asn Gln Ser Pro Arg Ser Phe Gln Lys
                805                 810                 815

Lys Thr Arg His Tyr Phe Ile Ala Ala Val Glu Arg Leu Trp Asp Tyr
            820                 825                 830

Gly Met Ser Ser Ser Pro His Val Leu Arg Asn Arg Ala Gln Ser Gly
            835                 840                 845

Ser Val Pro Gln Phe Lys Lys Val Val Phe Gln Glu Phe Thr Asp Gly
            850                 855                 860

Ser Phe Thr Gln Pro Leu Tyr Arg Gly Glu Leu Asn Glu His Leu Gly
865                 870                 875                 880

Leu Leu Gly Pro Tyr Ile Arg Ala Glu Val Glu Asp Asn Ile Met Val
                885                 890                 895

Thr Phe Arg Asn Gln Ala Ser Arg Pro Tyr Ser Phe Tyr Ser Ser Leu
            900                 905                 910

Ile Ser Tyr Glu Glu Asp Gln Arg Gln Gly Ala Glu Pro Arg Lys Asn
            915                 920                 925

Phe Val Lys Pro Asn Glu Thr Lys Thr Tyr Phe Trp Lys Val Gln His
            930                 935                 940

His Met Ala Pro Thr Lys Asp Glu Phe Asp Cys Lys Ala Trp Ala Tyr
945                 950                 955                 960

Phe Ser Asp Val Asp Leu Glu Lys Asp Val His Ser Gly Leu Ile Gly
                965                 970                 975

Pro Leu Leu Val Cys His Thr Asn Thr Leu Asn Pro Ala His Gly Arg
            980                 985                 990

Gln Val Thr Val Gln Glu Phe Ala Leu Phe Phe Thr Ile Phe Asp Glu
            995                1000                1005

Thr Lys Ser Trp Tyr Phe Thr Glu Asn Met Glu Arg Asn Cys Arg
    1010                1015                1020

Ala Pro Cys Asn Ile Gln Met Glu Asp Pro Thr Phe Lys Glu Asn
    1025                1030                1035

Tyr Arg Phe His Ala Ile Asn Gly Tyr Ile Met Asp Thr Leu Pro
    1040                1045                1050

Gly Leu Val Met Ala Gln Asp Gln Arg Ile Arg Trp Tyr Leu Leu
    1055                1060                1065

Ser Met Gly Ser Asn Glu Asn Ile His Ser Ile His Phe Ser Gly
    1070                1075                1080

His Val Phe Thr Val Arg Lys Lys Glu Glu Tyr Lys Met Ala Leu
    1085                1090                1095

Tyr Asn Leu Tyr Pro Gly Val Phe Glu Thr Val Glu Met Leu Pro
    1100                1105                1110

Ser Lys Ala Gly Ile Trp Arg Val Glu Cys Leu Ile Gly Glu His
    1115                1120                1125

Leu His Ala Gly Met Ser Thr Leu Phe Leu Val Tyr Ser Asn Lys
    1130                1135                1140

Cys Gln Thr Pro Leu Gly Met Ala Ser Gly His Ile Arg Asp Phe
    1145                1150                1155
```

| | | | | | | | | | |
|---|---|---|---|---|---|---|---|---|---|
| Gln | Ile | Thr | Ala | Ser | Gly | Gln | Tyr | Gly | Gln | Trp | Ala | Pro | Lys | Leu |
| | 1160 | | | | 1165 | | | | 1170 | | | |

Gln Ile Thr Ala Ser Gly Gln Tyr Gly Gln Trp Ala Pro Lys Leu
        1160                1165                1170

Ala Arg Leu His Tyr Ser Gly Ser Ile Asn Ala Trp Ser Thr Lys
        1175                1180                1185

Glu Pro Phe Ser Trp Ile Lys Val Asp Leu Leu Ala Pro Met Ile
        1190                1195                1200

Ile His Gly Ile Lys Thr Gln Gly Ala Arg Gln Lys Phe Ser Ser
        1205                1210                1215

Leu Tyr Ile Ser Gln Phe Ile Ile Met Tyr Ser Leu Asp Gly Lys
        1220                1225                1230

Lys Trp Gln Thr Tyr Arg Gly Asn Ser Thr Gly Thr Leu Met Val
        1235                1240                1245

Phe Phe Gly Asn Val Asp Ser Ser Gly Ile Lys His Asn Ile Phe
        1250                1255                1260

Asn Pro Pro Ile Ile Ala Arg Tyr Ile Arg Leu His Pro Thr His
        1265                1270                1275

Tyr Ser Ile Arg Ser Thr Leu Arg Met Glu Leu Met Gly Cys Asp
        1280                1285                1290

Leu Asn Ser Cys Ser Met Pro Leu Gly Met Glu Ser Lys Ala Ile
        1295                1300                1305

Ser Asp Ala Gln Ile Thr Ala Ser Ser Tyr Phe Thr Asn Met Phe
        1310                1315                1320

Ala Thr Trp Ser Pro Ser Lys Ala Arg Leu His Leu Gln Gly Arg
        1325                1330                1335

Ser Asn Ala Trp Arg Pro Gln Val Asn Asn Pro Lys Glu Trp Leu
        1340                1345                1350

Gln Val Asp Phe Gln Lys Thr Met Lys Val Thr Gly Val Thr Thr
        1355                1360                1365

Gln Gly Val Lys Ser Leu Leu Thr Ser Met Tyr Val Lys Glu Phe
        1370                1375                1380

Leu Ile Ser Ser Ser Gln Asp Gly His Gln Trp Thr Leu Phe Phe
        1385                1390                1395

Gln Asn Gly Lys Val Lys Val Phe Gln Gly Asn Gln Asp Ser Phe
        1400                1405                1410

Thr Pro Val Val Asn Ser Leu Asp Pro Pro Leu Leu Thr Arg Tyr
        1415                1420                1425

Leu Arg Ile His Pro Gln Ser Trp Val His Gln Ile Ala Leu Arg
        1430                1435                1440

Met Glu Val Leu Gly Cys Glu Ala Gln Asp Leu Tyr
        1445                1450                1455

<210> SEQ ID NO 13
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgcagattg agctgtccac ctgcttcttt ctgtgcctgc tgagattctg cttctctgcc      60
accaggagat actacctggg ggctgtggaa ctttcttggg actacatgca gtctgacctg     120
ggagagctgc ctgtggatgc caggttccca cccagagtgc ccaagtcctt cccattcaac     180
acctctgtgg tctacaagaa gacactcttt gtggaattca ctgaccacct gttcaacatt     240

```
gcaaaaccca gaccaccctg gatgggactc ctgggaccca ccattcaggc tgaggtgtat    300
gacactgtgg tcatcaccct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc catttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga agtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg acccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc   2100 atggagaacc ctggactgtg gattctggga tgccacaact ctgacttcag aaacagggga   2160
atgactgcac tgctcaaagt ctcctcctgt gacaagaaca ctgggggacta ctatgaggac   2220 tcttatgagg acatctctgc ctacctgctc agcaagaaca atgccattga gcccagaagc   2280
ttctctcaga atcccacctgt cctgaagaga caccagagag agatcaccag gacaaccctc   2340
cagtctgacc aggaagagat tgactatgat gacaccattt ctgtggagat gaagaaggag   2400
gactttgaca tctatgatga ggacgagaac cagtctccaa gatcattcca gaagaagaca   2460
agacactact tcattgctgc tgtggaaaga ctgtgggact atggcatgtc ttcctctccc   2520
catgtcctca ggaacagggc acagtctggc tctgtgccac agttcaagaa agtggtcttc   2580
```

```
caggagttca ctgatggctc attcacccag cccctgtaca gaggggaact gaatgagcac    2640
ctgggactcc tgggaccata catcagggct gaggtggaag acaacatcat ggtgacattc    2700
agaaaccagg cctccaggcc ctacagcttc tactcttccc tcatcagcta tgaggaagac    2760
cagagacaag gggctgagcc aagaaagaac tttgtgaaac ccaatgaaac caagacctac    2820
ttctggaaag tccagcacca catggcaccc accaaggatg agtttgactg caaggcctgg    2880
gcatacttct ctgatgtgga cctggagaaa gatgtgcact ctggcctgat tgcccactc    2940 ctggtctgcc acaccaacac cctgaaccct gcacatggaa ggcaagtgac tgtgcaggag    3000
tttgccctct tcttcaccat ctttgatgaa accaagtcat ggtacttcac tgagaacatg    3060
gagagaaact gcagagcacc atgcaacatt cagatggaag accccacctt caaggagaac    3120
tacaggttcc atgccatcaa tggctacatc atggacaccc tgcctgggct tgtcatggca    3180
caggaccaga gaatcagatg gtacctgctt tctatgggat ccaatgagaa cattcactcc    3240
atccacttct ctgggcatgt cttcactgtg agaaagaagg aggaatacaa gatggccctg    3300
tacaacctct accctggggt cttttgagact gtggagatgc tgccctccaa agctggcatc    3360
tggagggtgg aatgcctcat tggggagcac ctgcatgctg gcatgtcaac cctgttcctg    3420
gtctacagca acaagtgcca gacaccctg ggaatggcct ctggccacat cagggacttc    3480
cagatcactg cctctggcca gtatggccag tgggcaccca aactggccag gctccactac    3540
tctggctcca tcaatgcatg gtcaaccaag gagccattct cttggatcaa ggtggacctg    3600
ctggcaccca tgatcattca tggcatcaag acacagggg caagacagaa attctcctct    3660
ctgtacatct cacagttcat catcatgtac tctctggatg gcaagaagtg gcagacatac    3720
agaggcaact ccactggcac cctcatggtc ttctttggca atgtggacag ctctggcatc    3780
aagcacaaca tcttcaaccc tcccatcatt gccagataca tcaggctgca ccccacccac    3840
tactcaatca gatcaacct caggatggaa ctgatgggat gtgacctgaa ctcctgctca    3900
atgcccctgg gaatggagag caaggccatt tctgatgccc agatcactgc atcctcttac    3960
ttcaccaaca tgtttgccac ctggtcacca tcaaaagcca ggctgcacct ccagggaaga    4020
agcaatgcct ggagacccca ggtcaacaac ccaaaggaat ggctgcaagt ggacttccag    4080
aagacaatga agtcactgg ggtgacaacc caggggtca agtctctgct cacctcaatg    4140
tatgtgaagg agttcctgat ctcttcctca caggatggcc accagtggac actcttcttc    4200
cagaatggca agtcaaggt gttccagggc aaccaggact ctttcacacc tgtggtgaac    4260
tcactggacc ccccctcct gacaagatac ctgagaattc accccagtc ttgggtccac    4320 cagattgccc tgagaatgga agtcctggga tgtgaggcac aagacctgta ctga         4374

<210> SEQ ID NO 14
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgcagatcg aactgagcac ttgcttcttc ctgtgtctcc tgcgcttttg cttctccgcc      60
acaaggagat actatctcgg tgccgtggag ctcagctggg actacatgca gagcgacttg     120
ggtgaactgc ctgtggacgc caggtttcca ccccgcgtgc ccaagagttt cccgttcaac     180
accagtgtcg tgtacaagaa aaccctcttc gtggaattca ccgaccacct gttcaacatc     240
```

```
gccaaaccgc gccctccctg gatggggctg ctcggcccga cgatccaggc tgaggtctat    300
gacacggtgg tgattaccct caagaacatg gctagccacc cggtgagcct gcacgccgtg    360
ggcgtgtcct attggaaagc gtccgagggt gcggagtacg atgaccagac ttcacagcgg    420
gagaaggaag acgacaaagt gttccccggg ggttcccaca cctatgtctg gcaggtcctg    480
aaggagaatg gtcctatggc ctccgaccca ttgtgcctca cctactctta cctaagccat    540
gtggatctcg tcaaggacct gaactcgggg ctgatcggcg ccctgctcgt gtgccgggag    600
ggctcactgg ccaaggagaa gacccaaact ctgcacaagt tcatcctgct gttcgcggta    660
ttcgacgagg ggaagtcctg gcactccgag accaagaaca gcctgatgca ggaccgcgac    720
gcagcctcgg cccgtgcgtg gccaaagatg cacaccgtga acggctacgt taacaggagc    780
ctacccggcc tgatcggctg ccaccgcaaa tcggtctact ggcatgtgat cggaatgggc    840
acaacgcccg aggtccacag tatcttcctc gagggccaca ctttcctggt ccggaatcac    900
cgccaggcca gcctggagat cagccccata acctttctga cggcgcagac cttactcatg    960
gatctcggcc agttcctcct gttctgccac atttcgtccc accagcacga tgggatggaa   1020
gcatatgtga agtggactc ctgccccgag gaaccccagc ttaggatgaa gaacaatgag   1080
gaggccgagg actacgacga tgaccttacc gattcagaaa tggacgtagt acgctttgac   1140
gacgacaact ctccatcctt catacagatt cgctccgtcg ccaagaagca ccctaagact   1200
tgggtgcact acatcgcggc cgaggaggag gactgggatt atgctcccct ggtgctggcc   1260
cccgacgacc gcagctacaa gagccagtac ctgaataacg ggccccagcg catcggccgg   1320
aagtacaaga agtgcggtt catggcttac acggacgaga ccttcaagac ccgggaggct   1380
atccagcatg agagcggcat cttggggccc ctcctgtacg gcaagttgg agacacactg   1440 ctgatcatct tcaagaacca ggcgagcagg ccctacaaca tctacccca cggcattacc   1500 gatgtccggc cgttgtacag ccgacggctg cccaagggcg tgaagcacct gaaggacttt   1560
ccgatcctgc cgggcgagat cttcaagtac aagtggactg tgaccgtgga ggatgggccg   1620
accaagagcg atccgcgctg cctgacccgt tactactcca gctttgtcaa tatggagcgc   1680
gacctcgcta gcggcttgat tggccctctg ctgatctgct acaaggagtc cgtggaccag   1740 aggggggaatc agatcatgag tgacaagagg aacgtgatcc tgttctccgt gttcgacgaa   1800
aaccgcagct ggtatctcac cgagaatatc cagcgcttcc tgcccaaccc ggccggtgtg   1860
cagctggagg accccgagtt tcaggccagc aacatcatgc attctatcaa cggatatgtg   1920
tttgattccc tgcagctctc agtgtgtctg cacgaggtcg cctactggta tatcctcagc   1980
attggggcac agaccgactt cctgagcgtg ttcttctccg ggtataccct caagcacaag   2040
atggtgtacg aggatacect gaccetgttc cectttageg gegaaacegt gtttatgtct   2100 atggagaacc ccgggctctg gatccttggc tgccataact ccgacttccg caaccgcgga   2160
atgaccgcgc tcctgaaagt gtcgagttgt gacaagaaca ccggcgacta ttacgaggac   2220
agttacgagg acatctctgc gtacctcctt agcaagaata cgccatcga gccaagatcc   2280 ttcagccaga acccccagt gctgaagagg catcagcggg agatcacccg cacgaccctg   2340
cagtcggatc aggaggagat tgattacgac gacacgatca gtgtggagat gaagaaggag   2400
gacttcgaca tctacgacga agatgaaaac cagtcccctc ggtccttcca aaagaagacc   2460
cggcactact tcatcgccgc tgtggaacgc ctgtgggact atggaatgtc ttctagccct   2520
cacgttttga ggaaccgcgc ccagtcgggc agcgtgcccc agttcaagaa agtggtgttc   2580
caggagttca ccgacggctc cttcacccag ccactttacc ggggcgagct caatgaacat   2640
```

-continued

```
ctgggcctgc tgggacccta catcagggct gaggtggagg acaacatcat ggtgacattc    2700
cggaatcagg ccagcagacc atacagtttc tacagttcac tcatctccta cgaggaggac    2760
cagcgccagg gggctgaacc ccgtaagaac ttcgtgaagc caaacgaaac aaagacctac    2820
ttctggaagg tccagcacca catggcacct accaaggacg agttcgattg caaggcctgg    2880
gcctacttct ccgacgtgga cctggagaaa gatgtgcaca gcggcctgat tggccctctg    2940
ctggtgtgtc acacgaacac actcaaccct gcacacgggc ggcaggtcac tgtgcaggaa    3000
ttcgccctgt tctttaccat ctttgatgag acgaagtcct ggtatttcac cgaaaacatg    3060
gagaggaact gccgcgcacc ctgcaacatc cagatggaag atccgacatt caaggagaac    3120
taccggttcc atgccatcaa tggctacatc atggacaccc tgcctggcct cgtgatggcc    3180
caagaccagc gtatccgctg gtatctgctg tcgatgggct ccaacgagaa catccatagt    3240
atccacttca gcgggcatgt cttcacggtg aggaaaaagg aggagtacaa gatggcactg    3300
tacaacctct atcccggcgt gttcgagacc gtggagatgc tgccctccaa ggccggcatc    3360
tggagagtgg aatgcctgat cggcgagcac ctccacgctg ggatgtccac gctgttcctc    3420
gtttacagca ataagtgcca gacccctctg ggcatggcga gcggccacat ccgcgacttc    3480
cagattacag ccagcggcca gtacggtcag tgggctccaa agctggcccg tctgcactac    3540
tccggatcca tcaacgcctg gtccaccaag gaaccgttct cctggatcaa gtagacctg    3600
ctagccccca tgatcattca cggcatcaag acacaaggcg cccgacagaa gttctcgagc    3660
ctctatatct cccagttcat catcatgtat agcctggacg gaaagaagtg gcagacttac    3720
cgcggaaact cgacagggac cctgatggta ttcttcggta acgtggacag ctccggaatc    3780
aagcacaaca tcttcaaccc acccattatc gcccgctaca tccgcctgca ccccactcac    3840
tatagcatta ggtccaccct gcgaatggag ctcatgggct gtgacctgaa cagctgtagc    3900
atgcccctcg gcatggagtc taaggcgatc tccgacgcac agataacggc atcatcctac    3960
tttaccaaca tgttcgctac ctggtccccc tccaaggccc gactccacct gcaagggaga    4020
tccaacgcct ggcggccaca ggtcaacaat cccaaggagt ggctgcaagt ggactttcag    4080
aaaactatga aagtcaccgg agtgaccaca cagggagtga agtctctgct gaccagcatg    4140
tacgtgaagg agttcctcat ctccagttcg caggatggcc accagtggac gttgttcttc    4200
caaaacggta aagtcaaagt cttccaaggg aaccaggaca gctttacacc cgtcgtgaac    4260
tccctggacc cccgcttcct cactagatac ctccgcatcc accctcagag ctgggtgcac    4320
cagattgccc tgcgcatgga ggttctgggg tgtgaagccc aggacctgta ctaa          4374
```

<210> SEQ ID NO 15
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgcagattg agctctccac ctgcttcttt ctctgccttc ttcgcttctg cttttctgcc      60
acacgcaggt actatttggg agcagtggaa ctgagctggg attacatgca gagtgacctt     120
ggtgaacttc ctgtggacgc tcgttttcca cctagagttc ccaagtcctt cccccttcaac    180
acctcagtgg tctacaagaa aacgctgttt gtggagttca ctgaccacct cttcaacatt     240
gccaaaccaa gaccccttg gatgggattg ctgggaccca aatacaagc agaagtctac       300
```

```
gacacggtgg tgattaccct gaagaacatg gcgtcacacc ctgtttcact tcacgctgtt    360 gggtcagtt attggaaagc ctcagagggt gcggaatacg atgatcaaac cagccagagg    420
gagaaggaag atgacaaggt cttccctggg ggtagccata cctatgtttg caggtgctg    480 aaagagaatg ggcctatggc ctctgatccc ttgtgcctca catactctta cctgagtcac    540
gtcgacctgg tgaaagacct gaatagcggt ctgattggtg cactgcttgt tgtagagag    600 gggagtttgg ccaaggagaa aactcagact ctccacaagt ttatcctcct gtttgctgtg    660
ttcgacgagg gcaagtcttg gcactctgaa acaaagaact ccctgatgca ggacagagat    720
gctgcatctg caagggcttg gccaaaaatg cacacagtga acggctatgt gaatcgatca    780
ctgccaggac tgataggctg tcatcgcaag tcagtgtatt ggcacgttat cgggatggga    840
acaactccag aagtgcacag catcttcctt gagggccaca ctttcctggt tcggaatcat    900
agacaggcca gccttgagat cagcccaatc acctttctga ctgcccaaac cttgctgatg    960
gatctgggac agttcctcct gttttgtcac atctcctccc accaacatga cgggatggag   1020
gcttatgtga aggtcgatag ctgtccggag gaaccacaac tgaggatgaa gaacaacgaa   1080
gaggcagagg actatgacga cgatctgact gacagtgaaa tggacgtggt tcggttcgac   1140
gatgacaatt ctccttcatt tatccagatc cgttccgtgg ccaagaagca ccccaagact   1200
tgggttcatt acatcgctgc tgaggaggag gattgggact acgcgccctt ggtgttggcc   1260
ccagacgatc gctcatacaa gagccagtac cttaacaatg gtccacaaag gatcggccgg   1320
aagtacaaga aggttagatt tatggcttat accgacgaga cttttaaaac tagggaagca   1380
attcagcatg aaagtggcat tcttggaccc ctgctgtatg gcgaggttgg cgacaccctg   1440
ctgattatct ttaagaacca ggcaagccgg ccctacaaca tctacccgca cggcataacc   1500
gatgtacgac ccctgtacag tcgcagactt cctaaagggg tgaaacacct gaaggacttc   1560
ccaattctgc ccggggagat cttcaagtat aaatggaccg tgacggttga ggatggtccc   1620
acaaagtccg atccgagatg ccttacccga tattattcca gcttcgtgaa catggaaagg   1680
gacctggcca gcgggctgat tggcccactg ctgatttgtt acaaggagtc tgtcgatcaa   1740
agaggaaacc aaataatgag cgacaaacgt aacgtcatcc tgttcagcgt ctttgatgag   1800
aatagaagct ggtacctcac agaaaatatt cagcggtttc tgcctaaccc cgcaggcgtc   1860
cagctggaag atcccgagtt ccaagcctca aacatcatgc atagcatcaa cggatacgta   1920
ttcgatagcc tgcagctgtc cgtctgtctc catgaagtgg catattggta catcctgagt   1980
atcggggcgc agaccgactt cctgagcgtg ttctttctg gatacacgtt caaacacaaa   2040
atggtctatg aagatacccct gactctgttt ccattctcag gagagacagt ctttatgagt   2100
atggaaaatc ctggactgtg gatcctgggc tgtcacaatt ctgattttcg gaacagaggc   2160
atgacagccc tgcttaaagt gagctcatgc gacaagaaca ccggtgatta ctacgaagat   2220
agctatgagg acatcagtgc gtatttgctc tccaagaaca acgctatcga ccacggtct   2280 ttcagtcaga atcctcccgt tctgaagcgg catcagcgcg aaataacacg cacaaccctt   2340
cagtcagacc aagaggaaat cgactacgat gatactatct ctgtggagat gaagaaggag   2400
gatttcgaca tttacgacga ggacgagaat cagtccccaa ggagctttca agagaaaaca   2460
agacactatt tcattgccgc cgtggagcga ctgtgggact acggcatgtc tagctctccg   2520
catgtactta gaaataggg acaaagcgga tccgtgcctc agtttaagaa gttgtcttt   2580 cagggagttta cagatggctc cttcacccag cccttgtatc gcggggaact caatgaacac   2640
```

```
ctgggcctcc tgggtcctta tattagggcc gaagtcgagg acaatatcat ggtgacctttt      2700 aggaaccagg catctagacc ttactctttc tactcctccc tgatatccta tgaggaggac      2760
cagcggcaag gcgctgagcc tcggaagaac tttgtgaagc caaatgaaac caaaacatac      2820
ttttggaaag ttcagcacca catggctccc acgaaggacg aatttgactg taaagcctgg      2880
gcctacttct cagatgtaga tctcgagaaa gacgtgcact cagggctcat tggtcccctc      2940
ctggtctgtc atactaatac cctcaatcca gcacacggac gtcaggtaac cgtccaggaa      3000
tttgccctgt tctttaccat tttcgatgag actaaatcct ggtactttac cgaaaacatg      3060
gagaggaatt gcagagcccc atgcaacatc cagatggagg accctacctt caaagagaac      3120
tatcgcttcc atgccattaa cggttacatt atggatactc tcccaggact tgtgatggca      3180
caggatcagc ggataagatg gtatctgttg agcatgggct ccaacgagaa tattcacagc      3240
atccatttct ccggtcacgt gtttacagtg agaaagaaag aagagtacaa gatggctctg      3300
tataatctct atccaggcgt attcgaaacg gtggagatgt tgcctagcaa ggccggcatt      3360
tggcgagtag aatgccttat cggggaacat ctgcatgccg aatgagcac gctcttcctg       3420 gtgtatagta acaagtgcca gactccgctg gcatggcat ctggccatat acgggactttt     3480 cagattacgg ctagcgggca gtatgggcag tgggcaccca acttgcgcg actgcactat      3540 tcaggctcta tcaatgcatg gtccaccaag gaaccttct cttggattaa ggtggacctt      3600
ttggcgccca tgataatcca tgggatcaaa acccagggcg ctcgtcagaa attctcatca     3660
ctctacatct ctcagttcat aataatgtat tcactggatg ggaagaaatg gcagacttac      3720
agaggaaaca gcaccgggac gctgatggtg ttctttggca acgtggacag cagcggcatc      3780
aaacacaaca tcttcaatcc tcccattatt gcccgttata ttagactgca tcccactcac      3840
tactctatac gcagcacact taggatggag ctcatgggat gcgacctgaa cagttgtagt      3900
atgcccttgg ggatggagtc caaagctata agcgacgcac aaattacagc tagctcttac      3960
tttacgaata tgttcgccac gtggagccca agcaaagccc ggctgcattt gcagggtcgg      4020
agtaatgctt ggcgcccaca ggtgaataac cctaaggaat ggttgcaagt agatttccag      4080
aaaactatga aggtaaccgg cgtcactaca cagggagtca agtccctctt gacctctatg      4140
tacgtcaagg agttcctgat tagcagcagt caggatgggc accaatggac actgttcttc      4200
cagaatggga aagttaaagt atttcagggt aaccaggact cctttacacc tgtggtgaat      4260
agcctcgacc cacccctgct gacacgatac ctccgcatcc accctcagtc ttgggtgcat      4320
caaattgccc tgcgaatgga ggtgttggga tgcgaagctc aggacctcta ctga           4374
```

<210> SEQ ID NO 16
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgcagatcg aactctctac ttgcttcttc ctgtgcctc tgaggttctg cttctctgcc        60
actcgccgat attacctcgg ggccgtggag ttgagttggg actacatgca atcagatctg      120
ggcgaactcc ctgtggatgc ccgattccca ccgcgcgtgc ccaagtctttt cccatttaat     180 acttctgtgg tgtacaagaa gacattgttt gtggagttta ccgatcacct gttcaacatc      240
gccaaaccgc ggccccccatg gatgggtctg cttgggccca ccattcaagc ggaggtctat     300
```

```
gatacagtgg tgataacgct taagaacatg gcgagccacc cagtgtctct gcatgccgtt      360
ggtgtatcat attggaaggc cagcgaagga gcggagtacg atgaccagac ctctcagaga      420
gagaaggaag acgataaggt ttttcctggc ggaagtcata catatgtatg gcaggtcctg      480
aaagagaatg ggccgatggc ttctgacccc ctttgtctta cctatagtta tctgagccac      540
gtggacctgg tcaaggacct caacagtggt ctgattgggg ctctgcttgt ttgtagagag      600
ggtagcttgg ctaaggagaa aacccaaaca ctccataagt tcattttgct gttcgcggtg      660
ttcgacgagg gaaagagttg gcacagcgaa acaaagaatt cactgatgca agacagggac      720
gccgcttccg caagggcttg gcctaagatg catacggtga atgggtatgt gaaccggagc      780
ctcccggggc tgatcgggtg ccatcgcaag tctgtttact ggcacgtcat tggaatgggg      840
acaacgccag aggtacatag tatatttctt gaaggccaca cgttcctcgt acggaaccac      900
cgacaggctt ccctggagat aagccccatt acctttctga ccgctcagac tctgctgatg      960
gaccttggcc agtttctcct gttctgccat attagcagcc accagcacga cggtatggaa     1020
gcatacgtga aagtcgatag ctgtcctgag gagcctcagc tcagaatgaa gaacaacgag     1080
gaggccgaag actatgacga tgaccttaca gattccgaga tggacgtggt gcgctttgac     1140
gacgataaca gtcctagttt cattcaaatc agatccgtag ccaaaaagca tccaaagaca     1200
tgggtgcatt acattgcagc cgaagaggag gattgggatt atgcgcccct tgttctggct     1260
ccagatgaca ggagctataa gtcccagtac ttgaacaacg ggccacagcg aatcggtaga     1320
aaatataaga aggtaagatt catggcctac actgacgaaa catttaaaac cagggaagct     1380
atccaacacg aatctggaat tctcggccct ctgctctacg tgaggtggg ggacaccttg      1440 ctgatcattt tcaaaaatca ggcatccagg ccttacaaca tatacccca tggcatcacc      1500 gatgtccgcc cgctgtattc cagaagactc cccaagggga tgaaacatct gaaagatttt     1560
cccatcctgc cgggcgagat ctttaaatac aaatggactg tgactgtaga ggacgggcct     1620
acaaaatcag acccacggtg cctgacaagg tattacagta gcttcgtcaa catggaacgc     1680
gacctcgcca gcggactcat tggcccactg ttgatctgtt acaaagagtc agtggatcag     1740
aggggaaatc agatcatgag cgataagaga aacgttatcc tgtttagtgt cttcgacgag     1800
aaccggtctt ggtaccttac tgagaacatc cagaggttcc tgccgaatcc ggctggcgtt     1860
cagctcgagg acccagagtt ccaggccagt aatataatgc actcaatcaa cggttatgtg     1920
ttcgatagcc tgcagctgag cgtctgcctc cacgaggtag cctattggta catattgtcc     1980 atcgggctc agaccgattt tctgtccgtg ttctttagcg ggtataccttt aaacataaa     2040 atggtctatg aagacacccct gaccctgttc ccattctccg gtgagactgt gttcatgtcc     2100
atggagaacc cagggctgtg gatcctgggg tgtcacaata gtgactttag gaatcgggga     2160
atgacggcac tgctgaaggt gagttcttgc gataaaaata caggagatta ctatgaggat     2220
agttacgagg atatcagtgc ctatctgctt tcaaaaaaca acgcaattga gccccggtct     2280
ttctcacaaa acccccggt gctgaagcgc accagcgcg aaattacccg acaaccttg       2340 cagtccgacc aggaggaaat cgattatgac gatactatca gtgtagaaat gaaaaggag     2400 gattttgata tttacgacga agacgagaac cagtctccgc gaagttttca gaagaaaacg     2460
cgacactact ttatagctgc cgtggaacga ctctgggatt atggcatgtc ctccagccct     2520
catgtcctta ggaatcgagc gcagagtggc tctgtgcctc agttcaaaaa ggttgtgttc     2580
caggaattca ccgacggctc atttacccag ccgctgtaca gaggcgaact caacgaacac     2640
cttgggctgc ttgggccata tattcgagca gaggtggaag ataatatcat ggtaacctt     2700
```

```
agaaaccagg cgtcaagacc ctattccttc tacagttctc tgatcagcta cgaggaggac    2760
caaagacagg gagctgaacc caggaagaac tttgtgaaac ctaatgagac caagacctac    2820
ttctggaagg tccagcacca tatggcccca actaaagatg aattcgattg caaggcctgg    2880
gcttatttca gcgacgtgga tctcgaaaag gatgtgcaca gcgggttgat cggaccgctt    2940
ttggtgtgcc acacaaatac cctcaatcct gcccacgggc ggcaggtcac agttcaagag    3000
tttgcactct tctttacaat atttgacgag acaaagtcat ggtattttac agagaatatg    3060
gagagaaatt gtcgcgcacc ttgcaacatt cagatggagg accccacatt taaggagaat    3120
tacagatttc atgctatcaa tgggtacatt atggatactc tgcctggtct ggtcatggcc    3180
caggatcagc gcataaggtg gtacttgctg agcatgggat ctaatgagaa tatacacagc    3240
attcacttca gtggccacgt ttttactgtt agaaagaagg aggagtacaa aatggcgctc    3300
tacaaccttt acccgggtgt gtttgagaca gtggagatgc tgccaagcaa ggcaggcatc    3360
tggagggttg agtgtcttat tggggagcat ctgcatgctg gaatgtccac cctctttctt    3420
gtgtacagca ataagtgcca gacaccgctt ggcatggcca gcggccacat tagggacttt    3480
cagataactg ccagtggaca gtacggccag tgggctccca agcttgcaag actccactac    3540
tccggaagca taaacgcatg gagcaccaag gaacccttct cttggattaa ggtggacctg    3600
ctggcgccaa tgatcattca cggcataaaa acccaagggg cacgacagaa attttcatct    3660
ttgtatatta gtcagtttat catcatgtac agcttggatg gaaagaagtg gcagacgtac    3720
aggggcaatt ctacaggaac acttatggtg tttttttggga atgtcgattc cagcgggatc    3780
aaacataaca tcttcaatcc tcctattatc gcccgatata tccgcctgca ccctacgcat    3840
tactccatca ggtccacatt gagaatgaaa ctgatggggt gcgacctgaa tagttgtagt    3900
atgccactgg gcatggagtc taaagccatc agcgatgcac agatcactgc cagctcttac    3960
ttcaccaaca tgtttgcaac ttggtccccc tctaaagctc gcctgcatct gcagggacgc    4020
tcaaatgcat ggcgaccaca ggtgaacaat ccaaaagagt ggctccaggt cgactttcag    4080
aagacaatga aggtaacagg agtgacaacc caggtgtaa aaagcctcct tacgagtatg    4140
tacgttaagg agtttctgat ttctagctcc caggacggac accagtggac tctgttcttc    4200
cagaacggca aagtgaaggt atttcaggga aaccaggatt cttttacccc ggtagtgaat    4260
agcctggatc caccgttgct gacccgctat ctgagaattc atccacaatc ctgggtgcat    4320
cagattgccc tccggatgga agtgctcggc tgtgaagctc aggatctgta ttag          4374
```

<210> SEQ ID NO 17
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
```

```
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccct agtcctcgcc   1260
cccgatgaca aagttataaa agtcaatat ttgaacaatg ccctcagcg gattggtagg    1320 aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccct caaacacaaa   2040
atggtctatg aagacacact caccctattc ccattctcag agaaactgt cttcatgtcg    2100 atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga tccaccagt cttgaaacgc atcaacggg aataactcg tactactctt    2340 cagtcagatc aagaggaaat tgactatgat gataccatat cagttgaaat gaagaaggaa   2400
gattttgaca tttatgatga ggatgaaaat cagagccccc gcagcttca aaagaaaaca    2460 cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
```

```
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg     3420 gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg gcagacttat     3720 cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa atctctgct taccagcatg     4140 tatgtgaagg agttcctcat ctccagcagt caagatggcc atcagtggac tctcttttt     4200 cagaatggca aagtaaaggt ttttcaggga aatcaagact ccttcacacc tgtggtgaac    4260
tctctagacc caccgttact gactcgctac cttcgaattc accccagag ttgggtgcac     4320 cagattgccc tgaggatgga ggttctgggc tgcgaggcac aggacctcta ctga          4374
```

<210> SEQ ID NO 18
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgcagatcg agctgtccac atgcttttt ctgtgcctgc tgcggttctg cttcagcgcc       60
acccggcggt actacctggg cgccgtggag ctgtcctggg actacatgca gagcgacctg     120
ggcgagctgc ccgtggacgc ccggttcccc ccagagtgc caagagctt ccccttcaac      180 accagcgtgg tgtacaagaa aaccctgttc gtggagttca ccgaccacct gttcaacatc    240
gccaagccca ggccccctg gatgggcctg ctgggcccca ccatccaggc cgaggtgtac    300
gacaccgtgg tgatcaccct gaagaacatg gccagccacc ccgtgagcct gcacgccgtg    360
```

```
ggcgtgagct actggaaggc ctccgagggc gccgagtacg acgaccagac cagccagcgg      420
gagaaagagg acgacaaagt cttcctggc ggcagccaca cctacgtgtg gcaggtcctg       480
aaagaaaacg gccccatggc ctccgacccc ctgtgcctga cctacagcta cctgagccac     540
gtggacctgg tgaaggacct gaacagcggg ctgattgggg ccctgctggt ctgccgggag     600
ggcagcctgg ccaaagagaa acccagacc ctgcacaagt tcatcctgct gttcgccgtg     660
ttcgacgagg gcaagagctg gcacagcgag accaagaaca gcctgatgca ggaccgggac   720
gccgcctctg ccagagcctg gcccaagatg cacaccgtga acggctacgt gaacagaagc    780
ctgcccggcc tgattggctg ccaccggaag agcgtgtact ggcacgtgat cggcatgggc     840
accacacccg aggtgcacag catctttctg aagggcaca cctttctggt gcggaaccac       900
cggcaggcca gcctgaaaat cagccctatc accttcctga ccgcccagac actgctgatg    960
gacctgggcc agttcctgct gttttgccac atcagctctc accagcacga cggcatggaa   1020
gcctacgtga aggtggactc ctgccccgag aaccccagc tgcggatgaa gaacaacgag   1080
gaagccgagg actacgacga cgacctgacc gacagcgaga tggacgtggt gcggttcgac   1140
gacgacaaca gccccagctt catccagatc agaagcgtgg ccaagaagca ccccaagacc   1200
tgggtgcact acatcgccgc cgaggaagag gactgggact acgccccct ggtgctggcc     1260 cccgacgaca aagctacaa gagccagtac ctgaacaatg ccccagcg atcggccgg       1320 aagtacaaga agtgcggtt catggcctac accgacgaga ccttcaagac ccggagcc       1380 atccagcacg agagcggcat cctgggcccc ctgctgtacg gcgaagtggg cgacacactg   1440
ctgatcatct tcaagaacca ggccagccgg ccctacaaca tctacccca cggcatcacc     1500 gacgtgcggc ccctgtacag caggcggctg cccaagggcg tgaagcacct gaaggacttc   1560
cccatcctgc ccggcgagat cttcaagtac aagtggaccg tgaccgtgga ggacggcccc   1620
accaagagcg acccagatg cctgacccgg tactacagca gcttcgtgaa catggaacgg   1680
gacctggcct ccgggctgat cggacctctg ctgatctgct acaaagaaag cgtggaccag   1740
cggggcaacc agatcatgag cgacaagcgg aacgtgatcc tgttcagcgt gttcgatgag   1800
aaccggtcct ggtatctgac cgagaacatc cagcggttc tgcccaaccc tgccggggtg    1860
cagctggaag atcccgagtt ccaggccagc aacatcatgc actccatcaa tggctacgtg   1920
ttcgacagcc tgcagctgtc cgtgtgtctg cacgaggtgg cctactggta catcctgagc   1980
atcggcgccc agaccgactt cctgagcgtg ttcttcagcg gctacacctt caagcacaag  2040
atggtgtacg aggacaccct gaccctgttc cctttcagcg gcgagaccgt gttcatgagc   2100
atggaaaacc ccggcctgtg gatcctgggc tgccacaaca gcgacttccg gaaccggggc   2160
atgaccgccc tgctgaaggt gtccagctgc gacaagaaca ccggcgacta ctacgaggac   2220
agctacgagg atatcagcgc ctacctgctg tccaagaaca cgccatcga gcccagaagc   2280 ttcagccaga ccccccctgt gctgaagcgg caccagagag atcacccg gaccaccctg      2340 cagtccgacc aggaagagat cgattacgac gacaccatca gcgtggagat gaaaaagaa  2400 gatttcgaca tctacgacga ggacgagaac cagagccccc ggtccttcca gaagaaaacc  2460
cggcactact tatcgccgc cgtggagcgg ctgtgggact acggcatgag cagcagccc       2520 cacgtgctgc ggaaccgggc cagagcggc agcgtgcccc agttcaagaa agtggtgttc    2580
caggaattca ccgacggcag cttcacccag cccctgtacc ggggcgagct gaacgagcac  2640
ctggggctgt gggcccta catcagggcc gaagtggagg acaacatcat ggtgaccttc         2700
cggaatcagg ccagcagacc ctactccttc tacagcagcc tgatcagcta cgaagaggac   2760
```

| | |
|---|---|
| cagcggcagg gcgctgaacc ccggaagaac ttcgtgaagc ccaatgagac caagacctac | 2820 |
| ttctggaaag tgcagcacca catggccccc accaaggacg agttcgactg caaggcctgg | 2880 |
| gcctacttca gcgacgtgga tctggaaaag gacgtgcact ctggactgat tggccctctg | 2940 |
| ctggtgtgcc acaccaacac cctgaacccc gcccacggcc ggcaggtgac cgtgcaggaa | 3000 |
| ttcgccctgt tcttcaccat cttcgacgag accaagtcct ggtacttcac cgagaatatg | 3060 |
| gaacggaact gcagagcccc ctgcaacatc cagatggaag atcctacctt caaagagaac | 3120 |
| taccggttcc acgccatcaa cggctacatc atggacaccc tgcctggcct ggtgatggcc | 3180 |
| caggaccaga ggatccggtg gtatctgctg tccatgggca gcaacgagaa tatccacagc | 3240 |
| atccacttca gcggccacgt gttcaccgtg aggaagaaag aagagtacaa gatggccctg | 3300 |
| tacaacctgt accccggcgt gttcgagacc gtggagatgc tgcccagcaa ggccggcatc | 3360 |
| tggcgggtgg agtgtctgat cggcgagcac ctgcatgccg ggatgagcac cctgtttctg | 3420 |
| gtgtacagca caagtgcca gaccccctg ggcatggcca cggccacat ccggcttc | 3480 |
| cagatcaccg cctccggcca gtacggccag tgggccccca gctggcccg gctgcactac | 3540 |
| agcggcagca tcaacgcctg gtccaccaaa gagccttca gctggatcaa ggtgacctg | 3600 |
| ctggccccta tgatcatcca cggcattaag acccagggcg ccaggcagaa gttcagcagc | 3660 |
| ctgtacatca gccagttcat catcatgtac agcctggacg gcaagaagtg gcagacctac | 3720 |
| cggggcaaca gcaccggcac cctgatggtg ttcttcggca acgtggacag cagcggcatc | 3780 |
| aagcacaaca tcttcaaccc ccccatcatc gcccggtaca tccggctgca ccccaccca | 3840 |
| tacagcatca gatccaccct gcggatggaa ctgatgggct gcgacctgaa ctcctgcagc | 3900 |
| atgcctctgg gcatggaaag caaggccatc agcgacgccc agatcacagc cagcagctac | 3960 |
| ttcaccaaca tgttcgccac ctggtccccc tccaaggcca ggctgcacct gcagggccgg | 4020 |
| tccaacgcct ggcggcctca ggtgaacaac cccaaagaat ggctgcaggt ggactttcag | 4080 |
| aaaaccatga aggtgaccgg cgtgaccacc cagggcgtga aaagcctgct gaccagcatg | 4140 |
| tacgtgaaag agtttctgat cagcagcagc caggacggcc accagtggac cctgttctt | 4200 |
| cagaacggca aggtgaaagt gttccagggc aaccaggact ccttcacccc cgtggtgaac | 4260 |
| tccctggacc ccccctgct gacccgctac ctgcggatcc acccccagtc ttgggtgcac | 4320 |
| cagatcgccc tgaggatgga agtgctggga tgtgaggccc aggatctgta ctga | 4374 |

<210> SEQ ID NO 19
<211> LENGTH: 2351
<212> TYPE: PRT
<213> ORGANISM: Homo sapiens

<400> SEQUENCE: 19

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln

-continued

```
            85                  90                  95
Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
                130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
                210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
                290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asp Asn Ser
                370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510
```

```
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
        530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
        835                 840                 845
Ser Leu Ser Glu Met Thr His Phe Arg Pro Gln Leu His His Ser Gly
    850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
            900                 905                 910
Leu Ala Ala Gly Thr Asp Asn Thr Ser Ser Leu Gly Pro Pro Ser Met
        915                 920                 925
```

```
Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
```

-continued

```
            1325                1330                1335
Leu Pro Leu Glu Glu Thr Glu Leu Glu Lys Arg Ile Ile Val Asp
            1340                1345                1350
Asp Thr Ser Thr Gln Trp Ser Lys Asn Met Lys His Leu Thr Pro
            1355                1360                1365
Ser Thr Leu Thr Gln Ile Asp Tyr Asn Glu Lys Glu Lys Gly Ala
            1370                1375                1380
Ile Thr Gln Ser Pro Leu Ser Asp Cys Leu Thr Arg Ser His Ser
            1385                1390                1395
Ile Pro Gln Ala Asn Arg Ser Pro Leu Pro Ile Ala Lys Val Ser
            1400                1405                1410
Ser Phe Pro Ser Ile Arg Pro Ile Tyr Leu Thr Arg Val Leu Phe
            1415                1420                1425
Gln Asp Asn Ser Ser His Leu Pro Ala Ala Ser Tyr Arg Lys Lys
            1430                1435                1440
Asp Ser Gly Val Gln Glu Ser Ser His Phe Leu Gln Gly Ala Lys
            1445                1450                1455
Lys Asn Asn Leu Ser Leu Ala Ile Leu Thr Leu Glu Met Thr Gly
            1460                1465                1470
Asp Gln Arg Glu Val Gly Ser Leu Gly Thr Ser Ala Thr Asn Ser
            1475                1480                1485
Val Thr Tyr Lys Lys Val Glu Asn Thr Val Leu Pro Lys Pro Asp
            1490                1495                1500
Leu Pro Lys Thr Ser Gly Lys Val Glu Leu Leu Pro Lys Val His
            1505                1510                1515
Ile Tyr Gln Lys Asp Leu Phe Pro Thr Glu Thr Ser Asn Gly Ser
            1520                1525                1530
Pro Gly His Leu Asp Leu Val Glu Gly Ser Leu Leu Gln Gly Thr
            1535                1540                1545
Glu Gly Ala Ile Lys Trp Asn Glu Ala Asn Arg Pro Gly Lys Val
            1550                1555                1560
Pro Phe Leu Arg Val Ala Thr Glu Ser Ser Ala Lys Thr Pro Ser
            1565                1570                1575
Lys Leu Leu Asp Pro Leu Ala Trp Asp Asn His Tyr Gly Thr Gln
            1580                1585                1590
Ile Pro Lys Glu Glu Trp Lys Ser Gln Glu Lys Ser Pro Glu Lys
            1595                1600                1605
Thr Ala Phe Lys Lys Lys Asp Thr Ile Leu Ser Leu Asn Ala Cys
            1610                1615                1620
Glu Ser Asn His Ala Ile Ala Ala Ile Asn Glu Gly Gln Asn Lys
            1625                1630                1635
Pro Glu Ile Glu Val Thr Trp Ala Lys Gln Gly Arg Thr Glu Arg
            1640                1645                1650
Leu Cys Ser Gln Asn Pro Pro Val Leu Lys Arg His Gln Arg Glu
            1655                1660                1665
Ile Thr Arg Thr Thr Leu Gln Ser Asp Gln Glu Glu Ile Asp Tyr
            1670                1675                1680
Asp Asp Thr Ile Ser Val Glu Met Lys Lys Glu Asp Phe Asp Ile
            1685                1690                1695
Tyr Asp Glu Asp Glu Asn Gln Ser Pro Arg Ser Phe Gln Lys Lys
            1700                1705                1710
Thr Arg His Tyr Phe Ile Ala Ala Val Glu Arg Leu Trp Asp Tyr
            1715                1720                1725
```

```
Gly Met Ser Ser Ser Pro His Val Leu Arg Asn Arg Ala Gln Ser
    1730            1735                1740

Gly Ser Val Pro Gln Phe Lys Lys Val Val Phe Gln Glu Phe Thr
    1745            1750                1755

Asp Gly Ser Phe Thr Gln Pro Leu Tyr Arg Gly Glu Leu Asn Glu
    1760            1765                1770

His Leu Gly Leu Leu Gly Pro Tyr Ile Arg Ala Glu Val Glu Asp
    1775            1780                1785

Asn Ile Met Val Thr Phe Arg Asn Gln Ala Ser Arg Pro Tyr Ser
    1790            1795                1800

Phe Tyr Ser Ser Leu Ile Ser Tyr Glu Glu Asp Gln Arg Gln Gly
    1805            1810                1815

Ala Glu Pro Arg Lys Asn Phe Val Lys Pro Asn Glu Thr Lys Thr
    1820            1825                1830

Tyr Phe Trp Lys Val Gln His His Met Ala Pro Thr Lys Asp Glu
    1835            1840                1845

Phe Asp Cys Lys Ala Trp Ala Tyr Phe Ser Asp Val Asp Leu Glu
    1850            1855                1860

Lys Asp Val His Ser Gly Leu Ile Gly Pro Leu Leu Val Cys His
    1865            1870                1875

Thr Asn Thr Leu Asn Pro Ala His Gly Arg Gln Val Thr Val Gln
    1880            1885                1890

Glu Phe Ala Leu Phe Phe Thr Ile Phe Asp Glu Thr Lys Ser Trp
    1895            1900                1905

Tyr Phe Thr Glu Asn Met Glu Arg Asn Cys Arg Ala Pro Cys Asn
    1910            1915                1920

Ile Gln Met Glu Asp Pro Thr Phe Lys Glu Asn Tyr Arg Phe His
    1925            1930                1935

Ala Ile Asn Gly Tyr Ile Met Asp Thr Leu Pro Gly Leu Val Met
    1940            1945                1950

Ala Gln Asp Gln Arg Ile Arg Trp Tyr Leu Leu Ser Met Gly Ser
    1955            1960                1965

Asn Glu Asn Ile His Ser Ile His Phe Ser Gly His Val Phe Thr
    1970            1975                1980

Val Arg Lys Lys Glu Glu Tyr Lys Met Ala Leu Tyr Asn Leu Tyr
    1985            1990                1995

Pro Gly Val Phe Glu Thr Val Glu Met Leu Pro Ser Lys Ala Gly
    2000            2005                2010

Ile Trp Arg Val Glu Cys Leu Ile Gly Glu His Leu His Ala Gly
    2015            2020                2025

Met Ser Thr Leu Phe Leu Val Tyr Ser Asn Lys Cys Gln Thr Pro
    2030            2035                2040

Leu Gly Met Ala Ser Gly His Ile Arg Asp Phe Gln Ile Thr Ala
    2045            2050                2055

Ser Gly Gln Tyr Gly Gln Trp Ala Pro Lys Leu Ala Arg Leu His
    2060            2065                2070

Tyr Ser Gly Ser Ile Asn Ala Trp Ser Thr Lys Glu Pro Phe Ser
    2075            2080                2085

Trp Ile Lys Val Asp Leu Leu Ala Pro Met Ile Ile His Gly Ile
    2090            2095                2100

Lys Thr Gln Gly Ala Arg Gln Lys Phe Ser Ser Leu Tyr Ile Ser
    2105            2110                2115
```

| | | | | | | | | | | | |
|---|---|---|---|---|---|---|---|---|---|---|---|
| Gln | Phe | Ile | Ile | Met | Tyr | Ser | Leu | Asp | Gly | Lys | Lys | Trp | Gln | Thr |
| | 2120 | | | | 2125 | | | | 2130 | | |

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr
2345                2350

<210> SEQ ID NO 20
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc ctgtggacgc caggttcccc cccagagtgc caagagcttc cccttcaac      180 acctcagtgg tgtacaagaa gaccctgttc gtggagttca ccgaccacct gttcaacatc     240
gccaagccca ggccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc ctctgagggc gccgagtatg acgaccagac cagccagagg     420
gagaaggagg acgacaaggt gttccccggc ggcagccaca cctacgtgtg gcaggtgctg     480
aaggagaacg gccccatggc cagcgacccc ctgtgcctga cctacagcta cctgagccac     540
gtggacctgg tgaaggacct gaactctggc ctgatcggcg ccctgctggt gtgcagggag     600

```
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840 accaccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgcccccct ggtgctggcc   1260
cccgacgaca ggagctacaa gagccagtac ctgaacaacg gccccagag gatcggcagg   1320 aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg cgagaccgt gttcatgagc   2100 atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga cccccccgt gctgaagagg caccagaggg agatcaccag gaccaccctg   2340
cagagcgacc aggaggagat cgactatgat gacaccatca gcgtggagat gaagaaggag   2400
gacttcgaca tctacgacga ggacgagaac cagagcccca ggagcttcca gaagaagacc   2460
aggcactact tcatcgccgc cgtggagagg ctgtgggact atggcatgag cagcagcccc   2520
cacgtgctga ggaacagggc ccagagcggc agcgtgcccc agttcaagaa ggtggtgttc   2580
caggagttca ccgacggcag cttcacccag cccctgtaca gaggcgagct gaacgagcac   2640
ctgggcctgc tgggccccta catcagggcc gaggtggagg acaacatcat ggtgaccttc   2700
aggaaccagg ccagcaggcc ctacagcttc tacagcagcc tgatcagcta cgaggaggac   2760
cagaggcagg gcgccgagcc caggaagaac ttcgtgaagc ccaacgagac caagacctac   2820
ttctggaagg tgcagcacca catggccccc accaaggacg agttcgactg caaggcctgg   2880
gcctacttct ctgatgtgga cctggagaag gacgtgcaca cgcctgat cggcccctg   2940 ctggtgtgcc acaccaacac cctgaacccc gcccacggca ggcaggtgac cgtgcaggag   3000
```

```
ttcgccctgt tcttcaccat cttcgacgag accaagagct ggtacttcac cgagaacatg    3060
gagaggaact gcagggcccc ctgcaacatc cagatggagg accccaccct caaggagaac    3120
tacaggttcc acgccatcaa cggctacatc atggacaccc tgcccggcct ggtgatggcc    3180
caggaccaga ggatcaggtg gtatctgctg agcatgggca gcaacgagaa catccacagc    3240
atccacttca gcggccacgt gttcaccgtg aggaagaagg aggagtacaa gatggccctg    3300
tacaacctgt accccggcgt gttcgagacc gtggagatgc tgcccagcaa ggccggcatc    3360
tggagggtgg agtgcctgat cggcgagcac ctgcacgccg gcatgagcac cctgttcctg    3420
gtgtacagca caagtgcca gaccccctg ggcatggcca gcggccacat cagggacttc    3480
cagatcaccg cctctggcca gtacggccag tgggccccca gctggccag gctgcactac    3540 agcggcagca tcaacgcctg gagcaccaag gagcccttca gctggatcaa ggtggacctg    3600
ctggccccca tgatcatcca cggcatcaag acccagggcg ccaggcagaa gttcagcagc    3660
ctgtacatca gccagttcat catcatgtac agcctggacg caagaagtg gcagacctac    3720 aggggcaaca gcaccggcac cctgatggtg ttcttcggca cgtggacag cagcggcatc    3780 aagcacaaca tcttcaaccc ccccatcatc gccaggtaca tcaggctgca ccccaccccac    3840 tacagcatca ggagcaccct gcggatggaa ctgatgggct gcgacctgaa cagctgcagc    3900
atgcccctgg gcatggagag caaggccatc tctgacgccc agatcaccgc cagcagctac    3960
ttcaccaaca tgttcgccac ctggagcccc agcaaggcca ggctgcacct gcagggcagg    4020
agcaacgcct ggaggcccca ggtgaacaac cccaaggagt ggctgcaggt ggacttccag    4080
aagaccatga aggtgaccgg cgtgaccacc cagggcgtga gagcctgct gaccagcatg    4140 tacgtgaagg agttcctgat cagcagcagc aggacggcc accagtggac cctgttcttc    4200
cagaacggca aagtgaaggt gttccagggc aaccaggaca gcttcacccc cgtggtgaac    4260
agcctggacc ccccctgct gaccaggtat ctgaggatcc accccagag ctgggtgcac    4320 cagatcgccc tgaaatgga agtgctggga tgcgaggccc aggacctgta ctga          4374
```

<210> SEQ ID NO 21
<211> LENGTH: 1457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110
```

-continued

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp

-continued

```
            530                 535                 540
Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
                820                 825                 830

Asp Tyr Gly Met Ser Ser Ser Pro His Val Leu Arg Asn Arg Ala Gln
                835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
                915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960
```

```
Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Glu Pro Phe Ser Trp Ile Lys Val Asp Leu Leu Ala Pro
        1190                1195                1200

Met Ile Ile His Gly Ile Lys Thr Gln Gly Ala Arg Gln Lys Phe
        1205                1210                1215

Ser Ser Leu Tyr Ile Ser Gln Phe Ile Ile Met Tyr Ser Leu Asp
        1220                1225                1230

Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn
        1250                1255                1260

Ile Phe Asn Pro Pro Ile Ile Ala Arg Tyr Ile Arg Leu His Pro
        1265                1270                1275

Thr His Tyr Ser Ile Arg Ser Thr Leu Arg Met Glu Leu Met Gly
        1280                1285                1290

Cys Asp Leu Asn Ser Cys Ser Met Pro Leu Gly Met Glu Ser Lys
        1295                1300                1305

Ala Ile Ser Asp Ala Gln Ile Thr Ala Ser Ser Tyr Phe Thr Asn
        1310                1315                1320

Met Phe Ala Thr Trp Ser Pro Ser Lys Ala Arg Leu His Leu Gln
        1325                1330                1335

Gly Arg Ser Asn Ala Trp Arg Pro Gln Val Asn Asn Pro Lys Glu
        1340                1345                1350
```

```
Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 22
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gccaccagga gatactacct gggcgccgtg gagctgagct gggactacat gcagtctgac      60
ctgggcgagc tgcctgtgga cgccaggttc ccccccagag tgcccaagag cttcccttc     120 aacacctcag tggtgtacaa gaagaccctg ttcgtggagt tcaccgacca cctgttcaac    180
atcgccaagc caggccccc tggatgggc ctgctgggcc ccaccatcca ggccgaggtg     240
tacgacaccg tggtgatcac cctgaagaac atggccagcc accccgtgag cctgcacgcc    300
gtgggcgtga gctactggaa ggcctctgag ggcgccgagt atgacgacca gaccagccag    360
agggagaagg aggacgacaa ggtgttcccc ggcggcagcc acacctacgt gtggcaggtg    420
ctgaaggaga acggccccat ggccagcgac cccctgtgcc tgacctacag ctacctgagc    480
cacgtggacc tggtgaagga cctgaactct ggcctgatcg cgccctgct ggtgtgcagg    540 gagggcagcc tggccaagga aagacccag accctgcaca gttcatcct gctgttcgcc     600 gtgttcgatg agggcaagag ctggcacagc gagaccaaga caagcctgat gcaggacagg    660
gatgccgcct ctgccagggc ctggccaaag atgcacaccg tgaacggcta cgtgaacagg    720
agcctgcccg gcctgatcgg ctgccacagg aagtctgtgt actggcacgt gatcggcatg    780
ggcaccaccc ccgaggtgca cagcatcttc ctggagggcc acaccttcct ggtgaggaac    840
cacaggcagg ccagcctgga gatcagcccc atcaccttcc tgaccgccca gaccctgctg    900
atggacctgg gccagttcct gctgttctgc cacatcagca gccaccagca cgacggcatg    960
gaggcctacg tgaaggtgga cagctgcccc gaggagcccc agctgaggat gaagaacaac   1020
gaggaggccg aggactatga tgatgacctg accgactctg agatggacgt ggtgaggttt   1080
gatgatgaca cagccccag cttcatccag atcaggtctg tggccaagaa gcaccccaag   1140
acctgggtgc actacatcgc cgccgaggag gaggactggg actacgcccc cctggtgctg    1200 gccccgacg acaggagcta caagagccag tacctgaaca cggcccca gaggatcggc     1260 aggaagtaca agaaggtcag attcatggcc tacaccgacg agaccttcaa gaccagggag    1320
gccatccagc acgagtctgg catcctgggc cccctgctgt acggcgaggt gggcgacacc    1380
ctgctgatca tcttcaagaa ccaggccagc aggcctaca acatctaccc ccacggcatc   1440
```

| | |
|---|---|
| accgatgtga ggcccctgta cagcaggagg ctgcccaagg gcgtgaagca cctgaaggac | 1500 |
| ttccccatcc tgcccggcga gatcttcaag tacaagtgga ccgtgaccgt ggaggatggc | 1560 |
| cccaccaagt ctgaccccag gtgcctgacc aggtactaca gcagcttcgt gaacatggag | 1620 |
| agggacctgg cctctggcct gatcggcccc ctgctgatct gctacaagga gagcgtggac | 1680 |
| cagaggggca accagatcat gtctgacaag aggaacgtga tcctgttctc tgtgttcgat | 1740 |
| gagaacagga gctggtatct gaccgagaac atccagaggt cctgcccaa ccccgccggc | 1800 |
| gtgcagctgg aggacccga gttccaggcc agcaacatca tgcacagcat caacggctac | 1860 |
| gtgttcgaca gcctgcagct gtctgtgtgc ctgcacgagg tggcctactg gtacatcctg | 1920 |
| agcatcggcg cccagaccga cttcctgtct gtgttcttct ctggctacac cttcaagcac | 1980 |
| aagatggtgt acgaggacac cctgaccctg ttccccttca gcggcgagac cgtgttcatg | 2040 |
| agcatggaga accccggcct gtggatcctg gctgccaca cagcgactt caggaacagg | 2100 |
| ggcatgaccg ccctgctgaa agtcagcagc tgcgacaaga caccggcga ctactacgag | 2160 |
| gacagctacg aggacatcag cgcctacctg ctgagcaaga caacgccat cgagcccagg | 2220 |

<210> SEQ ID NO 23
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | |
|---|---|
| gagatcacca ggaccaccct gcagagcgac caggaggaga tcgactatga tgacaccatc | 60 |
| agcgtggaga tgaagaagga ggacttcgac atctacgacg aggacgagaa ccagagcccc | 120 |
| aggagcttcc agaagaagac caggcactac ttcatcgccg ccgtggagag gctgtgggac | 180 |
| tatgcatga gcagcagccc ccacgtgctg aggaacaggg cccagagcgg cagcgtgccc | 240 |
| cagttcaaga aggtggtgtt ccaggagttc accgacggca gcttcaccca gccctgtac | 300 |
| agaggcgagc tgaacgagca cctgggcctg ctgggccct acatcagggc cgaggtggag | 360 |
| gacaacatca tggtgacctt caggaaccag gccagcaggc cctacagctt ctacagcagc | 420 |
| ctgatcagct acgaggagga ccagaggcag ggcgccgagc caggaagaa cttcgtgaag | 480 |
| cccaacgaga ccaagaccta cttctggaag gtgcagcacc atggcccc caccaaggac | 540 |
| gagttcgact gcaaggcctg gcctacttc tctgatgtgg acctggagaa ggacgtgcac | 600 |
| agcggcctga tcggccccct gctggtgtgc cacaccaaca ccctgaaccc cgcccacggc | 660 |
| aggcaggtga ccgtgcagga gttcgccctg ttcttcacca tcttcgacga gaccaagagc | 720 |
| tggtacttca ccgagaacat ggagaggaac tgcagggccc cctgcaacat ccagatggag | 780 |
| gaccccacct tcaaggagaa ctacaggttc cacgccatca cggctacat catggacacc | 840 |
| ctgcccggcc tggtgatggc ccaggaccag aggatcaggt ggtatctgct gagcatgggc | 900 |
| agcaacgaga acatccacag catccacttc agcggccacg tgttcaccgt gaggaagaag | 960 |
| gaggagtaca gatggccct gtacaacctg taccccggcg tgttcgagac cgtggagatg | 1020 |
| ctgcccagca aggccggcat ctggagggtg gagtgcctga tcggcgagca cctgcacgcc | 1080 |
| ggcatgagca ccctgttcct ggtgtacagc aacaagtgcc agaccccct gggcatggcc | 1140 |
| agcggccaca tcagggactt ccagatcacc gcctctggcc agtacggcca gtgggccccc | 1200 |
| aagctggcca ggctgcacta cagcggcagc atcaacgcct ggagcaccaa ggagcccttc | 1260 |

-continued

| | |
|---|---|
| agctggatca aggtggacct gctggccccc atgatcatcc acggcatcaa gacccagggc | 1320 |
| gccaggcaga agttcagcag cctgtacatc agccagttca tcatcatgta cagcctggac | 1380 |
| ggcaagaagt ggcagaccta caggggcaac agcaccggca ccctgatggt gttcttcggc | 1440 |
| aacgtggaca gcagcggcat caagcacaac atcttcaacc cccccatcat cgccaggtac | 1500 |
| atcaggctgc accccaccca ctacagcatc aggagcaccc tgcggatgga actgatgggc | 1560 |
| tgcgacctga cagctgcag catgcccctg gcatggaga gcaaggccat ctctgacgcc | 1620 |
| cagatcaccg ccagcagcta cttcaccaac atgttcgcca cctggagccc agcaaggcc | 1680 |
| aggctgcacc tgcagggcag gagcaacgcc tggaggcccc aggtgaacaa ccccaaggag | 1740 |
| tggctgcagg tggacttcca gaagaccatg aaggtgaccg gcgtgaccac ccagggcgtg | 1800 |
| aagagcctgc tgaccagcat gtacgtgaag gagttcctga tcagcagcag ccaggacggc | 1860 |
| caccagtgga ccctgttctt ccagaacggc aaagtgaagg tgttccaggg caaccaggac | 1920 |
| agcttcaccc ccgtggtgaa cagcctggac cccccctgc tgaccaggta tctgaggatc | 1980 |
| caccccaga gctgggtgca ccagatcgcc ctgagaatgg aagtgctggg atgcgaggcc | 2040 |
| caggacctgt ac | 2052 |

<210> SEQ ID NO 24
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | |
|---|---|
| gccaccagga gatactacct gggggctgtg aactttctt gggactacat gcagtctgac | 60 |
| ctgggagagc tgcctgtgga tgccaggttc ccacccagag tgcccaagtc cttcccattc | 120 |
| aacacctctg tggtctacaa gaagacactc tttgtggaat tcactgacca cctgttcaac | 180 |
| attgcaaaac ccagaccacc ctggatggga ctcctgggac ccaccattca ggctgaggtg | 240 |
| tatgacactg tggtcatcac cctcaagaac atggcatccc accctgtgtc tctgcatgct | 300 |
| gtgggagtct catactggaa agcctctgaa ggggctgagt atgatgacca gacatcccag | 360 |
| agagagaaag aggatgacaa ggtgttccct gggggatctc acacctatgt gtggcaagtc | 420 |
| ctcaaggaga atggacccat ggcatctgac ccactctgcc tgacatactc ctaccttttct | 480 |
| catgtggacc tggtcaagga cctcaactct ggactgattg ggcactgct ggtgtgcagg | 540 |
| gaaggatccc tggccaagga gaaacccag acactgcaca agttcattct cctgttttgct | 600 |
| gtctttgatg agggcaagtc ttggcactct gaaacaaaga actccctgat gcaagacagg | 660 |
| gatgctgcct ctgccagggc atggccaag atgcacactg tgaatggcta tgtgaacaga | 720 |
| tcactgcctg gactcattgg ctgccacagg aaatctgtct actggcatgt gattggcatg | 780 |
| gggacaaccc ctgaagtgca ctccattttc ctggaggac acaccttcct ggtcaggaac | 840 |
| cacagacaag cctctctgga gatctctccc atcaccttcc tcactgcaca gacactgctg | 900 |
| atggaccttg acagttcct gctgttctgc cacatctctt cccaccagca tgatggcatg | 960 |
| gaagcctatg tcaaggtgga ctcatgccct gaggaaccac agctcaggat gaagaacaat | 1020 |
| gaggaggctg aggactatga tgatgacctg actgactctg agatggatgt ggtcagattt | 1080 |
| gatgatgaca actctccatc cttcattcag atcaggtctg tggcaaagaa acaccccaag | 1140 |
| acatgggtgc actacattgc tgctgaggaa gaggactggg actatgcacc actggtcctg | 1200 |

```
gcccctgatg acaggagcta caagtctcag tacctcaaca atggcccaca aagaattgga    1260
agaaagtaca agaaagtcag attcatggcc tacactgatg aaaccttcaa gacaagagaa    1320
gccattcagc atgagtctgg cattctggga ccactcctgt atgggaagt gggagacacc     1380 ctgctcatca tcttcaagaa ccaggcctcc aggccctaca acatctaccc acatggcatc    1440
actgatgtca ggcccctgta cagcaggaga ctgccaaaag gggtgaaaca cctcaaggac    1500
ttccccattc tgcctggaga gatcttcaag tacaagtgga ctgtcactgt ggaggatgga    1560
ccaacaaagt ctgacccag gtgcctcacc agatactact cctcttttgt gaacatggag     1620
agagacctgg catctggact gattggacca ctgctcatct gctacaagga gtctgtggac    1680
cagagaggca accagatcat gtctgacaag agaaatgtga ttctgttctc tgtctttgat    1740
gagaacagat catggtacct gactgagaac attcagagat tcctgcccaa ccctgctggg    1800
gtgcaactgg aagaccctga gttccaggca agcaacatca tgcactccat caatggctat    1860
gtgtttgact ctctccagct ttctgtctgc ctgcatgagg tggcctactg gtacattctt    1920
tctattgggg cacaaactga cttcctttct gtcttcttct ctggatacac cttcaagcac    1980
aagatggtgt atgaggacac cctgacactc ttcccattct ctggggaaac tgtgttcatg    2040
agcatggaga accctggact gtggattctg ggatgccaca actctgactt cagaaacagg    2100
ggaatgactg cactgctcaa agtctcctcc tgtgacaaga acactgggga ctactatgag    2160
gactcttatg aggacatctc tgcctacctg ctcagcaaga acaatgccat tgagcccaga    2220
```

<210> SEQ ID NO 25
<211> LENGTH: 2052
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gagatcacca ggacaaccct ccagtctgac caggaagaga ttgactatga tgacaccatt     60
tctgtggaga tgaagaagga ggactttgac atctatgatg aggacgagaa ccagtctcca    120
agatcattcc agaagaagac aagacactac ttcattgctg ctgtggaaag actgtgggac    180
tatggcatgt cttcctctcc ccatgtcctc aggaacaggg cacagtctgg ctctgtgcca    240
cagttcaaga aagtggtctt ccaggagttc actgatggct cattcaccca gccctgtac     300 agagggggaac tgaatgagca cctgggactc tgggaccat acatcagggc tgaggtggaa    360
gacaacatca tggtgacatt cagaaaccag gcctccaggc cctacagctt ctactcttcc    420
ctcatcagct atgaggaaga ccagagacaa ggggctgagc aagaaagaa ctttgtgaaa     480 cccaatgaaa ccaagaccta cttctggaaa gtccagcacc acatggcacc caccaaggat    540
gagtttgact gcaaggcctg gcatacttc tctgatgtgg acctggagaa agatgtgcac     600
tctggcctga ttgcccact cctggtctgc cacaccaaca ccctgaaccc tgcacatgga    660
aggcaagtga ctgtgcagga gtttgccctc ttcttcacca tctttgatga aaccaagtca    720
tggtacttca ctgagaacat ggagagaaac tgcagagcac catgcaacat tcagatggaa    780
gaccccacct tcaaggagaa ctacaggttc catgccatca atggctacat catggacacc    840
ctgcctgggc ttgtcatggc acaggaccag agaatcagat ggtacctgct ttctatggga    900
tccaatgaga cattcactc catccacttc tctgggcatg tcttcactgt gagaaagaag    960
gaggaataca gatggccct gtacaacctc taccctgggg tctttgagac tgtggagatg   1020
```

```
ctgccctcca aagctggcat ctggagggtg gaatgcctca ttggggagca cctgcatgct    1080
ggcatgtcaa ccctgttcct ggtctacagc aacaagtgcc agacacccct gggaatggcc    1140
tctggccaca tcagggactt ccagatcact gcctctggcc agtatggcca gtgggcaccc    1200
aaactggcca ggctccacta ctctggctcc atcaatgcat ggtcaaccaa ggagccattc    1260
tcttggatca aggtggacct gctggcaccc atgatcattc atggcatcaa gacacagggg    1320
gcaagacaga aattctcctc tctgtacatc tcacagttca tcatcatgta ctctctggat    1380
ggcaagaagt ggcagacata cagaggcaac tccactggca ccctcatggt cttctttggc    1440
aatgtggaca gctctggcat caagcacaac atcttcaacc ctcccatcat tgccagatac    1500
atcaggctgc accccaccca ctactcaatc agatcaaccc tcaggatgga actgatggga    1560
tgtgacctga actcctgctc aatgcccctg gaatggaga gcaaggccat ttctgatgcc    1620
cagatcactg catcctctta cttcaccaac atgtttgcca cctggtcacc atcaaaagcc    1680
aggctgcacc tccagggaag aagcaatgcc tggagacccc aggtcaacaa cccaaaggaa    1740
tggctgcaag tggacttcca aagacaatg aaagtcactg gggtgacaac ccagggggtc    1800
aagtctctgc tcacctcaat gtatgtgaag gagttcctga tctcttcctc acaggatggc    1860
caccagtgga cactcttctt ccagaatggc aaagtcaagg tgttccaggg caaccaggac    1920
tctttcacac ctgtggtgaa ctcactggac ccccccctcc tgacaagata cctgagaatt    1980
cacccccagt cttgggtcca ccagattgcc ctgagaatgg aagtcctggg atgtgaggca    2040
caagacctgt ac                                                        2052
```

<210> SEQ ID NO 26
<211> LENGTH: 4332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgcagattg agctgtccac ctgcttcttt ctgtgcctgc tgagattctg cttctctgcc     60
accaggagat actacctggg ggctgtggaa cttttcttggg actacatgca gtctgacctg    120
ggagagctgc ctgtggatgc caggttccca cccagagtgc ccaagtcctt cccattcaac    180
acctctgtgg tctacaagaa gacactcttt gtggaattca ctgaccacct gttcaacatt    240
gcaaaaccca gaccccctg gatgggactc ctgggaccca ccattcaggc tgaggtgtat    300
gacactgtgg tcatcacct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcaggaa    600 ggatccctgg ccaaggagaa acccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840 acaaccctg aagtgcactc catttttcctg gagggacaca ccttcctggt caggaaccac    900
agacaagcct ctctggagat ctctcccatc accttcctca ctgcacagac actgctgatg    960
```

```
gaccttggac agttcctgct gttctgccac atctcttccc accagcatga tggcatggaa    1020
gcctatgtca aggtggactc atgccctgag gaaccacagc tcaggatgaa gaacaatgag    1080
gaggctgagg actatgatga tgacctgact gactctgaga tggatgtggt cagatttgat    1140
gatgacaact ctccatcctt cattcagatc aggtctgtgg caaagaaaca ccccaagaca    1200
tgggtgcact acattgctgc tgaggaagag gactgggact atgcaccact ggtcctggcc    1260
cctgatgaca ggagctacaa gtctcagtac ctcaacaatg gcccacaaag aattggaaga    1320
aagtacaaga aagtcagatt catggcctac actgatgaaa ccttcaagac aagagaagcc    1380
attcagcatg agtctggcat tctgggacca ctcctgtatg gggaagtggg agacaccctg    1440
ctcatcatct tcaagaacca ggcctccagg ccctacaaca tctacccaca tggcatcact    1500
gatgtcaggc cctgtacag caggagactg ccaaaagggg tgaaacacct caaggacttc    1560
cccattctgc ctggagagat cttcaagtac aagtggactg tcactgtgga ggatggacca    1620
acaaagtctg accccaggtg cctcaccaga tactactcct cttttgtgaa catggagaga    1680
gacctggcat ctggactgat tggaccactg ctcatctgct acaaggagtc tgtggaccag    1740
agaggcaacc agatcatgtc tgacaagaga aatgtgattc tgttctctgt ctttgatgag    1800
aacagatcat ggtacctgac tgagaacatt cagagattcc tgcccaaccc tgctggggtg    1860
caactggaag accctgagtt ccaggcaagc aacatcatgc actccatcaa tggctatgtg    1920
tttgactctc tccagctttc tgtctgcctg catgaggtgg cctactggta cattctttct    1980 attgggcac aaactgactt cctttctgtc ttcttctctg atacaccctt caagcacaag    2040
atggtgtatg aggacaccct gacactcttc ccattctctg ggaaactgt gttcatgagc    2100 atggagaacc ctggactgtg gattctggga tgccacaact ctgacttcag aaacagggga    2160
atgactgcac tgctcaaagt ctcctcctgt gacaagaaca ctggggacta ctatgaggac    2220
tcttatgagg acatctctgc ctacctgctc agcaagaaca atgccattga gcccagagag    2280
atcaccagga caaccctcca gtctgaccag gaagagattg actatgatga caccatttct    2340
gtggagatga agaaggagga cttgacatc tatgatgagg acgagaacca gtctccaaga    2400
tcattccaga agaagacaag acactacttc attgctgctg tggaaagact gtgggactat    2460
ggcatgtctt cctctcccca tgtcctcagg aacagggcac agtctggctc tgtgccacag    2520
ttcaagaaag tggtcttcca ggagttcact gatggctcat tcacccagcc cctgtacaga    2580
ggggaactga atgagcacct gggactcctg ggaccataca tcagggctga ggtggaagac    2640
aacatcatgg tgacattcag aaaccaggcc tccaggccct acagcttcta ctcttccctc    2700
atcagctatg aggaagacca gagacaaggg gctgagccaa gaaagaactt tgtgaaaccc    2760
aatgaaacca agacctactt ctggaaagtc cagcaccaca tggcacccac caaggatgag    2820
tttgactgca aggcctgggc atacttctct gatgtggacc tggagaaaga tgtgcactct    2880
ggcctgattg gccactcct ggtctgccac accaacaccc tgaaccctgc acatggaagg    2940
caagtgactg tgcaggagtt tgccctcttc ttcaccatct ttgatgaaac caagtcatgg    3000
tacttcactg agaacatgga gagaaactgc agagcaccat gcaacattca gatggaagac    3060
cccaccttca aggagaacta caggttccat gccatcaatg gctacatcat ggacacccctg    3120 cctgggcttg tcatggcaca ggaccagaga atcagatggt acctgctttc tatgggatcc    3180
aatgagaaca ttcactccat ccacttctct gggcatgtct tcactgtgag aaagaaggag    3240
gaatacaaga tggcccctgta caacctctac cctgggtct ttgagactgt ggagatgctg    3300
```

```
ccctccaaag ctggcatctg gagggtggaa tgcctcattg ggagcacct gcatgctggc      3360 atgtcaaccc tgttcctggt ctacagcaac aagtgccaga cacccctggg aatggcctct      3420
ggccacatca gggacttcca gatcactgcc tctggccagt atggccagtg ggcacccaaa      3480
ctggccaggc tccactactc tggctccatc aatgcatggt caaccaagga gccattctct      3540
tggatcaagg tggacctgct ggcacccatg atcattcatg catcaagac acagggggca      3600 agacagaaat tctcctctct gtacatctca cagttcatca tcatgtactc tctggatggc      3660
aagaagtggc agacatacag aggcaactcc actggcaccc tcatggtctt ctttggcaat      3720
gtggacagct ctggcatcaa gcacaacatc ttcaaccctc ccatcattgc cagatacatc      3780
aggctgcacc ccacccacta ctcaatcaga tcaaccctca ggatggaact gatgggatgt      3840
gacctgaact cctgctcaat gcccctggga atggagagca aggccatttc tgatgcccag      3900
atcactgcat cctcttactt caccaacatg tttgccacct ggtcaccatc aaaagccagg      3960
ctgcacctcc agggaagaag caatgcctgg agacccagg tcaacaaccc aaaggaatgg      4020
ctgcaagtgg acttccagaa gacaatgaaa gtcactgggg tgacaaccca gggggtcaag      4080
tctctgctca cctcaatgta tgtgaaggag ttcctgatct cttcctcaca ggatggccac      4140
cagtggacac tcttcttcca gaatggcaaa gtcaaggtgt tccagggcaa ccaggactct      4200
ttcacacctg tggtgaactc actggacccc cccctcctga caagatacct gagaattcac      4260
ccccagtctt gggtccacca gattgccctg agaatggaag tcctgggatg tgaggcacaa      4320
gacctgtact ga                                                          4332
```

<210> SEQ ID NO 27
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 27

```
atgcagattg agctgtccac ctgcttcttt ctgtgcctgc tgagattctg cttctctgcc       60
accaggagat actacctggg ggctgtggaa ctttcttggg actacatgca gtctgacctg      120
ggagagctgc ctgtggatgc caggttccca cccagagtgc ccaagtcctt cccattcaac      180
acctctgtgg tctacaagaa gacactcttt gtggaattca ctgaccacct gttcaacatt      240
gcaaaaccca gaccaccctg gatgggactc ctgggaccca ccattcaggc tgaggtgtat      300
gacactgtgg tcatcaccct caagaacatg gcatcccacc tgtgtctct gcatgctgtg      360 ggagtctcat actggaaagc ctctgaaggg gctgagtatg atgaccagac atcccagaga      420
gagaaagagg atgacaaggt gttccctggg ggatctcaca cctatgtgtg caagtcctc      480 aaggagaatg gacccatggc atctgaccca ctctgcctga catactccta cctttctcat      540
gtggacctgg tcaaggacct caactctgga ctgattgggg cactgctggt gtgcagggaa      600
ggatccctgg ccaaggagaa acccagaca ctgcacaagt tcattctcct gtttgctgtc      660
tttgatgagg gcaagtcttg gcactctgaa acaaagaact ccctgatgca agacagggat      720
gctgcctctg ccagggcatg gcccaagatg cacactgtga atggctatgt gaacagatca      780
ctgcctggac tcattggctg ccacaggaaa tctgtctact ggcatgtgat tggcatgggg      840 acaaccctg aagtgcactc catttttcct gagggacaca ccttcctggt caggaaccac      900
agacaagcct ctctggagat ctctcccatc accttcctca ctgcacagac actgctgatg      960
```

-continued

```
gaccttggac agttcctgct gttctgccac atctcttccc accagcatga tggcatggaa    1020
gcctatgtca aggtggactc atgcctgag gaaccacagc tcaggatgaa gaacaatgag     1080
gaggctgagg actatgatga tgacctgact gactctgaga tggatgtggt cagatttgat    1140
gatgacaact ctccatcctt cattcagatc aggtctgtgg caaagaaaca ccccaagaca    1200
tgggtgcact acattgctgc tgaggaagag gactgggact atgcaccact ggtcctggcc    1260
cctgatgaca ggagctacaa gtctcagtac ctcaacaatg gcccacaaag aattggaaga    1320
aagtacaaga aagtcagatt catggcctac actgatgaaa ccttcaagac aagagaagcc    1380
attcagcatg agtctggcat tctgggacca ctcctgtatg gggaagtggg agacaccctg    1440
ctcatcatct tcaagaacca ggcctccagg ccctacaaca tctacccaca tggcatcact    1500
gatgtcaggc cctgtacag caggagactg ccaaaagggg tgaaacacct caaggacttc      1560
cccattctgc ctggagagat cttcaagtac aagtggactg tcactgtgga ggatggacca    1620
acaaagtctg accccaggtg cctcaccaga tactactcct cttttgtgaa catggagaga    1680
gacctggcat ctggactgat tggaccactg ctcatctgct acaaggagtc tgtggaccag    1740
agaggcaacc agatcatgtc tgacaagaga aatgtgattc tgttctctgt ctttgatgag    1800
aacagatcat ggtacctgac tgagaacatt cagagattcc tgcccaaccc tgctggggtg    1860
caactggaag accctgagtt ccaggcaagc aacatcatgc actccatcaa tggctatgtg    1920
tttgactctc tccagctttc tgtctgcctg catgaggtgg cctactggta cattcttttct    1980 attggggcac aaactgactt cctttctgtc ttcttctctg atacaccttt caagcacaag    2040
atggtgtatg aggacaccct gacactcttc ccattctctg gggaaactgt gttcatgagc    2100
atggagaacc ctggactgtg gattctggga tgccacaact ctgacttcag aaacagggga    2160
atgactgcac tgctcaaagt ctcctcctgt gacaagaaca ctgggactga ctatgaggac    2220
tcttatgagg acatctctgc ctacctgctc agcaagaaca atgccattga gcccagaagc    2280
ttctctcaga attccagaca ccccagcacc agggagatca ccaggacaac cctccagtct    2340
gaccaggaag agattgacta tgatgacacc atttctgtgg agatgaagaa ggaggacttt    2400
gacatctatg atgaggacga gaaccagtct ccaagatcat tccagaagaa gacaagacac    2460
tacttcattg ctgctgtgga aagactgtgg gactatggca tgtcttcctc tcccatgtc      2520 ctcaggaaca gggcacagtc tggctctgtg ccacagttca gaaagtggt cttccaggag     2580 ttcactgatg gctcattcac ccagccctg tacagaggg aactgaatga gcacctggga       2640
ctcctgggac catacatcag ggctgaggtg aagacaaca tcatggtgac attcagaaac     2700
caggcctcca ggccctacag cttctactct tccctcatca gctatgagga agaccagaga    2760
caaggggctg agccaagaaa gaactttgtg aaacccaatg aaaccaagac ctacttctgg    2820
aaagtccagc accacatggc acccaccaag gatgagtttg actgcaaggc ctgggcatac    2880
ttctctgatg tggacctgga gaagatgtg cactctggcc tgattggccc actcctggtc      2940
tgccacacca acacctgaa ccctgcacat ggaaggcaag tgactgtgca ggagtttgcc      3000
ctcttcttca ccatctttga tgaaaccaag tcatggtact tcactgagaa catggagaga    3060
aactgcagag caccatgcaa cattcagatg gaagacccca ccttcaagga gaactacagg    3120
ttccatgcca tcaatggcta catcatggac accctgcctg gcttgtcat ggcacaggac       3180 cagagaatca gatggtacct gcttctctatg ggatccaatg agaacattca ctccatccac    3240
ttctctgggc atgtcttcac tgtgagaaag aaggaggaat acaagatggc cctgtacaac    3300
ctctaccctg ggtctttga gactgtggag atgctgccct ccaaagctgg catctggagg    3360
```

| | |
|---|---|
| gtggaatgcc tcattgggga gcacctgcat gctggcatgt caaccctgtt cctggtctac | 3420 |
| agcaacaagt gccagacacc cctgggaatg gcctctggcc acatcaggga cttccagatc | 3480 |
| actgcctctg gccagtatgg ccagtgggca cccaaactgg ccaggctcca ctactctggc | 3540 |
| tccatcaatg catggtcaac caaggagcca ttctcttgga tcaaggtgga cctgctggca | 3600 |
| cccatgatca ttcatggcat caagacacag ggggcaagac agaaattctc ctctctgtac | 3660 |
| atctcacagt tcatcatcat gtactctctg gatggcaaga agtggcagac atacagaggc | 3720 |
| aactccactg gcaccctcat ggtcttcttt gcaatgtgg acagctctgg catcaagcac | 3780 |
| aacatcttca accctcccat cattgccaga tacatcaggc tgcaccccac ccactactca | 3840 |
| atcagatcaa ccctcaggat ggaactgatg ggatgtgacc tgaactcctg ctcaatgccc | 3900 |
| ctgggaatgg agagcaaggc catttctgat gcccagatca ctgcatcctc ttacttcacc | 3960 |
| aacatgtttg ccacctggtc accatcaaaa gccaggctgc acctccaggg aagaagcaat | 4020 |
| gcctggagac cccaggtcaa caacccaaag gaatggctgc aagtggactt ccagaagaca | 4080 |
| atgaaagtca ctggggtgac aacccagggg gtcaagtctc tgctcacctc aatgtatgtg | 4140 |
| aaggagttcc tgatctcttc ctcacaggat ggccaccagt ggacactctt cttccagaat | 4200 |
| ggcaaagtca aggtgttcca gggcaaccag gactcttca cacctgtggt gaactcactg | 4260 |
| gaccccccc tcctgacaag ataccctgaga attcacccc agtcttgggt ccaccagatt | 4320 |
| gccctgagaa tggaagtcct gggatgtgag gcacaagacc tgtactga | 4368 |

<210> SEQ ID NO 28
<211> LENGTH: 4332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

| | |
|---|---|
| atgcagattg agctgagcac ctgcttcttc ctgtgcctgc tgaggttctg cttctctgcc | 60 |
| accaggagat actacctggg cgccgtggag ctgagctggg actacatgca gtctgacctg | 120 |
| ggcgagctgc ctgtggacgc caggttcccc ccagagtgc caagagctt ccccttcaac | 180 |
| acctcagtgg tgtacaagaa gaccctgttc gtggagttca ccgaccacct gttcaacatc | 240 |
| gccaagccca ggccccctg gatgggcctg ctgggcccca ccatccaggc cgaggtgtac | 300 |
| gacaccgtgg tgatcaccct gaagaacatg gccagccacc cgtgagcct gcacgccgtg | 360 |
| ggcgtgagct actggaaggc ctctgagggc gccgagtatg acgaccagac cagccagagg | 420 |
| gagaaggagg acgacaaggt gttccccggc ggcagccaca cctacgtgtg gcaggtgctg | 480 |
| aaggagaacg ccccatggc cagcgacccc ctgtgcctga cctacagcta cctgagccac | 540 |
| gtggacctgg tgaaggacct gaactctggc ctgatcggcg ccctgctggt gtgcagggag | 600 |
| ggcagcctgg ccaaggagaa gacccagacc ctgcacaagt catcctgct gttcgccgtg | 660 |
| ttcgatgagg gcaagagctg gcacagcgag accaagaaca gcctgatgca ggacagggat | 720 |
| gccgcctctg ccagggcctg gcccaagatg cacaccgtga acggctacgt gaacaggagc | 780 |
| ctgcccggcc tgatcggctg ccacaggaag tctgtgtact ggcacgtgat cggcatgggc | 840 |
| accaccccg aggtgcacag catcttcctg gagggccaca ccttcctggt gaggaaccac | 900 |
| aggcaggcca gcctggagat cagccccatc accttcctga ccgcccagac cctgctgatg | 960 |
| gacctgggcc agttcctgct gttctgccac atcagcagcc accagcacga cggcatggag | 1020 |

```
gcctacgtga aggtggacag ctgccccgag gagccccagc tgaggatgaa gaacaacgag      1080
gaggccgagg actatgatga tgacctgacc gactctgaga tggacgtggt gaggtttgat      1140
gatgacaaca gccccagctt catccagatc aggtctgtgg ccaagaagca ccccaagacc      1200
tgggtgcact acatcgccgc cgaggaggag gactgggact acgcccccct ggtgctggcc      1260
cccgacgaca ggagctacaa gagccagtac ctgaacaacg gcccccagag gatcggcagg      1320
aagtacaaga aggtcagatt catggcctac accgacgaga ccttcaagac cagggaggcc      1380
atccagcacg agtctggcat cctgggcccc ctgctgtacg gcgaggtggg cgacaccctg      1440
ctgatcatct tcaagaacca ggccagcagg ccctacaaca tctaccccca cggcatcacc      1500
gatgtgaggc ccctgtacag caggaggctg cccaagggcg tgaagcacct gaaggacttc      1560
cccatcctgc ccggcgagat cttcaagtac aagtggaccg tgaccgtgga ggatggcccc      1620
accaagtctg accccaggtg cctgaccagg tactacagca gcttcgtgaa catggagagg      1680
gacctggcct ctggcctgat cggccccctg ctgatctgct acaaggagag cgtggaccag      1740
aggggcaacc agatcatgtc tgacaagagg aacgtgatcc tgttctctgt gttcgatgag      1800
aacaggagct ggtatctgac cgagaacatc cagaggttcc tgcccaaccc cgccggcgtg      1860
cagctggagg accccgagtt ccaggccagc aacatcatgc acagcatcaa cggctacgtg      1920
ttcgacagcc tgcagctgtc tgtgtgcctg cacgaggtgg cctactggta catcctgagc      1980
atcggcgccc agaccgactt cctgtctgtg ttcttctctg gctacacctt caagcacaag      2040
atggtgtacg aggacaccct gaccctgttc cccttcagcg gcgagaccgt gttcatgagc      2100
atggagaacc ccggcctgtg gatcctgggc tgccacaaca gcgacttcag gaacaggggc      2160
atgaccgccc tgctgaaagt cagcagctgc gacaagaaca ccggcgacta ctacgaggac      2220
agctacgagg acatcagcgc ctacctgctg agcaagaaca acgccatcga gcccagggag      2280
atcaccagga ccaccctgca gagcgaccag gaggagatcg actatgatga ccaccatcagc      2340 gtggagatga agaaggagga cttcgacatc tacgacgagg acgagaacca gagccccagg      2400
agcttccaga gaagaccag gcactacttc atcgccgccg tggagaggct gtgggactat      2460
ggcatgagca gcagccccca cgtgctgagg aacagggccc agagcggcag cgtgccccag      2520
ttcaagaagg tggtgttcca ggagttcacc gacggcagct tcacccagcc cctgtacaga      2580
ggcgagctga cgagcacct gggcctgctg gcccctaca tcagggccga ggtggaggac      2640
aacatcatgg tgaccttcag gaaccaggcc agcaggccct acagcttcta cagcagcctg      2700
atcagctacg aggaggacca gaggcagggc gccgagccca ggaagaactt cgtgaagccc      2760
aacgagacca agacctactt ctggaaggtg cagcaccaca tggccccac caaggacgag      2820 ttcgactgca aggcctgggc ctacttctct gatgtggacc tggagaagga cgtgcacagc      2880
ggcctgatcg gccccctgct ggtgtgccac accaacaccc tgaacccgc ccacggcagg      2940 caggtgaccg tgcaggagtt cgccctgttc ttcaccatct tcgacgagac caagagctgg      3000
tacttcaccg agaacatgga gaggaactgc agggcccct gcaacatcca gatggaggac      3060
cccaccttca aggagaacta caggttccac gccatcaacg gctacatcat ggacaccctg      3120
cccggcctgg tgatggccca ggaccagagg atcaggtggt atctgctgag catgggcagc      3180
aacgagaaca tccacagcat ccacttcagc ggccacgtgt tcaccgtgag gaagaaggag      3240
gagtacaaga tggcccctgta caacctgtac cccggcgtgt tcgagaccgt ggagatgctg      3300
cccagcaagg ccggcatctg gagggtggag tgcctgatcg gcgagcacct gcacgccggc      3360
```

-continued

| | |
|---|---|
| atgagcaccc tgttcctggt gtacagcaac aagtgccaga ccccctggg catggccagc | 3420 |
| ggccacatca gggacttcca gatcaccgcc tctggccagt acggccagtg ggcccccaag | 3480 |
| ctggccaggc tgcactacag cggcagcatc aacgcctgga gcaccaagga gcccttcagc | 3540 |
| tggatcaagg tggacctgct ggcccccatg atcatccacg gcatcaagac ccagggcgcc | 3600 |
| aggcagaagt tcagcagcct gtacatcagc cagttcatca tcatgtacag cctggacggc | 3660 |
| aagaagtggc agacctacag gggcaacagc accggcaccc tgatggtgtt cttcggcaac | 3720 |
| gtggacagca gcggcatcaa gcacaacatc ttcaaccccc ccatcatcgc caggtacatc | 3780 |
| aggctgcacc ccacccacta cagcatcagg agcaccctgc ggatggaact gatgggctgc | 3840 |
| gacctgaaca gctgcagcat gcccctgggc atggagagca aggccatctc tgacgcccag | 3900 |
| atcaccgcca gcagctactt caccaacatg ttcgccacct ggagcccag caaggccagg | 3960 |
| ctgcacctgc agggcaggag caacgcctgg aggcccagg tgaacaaccc caaggagtgg | 4020 |
| ctgcaggtgg acttccagaa gaccatgaag gtgaccggcg tgaccaccca gggcgtgaag | 4080 |
| agcctgctga ccagcatgta cgtgaaggag ttcctgatca gcagcagcca ggacggccac | 4140 |
| cagtggaccc tgttcttcca gaacggcaaa gtgaaggtgt tccagggcaa ccaggacagc | 4200 |
| ttcacccccg tggtgaacag cctggacccc ccctgctga ccaggtatct gaggatccac | 4260 |
| ccccagagct gggtgcacca gatcgccctg agaatggaag tgctgggatg cgaggcccag | 4320 |
| gacctgtact ga | 4332 |

<210> SEQ ID NO 29
<211> LENGTH: 4368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

| | |
|---|---|
| atgcagattg agctgagcac ctgcttcttc ctgtgcctgc tgaggttctg cttctctgcc | 60 |
| accaggagat actacctggg cgccgtggag ctgagctggg actacatgca gtctgacctg | 120 |
| ggcgagctgc ctgtggacgc caggttcccc cccagagtgc ccaagagctt ccccttcaac | 180 |
| acctcagtgg tgtacaagaa gacccctgttc gtggagttca ccgaccacct gttcaacatc | 240 |
| gccaagccca ggccccctg gatgggcctg ctgggccca ccatccaggc cgaggtgtac | 300 |
| gacaccgtgg tgatcaccct gaagaacatg gccagccacc ccgtgagcct gcacgccgtg | 360 |
| ggcgtgagct actggaaggc ctctgagggc gccgagtatg acgaccagac cagcagagg | 420 |
| gagaaggagg acgacaaggt gttccccggc ggcagccaca cctacgtgtg gcaggtgctg | 480 |
| aaggagaacg gccccatggc cagcgacccc ctgtgcctga cctacagcta cctgagccac | 540 |
| gtggacctgg tgaaggacct gaactctggc ctgatcggcg ccctgctggt gtgcagggag | 600 |
| ggcagcctgg ccaaggagaa gacccagacc tgcacaagt tcatcctgct gttcgccgtg | 660 |
| ttcgatgagg gcaagagctg gcacagcgag accaagaaca gcctgatgca ggacagggat | 720 |
| gccgcctctg ccagggcctg gcccaagatg cacaccgtga acggctacgt gaacaggagc | 780 |
| ctgcccggcc tgatcggctg ccacaggaag tctgtgtact ggcacgtgat cggcatgggc | 840 |
| accaccccg aggtgcacag catcttcctg gagggccaca ccttcctggt gaggaaccac | 900 |
| aggcaggcca gctggagat cagccccatc accttcctga ccgcccagac cctgctgatg | 960 |
| gacctgggcc agttcctgct gttctgccac atcagcagcc accagcacga cggcatggag | 1020 |

| | |
|---|---|
| gcctacgtga aggtggacag ctgccccgag gagccccagc tgaggatgaa gaacaacgag | 1080 |
| gaggccgagg actatgatga tgacctgacc gactctgaga tggacgtggt gaggtttgat | 1140 |
| gatgacaaca gccccagctt catccagatc aggtctgtgg ccaagaagca ccccaagacc | 1200 |
| tgggtgcact acatcgccgc cgaggaggag gactgggact acgccccct ggtgctggcc | 1260 |
| cccgacgaca ggagctacaa gagccagtac ctgaacaacg ccccagag atcggcagg | 1320 |
| aagtacaaga aggtcagatt catggcctac accgacgaga ccttcaagac cagggaggcc | 1380 |
| atccagcacg agtctggcat cctgggcccc ctgctgtacg gcgaggtggg cgacaccctg | 1440 |
| ctgatcatct tcaagaacca ggccagcagg ccctacaaca tctacccca cggcatcacc | 1500 |
| gatgtgaggc ccctgtacag caggaggctg cccaagggcg tgaagcacct gaaggacttc | 1560 |
| cccatcctgc ccggcgagat cttcaagtac aagtggaccg tgaccgtgga ggatggcccc | 1620 |
| accaagtctg accccaggtg cctgaccagg tactacagca gcttcgtgaa catggagagg | 1680 |
| gacctggcct ctggcctgat cggccccctg ctgatctgct acaaggagag cgtggaccag | 1740 |
| aggggcaacc agatcatgtc tgacaagagg aacgtgatcc tgttctctgt gttcgatgag | 1800 |
| aacaggagct ggtatctgac cgagaacatc cagaggttcc tgcccaaccc cgccggcgtg | 1860 |
| cagctggagg accccgagtt ccaggccagc aacatcatgc acagcatcaa cggctacgtg | 1920 |
| ttcgacagcc tgcagctgtc tgtgtgcctg cacgaggtgg cctactggta catcctgagc | 1980 |
| atcggcgccc agaccgactt cctgtctgtg ttcttctctg gctacacctt caagcacaag | 2040 |
| atggtgtacg aggacaccct gaccctgttc cccttcagcg gcgagaccgt gttcatgagc | 2100 |
| atggagaacc ccgcctgtg gatcctgggc tgccacaaca gcgacttcag gaacaggggc | 2160 |
| atgaccgccc tgctgaaagt cagcagctgc gacaagaaca ccggcgacta ctacgaggac | 2220 |
| agctacgagg acatcagcgc ctacctgctg agcaagaaca cgccatcga gcccaggagc | 2280 |
| ttcagccaga actccagaca ccccagcacc agggagatca ccaggaccac cctgcagagc | 2340 |
| gaccaggagg agatcgacta tgatgacacc atcagcgtgg agatgaagaa ggaggacttc | 2400 |
| gacatctacg acgaggacga gaaccagagc cccaggagct tccagaagaa gaccaggcac | 2460 |
| tacttcatcg ccgccgtgga gaggctgtgg gactatggca tgagcagcag cccccacgtg | 2520 |
| ctgaggaaca gggcccagag cggcagcgtg ccccagttca gaaggtggt gttccaggag | 2580 |
| ttcaccgacg gcagcttcac ccagcccctg tacagaggcg agctgaacga gcacctgggc | 2640 |
| ctgctgggcc cctacatcag ggccgaggtg gaggacaaca tcatggtgac cttcaggaac | 2700 |
| caggccagca ggccctacag cttctacagc agcctgatca gctacgagga ggaccagagg | 2760 |
| cagggcgccg agcccaggaa gaacttcgtg aagcccaacg agaccaagac ctacttctgg | 2820 |
| aaggtgcagc accacatggc ccccaccaag gacgagttcg actgcaaggc ctgggcctac | 2880 |
| ttctctgatg tggacctgga aaggacgtg cacagcggcc tgatcggccc cctgctggtg | 2940 |
| tgccacacca cacccctgaa ccccgcccac ggcaggcagg tgaccgtgca ggagttcgcc | 3000 |
| ctgttcttca ccatcttcga cgagaccaag agctggtact tcaccgagaa catggagagg | 3060 |
| aactgcaggg ccccctgcaa catccagatg gaggacccca ccttcaagga aactacagg | 3120 |
| ttccacgcca tcaacggcta catcatggac accctgcccg gctggtgat ggcccaggac | 3180 |
| cagaggatca ggtggtatct gctgagcatg ggcagcaacg agaacatcca cagcatccac | 3240 |
| ttcagcggcc acgtgttcac cgtgaggaag aaggaggagt acaagatggc cctgtacaac | 3300 |
| ctgtaccccg gcgtgttcga gaccgtggag atgctgccca gcaaggccgg catctggagg | 3360 |
| gtggagtgcc tgatcggcga gcacctgcac gccggcatga gcaccctgtt cctggtgtac | 3420 |

```
agcaacaagt gccagacccc cctgggcatg gccagcggcc acatcaggga cttccagatc    3480
accgcctctg gccagtacgg ccagtgggcc cccaagctgg ccaggctgca ctacagcggc    3540
agcatcaacg cctggagcac caaggagccc ttcagctgga tcaaggtgga cctgctggcc    3600
cccatgatca tccacggcat caagacccag ggcgccaggc agaagttcag cagcctgtac    3660
atcagccagt tcatcatcat gtacagcctg gacggcaaga gtggcagac  ctacaggggc    3720 aacagcaccg gcaccctgat ggtgttcttc ggcaacgtgg acagcagcgg catcaagcac    3780
aacatcttca acccccccat catcgccagg tacatcaggc tgcaccccac ccactacagc    3840
atcaggagca ccctgcggat ggaactgatg ggctgcgacc tgaacagctg cagcatgccc    3900
ctgggcatgg agagcaaggc catctctgac gcccagatca ccgccagcag ctacttcacc    3960
aacatgttcg ccacctggag ccccagcaag gccaggctgc acctgcaggg caggagcaac    4020
gcctggaggc cccaggtgaa caaccccaag gagtggctgc aggtggactt ccagaagacc    4080
atgaaggtga ccggcgtgac cacccagggc gtgaagagcc tgctgaccag catgtacgtg    4140
aaggagttcc tgatcagcag cagccaggac ggccaccagt ggaccctgtt cttccagaac    4200
ggcaaagtga aggtgttcca gggcaaccag gacagcttca cccccgtggt gaacagcctg    4260 gaccccccc  tgctgaccag gtatctgagg atccaccccc agagctgggt gcaccagatc    4320
gccctgagaa tggaagtgct gggatgcgag gcccaggacc tgtactga             4368
```

```
<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Phe Ser Gln Asn Pro Pro Val Leu Lys Arg His Gln Arg
1               5                   10

<210> SEQ ID NO 31
<211> LENGTH: 24
<212> TYPE: PRT
<213> ORGANISM: Sus sp.

<400> SEQUENCE: 31

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 32
<211> LENGTH: 16
<212> TYPE: PRT
<213> ORGANISM: Sus sp.

<400> SEQUENCE: 32

Ser Phe Ser Gln Asn Ser Arg His Gln Ala Tyr Arg Tyr Arg Arg Gly
1               5                   10                  15

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 33

Thr Thr Tyr Val Asn Arg Ser Leu
1               5

<210> SEQ ID NO 34
<211> LENGTH: 7
<212> TYPE: PRT
<213> ORGANISM: Homo sapiens

<400> SEQUENCE: 34

Pro Gln Leu Arg Met Lys Asn
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Asp Gln Arg Gly Asn Gln
1               5

<210> SEQ ID NO 36
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agcttcagcc agaatgtgag caacaatgtg agcaacaatg ccaccaataa tgctaccaac    60
ccacctgtcc tgaaacgcca ccagagg                                       87

<210> SEQ ID NO 37
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcttcagcc agaatgtgag caacaatgcc accaacaatg tgagcaaccc acctgtcctg    60
aaacgccacc agagg                                                    75

<210> SEQ ID NO 38
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agcttcagcc agaatgtgag caataatgcc accaacccac ctgtcctgaa acgccaccag    60
agg                                                                 63

<210> SEQ ID NO 39

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agcttcagcc agaatgtgag caataatcca cctgtcctga aacgccacca gagg          54

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agcttcagcc agaataggag cctgccacct gtcctgaaac gccaccagag g             51

<210> SEQ ID NO 41
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agcttcagcc agaatgccac taatgtgtct aacaactctg ctacctctgc tgactctgct   60
gtgagcccac ctgtcctgaa acgccaccag agg                                93

<210> SEQ ID NO 42
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agcttcagcc agaatgccac caactatgtg aacaggagcc tgccacctgt cctgaaacgc   60
caccagagg                                                           69

<210> SEQ ID NO 43
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
agcttcagcc agaatgccac caactatgtg aacaggagcc tgtctgccac ctctgctgac   60
tctgctgtga gccagaatcc acctgtcctg aaacgccacc agagg                  105

<210> SEQ ID NO 44
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
```
agcttcagcc agaatgtgag caacaatgtg agcaatgctg tgtctgctgt gtctgctcca    60
cctgtcctga aacgccacca gagg                                           84

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agcttcagcc agaatatcac tgtggcctct gccacctcta acatcactgt ggcctctgct    60
gacccacctg tcctgaaacg ccaccagagg                                     90

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agcttcagcc agaatatcac tgtgaccaac atcactgtga ctgccccacc tgtcctgaaa    60
cgccaccaga gg                                                        72

<210> SEQ ID NO 47
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agcttcagcc agaatcagac tgtgaccaac atcactgtga ctgccccacc tgtcctgaaa    60
cgccaccaga gg                                                        72

<210> SEQ ID NO 48
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agcttcagcc agaatgccac taatgtgtct aacaacagca acaccagcaa tgacagcaat    60
gtgtctccac ctgtcctgaa acgccaccag agg                                 93

<210> SEQ ID NO 49
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgcagattg agctgtccac ctgcttcttt ctgtgcctgc tgagattctg cttctctgcc    60
accaggagat actacctggg ggctgtggaa ctttcttggg actacatgca gtctgacctg    120

```
ggagagctgc ctgtggatgc caggttccca cccagagtgc ccaagtcctt cccattcaac    180
acctctgtgg tctacaagaa gacactcttt gtggaattca ctgaccacct gttcaacatt    240
gcaaaaccca gaccaccctg gatgggactc ctgggaccca ccattcaggc tgaggtgtat    300
gacactgtgg tcatcaccct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
gtggacctgg tcaaggacct caactctgga ctgattgggg cactgctggt gtgcagggaa    600
ggatccctgg ccaaggagaa acccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gtcctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga agtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattcttttct  1980
attggggcac aaactgactt ccttttctgtc ttcttctctg gatacacctt caagcacaag  2040
atggtgtatg aggacacccct gacactcttc ccattctctg gggaaactgt gttcatgagc  2100
atggagaacc tggactgtgg attctgggga tgccacaact ctgacttcag aaacagggga  2160
atgactgcac tgctcaaagt ctcctcctgt gacaagaaca ctggggacta ctatgaggac  2220
tcttatgagg acatctctgc ctacctgctc agcaagaaca atgccattga gcccagaagc  2280
ttctctcaga atccacctgt cctgaagaga caccagagag agatcaccag gacaaccctc  2340
cagtctgacc aggaagagat tgactatgat gacaccattt ctgtggagat gaagaaggag  2400
gactttgaca tctatgatga ggacgagaac cagtctccaa gatcattcca gaagaagaca  2460
```

```
agacactact tcattgctgc tgtggaaaga ctgtgggact atggcatgtc ttcctctccc    2520
catgtcctca ggaacagggc acagtctggc tctgtgccac agttcaagaa agtggtcttc    2580
caggagttca ctgatggctc attcacccag ccctgtaca gaggggaact gaatgagcac    2640
ctgggactcc tgggaccata catcagggct gaggtggaag acaacatcat ggtgacattc    2700
agaaaccagg cctccaggcc ctacagcttc tactcttccc tcatcagcta tgaggaagac    2760
cagagacaag gggctgagcc aagaaagaac tttgtgaaac ccaatgaaac caagacctac    2820
ttctggaaag tccagcacca catggcaccc accaaggatg agtttgactg caaggcctgg    2880
gcatacttct ctgatgtgga cctggagaaa gatgtgcact ctggcctgat tggcccactc    2940
ctggtctgcc acaccaacac cctgaaccct gcacatggaa ggcaagtgac tgtgcaggag    3000
tttgccctct tcttcaccat ctttgatgaa accaagtcat ggtacttcac tgagaacatg    3060
gagagaaact gcagagcacc atgcaacatt cagatggaag accccacctt caaggagaac    3120
tacaggttcc atgccatcaa tggctacatc atggacaccc tgcctgggct tgtcatggca    3180
caggaccaga gaatcagatg gtacctgctt tctatgggat ccaatgagaa cattcactcc    3240
atccacttct ctgggcatgt cttcactgtg agaagaagg aggaatacaa gatggccctg    3300
tacaacctct accctggggt cttttgagact gtggagatgc tgccctccaa agctggcatc    3360
tggagggtgg aatgcctcat tggggagcac ctgcatgctg gcatgtcaac cctgttcctg    3420
gtctacagca caagtgcca gacacccctg ggaatggcct ctggccacat cagggacttc    3480
cagatcactg cctctggcca gtatggccag tgggcaccca aactggccag gctccactac    3540
tctggctcca tcaatgcatg gtcaaccaag gagccattct cttggatcaa ggtggacctg    3600
ctggcaccca tgatcattca tggcatcaag acacaggggg caagacagaa attctcctct    3660
ctgtacatct cacagttcat catcatgtac tctctggatg gcaagaagtg gcagacatac    3720
agaggcaact ccactggcac cctcatggtc ttctttggca atgtggacag ctctggcatc    3780
aagcacaaca tcttcaaccc tcccatcatt gccagataca tcaggctgca ccccaccac    3840 tactcaatca gatcaaccct caggatggaa ctgatgggat gtgacctgaa ctcctgctca    3900
atgcccctgg aatggagag caaggccatt tctgatgccc agatcactgc atcctcttac    3960
ttcaccaaca tgtttgccac ctggtcacca tcaaaagcca ggctgcacct ccagggaaga    4020
agcaatgcct ggagacccca ggtcaacaac ccaaaggaat ggctgcaagt ggacttccag    4080
aagacaatga aagtcactgg ggtgacaacc cagggggtca agtctctgct cacctcaatg    4140
tatgtgaagg agttcctgat ctcttcctca caggatggcc accagtggac actcttcttc    4200
cagaatggca aagtcaaggt gttccagggc aaccaggact ctttcacacc tgtggtgaac    4260
tcactggacc ccccctcct gacaagatac ctgagaattc accccagtc ttgggtccac    4320 cagattgccc tgagaatgga agtcctggga tgtgaggcac aagacctgta ctga         4374
```

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 50

```
gtg agc aac aat gtg agc aac aat gcc acc aat aat gct acc aac        45
```

Val Ser Asn Asn Val Ser Asn Asn Ala Thr Asn Asn Ala Thr Asn
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ser Asn Asn Val Ser Asn Asn Ala Thr Asn Asn Ala Thr Asn
1               5                   10                  15

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 52 gtg agc aac aat gcc acc aac aat gtg agc aac                        33
Val Ser Asn Asn Ala Thr Asn Asn Val Ser Asn
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Ser Asn Asn Ala Thr Asn Asn Val Ser Asn
1               5                   10

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 54 gtg agc aat aat gcc acc aac                                        21
Val Ser Asn Asn Ala Thr Asn
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ser Asn Asn Ala Thr Asn

```
<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 56 gtg agc aat aat                                                        12
Val Ser Asn Asn
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Ser Asn Asn
1

<210> SEQ ID NO 58
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(9)

<400> SEQUENCE: 58 agg agc ctg                                                             9
Arg Ser Leu
1

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Leu
1

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 60
```

```
gcc act aat gtg tct aac aac tct gct acc tct gct gac tct gct gtg      48
Ala Thr Asn Val Ser Asn Asn Ser Ala Thr Ser Ala Asp Ser Ala Val
1               5                   10                  15 agc                                                                   51
Ser
```

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Ala Thr Asn Val Ser Asn Asn Ser Ala Thr Ser Ala Asp Ser Ala Val
1               5                   10                  15

Ser
```

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 62

```
gcc acc aac tat gtg aac agg agc ctg                                  27
Ala Thr Asn Tyr Val Asn Arg Ser Leu
1               5
```

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Ala Thr Asn Tyr Val Asn Arg Ser Leu
1               5
```

<210> SEQ ID NO 64
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(63)

<400> SEQUENCE: 64

```
gcc acc aac tat gtg aac agg agc ctg tct gcc acc tct gct gac tct      48
Ala Thr Asn Tyr Val Asn Arg Ser Leu Ser Ala Thr Ser Ala Asp Ser
1               5                   10                  15 gct gtg agc cag aat                                                   63
Ala Val Ser Gln Asn
                20
```

```
<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Thr Asn Tyr Val Asn Arg Ser Leu Ser Ala Thr Ser Ala Asp Ser
1               5                   10                  15

Ala Val Ser Gln Asn
            20

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(42)

<400> SEQUENCE: 66 gtg agc aac aat gtg agc aat gct gtg tct gct gtg tct gct           42
Val Ser Asn Asn Val Ser Asn Ala Val Ser Ala Val Ser Ala
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ser Asn Asn Val Ser Asn Ala Val Ser Ala Val Ser Ala
1               5                   10

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 68 atc act gtg gcc tct gcc acc tct aac atc act gtg gcc tct gct gac    48
Ile Thr Val Ala Ser Ala Thr Ser Asn Ile Thr Val Ala Ser Ala Asp
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Thr Val Ala Ser Ala Thr Ser Asn Ile Thr Val Ala Ser Ala Asp
1               5                   10                  15
```

```
<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 70 atc act gtg acc aac atc act gtg act gcc                        30
Ile Thr Val Thr Asn Ile Thr Val Thr Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Thr Val Thr Asn Ile Thr Val Thr Ala
1               5                   10

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 72 cag act gtg acc aac atc act gtg act gcc                        30
Gln Thr Val Thr Asn Ile Thr Val Thr Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Thr Val Thr Asn Ile Thr Val Thr Ala
1               5                   10

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 74
```

```
gcc act aat gtg tct aac aac agc aac acc agc aat gac agc aat gtg    48
Ala Thr Asn Val Ser Asn Asn Ser Asn Thr Ser Asn Asp Ser Asn Val
 1               5                  10                  15 tct                                                                51
Ser
```

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Ala Thr Asn Val Ser Asn Asn Ser Asn Thr Ser Asn Asp Ser Asn Val
 1               5                  10                  15

Ser
```

<210> SEQ ID NO 76
<211> LENGTH: 405
<212> TYPE: PRT
<213> ORGANISM: Homo sapiens

<400> SEQUENCE: 76

```
Met Pro Leu Leu Leu Tyr Thr Cys Leu Leu Trp Leu Pro Thr Ser Gly
 1               5                  10                  15

Leu Trp Thr Val Gln Ala Met Asp Pro Asn Ala Ala Tyr Val Asn Met
             20                  25                  30

Ser Asn His His Arg Gly Leu Ala Ser Ala Asn Val Asp Phe Ala Phe
         35                  40                  45

Ser Leu Tyr Lys His Leu Val Ala Leu Ser Pro Lys Lys Asn Ile Phe
     50                  55                  60

Ile Ser Pro Val Ser Ile Ser Met Ala Leu Ala Met Leu Ser Leu Gly
 65                  70                  75                  80

Thr Cys Gly His Thr Arg Ala Gln Leu Leu Gln Gly Leu Gly Phe Asn
                 85                  90                  95

Leu Thr Glu Arg Ser Glu Thr Glu Ile His Gln Gly Phe Gln His Leu
            100                 105                 110

His Gln Leu Phe Ala Lys Ser Asp Thr Ser Leu Glu Met Thr Met Gly
        115                 120                 125

Asn Ala Leu Phe Leu Asp Gly Ser Leu Glu Leu Leu Glu Ser Phe Ser
    130                 135                 140

Ala Asp Ile Lys His Tyr Tyr Glu Ser Glu Val Leu Ala Met Asn Phe
145                 150                 155                 160

Gln Asp Trp Ala Thr Ala Ser Arg Gln Ile Asn Ser Tyr Val Lys Asn
                165                 170                 175

Lys Thr Gln Gly Lys Ile Val Asp Leu Phe Ser Gly Leu Asp Ser Pro
            180                 185                 190

Ala Ile Leu Val Leu Val Asn Tyr Ile Phe Phe Lys Gly Thr Trp Thr
        195                 200                 205

Gln Pro Phe Asp Leu Ala Ser Thr Arg Glu Glu Asn Phe Tyr Val Asp
    210                 215                 220

Glu Thr Thr Val Val Lys Val Pro Met Met Leu Gln Ser Ser Thr Ile
225                 230                 235                 240

Ser Tyr Leu His Asp Ser Glu Leu Pro Cys Gln Leu Val Gln Met Asn
                245                 250                 255
```

-continued

```
Tyr Val Gly Asn Gly Thr Val Phe Phe Ile Leu Pro Asp Lys Gly Lys
                260                 265                 270

Met Asn Thr Val Ile Ala Ala Leu Ser Arg Asp Thr Ile Asn Arg Trp
            275                 280                 285

Ser Ala Gly Leu Thr Ser Ser Gln Val Asp Leu Tyr Ile Pro Lys Val
        290                 295                 300

Thr Ile Ser Gly Val Tyr Asp Leu Gly Asp Val Leu Glu Glu Met Gly
305                 310                 315                 320

Ile Ala Asp Leu Phe Thr Asn Gln Ala Asn Phe Ser Arg Ile Thr Gln
                325                 330                 335

Asp Ala Gln Leu Lys Ser Ser Lys Val Val His Lys Ala Val Leu Gln
            340                 345                 350

Leu Asn Glu Glu Gly Val Asp Thr Ala Gly Ser Thr Gly Val Thr Leu
        355                 360                 365

Asn Leu Thr Ser Lys Pro Ile Ile Leu Arg Phe Asn Gln Pro Phe Ile
370                 375                 380

Ile Met Ile Phe Asp His Phe Thr Trp Ser Ser Leu Phe Leu Ala Arg
385                 390                 395                 400

Val Met Asn Pro Val
                405

<210> SEQ ID NO 77
<211> LENGTH: 4
<212> TYPE: PRT
<213> ORGANISM: Homo sapiens

<400> SEQUENCE: 77

Asn Met Ser Asn
1

<210> SEQ ID NO 78
<211> LENGTH: 4
<212> TYPE: PRT
<213> ORGANISM: Homo sapiens

<400> SEQUENCE: 78

Asn Leu Thr Glu
1

<210> SEQ ID NO 79
<211> LENGTH: 4
<212> TYPE: PRT
<213> ORGANISM: Homo sapiens

<400> SEQUENCE: 79

Asn Lys Thr Gln
1

<210> SEQ ID NO 80
<211> LENGTH: 4
<212> TYPE: PRT
<213> ORGANISM: Homo sapiens

<400> SEQUENCE: 80

Asn Gly Thr Val
1

<210> SEQ ID NO 81
<211> LENGTH: 4
<212> TYPE: PRT
<213> ORGANISM: Homo sapiens
```

```
<400> SEQUENCE: 81

Asn Phe Ser Arg
1

<210> SEQ ID NO 82
<211> LENGTH: 4
<212> TYPE: PRT
<213> ORGANISM: Homo sapiens

<400> SEQUENCE: 82

Asn Leu Thr Ser
1

<210> SEQ ID NO 83
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Ser Lys Asn Asn Ala Ile Glu Pro Arg Ser Phe Ser Gln Asn Ala
1               5                   10                  15

Thr Asn Val Ser Asn Asn Ser Asn Thr Ser Asn Asp Ser Asn Val Ser
            20                  25                  30

Pro Pro Val Leu Lys Arg His Gln Arg
        35                  40

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asn Ala Thr Asn
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Val Ser Asn
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asn Asn Ser Asn
1
```

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asn Thr Ser Asn
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Asp Ser Asn
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asn Val Ser Pro
1

<210> SEQ ID NO 90
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

| | | | | |
|---|---|---|---|---|
| atgcagattg | agctgtccac | ctgcttcttt | ctgtgcctgc | tgagattctg | cttctctgcc | 60 |
| accaggagat | actacctggg | ggctgtggaa | ctttcttggg | actacatgca | gtctgacctg | 120 |
| ggagagctgc | ctgtggatgc | caggttccca | cccagagtgc | ccaagtcctt | cccattcaac | 180 |
| acctctgtgg | tctacaagaa | gacactcttt | gtggaattca | ctgaccacct | gttcaacatt | 240 |
| gcaaaaccca | gaccaccctg | gatgggactc | tgggacccca | ccattcaggc | tgaggtgtat | 300 |
| gacactgtgg | tcatcaccct | caagaacatg | gcatcccacc | ctgtgtctct | gcatgctgtg | 360 |
| ggagtctcat | actggaaagc | tctgaaggg | gctgagtatg | atgaccagac | atcccagaga | 420 |
| gagaaagagg | atgacaaggt | gttccctggg | ggatctcaca | cctatgtgtg | gcaagtcctc | 480 |
| aaggagaatg | gacccatggc | atctgaccca | ctctgcctga | catactccta | cctttctcat | 540 |
| gtggacctgg | tcaaggacct | caactctgga | ctgattgggg | cactgctggt | gtgcagggaa | 600 |
| ggatccctgg | ccaaggagaa | aacccagaca | ctgcacaagt | tcattctcct | gtttgctgtc | 660 |
| tttgatgagg | gcaagtcttg | gcactctgaa | acaaagaact | ccctgatgca | agacagggat | 720 |
| gctgcctctg | ccagggcatg | gcccaagatg | cacactgtga | atggctatgt | gaacagatca | 780 |

```
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gtcctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg cccacaaag aattggaaga    1320
aagtacaaga aagtcagatt catggcctac actgatgaaa ccttcaagac aagagaagcc   1380
attcagcatg agtctggcat tctgggacca ctcctgtatg ggaagtggg agacaccctg     1440
ctcatcatct tcaagaacca ggcctccagg ccctacaaca tctacccaca tggcatcact   1500
gatgtcaggc cctgtacag caggagactg ccaaaaggg tgaaacacct caaggacttc      1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga atgtgattc tgttctctgt ctttgatgag    1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattcttttct   1980
attggggcac aaactgactt cctttctgtc ttcttctctg gatacacctt caagcacaag   2040
atggtgtatg aggacaccct gacactcttc ccattctctg gggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca taccaccta cgtgaaccgc    2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc aagatcatt ccagaagaag     2460
acaagacact acttcattgc tgctgtggaa agactgtggg actatggcat gtcttcctct   2520
ccccatgtcc tcaggaacag ggcacagtct ggctctgtgc acagttcaa gaaagtggtc     2580
ttccaggagt tcactgatgg ctcattcacc cagccctgt acagagggga actgaatgag     2640
cacctgggac tcctgggacc atacatcagg gctgaggtgg aagacaacat catggtgaca   2700
ttcagaaacc aggcctccag gccctacagc ttctactctt ccctcatcag ctatgaggaa   2760
gaccagagac aaggggctga gccaagaaag aactttgtga acccaatga aaccaagacc     2820
tacttctgga aagtccagca ccacatggca cccaccaagg atgagtttga ctgcaaggcc   2880
tgggcatact ctctgatgt ggacctggag aaagatgtgc actctggcct gattggccca    2940
ctcctggtct gccacaccaa caccctgaac cctgcacatg gaaggcaagt gactgtgcag   3000
gagtttgccc tcttcttcac catctttgat gaaaccaagt catggtactt cactgagaac   3060
atggagagaa actgcagagc accatgcaac attcagatga agaccccac cttcaaggag   3120
aactacaggt tccatgccat caatggctac atcatggaca ccctgcctgg gcttgtcatg   3180
```

```
gcacaggacc agagaatcag atggtacctg ctttctatgg gatccaatga gaacattcac    3240
tccatccact tctctgggca tgtcttcact gtgagaaaga aggaggaata caagatggcc    3300
ctgtacaacc tctaccctgg ggtctttgag actgtggaga tgctgccctc caaagctggc    3360
atctggaggg tggaatgcct cattggggag cacctgcatg ctggcatgtc aaccctgttc    3420
ctggtctaca gcaacaagtg ccagacaccc ctgggaatgg cctctggcca catcagggac    3480
ttccagatca ctgcctctgg ccagtatggc cagtgggcac ccaaactggc caggctccac    3540
tactctggct ccatcaatgc atggtcaacc aaggagccat tctcttggat caaggtggac    3600
ctgctggcac ccatgatcat tcatggcatc aagacacagg gggcaagaca gaaattctcc    3660
tctctgtaca tctcacagtt catcatcatg tactctctgg atggcaagaa gtggcagaca    3720
tacagaggca actccactgg cacccctcatg gtcttctttg gcaatgtgga cagctctggc    3780
atcaagcaca acatcttcaa ccctcccatc attgccagat acatcaggct gcaccccacc    3840
cactactcaa tcagatcaac cctcaggatg gaactgatgg gatgtgacct gaactcctgc    3900
tcaatgcccc tgggaatgga gagcaaggcc atttctgatg cccagatcac tgcatcctct    3960
tacttcacca acatgtttgc cacctggtca ccatcaaaag ccaggctgca cctccaggga    4020
agaagcaatg cctggagacc ccaggtcaac aacccaaagg aatggctgca agtggacttc    4080
cagaagacaa tgaaagtcac tgggggtgaca acccaggggg tcaagtctct gctcacctca    4140
atgtatgtga aggagttcct gatctcttcc tcacaggatg gccaccagtg gacactcttc    4200
ttccagaatg gcaaagtcaa ggtgttccag ggcaaccagg actctttcac acctgtggtg    4260
aactcactgg accccccccct cctgacaaga tacctgagaa ttcaccccca gtcttgggtc    4320
caccagattg ccctgagaat ggaagtcctg ggatgtgagg cacaagacct gtactga       4377
```

<210> SEQ ID NO 91
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
atgcagattg agctgtccac ctgcttcttt ctgtgcctgc tgagattctg cttctctgcc      60
accaggagat actacctggg ggctgtggaa cttcttgggg actacatgca gtctgacctg     120
ggagagctgc ctgtggatgc caggttccca cccagagtgc ccaagtcctt cccattcaac     180
acctctgtgg tctacaagaa gacactcttt gtggaattca ctgaccacct gttcaacatt     240
gcaaacccca gaccccctg atgggactc ctgggaccca ccattcaggc tgaggtgtat      300
gacactgtgg tcgtcaccct caagaacatg gcatcccacc ctgtgtctct gcatgctgtg     360
ggagtctcat actggaaatc ctctgaaggg gctgagtatg atgaccagac atcccagaga     420
gagaaagagg atgacaaggt gttccctggg aagtctcaca cctatgtgtg gcaagtcctc     480
aaggagaatg gacccactgc atctgaccca ccctgcctga catactccta cctttctcat     540
gtggacctgg tcaaggacct caactctgga ctgattgggg cactgctggt gtgcagggaa     600
ggatccctgg ccaaggagaa aacccagaca ctgcacaagt tcattctcct gtttgctgtc     660
tttgatgagg gcaagtcttg gcactctgaa acaaagaact ccctgatgca agacagggat     720
gctgcctctg ccagggcatg gcccaagatg cacactgtga atggctatgt gaacagatca     780
ctgcctggac tcattggctg ccacaggaaa tctgtctact ggcatgtgat tggcatgggg     840
```

```
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg ggaagtggg agacaccctg   1440
ctcatcatct tcaagaacca ggcctccagg ccctacaaca tctacccaca tggcatcact   1500
gatgtcaggc cctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg gatacacctt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca ataccaccta cgtgaaccgc   2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc caagatcatt ccagaagaag   2460
acaagacact acttcattgc tgctgtggaa agactgtggg actatggcat gtcttcctct   2520
ccccatgtcc tcaggaacag ggcacagtct ggctctgtgc acagttcaa gaaagtggtc   2580
ttccaggagt tcactgatgg ctcattcacc cagcccctgt acagagggga actgaatgag   2640
cacctgggac tcctgggacc atacatcagg gctgaggtgg aagacaacat catggtgaca   2700
ttcagaaacc aggcctccag gccctacagc ttctactctt ccctcatcag ctatgaggaa   2760
gaccagagac aaggggctga gccaagaaag aactttgtga acccaatga accaagacc   2820
tacttctgga aagtccagca ccacatggca cccaccaagg atgagtttga ctgcaaggcc   2880
tgggcatact ctctctgatgt ggacctggag aaagatgtgc actctggcct gattggccca   2940
ctcctggtct gccacaccaa caccctgaac cctgcacatg aaggcaagt gactgtgcag   3000
gagtttgccc tcttcttcac catctttgat gaaaccaagt catggtactt cactgagaac   3060
atggagagaa actgcagagc accatgcaac attcagatgg aagacccac cttcaaggag   3120
aactacaggt tccatgccat caatggctac atcatggaca ccctgcctgg gcttgtcatg   3180
```

```
gcacaggacc agagaatcag atggtacctg ctttctatgg gatccaatga gaacattcac   3240
tccatccact tctctgggca tgtcttcact gtgagaaaga aggaggaata caagatggcc   3300
ctgtacaacc tctaccctgg ggtctttgag actgtggaga tgctgccctc caaagctggc   3360
atctggaggg tggaatgcct cattggggag cacctgcatg ctggcatgtc aaccctgttc   3420
ctggtctaca gcaacaagtg ccagacaccc ctgggaatgg cctctggcca catcagggac   3480
ttccagatca ctgcctctgg ccagtatggc cagtgggcac ccaaactggc caggctccac   3540
tactctggct ccatcaatgc atggtcaacc aaggagccat tctcttggat caaggtggac   3600
ctgctggcac ccatgatcat tcatggcatc aagacacagg gggcaagaca gaaattctcc   3660
tctctgtaca tctcacagtt catcatcatg tactctctgg atggcaagaa gtggcagaca   3720
tacagaggca actccactgg cacccctcatg gtcttctttg gcaatgtgga cagctctggc   3780
atcaagcaca acatcttcaa ccctcccatc attgccagat acatcaggct gcaccccacc   3840
cactactcaa tcagatcaac cctcaggatg gaactgatgg gatgtgacct gaactcctgc   3900
tcaatgcccc tgggaatgga gagcaaggcc atttctgatg cccagatcac tgcatcctct   3960
tacttcacca acatgtttgc cacctggtca ccatcaaaag ccaggctgca cctccaggga   4020
agaagcaatg cctggagacc ccaggtcaac aacccaaagg aatggctgca agtggacttc   4080
cagaagacaa tgaaagtcac tggggtgaca acccaggggg tcaagtctct gctcacctca   4140
atgtatgtga aggagttcct gatctcttcc tcacaggatg ccaccagtga cactcttc    4200 ttccagaatg gcaaagtcaa ggtgttccag ggcaaccagg actctttcac acctgtggtg   4260
aactcactgg accccccccct cctgacaaga tacctgagaa ttcaccccca gtcttgggtc   4320
caccagattg ccctgagaat ggaagtcctg ggatgtgagg cacaagacct gtactga      4377
```

<210> SEQ ID NO 92
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
atgcagattg agctgtccac ctgcttcttt ctgtgcctgc tgagattctg cttctctgcc    60
accaggagat actacctggg ggctgtggaa ctttcttggg actacatgca gtctgacctg   120
ggagagctgc ctgtggatgc caggttccca cccagagtgc caagtccttc cccattcaac   180
acctctgtgg tctacaagaa gacactcttt gtggaattca ctgaccacct gttcaacatt   240
gcaaaaccca gaccaccctg gatgggactc ctgggaccca ccattcaggc tgaggtgtat   300
gacactgtgt catcacccct caagaacatg gcatcccacc ctgtgtctct gcatgctgtg   360
ggagtctcat actggaaagc ctctgaaggg gctgagtatg atgaccagac atcccagaga   420
gagaaagagg atgacaaggt gttccctggg ggatctcaca cctatgtgtg gcaagtcctc   480
aaggagaatg gacccatggc atctgaccca ctctgcctga catactccta cctttctcat   540
gtggacctgg tcaaggacct caactctgga ctgattgggg cactgctggt gtgcagggaa   600
ggatccctgg ccaaggagaa aacccagaca ctgcacaagt tcattctcct gtttgctgtc   660
tttgatgagg gcaagtcttg gcactctgaa acaaagaact ccctgatgca agacagggat   720
gctgcctctg ccagggcatg gcccaagatg cacactgtga atggctatgt gaacagatca   780
ctgcctggac tcattggctg ccacaggaaa tctgtctact ggcatgtgat tggcatgggg   840
```

```
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc cctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg atacaccttt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca ataccaccta cgtgaaccgc   2280
tccctgtctc agaatccacc tgtcctgaag agacaccaga gagagatcac caggacaacc   2340
ctccagtctg accaggaaga gattgactat gatgacacca tttctgtgga gatgaagaag   2400
gaggactttg acatctatga tgaggacgag aaccagtctc aagatcatt ccagaagaag   2460
acaagacact acttcattgc tgctgtggaa agactgtggg actatggcat gtcttcctct   2520
ccccatgtcc tcaggaacag ggcacagtct ggctctgtgc acagttcaa gaaagtggtc   2580
ttccaggagt tcactgatgg ctcattcacc cagcccctgt acagagggga actgaatgag   2640
cacctgggac tcctgggacc atacatcagg gctgaggtgg aagacaacat catggtgaca   2700
ttcagaaacc aggcctccag gccctacagc ttctactctt ccctcatcag ctatgaggaa   2760
gaccagagac aaggggctga gccaagaaag aactttgtga acccaatga accaagacc    2820
tacttctgga aagtccagca ccacatggca cccaccaagg atgagtttga ctgcaaggcc   2880
tgggcatact ctctgatgt ggacctggag aaagatgtgc actctggcct gattggccca   2940
ctcctggtct gccacaccaa caccctgaac cctgcacatg aaggcaagt gactgtgcag   3000
gagtttgccc tcttcttcac catctttgat gaaaccaagt catggtactt cactgagaac   3060
atggagagaa actgcagagc accatgcaac attcagatgg aagacccccac cttcaaggag   3120
aactacaggt tccatgccat caatggctac atcatggaca ccctgcctgg gcttgtcatg   3180
gcacaggacc agagaatcag atggtacctg cttctatgg gatccaatga gaacattcac   3240
```

```
tccatccact tctctgggca tgtcttcact gtgagaaaga aggaggaata caagatggcc   3300
ctgtacaacc tctaccctgg ggtctttgag actgtggaga tgctgccctc caaagctggc   3360
atctggaggg tggaatgcct cattgggag cacctgcatg ctggcatgtc aaccctgttc    3420
ctggtctaca gcaacaagtg ccagacaccc tgggaatgg cctctggcca catcagggac    3480
ttccagatca ctgcctctgg ccagtatggc cagtgggcac ccaaactggc caggctccac   3540
tactctggct ccatcaatgc atggtcaacc aaggagccat tctcttggat caaggtggac   3600
ctgctggcac ccatgatcat tcatggcatc aagacacagg gggcaagaca gaaattctcc   3660
tctctgtaca tctcacagtt catcatcatg tactctctgg atggcaagaa gtggcagaca   3720
tacagaggca actccactgg caccctcatg gtcttctttg gcaatgtgga cagctctggc   3780
atcaagcaca acatcttcaa ccctcccatc attgccagat acatcaggct gcaccccacc   3840
cactactcaa tcagatcaac cctcaggatg gaactgatgg gatgtgacct gaactcctgc   3900
tcaatgcccc tgggaatgga gagcaaggcc atttctgatg cccagatcac tgcatcctct   3960
tacttcacca acatgtttgc cacctggtca ccatcaaaag ccaggctgca cctccaggga   4020
agaagcaatg cctggagacc ccaggtcaac aacccaaagg aatggctgca agtggacttc   4080
cagaagacaa tgaaagtcac tggggtgaca acccaggggg tcaagtctct gctcacctca   4140
atgtatgtga aggagttcct gatctcttcc tcacaggatg ccaccagtg gacactcttc    4200
ttccagaatg gcaaagtcaa ggtgttccag ggcaaccagg actctttcac acctgtggtg   4260
aactcactgg accccccct cctgacaaga tacctgagaa ttcaccccca gtcttgggtc    4320
caccagattg ccctgagaat ggaagtcctg ggatgtgagg cacaagacct gtactga      4377
```

<210> SEQ ID NO 93
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
atgcagattg agctgtccac ctgcttcttt ctgtgcctgc tgagattctg cttctctgcc    60
accaggagat actacctggg ggctgtggaa ctttcttggg actacatgca gtctgacctg   120
ggagagctgc ctgtggatgc caggttccca cccagagtgc ccaagtcctt cccattcaac   180
acctctgtgg tctacaagaa gacactcttt gtggaattca ctgaccacct gttcaacatt   240
gcaaacccca gaccaccctg gatgggactc ctgggaccca ccattcaggc tgaggtgtat   300
gacactgtgg tcgtcacccct caagaacatg gcatcccacc ctgtgtctct gcatgctgtg   360
ggagtctcat actggaaatc ctctgaaggg gctgagtatg atgaccagac atcccagaga   420
gagaaagagg atgacaaggt gttccctggg aagtctcaca cctatgtgtg gcaagtcctc   480
aaggagaatg gacccactgc atctgaccca ccctgcctga catactccta cctttctcat   540
gtggacctgg tcaaggacct caactctgga ctgattgggg cactgctggt gtcagggaa    600
ggatccctgg ccaaggagaa acccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg   840
acaaccctg aagtgcactc catttttcctg gagggacaca ccttcctggt caggaaccac    900
```

```
agacaagcct ctctggagat ctctcccatc accttcctca ctgcacagac actgctgatg     960
gaccttggac agttcctgct gttctgccac atctcttccc accagcatga tggcatggaa    1020
gcctatgtca aggtggactc atgccctgag gaaccacagc tcaggatgaa gaacaatgag    1080
gaggctgagg actatgatga tgacctgact gactctgaga tggatgtggt cagatttgat    1140
gatgacaact ctccatcctt cattcagatc aggtctgtgg caaagaaaca ccccaagaca    1200
tgggtgcact acattgctgc tgaggaagag gactgggact atgcaccact ggtcctggcc    1260
cctgatgaca ggagctacaa gtctcagtac ctcaacaatg cccacaaag aattggaaga     1320 aagtacaaga aagtcagatt catggcctac actgatgaaa ccttcaagac aagagaagcc    1380
attcagcatg agtctggcat tctgggacca ctcctgtatg ggaagtggg agacaccctg      1440 ctcatcatct tcaagaacca ggcctccagg ccctacaaca tctacccaca tggcatcact    1500
gatgtcaggc cctgtacag caggagactg ccaaaagggg tgaaacacct caaggacttc      1560
cccattctgc ctggagagat cttcaagtac aagtggactg tcactgtgga ggatggacca    1620
acaaagtctg accccaggtg cctcaccaga tactactcct cttttgtgaa catggagaga    1680
gacctggcat ctggactgat tggaccactg ctcatctgct acaaggagtc tgtgaccag      1740 agaggcaacc agatcatgtc tgacaagaga aatgtgattc tgttctctgt ctttgatgag    1800
aacagatcat ggtacctgac tgagaacatt cagagattcc tgcccaaccc tgctggggtg    1860
caactggaag accctgagtt ccaggcaagc aacatcatgc actccatcaa tggctatgtg    1920
tttgactctc tccagctttc tgtctgcctg catgaggtgg cctactggta cattcttttct   1980 attggggcac aaactgactt ccttttctgtc ttcttctctg gatacacctt caagcacaag    2040
atggtgtatg aggacaccct gacactcttc ccattctctg gggaaactgt gttcatgagc     2100
atggagaacc tggactgtg gattctggga tgccacaact ctgacttcag aaacagggga     2160
atgactgcac tgctcaaagt ctcctcctgt gacaagaaca ctgggactta ctatgaggac    2220
tcttatgagg acatctctgc ctacctgctc agcaagaaca atgccattga gcccagaagc    2280
ttctctcaga atccacctgt cctgaagaga caccagagag agatcaccag gacaaccctc    2340
cagtctgacc aggaagagat tgactatgat gacaccattt ctgtggagat gaagaaggag    2400
gactttgaca tctatgatga ggacgagaac cagtctccaa gatcattcca agaagaagaca   2460 agacactact tcattgctgc tgtggaaaga ctgtgggact atggcatgtc ttcctctccc    2520
catgtcctca ggaacagggc acagtctggc tctgtgccac agttcaagaa agtggtcttc    2580
caggagttca ctgatggctc attcacccag ccctgtaca gaggggaact gaatgagcac      2640
ctgggactcc tgggaccata atcagggct gaggtggaag acaacatcat ggtgacattc      2700
agaaaccagg cctccaggcc ctacagcttc tactcttccc tcatcagcta tgaggaagac    2760
cagagacaag gggctgagcc aagaaagaac tttgtgaaac ccaatgaaac caagacctac    2820
ttctggaaag tccagcacca catggcaccc accaaggatg agtttgactg caaggcctgg    2880
gcatacttct ctgatgtgga cctggagaaa gatgtgcact ctggcctgat ggcccactc     2940 ctggtctgcc acaccaacac cctgaaccct gcacatggaa ggcaagtgac tgtgcaggag    3000
tttgccctct tcttcaccat ctttgatgaa accaagtcat ggtacttcac tgagaacatg    3060
gagagaaact gcagagcacc atgcaacatt cagatggaag accccacctt caaggagaac    3120
tacaggttcc atgccatcaa tggctacatc atggacaccc tgcctgggct tgtcatggca    3180
caggaccaga gaatcagatg gtacctgctt tctatgggat ccaatgagaa cattcactcc    3240
```

```
atccacttct ctgggcatgt cttcactgtg agaaagaagg aggaatacaa gatggccctg      3300
tacaacctct accctggggt ctttgagact gtggagatgc tgccctccaa agctggcatc      3360
tggagggtgg aatgcctcat tggggagcac ctgcatgctg gcatgtcaac cctgttcctg      3420
gtctacagca acaagtgcca gacaccctg ggaatggcct ctggccacat cagggacttc       3480
cagatcactg cctctggcca gtatggccag tgggcaccca aactggccag gctccactac      3540
tctggctcca tcaatgcatg gtcaaccaag gagccattct cttggatcaa ggtgacctg       3600 ctggcaccca tgatcattca tggcatcaag acacagggg caagacagaa attctcctct       3660
ctgtacatct cacagttcat catcatgtac tctctggatg gcaagaagtg gcagacatac      3720
agaggcaact ccactggcac cctcatggtc ttctttggca atgtggacag ctctggcatc      3780
aagcacaaca tcttcaaccc tcccatcatt gccagataca tcaggctgca ccccaccac      3840 tactcaatca gatcaaccct caggatggaa ctgatgggat gtgacctgaa ctcctgctca      3900
atgcccctgg gaatggagag caaggccatt tctgatgccc agatcactgc atcctcttac      3960
ttcaccaaca tgtttgccac ctggtcacca tcaaaagcca ggctgcacct ccagggaaga      4020
agcaatgcct ggagaccca ggtcaacaac ccaaaggaat ggctgcaagt ggacttccag       4080
aagacaatga aagtcactgg ggtgacaacc caggggtca gtctctgct cacctcaatg       4140 tatgtgaagg agttcctgat ctcttcctca caggatggcc accagtggac actcttcttc      4200
cagaatggca aagtcaaggt gttccagggc aaccaggact ctttcacacc tgtggtgaac      4260
tcactggacc ccccctcct gacaagatac ctgagaattc accccagtc ttgggtccac        4320 cagattgccc tgagaatgga agtcctggga tgtgaggcac aagacctgta ctga            4374
```

<210> SEQ ID NO 94  
<211> LENGTH: 4374  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 94

```
atgcagattg agctgagcac ctgcttcttc ctgtgcctgc tgaggttctg cttctctgcc        60
accaggagat actacctggg ggctgtggag ctttcttggg actacatgca gtctgacctg       120
ggggagctgc ctgtggatgc caggttccca cccagagtgc ccaaatcctt cccattcaac       180
acctctgtgg tctacaagaa gaccctcttt gtggagttca ctgaccacct gttcaacatt      240
gccaaaccca ggccaccctg gatgggactc ctggacccca ccattcaggc tgaggtgtat      300
gacactgtgg tcgtcaccct caagaacatg gcctcccacc ctgtgagcct gcatgctgtg      360
ggggtcagct actggaagtc ctctgagggg gctgagtatg atgaccagac ctcccagagg      420
gagaaggagg atgacaaagt gttccctggg aagagccaca cctatgtgtg gcaggtcctc      480
aaggagaatg cccccactgc ctctgaccca ccctgcctga cctactccta cctttctcat     540
gtggacctgg tcaaggacct caactctgga ctgattgggg ccctgctggt gtgcagggag     600
ggctccctgg ccaaagagaa gacccagacc ctgcacaagt tcattctcct gtttgctgtc     660
tttgatgagg caagagctg gcactctgaa accaagaact ccctgatgca ggacagggat      720
gctgcctctg ccaggggcctg gcccaagatg cacactgtga atggctatgt gaacaggagc    780
ctgcctggac tcattggctg ccacaggaaa tctgtctact ggcatgtgat tggcatgggg    840 acaaccctg aggtgcactc catttttcctg gagggccaca ccttcctggt caggaaccac    900
```

-continued

```
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga agtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tgcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg ctacaccctt caaacacaag   2040
atggtgtatg aggacaccct gaccctcttc ccattctctg gggagactgt gttcatgagc   2100
atggagaacc ctggcctgtg gattctggga tgccacaact ctgacttccg caacagggc    2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atccacctgt cctgaaacgc caccagaggg agatcaccag gaccacccte   2340
cagtctgacc aggaggagat tgactatgat gacaccattt ctgtggagat gaagaaagag   2400
gactttgaca tctatgacga ggacgagaac cagagcccaa ggagcttcca agaagacc     2460
aggcactact tcattgctgc tgtggagcgc tgtgggact atggcatgag ctccagcccc    2520
catgtcctca ggaacagggc ccagtctggc tctgtgccac agttcaagaa agtggtcttc   2580
caagagttca ctgatggcag cttcacccag cccctgtaca gggggagct gaatgagcac    2640
ctgggactcc tgggcccata catcagggct gaggtggagg acaacatcat ggtgaccttc   2700
cgcaaccagg cctccaggcc ctacagcttc tacagctccc tcatcagcta tgaggaggac   2760
cagaggcagg gggctgagcc acgcaagaac tttgtgaaac ccaatgaaac caagacctac   2820
ttctggaaag tccagcacca catggccccc accaaggatg agtttgactg caaggcctgg   2880
gcctacttct ctgatgtgga cctggagaag gatgtgcact ctggcctgat tgcccactc    2940
ctggtctgcc acaccaacac cctgaaccct gcccatggaa ggcaagtgac tgtgcaggag   3000
tttgccctct tcttcaccat ctttgatgaa accaagagct ggtacttcac tgagaacatg   3060
gagcgcaact gcagggcccc atgcaacatt cagatggagg accccaccttt caaagagaac   3120
taccgcttcc atgccatcaa tggctacatc atggacaccc tgcctgggct tgtcatggcc   3180
caggaccaga ggatcaggtg gtacctgctt ctctatgggc tcaatgagaa cattcactcc   3240
atccacttct ctgggcatgt cttcactgtg cgcaagaagg aggagtacaa gatggcctg   3300
```

```
tacaacctct accctggggt ctttgagact gtggagatgc tgccctccaa agctggcatc    3360
tggagggtgg agtgcctcat tggggagcac ctgcatgctg gcatgagcac cctgttcctg    3420
gtctacagca acaagtgcca gaccccctg ggaatggcct ctggccacat cagggacttc    3480
cagatcactg cctctggcca gtatggccag tgggcccca agctggccag gctccactac    3540
tctggatcca tcaatgcctg gagcaccaag gagccattca gctggatcaa agtggacctg    3600
ctggccccca tgatcatcca tggcatcaag acccaggggg ccaggcagaa gttctccagc    3660
ctgtacatca gccagttcat catcatgtac agcctggatg caagaaatg cagacctac    3720 agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcaccct caggatggag ctgatgggct gtgacctgaa ctcctgcagc    3900
atgcccctgg gcatggagag caaggccatt tctgatgccc agatcactgc ctccagctac    3960
ttcaccaaca tgtttgccac ctggagccca agcaaggcca ggctgcacct ccagggaagg    4020
agcaatgcct ggaggcccca ggtcaacaac ccaaaggagt ggctgcaggt ggacttccag    4080
aagaccatga aggtcactgg ggtgaccacc caggggtca agagcctgct caccagcatg    4140
tatgtgaagg agttcctgat cagctccagc caggatggcc accagtggac cctcttcttc    4200
cagaatggca aggtcaaggt gttccagggc aaccaggaca gcttcacccc tgtggtgaac    4260
agcctggacc cccccctcct gaccagatac ctgaggattc accccagag ctgggtccac    4320 cagattgccc tgaggatgga ggtcctggga tgtgaggccc aggacctgta ctga          4374

<210> SEQ ID NO 95
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgcagattg agctgagcac ctgcttcttc ctgtgcctgc tgaggttctg cttctctgcc      60
accaggagat actacctggg ggctgtggag ctttcttggg actacatgca gtctgacctg     120
ggggagctgc ctgtggatgc caggttccca cccagagtgc ccaaatcctt cccattcaac     180
acctctgtgg tctacaagaa gaccctcttt gtggagttca ctgaccacct gttcaacatt     240
gccaaaccca ggccaccctg gatgggactc ctgggaccca ccattcaggc tgaggtgtat     300
gacactgtgg tcatcaccct caagaacatg gcctcccacc ctgtgagcct gcatgctgtg     360
ggggtcagct actggaaggc ctctgagggg gctgagtatg atgaccagac ctcccagagg     420
gagaaggagg atgacaaagt gttccctggg ggcagccaca cctatgtgtg gcaggtcctc     480
aaggagaatg gccccatggc ctctgaccca ctctgcctga cctactccta cctttctcat     540
gtggacctgg tcaaggacct caactctgga ctgattgggg ccctgctggt gtgcagggag     600
ggctccctgg ccaaagagaa gacccagacc ctgcacaagt tcattctcct gtttgctgtc     660
tttgatgagg gcaagagctg gcactctgaa accaagaact ccctgatgca ggacagggat     720
gctgcctctg ccagggcctg gcccaagatg cacactgtga atggctatgt gaacaggagc     780
ctgcctggac tcattggctg ccacaggaaa tctgtctact ggcatgtgat tggcatgggg     840 acaaccctg aggtgcactc catttttctg gagggccaca ccttcctggt caggaaccac     900
agacaggcca gcctggagat cagccccatc accttcctca ctgcccagac cctgctgatg     960
```

```
gacctcggac agttcctgct gttctgccac atcagctccc accagcatga tggcatggag    1020
gcctatgtca aggtggacag ctgccctgag gagccacagc tcaggatgaa gaacaatgag    1080
gaggctgagg actatgatga tgacctgact gactctgaga tggatgtggt ccgctttgat    1140
gatgacaaca gcccatcctt cattcagatc aggtctgtgg ccaagaaaca ccccaagacc    1200
tgggtgcact acattgctgc tgaggaggag gactgggact atgccccact ggtcctggcc    1260
cctgatgaca ggagctacaa gagccagtac ctcaacaatg gcccacagag gattggacgc    1320
aagtacaaga aagtcaggtt catggcctac actgatgaaa ccttcaagac cagggaggcc    1380
attcagcatg agtctggcat cctgggccca ctcctgtatg gggaggtggg ggacaccctg    1440
ctcatcatct tcaagaacca ggcctccagg ccctacaaca tctacccaca tggcatcact    1500
gatgtcaggc cctgtacag ccgcaggctg ccaaagggg tgaaacacct caaggacttc    1560
cccattctgc tggggagat cttcaagtac aagtggactg tcactgtgga ggatggacca    1620
accaaatctg accccaggtg cctcaccaga tactactcca gctttgtgaa catggagagg    1680
gacctggcct ctggcctgat tgcccactg ctcatctgct acaaggagtc tgtggaccag    1740
aggggaaacc agatcatgtc tgacaagagg aatgtgattc tgttctctgt ctttgatgag    1800
aacaggagct ggtacctgac tgagaacatt cagcgcttcc tgcccaaccc tgctggggtg    1860
cagctggagg accctgagtt ccaggccagc aacatcatgc actccatcaa tggctatgtg    1920
tttgacagcc tccagctttc tgtctgcctg catgaggtgg cctactggta cattctttct    1980 attgggccc agactgactt cctttctgtc ttcttctctg gctacacctt caaacacaag    2040
atggtgtatg aggacaccct gaccctcttc ccattctctg gggagactgt gttcatgagc    2100
atggagaacc ctggcctgtg gattctggga tgccacaact ctgacttccg caacaggggc    2160
atgactgccc tgctcaaagt ctcctcctgt gacaagaaca ctgggactct atgaggac    2220 agctatgagg acatctctgc ctacctgctc agcaagaaca ataccaccta cgtgaaccgc    2280
tccctgagcc agaatccacc tgtcctgaaa cgccaccaga gggagatcac caggaccacc    2340
ctccagtctg accaggagga gattgactat gatgacacca tttctgtgga gatgaagaaa    2400
gaggactttg acatctatga cgaggacgag aaccagagcc caaggagctt ccagaagaag    2460
accaggcact acttcattgc tgctgtggag cgcctgtggg actatggcat gagctccagc    2520
ccccatgtcc tcaggaacag ggcccagtct ggctctgtgc acagttcaa gaaagtggtc    2580 ttccaagagt tcactgatgg cagcttcacc cagcccctgt acagagggga gctgaatgag    2640
cacctgggac tcctgggccc atacatcagg gctgaggtgg aggacaacat catggtgacc    2700
ttccgcaacc aggcctccag gccctacagc ttctacagct ccctcatcag ctatgaggag    2760
gaccagaggc aggggctga gccacgcaag aactttgtga acccaatga accaagacc    2820 tacttctgga aagtccagca ccacatggcc cccaccaagg atgagtttga ctgcaaggcc    2880
tgggcctact ctctgatgt ggacctggag aaggatgtgc actctggcct gattggccca    2940
ctcctggtct gccacaccaa caccctgaac cctgcccatg gaaggcaagt gactgtgcag    3000
gagtttgccc tcttcttcac catctttgat gaaaccaaga gctggtactt cactgagaac    3060
atggagcgca actgcagggc cccatgcaac attcagatgg aggaccccac cttcaaagag    3120
aactaccgct ccatgccat caatggctac atcatggaca ccctgcctgg gcttgtcatg    3180
gcccaggacc agaggatcag gtggtacctg ctttctatgg gctccaatga gaacattcac    3240
tccatccact tctctgggca tgtcttcact gtgcgcaaga aggaggagta caagatggcc    3300
```

```
ctgtacaacc tctaccctgg ggtctttgag actgtggaga tgctgccctc caaagctggc    3360
atctggaggg tggagtgcct cattggggag cacctgcatg ctggcatgag caccctgttc    3420
ctggtctaca gcaacaagtg ccagaccccc ctgggaatgg cctctggcca catcagggac    3480
ttccagatca ctgcctctgg ccagtatggc cagtgggccc ccaagctggc caggctccac    3540
tactctggat ccatcaatgc ctggagcacc aaggagccat tcagctggat caaagtggac    3600
ctgctggccc ccatgatcat ccatggcatc aagacccagg gggccaggca gaagttctcc    3660
agcctgtaca tcagccagtt catcatcatg tacagcctgg atggcaagaa atggcagacc    3720
tacagaggca actccactgg aacactcatg gtcttctttg gcaatgtgga cagctctggc    3780
atcaagcaca acatcttcaa ccccccaatc atcgccagat acatcaggct gcaccccacc    3840
cactacagca tccgcagcac cctcaggatg agctgatgg gctgtgacct gaactcctgc    3900
agcatgcccc tgggcatgga gagcaaggcc atttctgatg cccagatcac tgcctccagc    3960
tacttcacca acatgtttgc cacctggagc ccaagcaagg ccaggctgca cctccaggga    4020
aggagcaatg cctggaggcc ccaggtcaac aacccaaagg agtggctgca ggtggacttc    4080
cagaagacca tgaaggtcac tggggtgacc acccagggggg tcaagagcct gctcaccagc    4140
atgtatgtga aggagttcct gatcagctcc agccaggatg ccaccagtg gaccctcttc    4200 ttccagaatg gcaaggtcaa ggtgttccag ggcaaccagg acagcttcac ccctgtggtg    4260
aacagcctgg acccccccct cctgaccaga tacctgagga ttcacccccca gagctgggtc    4320 caccagattg ccctgaggat ggaggtcctg ggatgtgagg cccaggacct gtactga       4377
```

<210> SEQ ID NO 96
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
atgcagattg agctgagcac ctgcttcttc ctgtgcctgc tgaggttctg cttctctgcc     60
accaggagat actacctggg ggctgtggag ctttcttggg actacatgca gtctgacctg    120
ggggagctgc ctgtggatgc caggttccca cccagagtgc ccaaatcctt cccattcaac    180
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
gacactgtgg tcgtcaccct caagaacatg gcctcccacc ctgtgagcct gcatgctgtg    360
ggggtcagct actggaagtc ctctgagggg gctgagtatg atgaccagac ctcccagagg    420
gagaaggagg atgacaaagt gttccctggg aagagccaca cctatgtgtg gcaggtcctc    480
aaggagaatg gccccactgc ctctgaccca ccctgcctga cctactccta ccttttctcat    540 gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840 acaaccccctg aggtgcactc catttttcct gagggccaca ccttcctggt caggaaccac    900
agacaggcca gcctggagat cagccccatc accttcctca ctgcccagac cctgctgatg    960
```

```
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgcttttgat  1140 gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg cccacagag gattggacgc    1320 aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc cctgtacag ccgcaggctg ccaaaggggg tgaaacacct caaggacttc    1560
cccattctgc tggggagat cttcaagtac aagtggactg tcactgtgga ggatggacca    1620
accaaatctg accccaggtg cctcaccaga tactactcca gctttgtgaa catggagagg   1680
gacctggcct ctggcctgat tgcccactg ctcatctgct acaaggagtc tgtgaccag    1740 agggaaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg gggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca ataccaccta cgtgaaccgc   2280
tccctgagcc agaatccacc tgtcctgaaa cgccaccaga gggagatcac caggaccacc   2340
ctccagtctg accaggagga gattgactat gatgacacca tttctgtgga gatgaagaaa   2400
gaggactttg acatctatga cgaggacgag aaccagagcc caaggagctt ccagaagaag   2460
accaggcact acttcattgc tgctgtggag cgcctgtggg actatggcat gagctccagc   2520
ccccatgtcc tcaggaacag ggcccagtct ggctctgtgc acagttcaa gaaagtggtc   2580 ttccaagagt tcactgatgg cagcttcacc cagcccctgt acagagggga gctgaatgag   2640
cacctgggac tcctgggccc atacatcagg gctgaggtgg aggacaacat catggtgacc   2700
ttccgcaacc aggcctccag gccctacagc ttctacagct ccctcatcag ctatgaggag   2760
gaccagaggg aggggctga ccacgcaag aactttgtga acccaatga accaagacc     2820 tacttctgga aagtccagca ccacatggcc cccaccaagg atgagtttga ctgcaaggcc   2880
tgggcctact ctctctgatgt ggacctggag aaggatgtgc actctggcct gattggccca   2940
ctcctggtct gccacaccaa cacctgaac cctgcccatg aaggcaagt gactgtgcag    3000 gagtttgccc tcttcttcac catctttgat gaaaccaaga gctggtactt cactgagaac   3060
atggagcgca actgcagggc cccatgcaac attcagatgg aggaccccac cttcaaagag   3120
aactaccgct ccatgccat caatggctac atcatggaca ccctgcctgg gcttgtcatg   3180
gcccaggacc agaggatcag gtggtacctg ctttctatgg gctccaatga gaacattcac   3240
tccatccact tctctgggca tgtcttcact gtgcgcaaga aggaggagta caagatggcc   3300
ctgtacaacc tctaccctgg ggtctttgag actgtggaga tgctgccctc caaagctggc   3360
```

```
atctggaggg tggagtgcct cattggggag cacctgcatg ctggcatgag caccctgttc    3420
ctggtctaca gcaacaagtg ccagacccccc tgggaatgg cctctggcca catcagggac    3480
ttccagatca ctgcctctgg ccagtatggc cagtgggccc caagctggc caggctccac    3540 tactctggat ccatcaatgc ctggagcacc aaggagccat tcagctggat caaagtggac    3600
ctgctggccc ccatgatcat ccatggcatc aagacccagg gggccaggca gaagttctcc    3660
agcctgtaca tcagccagtt catcatcatg tacagcctgg atggcaagaa atggcagacc    3720
tacagaggca actccactgg aacactcatg gtcttctttg gcaatgtgga cagctctggc    3780
atcaagcaca acatcttcaa ccccccaatc atcgccagat acatcaggct gcaccccacc    3840
cactacagca tccgcagcac cctcaggatg gagctgatgg gctgtgacct gaactcctgc    3900
agcatgcccc tggcatgga gagcaaggc atttctgatg cccagatcac tgcctccagc    3960
tacttcacca acatgtttgc cacctggagc ccaagcaagg ccaggctgca cctccaggga    4020
aggagcaatg cctggaggcc ccaggtcaac aacccaaagg agtggctgca ggtggacttc    4080
cagaagacca tgaaggtcac tggggtgacc acccaggggg tcaagagcct gctcaccagc    4140
atgtatgtga aggagttcct gatcagctcc agccaggatg ccaccagtg gaccctcttc    4200 ttccagaatg gcaaggtcaa ggtgttccag ggcaaccagg acagcttcac ccctgtggtg    4260
aacagcctgg acccccccct cctgaccaga tacctgagga ttcacccca gagctgggtc    4320 caccagattg ccctgaggat ggaggtcctg ggatgtgagg cccaggacct gtactga      4377

<210> SEQ ID NO 97
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
atgcagattg agctgagcac ctgcttcttc ctgtgcctgc tgaggttctg cttctctgcc     60
accaggagat actacctggg ggctgtggag ctttcttggg actacatgca gtctgacctg    120
ggggagctgc ctgtggatgc caggttccca cccagagtgc ccaaatcctt cccattcaac    180
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
gacactgtgg tcatcacccct caagaacatg gcctccacc ctgtgagcct gcatgctgtg    360
ggggtcagct actggaaggc ctctgagggg gctgagtatg atgaccagac ctcccagagg    420
gagaaggagt tgacaaagt gttccctggg ggcagccaca cctatgtgtg gcaggtcctc    480
aaggagaatg cccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840 acaaccctg aggtgcactc catttttcctg gagggccaca ccttcctggt caggaaccac    900
agacaggcca gctggagat cagcccatc accttcctca ctgcccagac cctgctgatg    960
gacctcggac agttcctgct gtcctgccac atcagctccc accagcatga tggcatggag   1020
```

```
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg cccacagag gattggacgc   1320
aagtacaaga aagtcaggtt catggcctac actgatgaaa ccttcaagac cagggaggcc   1380
attcagcatg agtctggcat cctgggccca ctcctgtatg ggaggtggg ggacaccctg   1440
ctcatcatct tcaagaacca ggcctccagg ccctacaaca tctacccaca tggcatcact   1500
gatgtcaggc ccctgtacag ccgcaggctg ccaaagggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tgcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctgggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacaccttt caaacacaag   2040
atggtgtatg aggacacct gaccctcttc ccattctctg gggagactgt gttcatgagc   2100
atggagaacc ctggcctgtg gattctggga tgccacaact ctgacttccg caacagggc   2160
atgactgccc tgctcaaagt ctcctcctgt gacaagaaca ctgggactac tatgaggac   2220
agctatgagg acatctctgc ctacctgctc agcaagaaca atgccattga gcccaggagc   2280
ttcagccaga atccacctgt cctgaaacgc caccagaggg agatcaccag gaccacctc   2340
cagtctgacc aggaggagat tgactatgat gacaccattt ctgtggagat gaagaaagag   2400
gactttgaca tctatgacga ggacgagaac cagagcccaa ggagcttcca agaagacc    2460
aggcactact tcattgctgc tgtggagcgc ctgtgggact atggcatgag ctccagcccc   2520
catgtcctca ggaacagggc ccagtctggc tctgtgccac agttcaagaa agtggtcttc   2580
caagagttca ctgatggcag cttcacccag ccctgtaca gaggggagct gaatgagcac   2640
ctgggactcc tgggcccata catcagggct gaggtggagg acaacatcat ggtgaccttc   2700
cgcaaccagg cctccaggcc ctacagcttc tacagctccc tcatcagcta tgaggaggac   2760
cagaggcagg gggctgagcc acgcaagaac tttgtgaaac ccaatgaaac caagacctac   2820
ttctggaaag tccagcacca catggccccc accaaggatg agtttgactg caaggcctgg   2880
gcctacttct ctgatgtgga cctggagaag gatgtgcact ctggcctgat tggcccactc   2940
ctggtctgcc acaccaacac cctgaaccct gccatggaa ggcaagtgac tgtgcaggag   3000
tttgccctct tcttcaccat ctttgatgaa accaagagct ggtacttcac tgagaacatg   3060
gagcgcaact gcagggcccc atgcaacatt cagatggagg accccacctt caaagagaac   3120
taccgcttcc atgccatcaa tggctacatc atggacaccc tgcctgggct tgtcatggcc   3180
caggaccaga ggatcaggtg gtacctgctt tctatgggct ccaatgagaa cattcactcc   3240
atccacttct ctgggcatgt cttcactgtg cgcaagaagg aggagtacaa gatgcccctg   3300
tacaacctct accctgggt ctttgagact gtggagatgc tgccctccaa agctggcatc   3360
```

```
tggagggtgg agtgcctcat tggggagcac ctgcatgctg gcatgagcac cctgttcctg    3420
gtctacagca acaagtgcca gacccccctg ggaatggcct ctggccacat cagggacttc    3480
cagatcactg cctctggcca gtatggccag tgggccccca agctggccag gctccactac    3540
tctggatcca tcaatgcctg gagccaccaag gagccattca gctggatcaa agtggacctg    3600
```



```
tggagggtgg agtgcctcat tggggagcac ctgcatgctg gcatgagcac cctgttcctg    3420
gtctacagca acaagtgcca gacccccctg ggaatggcct ctggccacat cagggacttc    3480
cagatcactg cctctggcca gtatggccag tgggccccca agctggccag gctccactac    3540
tctggatcca tcaatgcctg gagccaccaag gagccattca gctggatcaa agtggacctg    3600 ctggcccca tgatcatcca tggcatcaag acccaggggg ccaggcagaa gttctccagc    3660
ctgtacatca gccagttcat catcatgtac agcctggatg caagaaatg gcagacctac    3720 agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcaccct caggatggag ctgatgggct gtgacctgaa ctcctgcagc    3900
atgcccctgg gcatggagag caaggccatt tctgatgccc agatcactgc ctccagctac    3960
ttcaccaaca tgttttgccac ctggagccca agcaaggcca ggctgcacct ccagggaagg    4020
agcaatgcct ggaggcccca ggtcaacaac ccaaaggagt ggctgcaggt ggacttccag    4080
aagaccatga aggtcactgg ggtgaccacc caggggtca agagcctgct caccagcatg    4140
tatgtgaagg agttcctgat cagctccagc caggatggcc accagtggac cctcttcttc    4200
cagaatggca aggtcaaggt gttccagggc aaccaggaca gcttcacccc tgtggtgaac    4260
agcctggacc ccccctcct gaccagatac ctgaggattc accccagag ctgggtccac    4320 cagattgccc tgaggatgga ggtcctggga tgtgaggccc aggacctgta ctga       4374
```

<210> SEQ ID NO 98
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
atgcagattg agctgagcac ctgcttcttc ctgtgcctgc tgaggttctg cttctctgcc      60
accaggagat actacctggg ggctgtggag ctttcttggg actacatgca gtctgacctg     120
ggggagctgc ctgtggatgc caggttccca cccagagtgc ccaaatcctt cccattcaac     180
acctctgtgg tctacaagaa gaccctcttt gtggagttca ctgaccacct gttcaacatt     240
gccaaaccca ggccacctg gatgggactc ctggacccca ccattcaggc tgaggtgtat     300
gacactgtgg tcatcaccct caagaacatg gcctcccacc ctgtgagcct gcatgctgtg     360
ggggtcagct actggaaggc ctctgagggg gctgagtatg atgaccagac ctcccagagg     420
gagaaggagg atgacaaagt gttccctggg ggcagccaca cctatgtgtg gcaggtcctc     480
aaggagaatg cccccatggc ctctgaccca ctctgcctga cctactccta cctttctcat     540
gtggacctgg tcaaggacct caactctgga ctgattgggg ccctgctggt gtgcagggag     600 ggctcccctgg ccaaagagaa gacccagacc ctgcacaagt tcattctcct gttttgctgtc     660 tttgatgagg gcaagagctg gcactctgaa accaagaact ccctgatgca ggacagggat     720
gctgcctctg ccagggcctg gcccaagatg cacactgtga atggctatgt gaacaggagc     780
ctgcctggac tcattggctg ccacaggaaa tctgtctact ggcatgtgat tggcatgggg     840 acaaccctg aggtgcactc catttttctg gagggccaca ccttcctggt caggaaccac     900
agacaggcca gctggagat cagccccatc accttcctca ctgcccagac cctgctgatg     960
gacctcggac agttcctgct gtcctgccac atcagctccc accagcatga tggcatggag    1020
```

-continued

```
gcctatgtca aggtggacag ctgccctgag gagccacagc tcaggatgaa gaacaatgag      1080
gaggctgagg actatgatga tgacctgact gactctgaga tggatgtggt ccgctttgat      1140
gatgacaaca gcccatcctt cattcagatc aggtctgtgg ccaagaaaca ccccaagacc      1200
tgggtgcact acattgctgc tgaggaggag gactgggact atgccccact ggtcctggcc      1260
cctgatgaca ggagctacaa gagccagtac ctcaacaatg cccacagag gattggacgc      1320 aagtacaaga agtcaggtt catggcctac actgatgaaa ccttcaagac cagggaggcc      1380
attcagcatg agtctggcat cctgggccca ctcctgtatg gggaggtggg ggacaccctg      1440
ctcatcatct tcaagaacca ggcctccagg ccctacaaca tctacccaca tggcatcact      1500
gatgtcaggc ccctgtacag ccgcaggctg ccaaaggggg tgaaacacct caaggacttc      1560
cccattctgc ctggggagat cttcaagtac aagtggactg tcactgtgga ggatggacca      1620
accaaatctg accccaggtg cctcaccaga tactactcca gctttgtgaa catggagagg      1680
gacctggcct ctggcctgat tgcccactg ctcatctgct acaaggagtc tgtggaccag      1740
aggggaaacc agatcatgtc tgacaagagg aatgtgattc tgttctctgt ctttgatgag      1800
aacaggagct ggtacctgac tgagaacatt cagcgcttcc tgcccaaccc tgctggggtg      1860
cagctggagg accctgagtt ccaggccagc aacatcatgc actccatcaa tggctatgtg      1920
tttgacagcc tccagctttc tgtctgcctg catgaggtgg cctactggta cattctttct      1980 attgggccc agactgactt cctttctgtc ttcttctctg ctacaccttc caaacacaag      2040
atggtgtatg aggacaccct gaccctcttc ccattctctg gggagactgt gttcatgagc      2100
atggagaacc ctggctgtg gattctggga tgccacaact ctgacttccg caacaggggc      2160
atgactgccc tgctcaaagt ctcctcctgt gacaagaaca ctggggacta ctatgaggac      2220
agctatgagg acatctctgc ctacctgctc agcaagaaca ataccaccta cgtgaaccgc      2280
tccctgagcc agaatccacc tgtcctgaaa cgccaccaga gggagatcac caggaccacc      2340
ctccagtctg accaggagga gattgactat gatgacacca tttctgtgga gatgaagaaa      2400
gaggactttg acatctatga cgaggacgag aaccagagcc caaggagctt ccagaagaag      2460
accaggcact acttcattgc tgctgtggag cgcctgtggg actatggcat gagctccagc      2520
ccccatgtcc tcaggaacag ggcccagtct ggctctgtgc acagttcaa gaaagtggtc      2580 ttccaagagt tcactgatgg cagcttcacc cagcccctgt acagagggga gctgaatgag      2640
cacctgggac tcctgggccc atacatcagg gctgaggtgg aggacaacat catggtgacc      2700
ttccgcaacc aggcctccag gccctacagc ttctacagct ccctcatcag ctatgaggag      2760
gaccagaggc agggggctga gccacgcaag aactttgtga acccaatga accaagacc      2820 tacttctgga aagtccagca ccacatggcc cccaccaagg atgagtttga ctgcaaggcc      2880
tgggcctact ctctgatgt ggacctggag aaggatgtgc actctggcct gattggccca      2940
ctcctggtct gccacaccaa cacccctgaac cctgcccatg gaaggcaagt gactgtgcag      3000
gagtttgccc tcttcttcac catctttgat gaaaccaaga gctggtactt cactgagaac      3060
atggagcgca actgcagggc cccatgcaac attcagatgg aggacccac cttcaaagag      3120 aactaccgct ccatgccat caatggctac atcatggaca ccctgcctgg gcttgtcatg      3180
gcccaggacc agaggatcag gtggtacctg ctttctatgg gctccaatga gaacattcac      3240
tccatccact ctctgggca tgtcttcact gtgcgcaaga aggaggagta caagatggcc      3300
ctgtacaacc tctaccctgg ggtctttgag actgtgcgaga tgctgccctc caaagctggc      3360
atctggaggg tggagtgcct cattggggag cacctgcatg ctggcatgag caccctgttc      3420
```

```
ctggtctaca gcaacaagtg ccagaccccc ctgggaatgg cctctggcca catcagggac    3480
ttccagatca ctgcctctgg ccagtatggc cagtgggccc ccaagctggc caggctccac    3540
tactctggat ccatcaatgc ctggagcacc aaggagccat tcagctggat caaagtggac    3600
ctgctggccc ccatgatcat ccatggcatc aagacccagg gggccaggca gaagttctcc    3660
agcctgtaca tcagccagtt catcatcatg tacagcctgg atggcaagaa atggcagacc    3720
tacagaggca actccactgg aacactcatg gtcttctttg caatgtgga cagctctggc    3780 atcaagcaca acatcttcaa ccccccaatc atcgccagat acatcaggct gcaccccacc    3840
cactacagca tccgcagcac cctcaggatg gagctgatgg gctgtgacct gaactcctgc    3900
agcatgcccc tgggcatgga gagcaaggcc atttctgatg cccagatcac tgcctccagc    3960
tacttcacca catgtttgc cacctggagc ccaagcaagg ccaggctgca cctccaggga    4020
aggagcaatg cctggaggcc ccaggtcaac aacccaaagg agtggctgca ggtggacttc    4080
cagaagacca tgaaggtcac tggggtgacc cccaggggg tcaagagcct gctcaccagc    4140
atgtatgtga aggagttcct gatcagctcc agccaggatg ccaccagtg gaccctcttc    4200 ttccagaatg gcaaggtcaa ggtgttccag ggcaaccagg acagcttcac ccctgtggtg    4260
aacagcctgg accccccct cctgaccaga tacctgagga ttcaccccca gagctgggtc    4320
caccagattg ccctgaggat ggaggtcctg ggatgtgagg cccaggacct gtactga      4377
```

<210> SEQ ID NO 99
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc ctgtggacgc caggttcccc cccagagtgc ccaagagctt ccccttcaac     180
acctcagtgg tgtacaagaa gaccctgttc gtggagttca ccgaccacct gttcaacatc     240
gccaagccca ggcccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc ctctgagggc gccgagtatg acgaccagac cagccagagg     420
gagaaggagg acgacaaggt gttccccggc ggcagccaca cctacgtgtg gcaggtgctg     480
aaggagaacg gccccatggc cagcgacccc tgtgcctga cctacagcta cctgagccac     540
gtggacctgg tgaaggacct gaactctggc ctgatcggcg ccctgctggt gtgcagggag     600
ggcagcctgg ccaaggagaa gacccagacc ctgcacaagt tcatcctgct gttcgccgtg     660
ttcgatgagg gcaagagctg gcacagcgag accaagaaca gcctgatgca ggacagggat     720
gccgcctctg ccagggcctg gcccaagatg cacaccgtga acggctacgt gaacaggagc     780
ctgcccggcc tgatcggctg ccacaggaag tctgtgtact ggcacgtgat cggcatgggc     840 accaccccg aggtgcacag catcttcctg gagggccaca ccttcctggt gaggaaccac     900
aggcaggcca gcctggagat cagccccatc accttcctga ccgcccagac cctgctgatg     960 gacctgggc agttcctgct gttcctgcac atcagcagcc accagcacga cggcatggag    1020
gcctacgtga aggtggacag ctgcccccga gagcccagc tgaggatgaa gaacaacgag    1080
```

```
gaggccgagg actatgatga tgacctgacc gactctgaga tggacgtggt gaggtttgat    1140
gatgacaaca gccccagctt catccagatc aggtctgtgg ccaagaagca ccccaagacc    1200
tgggtgcact acatcgccgc cgaggaggag gactgggact acgccccct ggtgctggcc     1260 cccgacgaca ggagctacaa gagccagtac ctgaacaacg cccccagag atcggcagg      1320 aagtacaaga aggtcagatt catggcctac accgacgaga ccttcaagac cagggaggcc    1380
atccagcacg agtctggcat cctgggcccc ctgctgtacg cgaggtggg cgacaccctg     1440 ctgatcatct tcaagaacca ggccagcagg ccctacaaca tctaccccca cggcatcacc    1500
gatgtgaggc ccctgtacag caggaggctg cccaagggcg tgaagcacct gaaggacttc    1560
cccatcctgc ccggcgagat cttcaagtac aagtggaccg tgaccgtgga ggatggcccc    1620
accaagtctg accccaggtg cctgaccagg tactacagca gcttcgtgaa catggagagg    1680
gacctggcct ctggcctgat cggccccctg ctgatctgct acaaggagag cgtggaccag    1740 agggcaacc agatcatgtc tgacaagagg aacgtgatcc tgttctctgt gttcgatgag     1800
aacaggagct ggtatctgac cgagaacatc cagaggttcc tgcccaaccc cgccggcgtg    1860
cagctggagg accccgagtt ccaggccagc aacatcatgc acagcatcaa cggctacgtg    1920
ttcgacagcc tgcagctgtc tgtgtgcctg cacgaggtgg cctactggta catcctgagc    1980
atcgccgccc agaccgactt cctgtctgtg ttcttctctg gctacacctt caagcacaag    2040
atggtgtacg aggacaccct gaccctgttc cccttcagcg gcgagaccgt gttcatgagc    2100
atggagaacc ccggcctgtg gatcctgggc tgccacaaca gcgacttcag gaacaggggc    2160
atgaccgccc tgctgaaagt cagcagctgc gacaagaaca ccggcgacta ctacgaggac    2220
agctacgagg acatcagcgc ctacctgctg agcaagaaca acaccaccta cgtgaaccgc    2280
tccctgagcc agaaccccc cgtgctgaag aggcaccaga gggagatcac caggaccacc     2340
ctgcagagcg accaggagga gatcgactat gatgacacca tcagcgtgga gatgaagaag    2400
gaggacttcg acatctacga cgaggacgag aaccagagcc caggagcttt ccagaagaag    2460
accaggcact acttcatcgc cgccgtggag aggctgtggg actatggcat gagcagcagc    2520
ccccacgtgc tgaggaacag ggcccagagc ggcagcgtgc cccagttcaa gaaggtggtg    2580
ttccaggagt tcaccgacgg cagcttcacc cagcccctgt acagaggcga gctgaacgag    2640
cacctgggcc tgctgggccc ctacatcagg gccgaggtgg aggacaacat catggtgacc    2700
ttcaggaacc aggccagcag gccctacagc ttctacagca gcctgatcag ctacgaggag    2760
gaccagaggc agggcgccga gcccaggaag aacttcgtga gcccaacga gaccaagacc     2820 tacttctgga aggtgcagca ccacatggcc cccaccaagg acgagttcga ctgcaaggcc    2880
tgggcctact ctctgatgt ggacctggag aaggacgtgc acagcggcct gatcggcccc     2940
ctgctggtgt gccacaccaa caccctgaac ccgcccacg gcaggcaggt gaccgtgcag     3000
gagttcgccc tgttcttcac catcttcgac gagaccaaga gctggtactt caccgagaac    3060
atggagagga actgcagggc ccctgcaac atccagatgg aggacccac cttcaaggag       3120 aactacaggt tccacgccat caacggctac atcatggaca ccctgccggg cctggtgatg    3180
gcccaggacc agaggatcag gtggtatctg ctgagcatgg gcagcaacga gaacatccac    3240
agcatccact tcagcggcca cgtgttcacc gtgaggaaga ggaggagta caagatggcc     3300 ctgtacaacc tgtaccccgg cgtgttcgag accgtggaga tgctgcccag caaggccggc    3360
atctggaggg tggagtgcct gatcggcgag cacctgcacg ccggcatgag cacccctgttc   3420
```

-continued

| | |
|---|---|
| ctggtgtaca gcaacaagtg ccagacccc ctgggcatgg ccagcggcca catcagggac | 3480 |
| ttccagatca ccgcctctgg ccagtacggc cagtgggccc ccaagctggc caggctgcac | 3540 |
| tacagcggca gcatcaacgc ctggagcacc aaggagccct tcagctggat caaggtggac | 3600 |
| ctgctggccc ccatgatcat ccacggcatc aagacccagg cgccaggca gaagttcagc | 3660 |
| agcctgtaca tcagccagtt catcatcatg tacagcctgg acggcaagaa gtggcagacc | 3720 |
| tacaggggca cagcaccgg caccctgatg gtgttcttcg gcaacgtgga cagcagcggc | 3780 |
| atcaagcaca acatcttcaa ccccccatc atcgccaggt acatcaggct gcaccccacc | 3840 |
| cactacagca tcaggagcac cctgcgatg gaactgatgg gctgcgacct gaacagctgc | 3900 |
| agcatgcccc tgggcatgga gagcaaggcc atctctgacg cccagatcac cgccagcagc | 3960 |
| tacttcacca acatgttcgc cacctggagc cccagcaagg ccaggctgca cctgcagggc | 4020 |
| aggagcaacg cctggaggcc ccaggtgaac aaccccaagg agtggctgca ggtggacttc | 4080 |
| cagaagacca tgaaggtgac cggcgtgacc acccagggcg tgaagagcct gctgaccagc | 4140 |
| atgtacgtga aggagttcct gatcagcagc agccaggacg ccaccagtg gaccctgttc | 4200 |
| ttccagaacg gcaaagtgaa ggtgttccag ggcaaccagg acagcttcac ccccgtggtg | 4260 |
| aacagcctgg accccccct gctgaccagg tatctgagga tccacccca gagctgggtg | 4320 |
| caccagatcg ccctgagaat ggaagtgctg ggatgcgagg cccaggacct gtactga | 4377 |

<210> SEQ ID NO 100
<211> LENGTH: 4377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

| | |
|---|---|
| atgcagattg agctgagcac ctgcttcttc ctgtgcctgc tgaggttctg cttctctgcc | 60 |
| accaggagat actacctggg cgccgtggag ctgagctggg actacatgca gtctgacctg | 120 |
| ggcgagctgc ctgtggacgc caggttcccc cccagagtgc ccaagagctt ccccttcaac | 180 |
| acctcagtgg tgtacaagaa gaccctgttc gtggagttca ccgaccacct gttcaacatc | 240 |
| gccaagccca ggcccccctg gatgggcctg ctgggccca ccatccaggc cgaggtgtac | 300 |
| gacaccgtgg tgatcaccct gaagaacatg gccagcacc ccgtgagcct gcacgccgtg | 360 |
| ggcgtgagct actggaaggc ctctgagggc gccgagtatg acgaccagac cagccagagg | 420 |
| gagaaggag acgacaaggt gttccccggc ggcagccaca cctacgtgtg gcaggtgctg | 480 |
| aaggagaacg cccccatggc cagcgacccc ctgtgcctga cctacagcta cctgagccac | 540 |
| gtggacctgt gaaggacct gaactctggc ctgatcggcg ccctgctggt gtgcaggag | 600 |
| ggcagcctgg ccaaggagaa gacccagacc ctgcacaagt tcatcctgct gttcgccgtg | 660 |
| ttcgatgagg gcaagagctg gcacagcgag accaagaaca gcctgatgca ggacagggat | 720 |
| gccgcctctg ccagggcctg gcccaagatg cacaccgtga acggctacgt gaacaggagc | 780 |
| ctgcccggcc tgatcggctg ccacaggaag tctgtgtact ggcacgtgat cggcatgggc | 840 |
| accaccccg aggtgcacag catcttcctg gagggccaca ccttcctggt gaggaaccac | 900 |
| aggcaggcca gctggagat cagccccatc accttcctga ccgcccagac cctgctgatg | 960 |
| gacctgggcc agttcctgct gttctgccac atcagcagcc accagcacga cggcatggag | 1020 |
| gcctacgtga aggtggacag ctgccccgag gagccccagc tgaggatgaa gaacaacgag | 1080 |

```
gaggccgagg actatgatga tgacctgacc gactctgaga tggacgtggt gaggtttgat      1140
gatgacaaca gccccagctt catccagatc aggtctgtgg ccaagaagca ccccaagacc      1200
tgggtgcact acatcgccgc cgaggaggag gactgggact acgccccect ggtgctggcc      1260 cccgacgaca ggagctacaa gagccagtac ctgaacaacg cccccagag gatcggcagg       1320 aagtacaaga aggtcagatt catggcctac accgacgaga ccttcaagac cagggaggcc      1380
atccagcacg agtctggcat cctgggcccc ctgctgtacg cgaggtggg cgacaccctg       1440 ctgatcatct tcaagaacca ggccagcagg ccctacaaca tctaccccca cggcatcacc      1500
gatgtgaggc ccctgtacag caggaggctg cccaagggcg tgaagcacct gaaggacttc      1560
cccatcctgc ccggcgagat cttcaagtac aagtggaccg tgaccgtgga ggatggcccc      1620
accaagtctg accccaggtg cctgaccagg tactacagca gcttcgtgaa catggagagg      1680
gacctggcct ctggcctgat cggccccctg ctgatctgct acaaggagag cgtggaccag      1740
aggggcaacc agatcatgtc tgacaagagg aacgtgatcc tgttctctgt gttcgatgag      1800
aacaggagct ggtatctgac cgagaacatc cagaggttcc tgcccaaccc cgccggcgtg      1860
cagctggagg accccgagtt ccaggccagc aacatcatgc acagcatcaa cggctacgtg      1920
ttcgacagcc tgcagctgtc tgtgtgcctg cacgaggtgg cctactggta catcctgagc      1980
atcggcgccc agaccgactt cctgtctgtg ttcttctctg gctacacctt caagcacaag      2040
atggtgtacg aggacaccct gaccctgttc cccttcagcg cgagaccgt gttcatgagc       2100 atggagaacc ccggcctgtg gatcctgggc tgccacaaca gcgacttcag gaacaggggc      2160
atgaccgccc tgctgaaagt cagcagctgc gacaagaaca ccggcgacta ctacgaggac      2220
agctacgagg acatcagcgc ctacctgctg agcaagaaca caccaccta cgtgaaccgc       2280 tccctgagcc agaacccccc cgtgctgaag aggcaccaga gggagatcac caggaccacc      2340
ctgcagagcg accaggagga gatcgactat gatgacacca tcagcgtgga gatgaagaag      2400
gaggacttcg acatctacga cgaggacgag aaccagagcc caggagctt ccagaagaag       2460 accaggcact acttcatcgc cgccgtggag aggctgtggg actatggcat gagcagcagc      2520
ccccacgtgc tgaggaacag ggcccagagc ggcagcgtgc cccagttcaa gaaggtggtg      2580
ttccaggagt tcaccgacgg cagcttcacc cagcccctgt acagaggcga gctgaacgag      2640
cacctgggcc tgctgggccc ctacatcagg gccgaggtgg aggacaacat catggtgacc      2700
ttcaggaacc aggccagcag gccctacagc ttctacagca gcctgatcag ctacgaggag      2760
gaccagaggg agggcgccga gccaggaag aacttcgtga agcccaacga gaccaagacc       2820
tacttctgga aggtgcagca ccacatggcc cccaccaagg acgagttcga ctgcaaggcc      2880
tgggcctact ctctgatgt ggacctggag aaggacgtgc acagcggcct gatcggcccc      2940
ctgctggtgt gccacaccaa caccctgaac cccgcccacg gcaggcaggt gaccgtgcag      3000
gagttcgccc tgttcttcac catcttcgac gagaccaaga ctggtactt caccgagaac       3060 atggagagga actgcagggc ccctgcaac atccagatgg aggacccac cttcaaggag        3120 aactacaggt tccacgccat caacggctac atcatggaca ccctgccgg cctggtgatg       3180 gcccaggacc agaggatcag gtggtatctg ctgagcatgg gcagcaacga gaacatccac      3240
agcatccact tcagcggcca cgtgttcacc gtgaggaaga aggaggagta caagatggcc      3300
ctgtacaacc tgtaccccgg cgtgttcgag accgtggaga tgctgcccag caaggccggc      3360
atctggaggg tggagtgcct gatcggcgag cacctgcacg ccggcatgag caccctgttc      3420
ctggtgtaca gcaacaagtg ccagacccccc ctgggcatgg ccagcggcca catcagggac     3480
```

| | |
|---|---|
| ttccagatca ccgcctctgg ccagtacggc cagtgggccc ccaagctggc caggctgcac | 3540 |
| tacagcggca gcatcaacgc ctggagcacc aaggagccct tcagctggat caaggtggac | 3600 |
| ctgctggccc ccatgatcat ccacggcatc aagacccagg gcgccaggca gaagttcagc | 3660 |
| agcctgtaca tcagccagtt catcatcatg tacagcctgg acggcaagaa gtggcagacc | 3720 |
| tacaggggca acagcaccgg caccctgatg gtgttcttcg gcaacgtgga cagcagcggc | 3780 |
| atcaagcaca acatcttcaa ccccccatc atcgccaggt acatcaggct gcaccccacc | 3840 |
| cactacagca tcaggagcac cctgcggatg gaactgatgg gctgcgacct gaacagctgc | 3900 |
| agcatgcccc tgggcatgga gagcaaggcc atctctgacg cccagatcac cgccagcagc | 3960 |
| tacttcacca acatgttcgc cacctggagc cccagcaagg ccaggctgca cctgcagggc | 4020 |
| aggagcaacg cctggaggcc ccaggtgaac aaccccaagg agtggctgca ggtggacttc | 4080 |
| cagaagacca tgaaggtgac cggcgtgacc acccagggcg tgaagagcct gctgaccagc | 4140 |
| atgtacgtga aggagttcct gatcagcagc agccaggacg ccaccagtg gaccctgttc | 4200 |
| ttccagaacg gcaaagtgaa ggtgttccag ggcaaccagg acagcttcac ccccgtggtg | 4260 |
| aacagcctgg acccccccct gctgaccagg tatctgagga tccaccccca gagctgggtg | 4320 |
| caccagatcg ccctgagaat ggaagtgctg ggatgcgagg cccaggacct gtactga | 4377 |

<210> SEQ ID NO 101
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

| | |
|---|---|
| atgcagattg agctgagcac ctgcttcttc ctgtgcctgc tgaggttctg cttctctgcc | 60 |
| accaggagat actacctggg cgccgtggag ctgagctggg actacatgca gtctgacctg | 120 |
| ggcgagctgc ctgtggacgc caggttcccc ccagagtgc caagagctt ccccttcaac | 180 |
| acctcagtgg tgtacaagaa gaccctgttc gtggagttca ccgaccacct gttcaacatc | 240 |
| gccaagccca ggccccctg gatgggcctg ctgggcccca ccatccaggc cgaggtgtac | 300 |
| gacaccgtgg tggtcaccct gaagaacatg gccagccacc ccgtgagcct gcacgccgtg | 360 |
| ggcgtgagct actggaagtc ctctgagggc gccgagtatg acgaccagac cagccagagg | 420 |
| gagaaggagg acgacaaggt gttccccggc aagagccaca cctacgtgtg gcaggtgctg | 480 |
| aaggagaacg cccccactgc cagcgacccc cctgcctga cctacagcta cctgagccac | 540 |
| gtggacctgg tgaaggacct gaactctggc ctgatcggcg ccctgctggt gtgcagggag | 600 |
| ggcagcctgg ccaaggagaa gacccagacc ctgcacaagt tcatcctgct gttcgccgtg | 660 |
| ttcgatgagg gcaagagctg gcacagcgag accaagaaca gcctgatgca ggacagggat | 720 |
| gccgcctctg ccagggcctg gcccaagatg cacaccgtga acggctacgt gaacaggagc | 780 |
| ctgcccggcc tgatcggctg ccacaggaag tctgtgtact ggcacgtgat cggcatgggc | 840 |
| accacccccg aggtgcacag catcttcctg gagggccaca ccttcctggt gaggaaccac | 900 |
| aggcaggcca gcctggagat cagccccatc accttcctga ccgcccagac cctgctgatg | 960 |
| gacctgggcc agttcctgct gttctgccac atcagcagcc accagcacga cggcatggag | 1020 |
| gcctacgtga aggtggacag ctgccccgag gagcccagc tgaggatgaa gaacaacgag | 1080 |
| gaggccgagg actatgatga tgacctgacc gactctgaga tggacgtggt gaggtttgat | 1140 |

```
gatgacaaca gccccagctt catccagatc aggtctgtgg ccaagaagca ccccaagacc   1200
tgggtgcact acatcgccgc cgaggaggag gactgggact acgcccccct ggtgctggcc   1260
cccgacgaca ggagctacaa gagccagtac ctgaacaacg cccccagag  gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca cgccatcga  gcccaggagc   2280
ttcagccaga ccccccccgt gctgaagagg caccagaggg agatcaccag gaccaccctg   2340
cagagcgacc aggaggagat cgactatgat gacaccatca gcgtggagat gaagaaggag   2400
gacttcgaca tctacgacga ggacgagaac cagagcccca ggagcttcca gaagaagacc   2460
aggcactact tcatcgccgc cgtggagagg ctgtgggact atggcatgag cagcagcccc   2520
cacgtgctga ggaacagggc ccagagcggc agcgtgcccc agttcaagaa ggtggtgttc   2580
caggagttca ccgacggcag cttcacccag cccctgtaca gaggcgagct gaacgagcac   2640
ctgggcctgc tgggccccta catcagggcc gaggtggagg acaacatcat ggtgaccttc   2700
aggaaccagg ccagcaggcc ctacagcttc tacagcagcc tgatcagcta cgaggaggac   2760
cagaggcagg gcgccgagcc caggaagaac ttcgtgaagc ccaacgagac caagacctac   2820
ttctggaagg tgcagcacca catggccccc accaaggacg agttcgactg caaggcctgg   2880
gcctacttct ctgatgtgga cctggagaag gacgtgcaca gcggcctgat cggccccctg   2940
ctggtgtgcc acaccaacac cctgaacccc gccacggca  ggcaggtgac cgtgcaggag   3000
ttcgccctgt tcttcaccat cttcgacgag accaagagct ggtacttcac cgagaacatg   3060
gagaggaact gcagggcccc ctgcaacatc cagatggagg accccacctt caaggagaac   3120
tacaggttcc acgccatcaa cggctacatc atggacaccc tgcccggcct ggtgatggcc   3180
caggaccaga ggatcaggtg gtatctgctg agcatgggca gcaacgagaa catccacagc   3240
atccacttca gcgccacgt  gttcaccgtg aggaagaagg aggagtacaa gatggccctg   3300
tacaacctgt accccggcgt gttcgagacc gtggagatgc tgcccagcaa ggccggcatc   3360
tggagggtgg agtgcctgat cggcgagcac ctgcacgccg gcatgagcac cctgttcctg   3420
gtgtacagca acaagtgcca gaccccctg  ggcatggcca gcggccacat cagggacttc   3480
```

| | | |
|---|---|---|
| cagatcaccg cctctggcca gtacggccag tgggccccca agctggccag gctgcactac | 3540 | |
| agcggcagca tcaacgcctg gagcaccaag gagcccttca gctggatcaa ggtggacctg | 3600 | |
| ctggccccca tgatcatcca cggcatcaag acccagggcg ccaggcagaa gttcagcagc | 3660 | |
| ctgtacatca gccagttcat catcatgtac agcctggacg gcaagaagtg gcagacctac | 3720 | |
| aggggcaaca gcaccggcac cctgatggtg ttcttcggca acgtggacag cagcggcatc | 3780 | |
| aagcacaaca tcttcaaccc ccccatcatc gccaggtaca tcaggctgca ccccacccac | 3840 | |
| tacagcatca ggagcaccct gcggatggaa ctgatgggct gcgacctgaa cagctgcagc | 3900 | |
| atgcccctgg gcatggagag caaggccatc tctgacgccc agatcaccgc cagcagctac | 3960 | |
| ttcaccaaca tgttcgccac ctggagcccc agcaaggcca ggctgcacct gcagggcagg | 4020 | |
| agcaacgcct ggaggcccca ggtgaacaac cccaaggagt ggctgcaggt ggacttccag | 4080 | |
| aagaccatga aggtgaccgg cgtgaccacc cagggcgtga gagcctgct gaccagcatg | 4140 | |
| tacgtgaagg agttcctgat cagcagcagc caggacggcc accagtggac cctgttcttc | 4200 | |
| cagaacggca aagtgaaggt gttccagggc aaccaggaca gcttcacccc cgtggtgaac | 4260 | |
| agcctggacc ccccccctgct gaccaggtat ctgaggatcc accccagag ctgggtgcac | 4320 | |
| cagatcgccc tgagaatgga agtgctggga tgcgaggccc aggacctgta ctga | 4374 | |

<210> SEQ ID NO 102
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

| | | |
|---|---|---|
| atgcagattg agctgagcac ctgcttcttc ctgtgcctgc tgaggttctg cttctctgcc | 60 | |
| accaggagat actacctggg cgccgtggag ctgagctggg actacatgca gtctgacctg | 120 | |
| ggcgagctgc ctgtggacgc caggttcccc cccagagtgc ccaagagctt cccccttcaac | 180 | |
| acctcagtgg tgtacaagaa gacccctgttc gtggagttca ccgaccacct gttcaacatc | 240 | |
| gccaagccca ggcccccctg gatgggcctg ctggccccca ccatccaggc cgaggtgtac | 300 | |
| gacaccgtgg tgatcaccct gaagaacatg gccagccacc ccgtgagcct gcacgccgtg | 360 | |
| ggcgtgagct actggaaggc ctctgagggc gccgagtatg acgaccagac cagccagagg | 420 | |
| gagaaggagg acgacaaggt gttccccggc ggcagccaca cctacgtgtg gcaggtgctg | 480 | |
| aaggagaacg cccccatggc cagcgacccc ctgtgcctga cctacagcta cctgagccac | 540 | |
| gtggacctgg tgaaggacct gaactctggc ctgatcggcg ccctgctggt gtgcagggag | 600 | |
| ggcagcctgg ccaaggagaa gacccagacc tgcacaagt tcatcctgct gttcgccgtg | 660 | |
| ttcgatgagg gcaagagctg gcacagcgag accaagaaca gcctgatgca ggacagggat | 720 | |
| gccgcctctg ccagggcctg gcccaagatg cacaccgtga acggctacgt gaacaggagc | 780 | |
| ctgcccggcc tgatcggctg ccacaggaag tctgtgtact ggcacgtgat cggcatgggc | 840 | |
| accacccccg aggtgcacag catcttcctg gagggccaca ccttcctggt gaggaaccac | 900 | |
| aggcaggcca gctggagat cagccccatc accttcctga ccgcccagac cctgctgatg | 960 | |
| gacctgggcc agttcctgct gttcctgcca tcagcagcc accagcacga cggcatggag | 1020 | |
| gcctacgtga aggtggacag ctgccccgag gagccccagc tgaggatgaa gaacaacgag | 1080 | |
| gaggccgagg actatgatga tgacctgacc gactctgaga tggacgtggt gaggtttgat | 1140 | |

-continued

```
gatgacaaca gccccagctt catccagatc aggtctgtgg ccaagaagca ccccaagacc    1200
tgggtgcact acatcgccgc cgaggaggag gactgggact acgcccccct ggtgctggcc    1260
cccgacgaca ggagctacaa gagccagtac ctgaacaacg ccccagag gatcggcagg      1320 aagtacaaga aggtcagatt catggcctac accgacgaga ccttcaagac cagggaggcc    1380
atccagcacg agtctggcat cctgggcccc ctgctgtacg gcgaggtggg cgacaccctg    1440
ctgatcatct tcaagaacca ggccagcagg ccctacaaca tctacccccca cggcatcacc   1500 gatgtgaggc ccctgtacag caggaggctg cccaagggcg tgaagcacct gaaggacttc    1560
cccatcctgc ccggcgagat cttcaagtac aagtggaccg tgaccgtgga ggatggcccc    1620
accaagtctg accccaggtg cctgaccagg tactacagca gcttcgtgaa catggagagg    1680
gacctggcct ctggcctgat cggcccctg ctgatctgct acaaggagag cgtggaccag     1740
aggggcaacc agatcatgtc tgacaagagg aacgtgatcc tgttctctgt gttcgatgag    1800
aacaggagct ggtatctgac cgagaacatc cagaggttcc tgcccaaccc cgccggcgtg    1860
cagctggagg accccgagtt ccaggccagc aacatcatgc acagcatcaa cggctacgtg    1920
ttcgacagcc tgcagctgtc tgtgtgcctg cacgaggtgg cctactggta catcctgagc    1980 atcgcgccc agaccgactt cctgtctgtg ttcttctctg gctacacctt caagcacaag     2040
atggtgtacg aggacaccct gaccctgttc cccttcagcg gcgagaccgt gttcatgagc    2100
atggagaacc ccgcctgtg gatcctgggc tgccacaaca gcgacttcag gaacaggggc    2160
atgaccgccc tgctgaaagt cagcagctgc gacaagaaca ccggcgacta ctacgaggac    2220
agctacgagg acatcagcgc ctacctgctg agcaagaaca acgccatcga gcccaggagc    2280
ttcagccaga accccccgt gctgaagagg caccagaggg agatcaccag gaccaccctg    2340
cagagcgacc aggaggagat cgactatgat gacaccatca gcgtggagat gaagaaggag    2400
gacttcgaca tctacgacga ggacgagaac cagagcccca ggagcttcca gaagaagacc    2460
aggcactact tcatcgccgc cgtggagagg ctgtgggact atggcatgag cagcagcccc    2520
cacgtgctga ggaacagggc ccagagcggc agcgtgcccc agttcaagaa ggtggtgttc    2580
caggagttca ccgacggcag cttcacccag ccctgtaca gaggcgagct gaacgagcac    2640
ctgggcctgc tgggccccta catcagggcc gaggtggagg acaacatcat ggtgaccttc    2700
aggaaccagg ccagcaggcc ctacagcttc tacagcagcc tgatcagcta cgaggaggac    2760
cagaggcagg gcgccgagcc caggaagaac ttcgtgaagc ccaacgagac caagacctac    2820
ttctggaagg tgcagcacca catggccccc accaaggacg agttcgactg caaggcctgg    2880
gcctacttct ctgatgtgga cctggagaag gacgtgcaca gcggcctgat cggcccctg    2940 ctggtgtgcc acaccaacac cctgaaccc gcccacggca gcaggtgac cgtgcaggag    3000 ttcgccctgt tcttcaccat cttcgacgag accaagagct ggtacttcac cgagaacatg    3060
gagaggaact gcagggcccc ctgcaacatc cagatggagg accccacctt caaggagaac    3120
tacaggttcc acgccatcaa cggctacatc atggacaccc tgcccggcct ggtgatggcc    3180
caggaccaga ggatcaggtg gtatctgctg agcatgggca gcaacgagaa catccacagc    3240
atccacttca gcgccacgt gttcaccgtg aggaagaagg aggagtacaa gatggccctg    3300
tacaacctgt accccggcgt gttcgagacc gtggagatgc tgcccagcaa ggccggcatc    3360
tggagggtgg agtgcctgat cggcgagcac ctgcacgccg gcatgagcac cctgttcctg    3420
gtgtacagca acaagtgcca gacccccctg ggcatggcca gcggccacat cagggacttc    3480
cagatcaccg cctctggcca gtacggccag tgggcccccca agctggccag gctgcactac    3540
```

```
agcggcagca tcaacgcctg gagcaccaag gagcccttca gctggatcaa ggtggacctg    3600
ctggccccca tgatcatcca cggcatcaag acccagggcg ccaggcagaa gttcagcagc    3660
ctgtacatca gccagttcat catcatgtac agcctggacg gcaagaagtg gcagacctac    3720
aggggcaaca gcaccggcac cctgatggtg ttcttcggca acgtggacag cagcggcatc    3780
aagcacaaca tcttcaaccc ccccatcatc gccaggtaca tcaggctgca ccccacccac    3840
tacagcatca ggagcaccct gcggatggaa ctgatgggct gcgacctgaa cagctgcagc    3900 atgccccctgg gcatggagag caaggccatc tctgacgccc agatcaccgc cagcagctac    3960
ttcaccaaca tgttcgccac ctggagcccc agcaaggcca ggctgcacct gcagggcagg    4020
agcaacgcct ggaggcccca ggtgaacaac cccaaggagt ggctgcaggt ggacttccag    4080
aagaccatga aggtgaccgg cgtgaccacc agggcgtga agagcctgct gaccagcatg    4140
tacgtgaagg agttcctgat cagcagcagc caggacggcc accagtggac cctgttcttc    4200
cagaacggca aagtgaaggt gttccagggc aaccaggaca gcttcacccc cgtggtgaac    4260
agcctggacc ccccctgct gaccaggtat ctgaggatcc accccagag ctgggtgcac    4320 cagatcgccc tgagaatgga agtgctggga tgcgaggccc aggacctgta ctga          4374
```

<210> SEQ ID NO 103
<211> LENGTH: 4377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc ctgtggacgc caggttcccc ccagagtgc caagagctt ccccttcaac     180 acctcagtgg tgtacaagaa gaccctgttc gtggagttca ccgaccacct gttcaacatc     240
gccaagccca ggcccccctg gatgggcctg ctgggcccca ccatccaggc cgaggtgtac     300
gacaccgtgg tggtcaccct gaagaacatg gccagccacc ccgtgagcct gcacgccgtg     360
ggcgtgagct actggaagtc ctctgagggc gccgagtatg acgaccagac cagccagagg     420
gagaaggagg acgacaaggt gttccccggc aagagccaca cctacgtgtg gcaggtgctg     480
aaggagaacg gccccactgc cagcgacccc cctgcctga cctacagcta cctgagccac     540
gtggacctgg tgaaggacct gaactctggc ctgatcggcg ccctgctggt gtgcagggag     600
ggcagcctgg ccaaggagaa gacccagacc ctgcacaagt tcatcctgct gttcgccgtg     660
ttcgatgagg gcaagagctg gcacagcgag accaagaaca gcctgatgca ggacagggat     720
gccgcctctg ccagggcctg gccaagatg cacaccgtga acggctacgt gaacaggagc     780
ctgcccggcc tgatcggctg ccacaggaag tctgtgtact ggcacgtgat cggcatgggc     840 accaccccg aggtgcacag catcttcctg gagggccaca ccttcctggt gaggaaccac     900
aggcaggcca gctggagat cagccccatc accttcctga ccgccagac cctgctgatg     960 gacctgggcc agttcctgct gttctgccac atcagcagcc accagcacga cggcatggag    1020
gcctacgtga aggtggacag ctgccccgag gagcccagc tgaggatgaa gaacaacgag    1080
gaggccgagg actatgatga tgacctgacc gactctgaga tggacgtggt gaggtttgat    1140
gatgacaaca gccccagctt catccagatc aggtctgtgg ccaagaagca ccccaagacc    1200
```

```
tgggtgcact acatcgccgc cgaggaggag gactgggact acgccccct ggtgctggcc   1260 cccgacgaca ggagctacaa gagccagtac ctgaacaacg cccccagag gatcggcagg   1320 aagtacaaga aggtcagatt catggcctac accgacgaga ccttcaagac cagggaggcc   1380
atccagcacg agtctggcat cctgggcccc tgctgtacg gcgaggtggg cgacaccctg   1440
ctgatcatct tcaagaacca ggccagcagg ccctacaaca tctacccca cggcatcacc   1500 gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggcccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980 atcgcgccc agaccgactt cctgtctgtg ttcttctctg gctacacctt caagcacaag   2040
atggtgtacg aggacacct gaccctgttc cccttcagcg gcgagaccgt gttcatgagc   2100
atggagaacc ccgcctgtg gatcctgggc tgccacaaca gcgacttcag gaacagggc   2160 atgaccgccc tgctgaaagt cagcagctgc gacaagaaca ccggcgacta ctacgaggac   2220
agctacgagg acatcagcgc ctacctgctg agcaagaaca acaccaccta cgtgaaccgc   2280
tccctgagcc agaacccccc cgtgctgaag aggcaccaga gggagatcac caggaccacc   2340
ctgcagagcg accaggagga gatcgactat gatgacacca tcagcgtgga gatgaagaag   2400
gaggacttcg acatctacga cgaggacgag aaccagagcc caggagctt ccagaagaag   2460 accaggcact acttcatcgc cgccgtggag aggctgtggg actatggcat gagcagcagc   2520
ccccacgtgc tgaggaacag ggcccagagc ggcagcgtgc cccagttcaa gaaggtggtg   2580
ttccaggagt tcaccgacgg cagcttcacc cagcccctgt acagaggcga gctgaacgag   2640
cacctgggcc tgctgggccc ctacatcagg gccgaggtgg aggacaacat catggtgacc   2700
ttcaggaacc aggccagcag gccctacagc ttctacagca gcctgatcag ctacgaggag   2760
gaccagaggc agggcgccga gcccaggaag aacttcgtga gcccaacga gaccaagacc   2820 tacttctgga aggtgcagca ccacatggcc cccaccaagg acgagttcga ctgcaaggcc   2880
tgggcctact ctctgatgt ggacctggag aaggacgtgc acagcggcct gatcggcccc   2940
ctgctggtgt gccacaccaa caccctgaac cccgcccacg gcaggcaggt gaccgtgcag   3000
gagttcgccc tgttcttcac catcttcgac gagaccaaga gctggtactt caccgagaac   3060
atggagagga actgcagggc ccctgcaac atccagatgg aggacccac cttcaaggag   3120 aactacaggt tccacgccat caacggctac atcatggaca ccctgcccgg cctggtgatg   3180
gcccaggacc agaggatcag gtggtatctg ctgagcatgg gcagcaacga gaacatccac   3240
agcatccact tcagcggcca cgtgttcacc gtgaggaaga aggaggagta caagatggcc   3300
ctgtacaacc tgtaccccgg cgtgttcgag accgtggaga tgctgcccag caaggccggc   3360
atctggaggg tggagtgcct gatcggcgag cacctgcacg ccggcatgag caccctgttc   3420
ctggtgtaca gcaacaagtg ccagacccc ctgggcatgg ccagcggcca catcagggac   3480
ttccagatca ccgcctctgg ccagtacggc cagtgggccc ccaagctggc caggctgcac   3540
```

```
tacagcggca gcatcaacgc ctggagcacc aaggagccct tcagctggat caaggtggac    3600
ctgctggccc ccatgatcat ccacggcatc aagacccagg gcgccaggca gaagttcagc    3660
agcctgtaca tcagccagtt catcatcatg tacagcctgg acggcaagaa gtggcagacc    3720
tacaggggca cagcaccgg caccctgatg gtgttcttcg gcaacgtgga cagcagcggc     3780
atcaagcaca acatcttcaa cccccccatc atcgccaggt acatcaggct gcaccccacc    3840
cactacagca tcaggagcac cctgcgatg gaactgatgg gctgcgacct gaacagctgc     3900
agcatgcccc tgggcatgga gagcaaggcc atctctgacg cccagatcac cgccagcagc    3960
tacttcacca acatgttcgc cacctggagc cccagcaagg ccaggctgca cctgcagggc    4020
aggagcaacg cctggaggcc ccaggtgaac aaccccaagg agtggctgca ggtggacttc    4080
cagaagacca tgaaggtgac cggcgtgacc acccagggcg tgaagagcct gctgaccagc    4140
atgtacgtga aggagttcct gatcagcagc agccaggacg ccaccagtg gaccctgttc      4200 ttccagaacg gcaaagtgaa ggtgttccag ggcaaccagg acagcttcac ccccgtggtg    4260
aacagcctgg accccccct gctgaccagg tatctgagga tccaccccca gagctgggtg     4320
caccagatcg ccctgagaat ggaagtgctg ggatgcgagg cccaggacct gtactga       4377
```

<210> SEQ ID NO 104
<211> LENGTH: 1458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Val Thr Leu Lys Asn Met Ala Ser
            100                 105                 110

His Pro Val Ser Leu His Ala Val Gly Val Ser Tyr Trp Lys Ser Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Lys Ser His Thr Tyr Val Trp Gln Val Leu
145                 150                 155                 160

Lys Glu Asn Gly Pro Thr Ala Ser Asp Pro Pro Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
```

-continued

```
            210                 215                 220
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
                290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Thr Thr Tyr Val Asn Arg Ser Leu Ser Gln Asn Pro Pro Val
        755                 760                 765
Leu Lys Arg His Gln Arg Glu Ile Thr Arg Thr Thr Leu Gln Ser Asp
    770                 775                 780
Gln Glu Glu Ile Asp Tyr Asp Asp Thr Ile Ser Val Glu Met Lys Lys
785                 790                 795                 800
Glu Asp Phe Asp Ile Tyr Asp Glu Asp Glu Asn Gln Ser Pro Arg Ser
                805                 810                 815
Phe Gln Lys Lys Thr Arg His Tyr Phe Ile Ala Ala Val Glu Arg Leu
            820                 825                 830
Trp Asp Tyr Gly Met Ser Ser Ser Pro His Val Leu Arg Asn Arg Ala
        835                 840                 845
Gln Ser Gly Ser Val Pro Gln Phe Lys Lys Val Val Phe Gln Glu Phe
    850                 855                 860
Thr Asp Gly Ser Phe Thr Gln Pro Leu Tyr Arg Gly Glu Leu Asn Glu
865                 870                 875                 880
His Leu Gly Leu Leu Gly Pro Tyr Ile Arg Ala Glu Val Glu Asp Asn
                885                 890                 895
Ile Met Val Thr Phe Arg Asn Gln Ala Ser Arg Pro Tyr Ser Phe Tyr
            900                 905                 910
Ser Ser Leu Ile Ser Tyr Glu Glu Asp Gln Arg Gln Gly Ala Glu Pro
        915                 920                 925
Arg Lys Asn Phe Val Lys Pro Asn Glu Thr Lys Thr Tyr Phe Trp Lys
    930                 935                 940
Val Gln His His Met Ala Pro Thr Lys Asp Glu Phe Asp Cys Lys Ala
945                 950                 955                 960
Trp Ala Tyr Phe Ser Asp Val Asp Leu Glu Lys Asp Val His Ser Gly
                965                 970                 975
Leu Ile Gly Pro Leu Leu Val Cys His Thr Asn Thr Leu Asn Pro Ala
            980                 985                 990
His Gly Arg Gln Val Thr Val Gln Glu Phe Ala Leu Phe Phe Thr Ile
        995                 1000                1005
Phe Asp Glu Thr Lys Ser Trp Tyr Phe Thr Glu Asn Met Glu Arg
    1010                1015                1020
Asn Cys Arg Ala Pro Cys Asn Ile Gln Met Glu Asp Pro Thr Phe
    1025                1030                1035
Lys Glu Asn Tyr Arg Phe His Ala Ile Asn Gly Tyr Ile Met Asp
    1040                1045                1050
```

-continued

Thr Leu Pro Gly Leu Val Met Ala Gln Asp Gln Arg Ile Arg Trp
1055            1060                1065

Tyr Leu Leu Ser Met Gly Ser Asn Glu Asn Ile His Ser Ile His
1070            1075                1080

Phe Ser Gly His Val Phe Thr Val Arg Lys Lys Glu Glu Tyr Lys
1085            1090                1095

Met Ala Leu Tyr Asn Leu Tyr Pro Gly Val Phe Glu Thr Val Glu
1100            1105                1110

Met Leu Pro Ser Lys Ala Gly Ile Trp Arg Val Glu Cys Leu Ile
1115            1120                1125

Gly Glu His Leu His Ala Gly Met Ser Thr Leu Phe Leu Val Tyr
1130            1135                1140

Ser Asn Lys Cys Gln Thr Pro Leu Gly Met Ala Ser Gly His Ile
1145            1150                1155

Arg Asp Phe Gln Ile Thr Ala Ser Gly Gln Tyr Gly Gln Trp Ala
1160            1165                1170

Pro Lys Leu Ala Arg Leu His Tyr Ser Gly Ser Ile Asn Ala Trp
1175            1180                1185

Ser Thr Lys Glu Pro Phe Ser Trp Ile Lys Val Asp Leu Leu Ala
1190            1195                1200

Pro Met Ile Ile His Gly Ile Lys Thr Gln Gly Ala Arg Gln Lys
1205            1210                1215

Phe Ser Ser Leu Tyr Ile Ser Gln Phe Ile Ile Met Tyr Ser Leu
1220            1225                1230

Asp Gly Lys Lys Trp Gln Thr Tyr Arg Gly Asn Ser Thr Gly Thr
1235            1240                1245

Leu Met Val Phe Phe Gly Asn Val Asp Ser Ser Gly Ile Lys His
1250            1255                1260

Asn Ile Phe Asn Pro Pro Ile Ile Ala Arg Tyr Ile Arg Leu His
1265            1270                1275

Pro Thr His Tyr Ser Ile Arg Ser Thr Leu Arg Met Glu Leu Met
1280            1285                1290

Gly Cys Asp Leu Asn Ser Cys Ser Met Pro Leu Gly Met Glu Ser
1295            1300                1305

Lys Ala Ile Ser Asp Ala Gln Ile Thr Ala Ser Ser Tyr Phe Thr
1310            1315                1320

Asn Met Phe Ala Thr Trp Ser Pro Ser Lys Ala Arg Leu His Leu
1325            1330                1335

Gln Gly Arg Ser Asn Ala Trp Arg Pro Gln Val Asn Asn Pro Lys
1340            1345                1350

Glu Trp Leu Gln Val Asp Phe Gln Lys Thr Met Lys Val Thr Gly
1355            1360                1365

Val Thr Thr Gln Gly Val Lys Ser Leu Leu Thr Ser Met Tyr Val
1370            1375                1380

Lys Glu Phe Leu Ile Ser Ser Gln Asp Gly His Gln Trp Thr
1385            1390                1395

Leu Phe Phe Gln Asn Gly Lys Val Lys Val Phe Gln Gly Asn Gln
1400            1405                1410

Asp Ser Phe Thr Pro Val Val Asn Ser Leu Asp Pro Pro Leu Leu
1415            1420                1425

Thr Arg Tyr Leu Arg Ile His Pro Gln Ser Trp Val His Gln Ile
1430            1435                1440

```
Ala Leu Arg Met Glu Val Leu Gly Cys Glu Ala Gln Asp Leu Tyr
    1445                1450                1455

<210> SEQ ID NO 105
<211> LENGTH: 1458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350
```

```
Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Thr Thr Tyr Val Asn Arg Ser Leu Ser Gln Asn Pro Pro Val
        755                 760                 765
```

-continued

```
Leu Lys Arg His Gln Arg Glu Ile Thr Arg Thr Thr Leu Gln Ser Asp
770                 775                 780
Gln Glu Glu Ile Asp Tyr Asp Asp Thr Ile Ser Val Glu Met Lys Lys
785                 790                 795                 800
Glu Asp Phe Asp Ile Tyr Asp Glu Asp Glu Asn Gln Ser Pro Arg Ser
            805                 810                 815
Phe Gln Lys Lys Thr Arg His Tyr Phe Ile Ala Ala Val Glu Arg Leu
        820                 825                 830
Trp Asp Tyr Gly Met Ser Ser Pro His Val Leu Arg Asn Arg Ala
                835                 840                 845
Gln Ser Gly Ser Val Pro Gln Phe Lys Lys Val Phe Gln Glu Phe
850                 855                 860
Thr Asp Gly Ser Phe Thr Gln Pro Leu Tyr Arg Gly Glu Leu Asn Glu
865                 870                 875                 880
His Leu Gly Leu Leu Gly Pro Tyr Ile Arg Ala Glu Val Glu Asp Asn
                885                 890                 895
Ile Met Val Thr Phe Arg Asn Gln Ala Ser Arg Pro Tyr Ser Phe Tyr
            900                 905                 910
Ser Ser Leu Ile Ser Tyr Glu Glu Asp Gln Arg Gln Gly Ala Glu Pro
        915                 920                 925
Arg Lys Asn Phe Val Lys Pro Asn Glu Thr Lys Thr Tyr Phe Trp Lys
930                 935                 940
Val Gln His His Met Ala Pro Thr Lys Asp Glu Phe Asp Cys Lys Ala
945                 950                 955                 960
Trp Ala Tyr Phe Ser Asp Val Asp Leu Glu Lys Asp Val His Ser Gly
                965                 970                 975
Leu Ile Gly Pro Leu Leu Val Cys His Thr Asn Thr Leu Asn Pro Ala
            980                 985                 990
His Gly Arg Gln Val Thr Val Gln Glu Phe Ala Leu Phe Phe Thr Ile
        995                1000                1005
Phe Asp Glu Thr Lys Ser Trp Tyr Phe Thr Glu Asn Met Glu Arg
1010                1015                1020
Asn Cys Arg Ala Pro Cys Asn Ile Gln Met Glu Asp Pro Thr Phe
1025                1030                1035
Lys Glu Asn Tyr Arg Phe His Ala Ile Asn Gly Tyr Ile Met Asp
1040                1045                1050
Thr Leu Pro Gly Leu Val Met Ala Gln Asp Gln Arg Ile Arg Trp
1055                1060                1065
Tyr Leu Leu Ser Met Gly Ser Asn Glu Asn Ile His Ser Ile His
1070                1075                1080
Phe Ser Gly His Val Phe Thr Val Arg Lys Lys Glu Glu Tyr Lys
1085                1090                1095
Met Ala Leu Tyr Asn Leu Tyr Pro Gly Val Phe Glu Thr Val Glu
1100                1105                1110
Met Leu Pro Ser Lys Ala Gly Ile Trp Arg Val Glu Cys Leu Ile
1115                1120                1125
Gly Glu His Leu His Ala Gly Met Ser Thr Leu Phe Leu Val Tyr
1130                1135                1140
Ser Asn Lys Cys Gln Thr Pro Leu Gly Met Ala Ser Gly His Ile
1145                1150                1155
Arg Asp Phe Gln Ile Thr Ala Ser Gly Gln Tyr Gly Gln Trp Ala
1160                1165                1170
```

Pro Lys Leu Ala Arg Leu His Tyr Ser Gly Ser Ile Asn Ala Trp
    1175                1180                1185

Ser Thr Lys Glu Pro Phe Ser Trp Ile Lys Val Asp Leu Leu Ala
    1190                1195                1200

Pro Met Ile Ile His Gly Ile Lys Thr Gln Gly Ala Arg Gln Lys
    1205                1210                1215

Phe Ser Ser Leu Tyr Ile Ser Gln Phe Ile Ile Met Tyr Ser Leu
    1220                1225                1230

Asp Gly Lys Lys Trp Gln Thr Tyr Arg Gly Asn Ser Thr Gly Thr
    1235                1240                1245

Leu Met Val Phe Phe Gly Asn Val Asp Ser Ser Gly Ile Lys His
    1250                1255                1260

Asn Ile Phe Asn Pro Pro Ile Ile Ala Arg Tyr Ile Arg Leu His
    1265                1270                1275

Pro Thr His Tyr Ser Ile Arg Ser Thr Leu Arg Met Glu Leu Met
    1280                1285                1290

Gly Cys Asp Leu Asn Ser Cys Ser Met Pro Leu Gly Met Glu Ser
    1295                1300                1305

Lys Ala Ile Ser Asp Ala Gln Ile Thr Ala Ser Ser Tyr Phe Thr
    1310                1315                1320

Asn Met Phe Ala Thr Trp Ser Pro Ser Lys Ala Arg Leu His Leu
    1325                1330                1335

Gln Gly Arg Ser Asn Ala Trp Arg Pro Gln Val Asn Asn Pro Lys
    1340                1345                1350

Glu Trp Leu Gln Val Asp Phe Gln Lys Thr Met Lys Val Thr Gly
    1355                1360                1365

Val Thr Thr Gln Gly Val Lys Ser Leu Leu Thr Ser Met Tyr Val
    1370                1375                1380

Lys Glu Phe Leu Ile Ser Ser Ser Gln Asp Gly His Gln Trp Thr
    1385                1390                1395

Leu Phe Phe Gln Asn Gly Lys Val Lys Val Phe Gln Gly Asn Gln
    1400                1405                1410

Asp Ser Phe Thr Pro Val Val Asn Ser Leu Asp Pro Pro Leu Leu
    1415                1420                1425

Thr Arg Tyr Leu Arg Ile His Pro Gln Ser Trp Val His Gln Ile
    1430                1435                1440

Ala Leu Arg Met Glu Val Leu Gly Cys Glu Ala Gln Asp Leu Tyr
    1445                1450                1455

<210> SEQ ID NO 106
<211> LENGTH: 1457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

-continued

```
Tyr Lys Lys Thr Leu Phe Val Glu Phe Thr Asp His Leu Phe Asn Ile
 65                  70                  75                  80
Ala Lys Pro Arg Pro Pro Trp Met Gly Leu Leu Gly Pro Thr Ile Gln
                 85                  90                  95
Ala Glu Val Tyr Asp Thr Val Val Thr Leu Lys Asn Met Ala Ser
            100                 105                 110
His Pro Val Ser Leu His Ala Val Gly Val Ser Tyr Trp Lys Ser Ser
            115                 120                 125
Glu Gly Ala Glu Tyr Asp Asp Gln Thr Ser Gln Arg Glu Lys Glu Asp
            130                 135                 140
Asp Lys Val Phe Pro Gly Lys Ser His Thr Tyr Val Trp Gln Val Leu
145                 150                 155                 160
Lys Glu Asn Gly Pro Thr Ala Ser Asp Pro Pro Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
            210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
            290                 295                 300
Leu Glu Ile Ser Pro Ile Thr Phe Leu Thr Ala Gln Thr Leu Leu Met
305                 310                 315                 320
Asp Leu Gly Gln Phe Leu Leu Ser Cys His Ile Ser Ser His Gln His
            325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895
```

-continued

```
Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
    915                 920                 925

Lys Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290
```

```
Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr
1445                1450                1455

<210> SEQ ID NO 107
<211> LENGTH: 1457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Thr Leu Lys Asn Met Ala Ser
                100                 105                 110

His Pro Val Ser Leu His Ala Val Gly Val Ser Tyr Trp Lys Ser Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Lys Ser His Thr Tyr Val Trp Gln Val Leu
145                 150                 155                 160

Lys Glu Asn Gly Pro Thr Ala Ser Asp Pro Pro Cys Leu Thr Tyr Ser
                165                 170                 175

Tyr Leu Ser His Val Asp Leu Val Lys Asp Leu Asn Ser Gly Leu Ile
            180                 185                 190
```

```
Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Ser Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605
```

-continued

```
Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
            805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
            885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020
```

```
Cys Arg Ala Pro Cys Asn Ile Gln Met Glu Asp Pro Thr Phe Lys
    1025            1030                1035

Glu Asn Tyr Arg Phe His Ala Ile Asn Gly Tyr Ile Met Asp Thr
    1040            1045                1050

Leu Pro Gly Leu Val Met Ala Gln Asp Gln Arg Ile Arg Trp Tyr
    1055            1060                1065

Leu Leu Ser Met Gly Ser Asn Glu Asn Ile His Ser Ile His Phe
    1070            1075                1080

Ser Gly His Val Phe Thr Val Arg Lys Lys Glu Glu Tyr Lys Met
    1085            1090                1095

Ala Leu Tyr Asn Leu Tyr Pro Gly Val Phe Glu Thr Val Glu Met
    1100            1105                1110

Leu Pro Ser Lys Ala Gly Ile Trp Arg Val Glu Cys Leu Ile Gly
    1115            1120                1125

Glu His Leu His Ala Gly Met Ser Thr Leu Phe Leu Val Tyr Ser
    1130            1135                1140

Asn Lys Cys Gln Thr Pro Leu Gly Met Ala Ser Gly His Ile Arg
    1145            1150                1155

Asp Phe Gln Ile Thr Ala Ser Gly Gln Tyr Gly Gln Trp Ala Pro
    1160            1165                1170

Lys Leu Ala Arg Leu His Tyr Ser Gly Ser Ile Asn Ala Trp Ser
    1175            1180                1185

Thr Lys Glu Pro Phe Ser Trp Ile Lys Val Asp Leu Leu Ala Pro
    1190            1195                1200

Met Ile Ile His Gly Ile Lys Thr Gln Gly Ala Arg Gln Lys Phe
    1205            1210                1215

Ser Ser Leu Tyr Ile Ser Gln Phe Ile Ile Met Tyr Ser Leu Asp
    1220            1225                1230

Gly Lys Lys Trp Gln Thr Tyr Arg Gly Asn Ser Thr Gly Thr Leu
    1235            1240                1245

Met Val Phe Phe Gly Asn Val Asp Ser Ser Gly Ile Lys His Asn
    1250            1255                1260

Ile Phe Asn Pro Pro Ile Ile Ala Arg Tyr Ile Arg Leu His Pro
    1265            1270                1275

Thr His Tyr Ser Ile Arg Ser Thr Leu Arg Met Glu Leu Met Gly
    1280            1285                1290

Cys Asp Leu Asn Ser Cys Ser Met Pro Leu Gly Met Glu Ser Lys
    1295            1300                1305

Ala Ile Ser Asp Ala Gln Ile Thr Ala Ser Ser Tyr Phe Thr Asn
    1310            1315                1320

Met Phe Ala Thr Trp Ser Pro Ser Lys Ala Arg Leu His Leu Gln
    1325            1330                1335

Gly Arg Ser Asn Ala Trp Arg Pro Gln Val Asn Asn Pro Lys Glu
    1340            1345                1350

Trp Leu Gln Val Asp Phe Gln Lys Thr Met Lys Val Thr Gly Val
    1355            1360                1365

Thr Thr Gln Gly Val Lys Ser Leu Leu Thr Ser Met Tyr Val Lys
    1370            1375                1380

Glu Phe Leu Ile Ser Ser Ser Gln Asp Gly His Gln Trp Thr Leu
    1385            1390                1395

Phe Phe Gln Asn Gly Lys Val Lys Val Phe Gln Gly Asn Gln Asp
    1400            1405                1410
```

```
Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 108
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atgcagattg agctgtccac ctgcttcttt ctgtgcctgc tgagattctg cttctctgcc      60
accaggagat actacctggg ggctgtggaa ctttcttggg actacatgca gtctgacctg     120
ggagagctgc ctgtggatgc caggttccca cccagagtgc ccaagtcctt cccattcaac     180
acctctgtgg tctacaagaa gacactcttt gtggaattca ctgaccacct gttcaacatt     240
gcaaaaccca gaccaccctg gatgggactc tgggaccca ccattcaggc tgaggtgtat     300
gacactgtgg tcgtcaccct caagaacatg gcatcccacc ctgtgtctct gcatgctgtg     360
ggagtctcat actggaaatc ctctgaaggg gctgagtatg atgaccagac atcccagaga     420
gagaaagagg atgacaaggt gttccctggg aagtctcaca cctatgtgtg gcaagtcctc     480
aaggagaatg gacccactgc atctgaccca ccctgcctga catactccta cctttctcat     540
gtggacctgg tcaaggacct caactctgga ctgattgggg cactgctggt gtgcagggaa     600
ggatccctgg ccaaggagaa aacccagaca ctgcacaagt tcattctcct gtttgctgtc     660
tttgatgagg gcaagtcttg gcactctgaa acaaagaact ccctgatgca agacagggat     720
gctgcctctg ccagggcatg gcccaagatg cacactgtga atggctatgt gaacagatca     780
ctgcctggac tcattggctg ccacaggaaa tctgtctact ggcatgtgat tggcatgggg     840 acaaccctg aagtgcactc cattttcctg gagggacaca ccttcctggt caggaaccac     900
agacaagcct ctctggagat ctctcccatc accttcctca ctgcacagac actgctgatg     960
gaccttggac agttcctgct gttcctgcca catctcttcc accagcatga tggcatggaa    1020
gcctatgtca aggtggactc atgccctgag gaaccacagc tcaggatgaa gaacaatgag    1080
gaggctgagg actatgatga tgacctgact gactctgaga tggatgtggt cagatttgat    1140
gatgacaact ctccatcctt cattcagatc aggtctgtgg caaagaaaca ccccaagaca    1200
tgggtgcact acattgctgc tgaggaagag gactgggact atgcaccact ggtcctggcc    1260
cctgatgaca ggagctacaa gtctcagtac ctcaacaatg gcccacaaag aattggaaga    1320
aagtacaaga agtcagatt catggcctac actgatgaaa ccttcaagac aagagaagcc    1380
attcagcatg agtctggcat tctgggacca ctcctgtatg gggaagtggg agacaccctg    1440
ctcatcatct tcaagaacca ggcctccagg ccctacaaca tctacccaca tggcatcact    1500
gatgtcaggc cctgtacag caggagactg ccaaaagggg tgaaacacct caaggacttc    1560
cccattctgc ctggagagat cttcaagtac aagtggactg tcactgtgga ggatggacca    1620
acaaagtctg accccaggtg cctcaccaga tactactcct cttttgtgaa catggagaga    1680
gacctggcat ctggactgat ggaccactg ctcatctgct acaaggagtc tgtggaccag    1740
agaggcaacc agatcatgtc tgacaagaga atgtgattc tgttctctgt ctttgatgag    1800
```

-continued

```
aacagatcat ggtacctgac tgagaacatt cagagattcc tgcccaaccc tgctggggtg      1860
caactggaag accctgagtt ccaggcaagc aacatcatgc actccatcaa tggctatgtg      1920
tttgactctc tccagctttc tgtctgcctg catgaggtgg cctactggta cattctttct      1980
attggggcac aaactgactt ccttctgtc ttcttctctg gatacacctt caagcacaag       2040
atggtgtatg aggacaccct gacactcttc ccattctctg ggaaactgt gttcatgagc       2100 atggagaacc ctggactgtg gattctggga tgccacaact ctgacttcag aaacagggga     2160
atgactgcac tgctcaaagt ctcctcctgt gacaagaaca ctggggacta ctatgaggac      2220
tcttatgagg acatctctgc ctacctgctc agcaagaaca atgccattga gcccagaagc      2280
ttctctcaga atccacctgt cctgaagaga caccagagag atcaccag gacaaccctc        2340 cagtctgacc aggaagagat tgactatgat gacaccattt ctgtggagat gaagaaggag      2400
gactttgaca tctatgatga ggacgagaac cagtctccaa gatcattcca gaagaagaca      2460
agacactact tcattgctgc tgtggaaaga ctgtgggact atggcatgtc ttcctctccc      2520
catgtcctca ggaacagggc acagtctggc tctgtgccac agttcaagaa agtggtcttc     2580
caggagttca ctgatggctc attcacccag ccctgtaca gagggaact gaatgagcac        2640 ctgggactcc tgggaccata catcagggct gaggtggaag acaacatcat ggtgacattc     2700
agaaaccagg cctccaggcc ctacagcttc tactcttccc tcatcagcta tgaggaagac     2760
cagagacaag gggctgagcc aagaaagaac tttgtgaaac ccaatgaaac caagacctac     2820
ttctggaaag tccagcacca catggcaccc accaaggatg agtttgactg caaggcctgg     2880
gcatacttct ctgatgtgga cctggagaaa gatgtgcact ctggcctgat ggcccactc     2940 ctggtctgcc acaccaacac cctgaacccct gcacatggaa ggcaagtgac tgtgcaggag    3000
tttgccctct tcttcaccat cttgatgaa accaagtcat ggtacttcac tgagaacatg      3060
gagagaaact gcagagcacc atgcaacatt cagatggaag accccacctt caggagaac      3120 tacaggttcc atgccatcaa tggctacatc atggacaccc tgcctgggct tgtcatggca     3180
caggaccaga gaatcagatg gtacctgctt tctatgggat ccaatgagaa cattcactcc     3240
atccacttct ctgggcatgt cttcactgtg agaaagaagg aggaatacaa gatggccctg     3300
tacaacctct accctggggt cttttgagact gtggagatgc tgccctccaa agctggcatc    3360
tggagggtgg aatgcctcat tggggagcac ctgcatgctg gcatgtcaac cctgttcctg    3420
gtctacagca acaagtgcca gacaccctg ggaatggcct ctggccacat cagggacttc     3480
cagatcactg cctctggcca gtatggccag tgggcaccca aactggccag gctccactac     3540
tctggctcca tcaatgcatg gtcaaccaag gagccattct cttggatcaa ggtggaccttg   3600 ctggcaccca tgatcattca tggcatcaag acacaggggg caagacagaa attctcctct    3660
ctgtacatct cacagttcat catcatgtac tctctggatg gcaagaagtg gcagacatac    3720
agaggcaact ccactggcac cctcatggtc ttctttggca atgtggacag ctctggcatc    3780
aagcacaaca tcttcaaccc tcccatcatt gccagataca tcaggctgca ccccacccac    3840
tactcaatca gatcaaccct caggatggaa ctgatgggat gtgacctgaa ctcctgctca    3900
atgcccctgg gaatggagag caaggccatt tctgatgccc agatcactgc atcctcttac   3960
ttcaccaaca tgtttgccac ctggtcacca tcaaaagcca ggctgcacct ccagggaaga    4020
agcaatgcct ggagaccca ggtcaacaac ccaaaggaat ggctgcaagt ggacttccag     4080
aagacaatga aagtcactgg ggtgacaacc caggggggtca agtctctgct cacctcaatg    4140
tatgtgaagg agttcctgat ctcttcctca caggatggcc accagtggac actcttcttc    4200
```

```
cagaatggca aagtcaaggt gttccagggc aaccaggact ctttcacacc tgtggtgaac    4260
tcactggacc cccccctcct gacaagatac ctgagaattc accccagtc ttgggtccac     4320 cagattgccc tgagaatgga agtcctggga tgtgaggcac aagacctgta ctga          4374

<210> SEQ ID NO 109
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
atgcagattg agctgagcac ctgcttcttc ctgtgcctgc tgaggttctg cttctctgcc      60
accaggagat actacctggg ggctgtggag ctttcttggg actacatgca gtctgacctg     120
ggggagctgc ctgtggatgc caggttccca cccagagtgc ccaaatcctt cccattcaac     180
acctctgtgg tctacaagaa gaccctcttt gtggagttca ctgaccacct gttcaacatt     240
gccaaaccca ggccacccctg gatgggactc ctgggaccca ccattcaggc tgaggtgtat     300
gacactgtgg tcgtcaccct caagaacatg gcctcccacc ctgtgagcct gcatgctgtg     360
ggggtcagct actggaagtc ctctgagggg gctgagtatg atgaccagac ctcccagagg     420
gagaaggagg atgacaaagt gttccctggg aagagccaca cctatgtgtg gcaggtcctc     480
aaggagaatg cccccactgc ctctgaccca ccctgcctga cctactccta cctttctcat     540
gtggacctgg tcaaggacct caactctgga ctgattgggg ccctgctggt gtgcagggag     600
ggctccctgg ccaaagagaa gacccagacc ctgcacaagt tcattctcct gtttgctgtc     660
tttgatgagg gcaagagctg gcactctgaa accaagaact ccctgatgca ggacagggat     720
gctgcctctg ccagggcctg gcccaagatg cacactgtga atggctatgt gaacaggagc     780
ctgcctggac tcattggctg ccacaggaaa tctgtctact ggcatgtgat tggcatgggg     840
acaacccctg aggtgcactc catttttcctg gagggccaca ccttcctggt caggaaccac     900
agacaggcca gctggagat cagccccatc accttcctca ctgcccagac cctgctgatg     960
gacctcggac agttcctgct gtcctgccac atcagctccc accagcatga tggcatggag    1020
gcctatgtca aggtggacag ctgccctgag gagccacagc tcaggatgaa gaacaatgag    1080
gaggctgagg actatgatga tgacctgact gactctgaga tggatgtggt ccgctttgat    1140
gatgacaaca gcccatcctt cattcagatc aggtctgtgg ccaagaaaca ccccaagacc    1200
tgggtgcact acattgctgc tgaggaggag gactgggact atgccccact ggtcctggcc    1260
cctgatgaca ggagctacaa gagccagtac ctcaacaatg gcccacagag gattggacgc    1320
aagtacaaga aagtcaggtt catggcctac actgatgaaa ccttcaagac cagggaggcc    1380
attcagcatg agtctggcat cctgggccca ctcctgtatg gggaggtggg ggacaccctg    1440
ctcatcatct tcaagaacca ggcctccagg ccctacaaca tctacccaca tggcatcact    1500
gatgtcaggc cctgtacag ccgcaggctg ccaaggggg tgaaacacct caaggacttc    1560
cccattctgc tggggagat cttcaagtac aagtggactg tcactgtgga ggatggacca    1620
accaaatctg accccaggtg cctcaccaga tactactcca gctttgtgaa catggagagg    1680
gacctggcct ctggcctgat tgcccactg ctcatctgct acaaggagtc tgtggaccag    1740
aggggaaacc agatcatgtc tgacaagagg aatgtgattc tgttctctgt ctttgatgag    1800
aacaggagct ggtacctgac tgagaacatt cagcgcttcc tgcccaaccc tgctggggtg    1860
```

```
cagctggagg accctgagtt ccaggccagc aacatcatgc actccatcaa tggctatgtg    1920
tttgacagcc tccagctttc tgtctgcctg catgaggtgg cctactggta cattctttct    1980
attggggccc agactgactt cctttctgtc ttcttctctg gctacacctt caaacacaag    2040
atggtgtatg aggacaccct gaccctcttc ccattctctg ggagactgt gttcatgagc     2100 atggagaacc ctggcctgtg gattctggga tgccacaact ctgacttccg caacaggggc    2160
atgactgccc tgctcaaagt ctcctcctgt gacaagaaca ctggggacta ctatgaggac    2220
agctatgagg acatctctgc ctacctgctc agcaagaaca atgccattga gcccaggagc    2280
ttcagccaga atccacctgt cctgaaacgc caccagaggg agatcaccag gaccaccctc    2340
cagtctgacc aggaggagat tgactatgat gacaccattt ctgtggagat gaagaaagag    2400
gactttgaca tctatgacga ggacgagaac cagagcccaa ggagcttcca gaagaagacc    2460
aggcactact tcattgctgc tgtggagcgc ctgtgggact atggcatgag ctccagcccc    2520
catgtcctca ggaacagggc ccagtctggc tctgtgccac agttcaagaa agtggtcttc    2580
caagagttca ctgatggcag cttcacccag cccctgtaca gagggagct gaatgagcac     2640 ctgggactcc tgggcccata catcagggct gaggtggagg acaacatcat ggtgaccttc    2700
cgcaaccagg cctccaggcc ctacagcttc tacagctccc tcatcagcta tgaggaggac    2760
cagaggcagg gggctgagcc acgcaagaac tttgtgaaac ccaatgaaac caagacctac    2820
ttctggaaag tccagcacca catggccccc accaaggatg agtttgactg caaggcctgg    2880
gcctacttct ctgatgtgga cctggagaag gatgtgcact ctggcctgat ggcccactc     2940 ctggtctgcc acaccaacac cctgaaccct gcccatggaa ggcaagtgac tgtgcaggag    3000
tttgccctct tcttcaccat ctttgatgaa accagagct ggtacttcac tgagaacatg     3060
gagcgcaact gcagggcccc atgcaacatt cagatggagg accccacctt caaagagaac    3120
taccgcttcc atgccatcaa tggctacatc atggacaccc tgcctgggct tgtcatggcc    3180
caggaccaga ggatcaggtg gtacctgctt tctatgggct ccaatgagaa cattcactcc    3240
atccacttct ctgggcatgt cttcactgtg cgcaagaagg aggagtacaa gatggcctg     3300 tacaacctct accctgggt cttttgagact gtggagatgc tgccctccaa agctggcatc    3360
tggagggtgg agtgcctcat tggggagcac ctgcatgctg gcatgagcac cctgttcctg    3420
gtctacagca caagtgcca gaccccctg ggaatggcct ctggccacat cagggacttc     3480
cagatcactg cctctggcca gtatggccag tgggccccca gctggccag ctccactac      3540 tctggatcca tcaatgcctg gagcaccaag gagccattca gctggatcaa agtggacctg    3600 ctggcccca tgatcatcca tggcatcaag acccaggggg ccaggcagaa gttctccagc     3660
ctgtacatca gccagttcat catcatgtac agcctggatg gcaagaaatg gcagacctac    3720
agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcacct caggatggag ctgatgggct gtgacctgaa ctcctgcagc     3900
atgcccctgg gcatggagag caaggccatt tctgatgccc agatcactgc ctccagctac    3960
ttcaccaaca tgtttgccac ctggagccca agcaaggcca ggctgcacct ccagggaagg    4020
agcaatgcct ggaggcccca ggtcaacaac ccaaaggagt ggctgcaggt ggacttccag    4080
aagaccatga aggtcactgg ggtgaccacc cagggggtca agagcctgct caccagcatg    4140
tatgtgaagg agttcctgat cagctccagc caggatggcc accagtggac cctcttcttc    4200
cagaatggca aggtcaaggt gttccagggc aaccaggaca gcttcacccc tgtggtgaac    4260
```

-continued

```
agcctggacc ccccctcct gaccagatac ctgaggattc accccagag ctgggtccac    4320 cagattgccc tgaggatgga ggtcctggga tgtgaggccc aggacctgta ctga        4374
```

VIRAL VECTORS ENCODING RECOMBINANT FVIII VARIANTS WITH INCREASED EXPRESSION FOR GENE THERAPY OF HEMOPHILIA A

CROSS REFERENCE TO RELATED APPLICATIONS

This application claims priority to U.S. Provisional Patent Application No. 62/255,317, filed Nov. 13, 2015, the content of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Nov. 9, 2016, is named 008073_5107_US_Sequence_Listing.txt and is 353,479 bytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) is a key component in the cascade. Factor VIII is recruited to bleeding sites, and forms a Xase complex with activated Factor IX (FIXa) and Factor X (FX). The Xase complex activates FX, which in turn activates prothrombin to thrombin, which then activates other components in the coagulation cascade to generate a stable clot (reviewed in Saenko et al., *Trends Cardiovasc. Med.*, 9:185-192 (1999); Lenting et al., *Blood*, 92:3983-3996 (1998)).

Hemophilia A is a congenital X-linked bleeding disorder characterized by a deficiency in Factor VIII activity. Diminished Factor VIII activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases (Zhang et al., *Clinic. Rev. Allerg. Immunol.*, 37:114-124 (2009)).

Conventionally, hemophilia A is treated by Factor VIII replacement therapy, which consists of administering Factor VIII protein (e.g., plasma-derived or recombinantly-produced Factor VIII) to an individual with hemophilia A. Factor VIII is administered prophylactically to prevent or reduce frequency of bleeding episodes, in response to an acute bleeding episode, and/or perioperatively to manage bleeding during surgery. However, there are several undesirable features of Factor VIII replacement therapy.

First, Factor VIII replacement therapy is used to treat or manage hemophilia A, but does not cure the underlying Factor VIII deficiency. Because of this, individuals with hemophilia A require Factor VIII replacement therapy for the duration of their lives. Continuous treatment is expensive and requires the individual to maintain strict compliance, as missing only a few prophylactic doses can have serious consequences for individuals with severe hemophilia A.

Second, because Factor VIII has a relatively short half-life in vivo, conventional prophylactic Factor VIII replacement therapy requires administration every second or third day. This places a burden on the individual to maintain compliance throughout their life. While third generation "long-acting" Factor VIII drugs may reduce the frequency of administration, prophylactic Factor FVIII replacement therapy with these drugs still requires monthly, weekly, or more frequent administration in perpetuity. For example, prophylactic treatment with ELOCTATE™ [Antihemophilic Factor (Recombinant), Fc Fusion Protein] requires administration every three to five days (ELOCTATE™ Prescribing Information, Biogen Idec Inc., (2015)). Moreover, the long-term effects of chemically modified biologics (e.g., pegylated polypeptides) are not yet fully understood.

Third, between 15% and 30% of all individuals receiving Factor VIII replacement therapy form anti-Factor VIII inhibitor antibodies, rendering the therapy inefficient. Factor VIII bypass therapy (e.g., administration of plasma-derived or recombinantly-produced prothrombin complex concentrates) can be used to treat hemophilia in individuals that form inhibitor antibodies. However, Factor VIII bypass therapy is less effective than Factor VIII replacement therapy (Mannucci P. M., J Thromb Haemost., 1(7):1349-55 (2003)) and may be associated with an increased risk of cardiovascular complication (Luu and Ewenstein, Haemophilia, 10 Suppl. 2:10-16 (2004)).

Somatic gene therapy holds great promise for the treatment of hemophilia A because it would remedy the underlying under-expression functional Factor VIII activity (e.g., due to missense or nonsense mutations), rather than provide a one-time dose of Factor VIII activity to the individual. Because of this difference in the mechanism of action, as compared to Factor VIII replacement therapy, one-time administration of a Factor VIII gene therapy vector may provide an individual with Factor VIII for several years, reducing the cost of treatment and eliminating the need for continued patient compliance.

Coagulation Factor IX (FIX) gene therapy has been used effectively to treat individuals with hemophilia B, a related blood coagulation condition characterized by diminished Factor IX activity (Manno C. S., et al., Nat Med., 12(3): 342-47 (2006)). However, Factor VIII gene therapy presents several unique challenges. For example, the full-length, wild-type Factor VIII polypeptide (2351 amino acids; UniProt accession number P00451) is five times larger than the full-length, wild-type Factor IX polypeptide (461 amino acids; UniProt accession number P00740). As such, the coding sequence of wild-type Factor VIII is 7053 base pairs, which is too large to be packaged in conventional AAV gene therapy vectors. Further, reported recombinant expression of B-domain deleted variants of Factor VIII (BDD-FVIII) has been poor. As such, several groups have attempted to alter the codon usage of BDD-FVIII constructs, with limited success.

BRIEF SUMMARY OF DISCLOSURE

Accordingly, there is a need for Factor VIII variants whose coding sequences are more efficiently packaged into, and delivered via, gene therapy vectors. There is also a need for synthetic, codon-altered nucleic acids which express Factor VIII more efficiently. Such Factor VIII variants and codon-altered nucleic acids allow for improved treatment of Factor VIII deficiencies (e.g., hemophilia A). The above deficiencies and other problems associated with the treatment of Factor VIII deficiencies (e.g., hemophilia A) are reduced or eliminated by the disclosed codon-altered Factor VIII variants.

In accordance with some embodiments, the present disclosure provides nucleic acids encoding Factor VIII variants that have high sequence identity to the disclosed codon-altered sequences of the Factor VIII heavy chain (e.g., CS01-HC-NA, CS04-HC-NA, or CS23-HC-NA) and light chain (CS01-LC-NA, CS04-LC-NA, or CS23-LC-NA). In some embodiments, these nucleic acids further include a sequence encoding a linker sequence that replaces the native Factor VIII B-domain (e.g., a linker sequences comprising a furin cleavage site), between the sequences coding for the Factor VIII heavy and light chains.

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS04-HC-NA (SEQ ID NO: 3). The light chain of the Factor FVIII polypeptide is encoded by a second nucleotide sequence having at least 95% identity to CS04-LC-NA (SEQ ID NO: 4). The polypeptide linker comprises a furin cleavage site.

In one embodiment of the polynucleotides described above, the polypeptide linker is encoded by a third nucleotide sequence having at least 95% identity to BDLO04 (SEQ ID NO: 6).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS01-HC-NA (SEQ ID NO: 24). The light chain of the Factor FVIII polypeptide is encoded by a second nucleotide sequence having at least 95% identity to CS01-LC-NA (SEQ ID NO: 25). The polypeptide linker comprises a furin cleavage site.

In one embodiment of the polynucleotides described above, the polypeptide linker is encoded by a third nucleotide sequence having at least 95% identity to BDLO01 (SEQ ID NO: 5).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS23-HC-NA (SEQ ID NO: 22). The light chain of the Factor FVIII polypeptide is encoded by a second nucleotide sequence having at least 95% identity to CS23-LC-NA (SEQ ID NO: 23). The polypeptide linker comprises a furin cleavage site.

In one embodiment of the polynucleotides described above, the polypeptide linker is encoded by a third nucleotide sequence having at least 95% identity to BDLO23 (SEQ ID NO: 7).

In one embodiment of the polynucleotides described above, the first nucleotide sequence encoding the heavy chain of the Factor VIII polypeptide has at least 96% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 96% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 97% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 97% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 98% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 98% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.5% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.5% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.9% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.9% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide is CS04-HC-NA (SEQ ID NO: 3), and the second nucleotide sequence encoding the light chain of the Factor FVIII polypeptide is CS04-LC-NA (SEQ ID NO: 4).

In one embodiment of the polynucleotides described above, the first nucleotide sequence encoding the heavy chain of the Factor VIII polypeptide is CS01-HC-NA (SEQ ID NO: 24), and the second nucleotide sequence encoding the light chain of the Factor FVIII polypeptide is CS01-LC-NA (SEQ ID NO: 25).

In one embodiment of the polynucleotides described above, the first nucleotide sequence encoding the heavy chain of the Factor VIII polypeptide is CS23-HC-NA (SEQ ID NO: 22), and the second nucleotide sequence encoding the light chain of the Factor FVIII polypeptide is CS23-LC-NA (SEQ ID NO: 23).

In one aspect, the disclosure provides a polynucleotide comprising a nucleotide sequence having at least 95% identity to CS04-FL-NA, wherein the polynucleotide encodes a Factor VIII polypeptide.

In one aspect, the disclosure provides a polynucleotide comprising a nucleotide sequence having at least 95% identity to CS01-FL-NA, wherein the polynucleotide encodes a Factor VIII polypeptide.

In one aspect, the disclosure provides a polynucleotide comprising a nucleotide sequence having at least 95% identity to CS23-FL-NA, wherein the polynucleotide encodes a Factor VIII polypeptide.

In one embodiment of the polynucleotides described above, the nucleotide sequence has at least 96% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 97% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 98% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.5% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.9% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence is CS04-FL-NA (SEQ ID NO: 1).

In one embodiment of the polynucleotides described above, the nucleotide sequence is CS01-FL-NA (SEQ ID NO: 13).

In one embodiment of the polynucleotides described above, the nucleotide sequence is CS23-FL-NA (SEQ ID NO: 20).

In one embodiment of the polynucleotides described above, the polynucleotide encodes a Factor VIII polypeptide comprising an amino acid sequence having at least 95% identity to CS04-FL-AA (SEQ ID NO: 2).

In one embodiment of the polynucleotides described above, the polynucleotide encodes a Factor VIII polypeptide comprising an amino acid sequence having at least 96% identity to CS04-FL-AA (SEQ ID NO: 2).

In one embodiment of the polynucleotides described above, the polynucleotide encodes a Factor VIII polypeptide comprising an amino acid sequence having at least 97% identity to CS04-FL-AA (SEQ ID NO: 2).

In one embodiment of the polynucleotides described above, the polynucleotide encodes a Factor VIII polypeptide comprising an amino acid sequence having at least 98% identity to CS04-FL-AA (SEQ ID NO: 2).

In one embodiment of the polynucleotides described above, the polynucleotide encodes a Factor VIII polypeptide comprising an amino acid sequence having at least 99% identity to CS04-FL-AA (SEQ ID NO: 2).

In one embodiment of the polynucleotides described above, the polynucleotide encodes a Factor VIII polypeptide comprising an amino acid sequence having at least 99.5% identity to CS04-FL-AA (SEQ ID NO: 2).

In one embodiment of the polynucleotides described above, the polynucleotide encodes a Factor VIII polypeptide comprising an amino acid sequence having at least 99.9% identity to CS04-FL-AA (SEQ ID NO: 2).

In one embodiment of the polynucleotides described above, the polynucleotide encodes a Factor VIII polypeptide comprising the amino acid sequence of CS04-FL-AA (SEQ ID NO: 2).

In one aspect, the disclosure provides a polynucleotide comprising a nucleotide sequence having at least 95% identity to CS04-SC1-NA (SEQ ID NO: 9), wherein the polynucleotide encodes a single-chain Factor VIII polypeptide.

In one aspect, the disclosure provides a polynucleotide comprising a nucleotide sequence having at least 95% identity to CS04-SC2-NA (SEQ ID NO: 11), wherein the polynucleotide encodes a single-chain Factor VIII polypeptide.

In one aspect, the disclosure provides a polynucleotide comprising a nucleotide sequence having at least 95% identity to CS01-SC1-NA (SEQ ID NO: 26), wherein the polynucleotide encodes a single-chain Factor VIII polypeptide.

In one aspect, the disclosure provides a polynucleotide comprising a nucleotide sequence having at least 95% identity to CS01-SC2-NA (SEQ ID NO: 27), wherein the polynucleotide encodes a single-chain Factor VIII polypeptide.

In one aspect, the disclosure provides a polynucleotide comprising a nucleotide sequence having at least 95% identity to CS23-SC1-NA (SEQ ID NO: 28), wherein the polynucleotide encodes a single-chain Factor VIII polypeptide.

In one aspect, the disclosure provides a polynucleotide comprising a nucleotide sequence having at least 95% identity to CS23-SC2-NA (SEQ ID NO: 29), wherein the polynucleotide encodes a single-chain Factor VIII polypeptide.

In one embodiment of the polynucleotides described above, the nucleotide sequence has at least 96% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 97% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 98% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.5% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.9% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence is CS04-SC1-NA (SEQ ID NO: 9).

In one embodiment of the polynucleotides described above, the nucleotide sequence is CS04-SC2-NA (SEQ ID NO: 11).

In one embodiment of the polynucleotides described above, the nucleotide sequence is CS01-SC1-NA (SEQ ID NO: 26).

In one embodiment of the polynucleotides described above, the nucleotide sequence is CS01-SC2-NA (SEQ ID NO: 27).

In one embodiment of the polynucleotides described above, the nucleotide sequence is CS23-SC1-NA (SEQ ID NO: 28).

In one embodiment of the polynucleotides described above, the nucleotide sequence is CS23-SC2-NA (SEQ ID NO: 29).

In one embodiment of the polynucleotides described above, the nucleotide sequence has at least 95% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 96% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 97% identity to a sequence selected from the group consisting of CS01-FL-NA, CS01-HC-NA, CS01-LC-NA, CS04-FL-NA, CS04-

HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 98% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the nucleotide sequence is NA, CS04-HC-NA, CS04-LC-NA, CS23-FL-NA, CS23-HC-NA, CS23-LC-NA, CS01m1-FL-NA, CS01m2-FL-NA, CS01m3-FL-NA, CS01m4-FL-NA, CS01m12-FL-NA, CS01m13-FL-NA, CS01m23-FL-NA, CS01m24-FL-NA, CS01m34-FL-NA, CS01m123-FL-NA, CS01m234-FL-NA, CS04m1-FL-NA, CS04m2-FL-NA, CS04m3-FL-NA, CS04m4-FL-NA, CS04m12-FL-NA, CS04m13-FL-NA, CS04m23-FL-NA, CS04m24-FL-NA, CS04m34-FL-NA, CS04m123-FL-NA, CS04m234-FL-NA, CS23m1-FL-NA, CS23m2-FL-NA, CS23m3-FL-NA, CS23m4-FL-NA, CS23m12-FL-NA, CS23m13-FL-NA, CS23m23-FL-NA, CS23m24-FL-NA, CS23m34-FL-NA, CS23m123-FL-NA, CS23m234-FL-NA, CS01-SC1-NA, CS04-SC1-NA, CS23-SC1-NA, CS01m1-SC1-NA, CS01m2-SC1-NA, CS01m3-SC1-NA, CS01m4-SC1-NA, CS01m12-SC1-NA, CS01m13-SC1-NA, CS01m23-SC1-NA, CS01m24-SC1-NA, CS01m34-SC1-NA, CS01m123-SC1-NA, CS01m234-SC1-NA, CS04m1-SC1-NA, CS04m2-SC1-NA, CS04m3-SC1-NA, CS04m4-SC1-NA, CS04m12-SC1-NA, CS04m13-SC1-NA, CS04m23-SC1-NA, CS04m24-SC1-NA, CS04m34-SC1-NA, CS04m123-SC1-NA, CS04m234-SC1-NA, CS23m1-SC1-NA, CS23m2-SC1-NA, CS23m3-SC1-NA, CS23m4-SC1-NA, CS23m12-SC1-NA, CS23m13-SC1-NA, CS23m23-SC1-NA, CS23m24-SC1-NA, CS23m34-SC1-NA, CS23m123-SC1-NA, CS23m234-SC1-NA, CS01-SC2-NA, CS04-SC2-NA, CS23-SC2-NA, CS01m1-SC2-NA, CS01m2-SC2-NA, CS01m3-SC2-NA, CS01m4-SC2-NA, CS01m12-SC2-NA, CS01m13-SC2-NA, CS01m23-SC2-NA, CS01m24-SC2-NA, CS01m34-SC2-NA, CS01m123-SC2-NA, CS01m234-SC2-NA, CS04m1-SC2-NA, CS04m2-SC2-NA, CS04m3-SC2-NA, CS04m4-SC2-NA, CS04m12-SC2-NA, CS04m13-SC2-NA, CS04m23-SC2-NA, CS04m24-SC2-NA, CS04m34-SC2-NA, CS04m123-SC2-NA, CS04m234-SC2-NA, CS23m1-SC2-NA, CS23m2-SC2-NA, CS23m3-SC2-NA, CS23m4-SC2-NA, CS23m12-SC2-NA, CS23m13-SC2-NA, CS23m23-SC2-NA, CS23m24-SC2-NA, CS23m34-SC2-NA, CS23m123-SC2-NA, and CS23m234-SC2-NA.

In one embodiment of the polynucleotides described above, the encoded Factor VIII polypeptide comprises a glycosylation polypeptide positioned between two consecutive amino acids.

In one embodiment of the polynucleotides described above, the encoded polypeptide linker includes a glycosylation peptide with an amino acid sequence having at least 92% identity to a glycosylation peptide selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the polynucleotides described above, the encoded polypeptide linker comprises a glycosylation peptide with an amino acid sequence selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the polynucleotides described above, the glycosylation peptide is encoded by a polynucleotide with a nucleotide sequence having at least 95% identity to a sequence selected from the group consisting of NG1-NA, NG4-NA, NG5-NA, NG6-NA, NG7-NA, NG9-NA, NG10-NA, NG16-NA, NG17-NA, NG18-NA, NG19-NA, NG20-NA, NG21-NA and NGV-NA.

In one embodiment of the polynucleotides described above, the glycosylation peptide is encoded by a polynucleotide with a nucleotide sequence selected from one of NG1-NA, NG4-NA, NG5-NA, NG6-NA, NG7-NA, NG9-NA, NG10-NA, NG16-NA, NG17-NA, NG18-NA, NG19-NA, NG20-NA, NG21-NA and NGV-NA.

In one embodiment of the polynucleotides described above, the polypeptide linker is encoded by a third nucleotide sequence having at least 95% identity to a sequence selected from the group consisting of BDLNG1-NA, BDLNG3-NA, BDLNG5-NA, BDLNG6-NA, BDLNG9-NA, BDLNG10-NA, BDLNG16-NA, BDLNG17-NA, BDLNG18-NA, BDLNG19-NA, BDLNG20-NA and BDLNG21-NA.

In one embodiment of the polynucleotides described above, the encoded Factor VIII polypeptide includes an F328S (SPI, F309S SPE) amino acid substitution, relative to FVIII-FL-AA (SEQ ID NO: 19).

In one embodiment of the polynucleotides described above, the encoded Factor VIII polypeptide includes I105V, A127S, G151K, M166T, and L171P (SPI; I86V, A108S, G132K, M147T, and L152P, SPE, respectively) amino acid substitutions, relative to FVIII-FL-AA (SEQ ID NO: 19).

In one embodiment of the polynucleotides described above, the encoded Factor VIII polypeptide includes a) a deletion of amino acids AIEPR755-759, relative to FVIII-FL-AA (SEQ ID NO: 19), and b) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) an F328S (SPI; F309S SPE) amino acid substitution, relative to FVIII-FL-AA (SEQ ID NO: 19), and b) C1918G and C1922G (SPI; C1899G and C1903 SPE, respectively) amino acid substitutions, relative to FVIII-FL-AA (SEQ ID NO: 19).

In one embodiment of the polynucleotides described above, the encoded Factor VIII polypeptide includes a) an F328S (SPI; F309S SPE) amino acid substitution, relative to FVIII-FL-AA (SEQ ID NO: 19), and b) I105V, A127S, G151K, M166T, and L171P (SPI; I86V, A108S, G132K, M147T, and L152P, SPE, respectively) amino acid substitutions, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) a deletion of amino acids AIEPR755-759, relative to FVIII-FL-AA (SEQ ID NO: 19), and c) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) I105V, A127S, G151K, M166T, and L171P amino acid substitutions, relative to FVIII-FL-AA (SEQ ID NO: 19), b) a deletion of amino acids AIEPR755-759, relative to FVIII-FL-AA (SEQ ID NO: 19), and c) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) C1918G and C1922G amino acid substitutions, relative to FVIII-FL-AA (SEQ ID NO: 19), and c) I105V, A127S, G151K, M166T, and L171P amino acid substitutions, relative to FVIII-FL-AA (SEQ ID NO: 19).

In one embodiment of the polynucleotides described above, the encoded Factor VIII polypeptide includes a) an F328S amino acid substitution, relative to FVIII-FL-AA (SEQ ID NO: 19), b) C1918G and C1922G amino acid substitutions, relative to FVIII-FL-AA (SEQ ID NO: 19), c) a deletion of amino acids AIEPR755-759, relative to FVIII-FL-AA (SEQ ID NO: 19), and d) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the encoded Factor VIII polypeptide includes a) I105V, A127S, G151K, M166T, and L171P amino acid substitutions, relative to FVIII-FL-AA (SEQ ID NO: 19), b) an F328S amino acid substitution, relative to FVIII-FL-AA (SEQ ID NO: 19), c) C1918G and C1922G amino acid substitutions, relative to FVIII-FL-AA (SEQ ID NO: 19), d) a deletion of amino acids AIEPR755-759, relative to FVIII-FL-AA (SEQ ID NO: 19), and e) an insertion of amino acids TTYVNRSL (SEQ ID NO: 33) after N754, relative to FVIII-FL-AA (SEQ ID NO: 19). In some embodiments (e.g., where the encoded FVIII molecule includes a portion of the N-terminal region of the wild-type B-domain), the encoded Factor VIII polypeptide also includes a deletion of amino acids SF760-761, relative to FVIII-FL-AA (SEQ ID NO: 19).

In one embodiment of the polynucleotides described above, the polynucleotide also includes a promoter element operably linked to the polynucleotide encoding the Factor VIII polypeptide.

In one embodiment of the polynucleotides described above, the polynucleotide also includes an enhancer element operably linked to the polynucleotide encoding the Factor VIII polypeptide.

In one embodiment of the polynucleotides described above, the polynucleotide also includes a polyadenylation element operably linked to the polynucleotide encoding the Factor VIII polypeptide.

In one embodiment of the polynucleotides described above, the polynucleotide also includes an intron operatively linked to the nucleotide sequence encoding the Factor VIII polypeptide.

In one embodiment of the polynucleotides described above, the intron is positioned between a promoter element and the translation initiation site (e.g., the first coding ATG) of the nucleotide sequence encoding a Factor VIII polypeptide.

In another aspect, the disclosure provides a mammalian gene therapy vector including a polynucleotide as described above.

In one embodiment of the mammalian gene therapy vector described above, the mammalian gene therapy vector is an adeno-associated virus (AAV) vector.

In one embodiment of the mammalian gene therapy vector described above, the AAV vector is an AAV-8 vector.

In another aspect, the disclosure provides a method for treating hemophilia A including administering, to a patient in need thereof, a mammalian gene therapy vector as described above.

In another aspect, the disclosure provides a mammalian gene therapy vector as described above for treating hemophilia A.

In another aspect, the disclosure provides the use of a mammalian gene therapy vector as described above for the manufacture of a medicament for treating hemophilia A.

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm23. The light chain of the Factor VIII polypeptide has a sequence at least 95% identical to the sequence CS01-LC-AAm23. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), and iii) an insertion of amino acids TTYVNRSL (SEQ ID NO: 33) after N754, relative to FVIII-FL-AA (SEQ ID NO: 19).

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm123. The light chain of the Factor VIII polypeptide has a sequence at least 95% identical to the sequence CS01-LC-AAm123. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) an F328S amino acid substitution.

In another aspect, the disclosure provides a Factor VIII polypeptide including a light chain, a heavy chain, and a polypeptide linker joining the C-terminus of the heavy chain to the N-terminus of the light chain. The heavy chain of the Factor VIII polypeptide has a sequence at least 95% identical to the sequence CS01-HC-AAm234. The light chain of the Factor VIII polypeptide has a sequence at least 95% identical to the sequence CS01-LC-AAm234. The polypeptide linker of the Factor VIII polypeptide includes a furin cleavage site. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) F328S/C1918G/C1922G amino acid substitutions.

In one embodiment of the Factor VIII polypeptides described, the heavy chain of the Factor VIII polypeptide has a sequence at least 96% identical to the respective heavy chain sequence (e.g., CS01-HC-AAm23, CS01-HC-AAm123, or CS01-HC-AAm234), and the light chain of the Factor FVIII polypeptide has a sequence at least 96% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 97% identical to the respective heavy chain sequence (e.g., CS01-HC-AAm23, CS01-HC-AAm123, or CS01-HC-AAm234), and the light chain of the Factor FVIII polypeptide has a sequence at least 97% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 98% identical to the respective heavy chain sequence (e.g., CS01-HC-AAm23, CS01-HC-AAm123, or CS01-HC-AAm234), and the light chain of the Factor FVIII polypeptide has a sequence at least 98% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 99% identical to the respective heavy chain sequence (e.g., CS01-HC-AAm23, CS01-HC-AAm123, or CS01-HC-AAm234), and the light chain of the Factor FVIII polypeptide has a sequence at least 99% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence at least 99.5% identical to the respective heavy chain sequence (e.g., CS01-HC-AAm23, CS01-HC-AAm123, or CS01-HC-AAm234), and the light chain of the Factor FVIII polypeptide has a sequence at least 99.5% identical to the respective light chain sequence (e.g., CS01-LC-AAm23, CS01-LC-AAm123, or CS01-LC-AAm234).

In one embodiment of the Factor VIII polypeptides described, the heavy chain of the Factor VIII polypeptide has a sequence identical to the respective heavy chain sequence (e.g., CS01-HC-AAm23, CS01-HC-AAm123, or CS01-HC-AAm234), and the light chain of the Factor FVIII polypeptide has a sequence identical to the respective light chain sequence (e.g., CS01-LC-AAm23, CS01-LC-AAm123, or CS01-LC-AAm234).

In one embodiment of the Factor VIII polypeptides described above, the polypeptide linker has at least 95% identity to BDL-SQ-AA (SEQ ID NO: 30).

In one embodiment of the Factor VIII polypeptides described above, the polypeptide linker has the amino acid sequence of BDL-SQ-AA (SEQ ID NO: 30).

In one embodiment of the Factor VIII polypeptides described above, the polypeptide linker includes a glycosylation peptide with an amino acid sequence having at least 92% identity to a glycosylation peptide selected from the group consisting of NG1-AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the Factor VIII polypeptides described above, the polypeptide linker includes a glycosylation peptide selected from the group consisting of NG1-

AA, NG4-AA, NG5-AA, NG6-AA, NG7-AA, NG9-AA, NG10-AA, NG16-AA, NG17-AA, NG18-AA, NG19-AA, NG20-AA, NG21-AA and NGV-AA.

In one embodiment of the Factor VIII polypeptides described above, the polypeptide linker has an amino acid sequence having at least 95% identity to a sequence selected from the group consisting of BDLNG1-AA, BDLNG3-AA, BDLNGS-AA, BDLNG6-AA, BDLNG9-AA, BDLNG10-AA, BDLNG16-AA, BDLNG17-AA, BDLNG18-AA, BDLNG19-AA, BDLNG20-AA and BDLNG21-AA.

In one embodiment of the Factor VIII polypeptides described above, the polypeptide linker has an amino acid sequence selected from the group consisting of BDLNG1-AA, BDLNG3-AA, BDLNGS-AA, BDLNG6-AA, BDLNG9-AA, BDLNG10-NA, BDLNG16-AA, BDLNG17-AA, BDLNG18-AA, BDLNG19-AA, BDLNG20-AA and BDLNG21-AA.

In another aspect, the disclosure provides a Factor VIII polypeptide having an amino acid sequence with at least 95% identity to CS40-FL-AAm23 (SEQ ID NO: 104). The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), and iii) an insertion of amino acids TTYVNRSL (SEQ ID NO: 33) after N754, relative to FVIII-FL-AA (SEQ ID NO: 19).

In another aspect, the disclosure provides a Factor VIII polypeptide having an amino acid sequence with at least 95% identity to CS40-FL-AAm123. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) an F328S amino acid substitution.

In another aspect, the disclosure provides a Factor VIII polypeptide having an amino acid sequence with at least 95% identity to CS40-FL-AAm234. The Factor VIII polypeptide includes i) I105V, A127S, G151K, M166T, and L171P amino acid substitutions, ii) a deletion of amino acids AIEPR755-759, relative to FVIII-FL-AA (SEQ ID NO: 19), iii) an insertion of amino acids TTYVNRSL (SEQ ID NO: 33) after N754, relative to FVIII-FL-AA (SEQ ID NO: 19), and iv) F328S/C1918G/C1922G amino acid substitutions.

In one embodiment of the Factor VIII polypeptides described, the Factor VIII polypeptide has a sequence at least 96% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 97% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 98% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 99% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence at least 99.5% identical to the respective full-length sequence (e.g., CS40-FL-AAm23 (SEQ ID NO: 104), CS40-FL-AAm123, or CS40-FL-AAm234).

In one embodiment of the Factor VIII polypeptides described, the Factor VIII polypeptide has a sequence identical to the respective full-length sequence (e.g., CS40-FL-AAm23 (SEQ ID NO: 104), CS40-FL-AAm123, or CS40-FL-AAm234).

BRIEF DESCRIPTION OF DRAWINGS

FIGS. 2A and 2B show the CS04 codon-altered nucleotide sequence (SEQ ID NO: 1) encoding a Factor VIII variant in accordance with some embodiments ("CS04-FL-NA" for full-length coding sequence).

FIG. 3 shows the Factor VIII variant amino acid sequence (SEQ ID NO: 2) encoded by the CS04 codon-altered nucleotide sequence in accordance with some embodiments ("CS04-FL-AA" for full-length amino acid sequence).

FIG. 4 shows the portion of the CS04 codon-altered nucleotide sequence (SEQ ID NO: 3) encoding the heavy chain of a Factor VIII variant in accordance with some embodiments ("CS04-HC-NA").

FIG. 5 shows the portion of the CS04 codon-altered nucleotide sequence (SEQ ID NO: 4) encoding the light chain of a Factor VIII variant in accordance with some embodiments ("CS04-LC-NA").

FIG. 6 shows exemplary coding sequences (SEQ ID NOS 5-7 and 36-48, respectively, in order of appearance) for B-domain substituted linkers in accordance with some embodiments. BDLO01 (SEQ ID NO: 5), BDLO04 (SEQ ID NO: 6), and BDLO23 (SEQ ID NO: 7) are the respective portions of the CS01, CS04, and CS23 codon-altered nucleotide sequences that encode a B-domain substituted linker, respectively.

FIGS. 7A, 7B, and 7C show an AAV vector sequence (SEQ ID NO: 8) containing an CS04 codon-altered nucleotide sequence in accordance with some embodiments ("CS04-AV-NA").

FIGS. 8A and 8B show the CS01m1 codon-altered nucleotide sequence (SEQ ID NO: 49) encoding a Factor VIII variant with an F328S amino acid substitution in accordance with some embodiments ("CS01m1-FL-NA").

FIGS. 9A and 9B show the CS04Δ(760-1667) (SPI; CS04Δ(741-1648), SPE) codon-altered nucleotide sequence (SEQ ID NO: 9) encoding a single-chain Factor VIII variant in accordance with some embodiments ("CS04-SC1-NA").

FIG. 10 shows the Factor VIII variant amino acid sequence (SEQ ID NO: 10) encoded by the CS01Δ(760-1667) (SPI; CS01Δ(741-1648), SPE), CS04Δ(760-1667) (SPI; CS04Δ(741-1648), SPE), and CS23Δ(760-1667) (SPI; CS23Δ(741-1648), SPE) codon-altered nucleotide sequences in accordance with some embodiments ("CS01-SC1-AA," "CS04-SC1-AA," and "CS23-SC1-AA," respectively).

FIGS. 11A and 11B show the CS04Δ(772-1667) (SPI; CS04Δ(753-1648), SPE) codon-altered nucleotide sequence (SEQ ID NO: 11) encoding a single-chain Factor VIII variant in accordance with some embodiments ("CS04-SC2-NA").

FIG. 12 shows the Factor VIII variant amino acid sequence (SEQ ID NO: 12) encoded by the CS01Δ(772-1667) (SPI; CS01Δ(753-1648), SPE), CS04Δ(772-1667) (SPI; CS04Δ(753-1648), SPE), and CS23Δ(772-1667) (SPI; CS23Δ(753-1648), SPE) codon-altered nucleotide sequence in accordance with some embodiments ("CS01-SC2-AA," "CS04-SC2-AA," and "C523-SC2-AA," respectively).

FIGS. 13A and 13B show amino acid and nucleotide sequences for exemplary glycosylation peptides that are inserted into the B-domain substituted linker in accordance with some embodiments. "NG1" or NG1-AA" is the code for the amino acid sequence, shown in the top line. "NG1-NA" is the code for the nucleic acid sequence, shown in the bottom line for each set. FIGS. 13A and 13B disclose the amino acid sequences as SEQ ID NOS 51, 53, 55, 57, 59, 61, 63, 65, 67, 69, 71, 73, and 75, and the nucleotide sequences as SEQ ID NOS 50, 52, 54, 56, 58, 60, 62, 64, 66, 68, 70, 72, and 74, all respectively, in order of appearance.

FIG. 14 shows the results of in silico prediction of in vivo N-glycosylation of the wild-type Factor VIII B-domain. Figure discloses SEQ ID NOS 76 and 76-82, respectively, in order of appearance.

FIG. 15 shows the results of in silico prediction of in vivo N-glycosylation of the V3 peptide linker. Figure discloses SEQ ID NOS 83 and 83-89, respectively, in order of appearance.

FIGS. 16A and 16B show the CS01 codon-altered nucleotide sequence (SEQ ID NO: 13) encoding a Factor VIII variant in accordance with some embodiments ("CS01-FL-NA").

FIGS. 17A and 17B show the CS08 codon-altered nucleotide sequence (SEQ ID NO: 14) encoding a Factor VIII variant in accordance with some embodiments ("CS08-FL-NA").

FIGS. 18A and 18B show the CS10 codon-altered nucleotide sequence (SEQ ID NO: 15) encoding a Factor VIII variant in accordance with some embodiments ("CS10-FL-NA").

FIGS. 19A and 19B show the CS11 codon-altered nucleotide sequence (SEQ ID NO: 16) encoding a Factor VIII variant in accordance with some embodiments ("CS11-FL-NA").

FIGS. 20A and 20B show the CS40 wild-type ReFacto coding sequence (SEQ ID NO: 17), in accordance with some embodiments ("CS40-FL-NA").

FIGS. 21A and 21B show the CH25 codon-altered nucleotide sequence (SEQ ID NO: 18) encoding a Factor VIII variant in accordance with some embodiments ("CH25-FL-NA").

FIG. 22 shows a wild-type human Factor VIII amino acid sequence (SEQ ID NO: 19), in accordance with some embodiments ("FVIII-FL-AA").

FIGS. 26A and 26B show the CS23 codon-altered nucleotide sequence (SEQ ID NO: 20) encoding a Factor VIII variant in accordance with some embodiments ("CS23-FL-NA").

FIG. 27 shows the Factor VIII variant amino acid sequence (SEQ ID NO: 21) encoded by the CS23 codon-altered nucleotide sequence in accordance with some embodiments ("CS23-FL-AA").

FIG. 28 shows the portion of the CS23 codon-altered nucleotide sequence (SEQ ID NO: 22) encoding the heavy chain of a Factor VIII variant in accordance with some embodiments ("CS23-HC-NA").

FIG. 29 shows the portion of the CS23 codon-altered nucleotide sequence (SEQ ID NO: 23) encoding the light chain of a Factor VIII variant in accordance with some embodiments ("CS23-LC-NA").

FIGS. 30A and 30B show the CS01m13 codon-altered nucleotide sequence (SEQ ID NO: 90) encoding a Factor VIII variant with m1 (F328S) and m3 amino acid substitutions in accordance with some embodiments ("CS01-FL-NA-m13").

FIGS. 31A and 31B show the CS01m23 codon-altered nucleotide sequence (SEQ ID NO: 91) encoding a Factor VIII variant with the m2 and m3 mutation sets in accordance with some embodiments ("CS01-FL-NA-m23").

FIGS. 32A and 32B show the CS01m3 codon-altered nucleotide sequence (SEQ ID NO: 92) encoding a Factor VIII variant with m3 amino acid substitutions in accordance with some embodiments ("CS01-FL-NA-m3").

FIGS. 33A and 33B show the CS01m2 codon-altered nucleotide sequence (SEQ ID NO: 93) encoding a Factor VIII variant with the m2 mutation set (I105V/A127S/G151K/M166T/L171P (SPI)) amino acid substitutions in accordance with some embodiments ("CS01-FL-NA-m2").

FIGS. 34A and 34B show the CS04m2 codon-altered nucleotide sequence (SEQ ID NO: 94) encoding a Factor VIII variant with the m2 mutants (I105V/A127S/G151K/M166T/L171P (SPI)) amino acid substitutions in accordance with some embodiments ("CS01-FL-NA-m2").

FIGS. 35A and 35B show the CS04m3 codon-altered nucleotide sequence (SEQ ID NO: 95) encoding a Factor VIII variant with m3 amino acid substitutions in accordance with some embodiments ("CS04-FL-NA-m3").

FIGS. 36A and 36B show the CS04m23 codon-altered nucleotide sequence (SEQ ID NO: 96) encoding a Factor VIII variant with the m2 mutant set (I105V/A127S/G151K/M166T/L171P (SPI)) and m3 amino acid substitutions in accordance with some embodiments ("CS04-FL-NA-m23").

FIGS. 37A and 37B show the CS04m1 codon-altered nucleotide sequence (SEQ ID NO: 97) encoding a Factor VIII variant with an m1 (F328S) amino acid substitution in accordance with some embodiments ("CS04-FL-NA-m1").

FIGS. 38A and 38B show the CS04m13 codon-altered nucleotide sequence (SEQ ID NO: 98) encoding a Factor VIII variant with m1 and m3 amino acid substitutions in accordance with some embodiments ("CS04-FL-NA-m13")

FIGS. 39A and 39B show the CS23m13 codon-altered nucleotide sequence (SEQ ID NO: 99) encoding a Factor VIII variant with m1 and m3 amino acid substitutions in accordance with some embodiments ("CS23m13-FL-NA")

FIGS. 40A and 40B show the CS23m3 codon-altered nucleotide sequence (SEQ ID NO: 100) encoding a Factor VIII variant with m3 amino acid substitutions in accordance with some embodiments ("C523-FL-NA-m3")

FIGS. 41A and 41B show the CS23m2 codon-altered nucleotide sequence (SEQ ID NO: 101) encoding a Factor VIII variant with the m2 mutant set (I105V/A127S/G151K/

M166T/L171P amino acid substitutions) in accordance with some embodiments ("CS23-FL-NA-m2").

FIGS. 42A and 42B show the CS23m1 codon-altered nucleotide sequence (SEQ ID NO: 102) encoding a Factor VIII variant with an m1 (F328S) amino acid substitution in accordance with some embodiments ("CS23-FL-NA-m1").

FIGS. 43A and 43B show the CS23m23 codon-altered nucleotide sequence (SEQ ID NO: 103) encoding a Factor VIII variant with the m2 mutant set (I105V/A127S/G151K/M166T/L171P) and m3 amino acid substitutions in accordance with some embodiments ("C523-FL-NA-m23").

Figure 44:
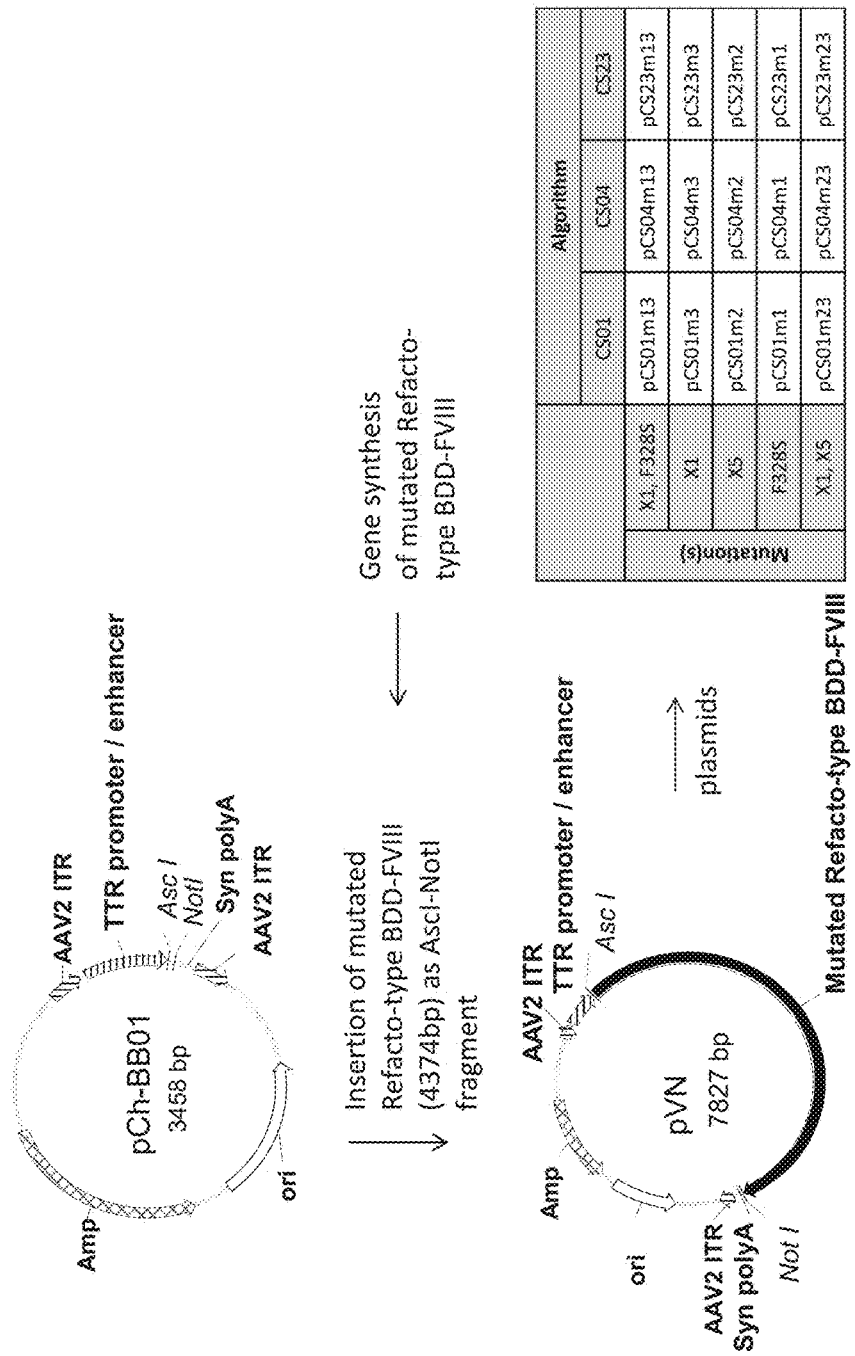

FIG. 44 depicts cloning of the pCS constructs, done by inserting synthetic Refacto-type BDD-FVIII carrying different mutations (see inserted table) into the vector backbone pCh-BB01 via AscI and NotI restriction sites.

Figure 45:
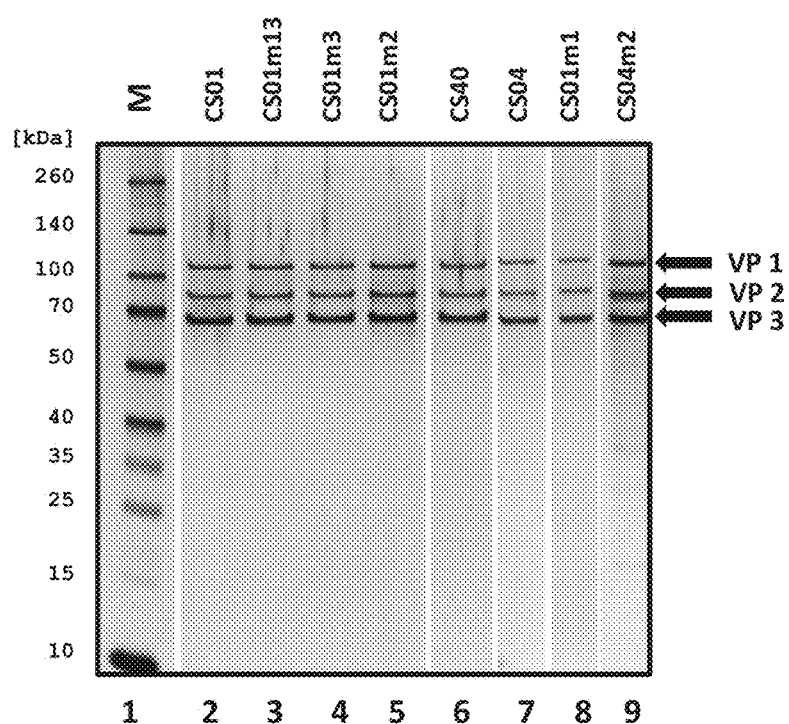

FIG. 45 depicts the protein analysis of AAV vector preparations by PAGE and silver staining. Lane 1, protein marker (M); lane 2, vCS01, lane 3, vCS17; lane 4, vCS19; lane 5, vCS20; lane 6, vCS40; lane 7, vCS04; lane 8, vCS17; lane 9, vCS24 construct. The constructs have all the same AAV8 capsids consisting of VP1, VP2 and VP3 (arrows right side). The scale on the left side indicates size of the protein marker in kilo Daltons (kDa).

Figure 46:
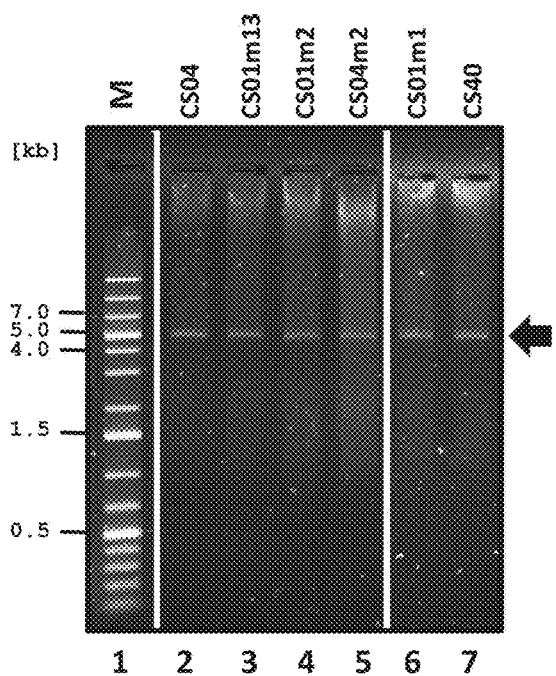

FIG. 46 depicts the integrity of AAV vector genome preparations analyzed by agarose gel electrophoresis. Lane 1, DNA marker (M); lane 2, vCS04, lane 3, vCS17; lane 4, vCS20; lane 5, vCS24; lane 6, vCS16; lane 7, vCS40 construct. Vector load is 1.5E10 vg per lane. The AAV vectors have the same-sized genomes, migrating at approximately 5 kb (arrow, right side). The scale on the left side indicates size of the DNA fragments in kilobases (kb).

FIG. 47 shows the portion of the CS01 codon-altered nucleotide sequence (SEQ ID NO: 24) encoding the heavy chain of a Factor VIII variant in accordance with some embodiments ("CS01-HC-NA").

FIG. 48 shows the portion of the CS01 codon-altered nucleotide sequence (SEQ ID NO: 25) encoding the light chain of a Factor VIII variant in accordance with some embodiments ("CS01-LC-NA").

FIGS. 49A and 49B show the CS01Δ(760-1667) (SPI; CS01Δ(741-1648), SPE) codon-altered nucleotide sequence (SEQ ID NO: 26) encoding a single-chain Factor VIII variant in accordance with some embodiments ("CS01-SC1-NA").

FIGS. 50A and 50B show the CS01Δ(772-1667) (SPI; CS01Δ(753-1648), SPE) codon-altered nucleotide sequence (SEQ ID NO: 27) encoding a single-chain Factor VIII variant in accordance with some embodiments ("CS01-SC2-NA").

FIGS. 51A and 51B show the CS23Δ(760-1667) (SPI; CS23Δ(741-1648), SPE) codon-altered nucleotide sequence (SEQ ID NO: 28) encoding a single-chain Factor VIII variant in accordance with some embodiments ("CS23-SC1-NA").

FIGS. 52A and 52B show the CS23Δ(772-1667) (SPI; CS234 (753-1648), SPE) codon-altered nucleotide sequence (SEQ ID NO: 29) encoding a single-chain Factor VIII variant in accordance with some embodiments ("C523-SC2-NA").

FIG. 53 shows the Factor VIII variant amino acid sequence (SEQ ID NO: 104) encoded by the CS01m23 codon-altered nucleotide sequence in accordance with some embodiments ("CS01m23-FL-AA").

FIG. 54 shows the Factor VIII variant amino acid sequence (SEQ ID NO: 105) encoded by the CS04m3 codon-altered nucleotide sequence in accordance with some embodiments ("CS01m23-FL-AA").

FIG. 55 shows the Factor VIII variant amino acid sequence (SEQ ID NO: 106) encoded by the CS01m12 codon-altered nucleotide sequence in accordance with some embodiments ("CS01m12-FL-AA").

FIG. 56 shows the Factor VIII variant amino acid sequence (SEQ ID NO: 107) encoded by the CS04m12 codon-altered nucleotide sequence in accordance with some embodiments ("CS04m12-FL-AA").

FIGS. 57A and 57B show the CS01m12 codon-altered nucleotide sequence (SEQ ID NO: 108) encoding a Factor VIII variant with m1 (F328S) and m2 amino acid substitutions in accordance with some embodiments ("CS01-FL-NAm12").

FIGS. 58A and 58B show the CS04m12 codon-altered nucleotide sequence (SEQ ID NO: 109) encoding a Factor VIII variant with m1 (F328S) and m2 amino acid substitutions in accordance with some embodiments ("CS04-FL-NAm12").

DETAILED DESCRIPTION OF DISCLOSURE

I. Introduction

AAV-based gene therapy holds great promise for the treatment of hemophiliacs. For hemophilia B, first clinical data are encouraging in that FIX levels of about 10% can be maintained in at least some patients for more than 1 year. For hemophilia A however, achieving therapeutic expression levels of 5-10% with AAV vectors remains challenging for various reasons. First, the Factor VIII coding sequence is too large for conventional AAV-based vectors. Second, engineered B-domain deleted or truncated Factor VIII constructs suffer from poor expression in vivo, even when codon-optimized. Third, these B-domain deleted or truncated Factor VIII variant constructs have short half-lives in vivo, exacerbating the effects of poor expression. Fourth, even when expressed, FVIII is not efficiently secreted from cells, as are other coagulation factors, such as Factor IX.

Moreover, these challenges cannot be addressed by simply administering higher doses of the gene therapy construct. According to current knowledge, the vector dose of an AAV-based gene therapy vector should be increased above $2\times10^2$ vg/kg bodyweight. This is because at such high doses a T cell immune response is triggered, which destroys transduced cells and, as a consequence, transgene expression is reduced or even eliminated. Therefore, strategies to improve the expression of FVIII are needed to make FVIII gene therapy a viable therapeutic option for hemophilia A patients.

The present disclosure relates to the discovery of codon-altered Factor VIII variant coding sequences that solve these and other problems associated with Factor VIII gene therapy. For example, the polynucleotides disclosed herein provide markedly improved expression in mammalian cells, and display improved virion packaging due to stabilized packing interactions. In some implementations, these advantages are realized by using coding sequences for the heavy and light chains of Factor VIII with high sequence identity to the codon altered CS01, CS04, and CS23 constructs (e.g., with high sequence identity to one of the CS01-HC, CS04-HC, and CS23-HC heavy chain coding sequences and high sequence identity to one of the CS01-LC, CS04-LC, and CS23-LC light chain coding sequences).

In some implementations, the Factor VIII molecules encoded by the polynucleotides described herein have been shortened by truncating, deleting, or replacing the wild-type B-domain. As such, the polynucleotides are better suited for expressing Factor VIII via conventional gene therapy vectors, which inefficiently express larger polypeptides, such as the wild-type Factor VIII.

Advantageously, it is shown herein that the CS01, CS04, and CS23 codon-altered Factor VIII variant coding sequences provide superior expression of a B-domain deleted Factor VIII construct in vivo. For example, it is demonstrated in Example 2 and Example 4 that intravenous administration of AAV-based gene therapy vectors having the CS01 (SEQ ID NO: 13), CS04 (SEQ ID NO: 1), and CS23 (SEQ ID NO: 20) coding sequence provide 18-fold, 74-fold, and 30-fold increases in Factor VIII expression, relative to the corresponding CS40 construct encoded with the wild-type polynucleotide sequence (SEQ ID NO: 17), in Factor VIII knock-out mice (Table 4 and Table 7).

Further, it also shown herein that the CS01 and CS04 codon-altered Factor VIII variant coding sequences provide superior virion packaging and virus production. For example, it is demonstrated in Example 1 that AAV vector constructs containing the CS01 and CS04 constructs provided 5 to 7-fold greater viral yield, relative to the corresponding CS40 construct encoded with the wild-type polynucleotide sequence, when isolated from the same amount of cell pellet.

Advantageously, Applicants also found that the improved Factor VIII activity generated from the CS01, CS04, and CS23 codon altered sequences could be further enhanced by introducing mutations into the underlying Factor VIII polypeptide sequence. For example, as demonstrated in Example 4, the F328S, X5, and X1 mutations, alone and in combination with one another, further increased FVIII activity when expressed in vivo in the CS01 or CS04 codon altered background 2 to 7-fold, relative to the wild type, codon altered constructs (Table 7). More strikingly, these codon altered sequences, encoding the mutant Factor VIII mutants, provided up to 246-fold greater increase as compared to the corresponding CS40 construct encoded with the wild-type polynucleotide sequence (Table 7).

II. Definitions

As used herein, the following terms have the meanings ascribed to them unless specified otherwise.

As used herein, the terms "Factor VIII" and "FVIII" are used interchangeably, and refer to any protein with Factor VIII activity (e.g., active FVIII, often referred to as FVIIIa) or protein precursor (e.g., pro-protein or pre-pro-protein) of a protein with Factor VIII activity, particularly Factor IXa cofactor activity. In an exemplary embodiment, a Factor VIII polypeptide refers to a polypeptide that has sequences with high sequence identity (e.g., at least 70%, 75%, 80%, 85%, 90%, 95%, 99%, or more) to the heavy and light chains of a wild type Factor VIII polypeptide. In some embodiments, the B-domain of a Factor VIII polypeptide is deleted, truncated, or replaced with a linker polypeptide to reduce the size of the polynucleotide encoding the Factor VIII polypeptide. In an exemplary embodiment, amino acids 20-1457 of SEQ ID NO: 2 constitute a Factor VIII polypeptide.

Non-limiting examples of wild type Factor VIII polypeptides include human pre-pro-Factor VIII (e.g., GenBank accession nos. AAA52485, CAA25619, AAA58466, AAA52484, AAA52420, AAV85964, BAF82636, BAG36452, CAI41660, CAI41666, CAI41672, CAI43241, CA003404, EAW72645, AAH22513, AAH64380, AAH98389, AAI11968, AAI11970, or AAB61261), corresponding pro-Factor VIII, and natural variants thereof; porcine pre-pro-Factor VIII (e.g., UniProt accession nos. F1RZ36 or K7GSZ5), corresponding pro-Factor VIII, and natural variants thereof; mouse pre-pro-Factor VIII (e.g., GenBank accession nos. AAA37385, CAM15581, CAM26492, or EDL29229), corresponding pro-Factor VIII, and natural variants thereof; rat pre-pro-Factor VIII (e.g., GenBank accession no. AAQ21580), corresponding pro-Factor VIII, and natural variants thereof; rat pre-pro-Factor VIII; and other mammalian Factor VIII homologues (e.g., monkey, ape, hamster, guinea pig, etc.).

As used herein, a Factor VIII polypeptide includes natural variants and artificial constructs with Factor IX cofactor activity. As used in the present disclosure, Factor VIII encompasses any natural variants, alternative sequences, isoforms, or mutant proteins that retain some basal Factor IX cofactor activity (e.g., at least 5%, 10%, 25%, 50%, 75%, or more of the corresponding wild type activity). Examples of Factor VIII amino acid variations (relative to FVIII-FL-AA (SEQ ID NO: 19)) found in the human population include, without limitation, S19R, R22T, Y24C, Y25C, L26P/R, E30V, W33G, Y35C/H, G41C, R48C/K, K67E/N, L69P, E72K, D75E/V/Y, P83R, G89D/V, G92A/V, A97P, E98K, V99D, D101G/H/V, V104D, K108T, M110V, A111T/V, H113R/Y, L117F/R, G121S, E129V, G130R, E132D, Y133C, D135G/Y, T137A/I, S138R, E141K, D145H, V147D, Y155H, V159A, N163K, G164D/V, P165S, C172W, S176P, S179P, V181E/M, K185T, D186G/N/Y, S189L, L191F, G193R, L195P, C198G, S202N/R, F214V, L217H, A219D/T, V220G, D222V, E223K, G224W, T252I, V253F, N254I, G255V, L261P, P262L, G263S, G266F, C267Y, W274C, H275L, G278R, G280D, E284K, V285G, E291G/K, T294I, F295L, V297A, N299I, R301C/H/L, A303E/P, I307S, S308L, F312S, T314A/I, A315V, G323E, L326P, L327P/V, C329F, I331V, M339T, E340K, V345A/L, C348R/S/Y, Y365C, R391C/H/P, S392L/P, A394S, W401G, I405F/S, E409G, W412G/R, K427I, L431F/S, R437P/W, I438F, G439D/S/V, Y442C, K444R, Y450D/N, T454I, F455C, G466E, P470L/R/T, G474E/R/V, E475K, G477V, D478N, T479R, F484C, A488G, R490G, Y492C/H, Y492H, I494T, P496R, G498R, R503H, G513S/V, I522Y, K529E, W532G, P540T, T541S, D544N, R546W, R550C/G/H, S553P, S554C/G, V556D, R560T, D561G/H/Y, I567T, P569R, S577F, V578A, D579A/H, N583S, Q584H/K/R, I585R/T, M586V, D588G/Y, L594Q, S596P, N601D/K, R602G, S603I/R, W604C, Y605H/S, N6091, R612C, N631K/S, M633I, S635N, N637D/I/S, Y639C, L644V, L650F, V653A/M, L659P, A663V, Q664P, F677L, M681I, V682F, Y683C/N, T686R, F698L, M699T/V, M701I, G705V, G710W, N713I, R717L/W, G720D/S, M721I/L, A723T, L725Q, V727F, E739K, Y742C, R795G, P947R, V1012L, E1057K, H1066Y, D1260E, K1289Q, Q1336K, N1460K, L1481P, A1610S, I1698T, Y1699C/F, E1701K, Q1705H, R1708C/H, T1714S, R1715G, A1720V, E1723K, D1727V, Y1728C, R1740G, K1751Q, F1762L, R1768H, G1769R, L1771P, L1775F/V, L1777P, G1779E/R, P1780L, I1782R, D1788H, M1791T, A1798P, S1799H, R1800C/G/H, P1801A, Y1802C, S1803Y, F1804S, L1808F, M1842I, P1844S, T1845P, E1848G, A1853T/V, S1858C, K1864E, D1865N/Y, H1867P/R, G1869D/V, G1872E, P1873R, L1875P, V1876L, C1877R/Y, L1882P, R1888I, E1894G, I1901F, E1904D/K, S1907C/R, W1908L, Y1909C, A1939T/V, N1941D/S, G1942A, M1945V, L1951F, R1960L/Q, L1963P, S1965I, M1966I/V, G1967D, S1968R, N1971T, H1973L, G1979V, H1980P/Y, F1982I, R1985Q, L1994P, Y1998C, G2000A, T2004R, M2007I, G2013R, W2015C, R2016P/W, E2018G, G2022D, G2028R, G2030N, V2035A, Y2036C, N2038S, 2040Y, G2045E/V, I2051S, I2056N, A2058P, W2065R, P2067L, A2070V, S2082N, S2088F, D2093G/Y, H2101D, T2105N, Q2106E/P/R, G2107S, R2109C, I2117F/S, Q2119R, F2120C/L, Y2124C, R2135P, S2138Y, T2141N, M2143V, F2145C, N2148S, N2157D, P2162L, R2169C/H, P2172L/Q/R, T2173A/I, H2174D, R2178C/H/L, R2182C/H/P, M2183R/V, L2185S/W, S2192I, C2193G, P2196R, G2198V, E2200D, I2204T, I2209N, A2211P, A2220P, P2224L, R2228G/L/P/Q, L2229F, V2242M, W2248C/S, V2251A/E, M2257V, T2264A, Q2265R, F2279C/I, I2281T, D2286G, W2290L, G2304V, D2307A, P2319L/S, R2323C/G/H/L, R2326G/L/P/Q, Q2330P, W2332R, I2336F, R2339T, G2344C/D/S, and C2345S/Y. Factor VIII proteins also include polypeptides containing post-translational modifications.

Figure 1:
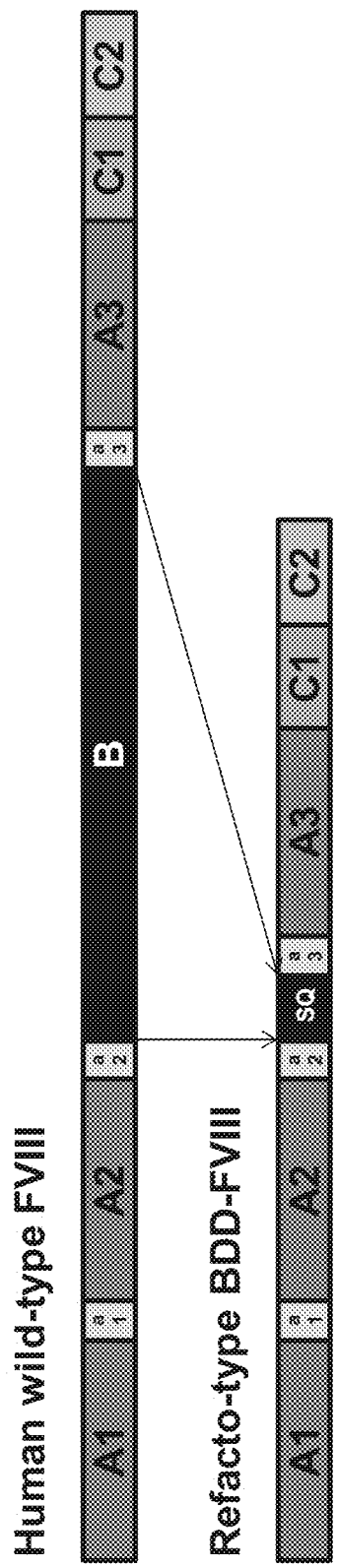
FIG. 1 shows schematic illustrations of the wild-type and ReFacto-type human Factor VIII protein constructs.

Generally, polynucleotides encoding Factor VIII encode for an inactive single-chain polypeptide (e.g., a pre-pro-protein) that undergoes post-translational processing to form an active Factor VIII protein (e.g., FVIIIa). For example, referring to FIG. 1, the wild type human Factor VIII pre-pro-protein is first cleaved to release the encoded signal peptide (not shown), forming a first single-chain pro-protein (shown as "human wild-type FVIII). The pro-protein is then cleaved between the B and A3 domains to form a first polypeptide that includes the Factor VIII heavy chain (e.g., the A1 and A2 domains) and B-domain, and a second polypeptide that includes the Factor VIII light chain (e.g., including the A3, C1, and C3 domains). The first polypeptide is further cleaved to remove the B-domain, and also to separate the A1 and A2 domains, which remain associated with the Factor VIII light chain in the mature Factor VIIIa protein. For review of the Factor VIII maturation process, see Graw et al., Nat Rev Genet., 6(6):488-501 (2005), the content of which is incorporated herein by reference in its entirety for all purposes.

However, in some embodiments, the Factor VIII polypeptide is a single-chain Factor VIII polypeptide. Single-chain Factor VIII polypeptides are engineered to remove natural cleavage sites, and optionally remove, truncate, or replace the B-domain of Factor VIII. As such, they are not matured by cleavage (other than cleavage of an optional signal and/or leader peptide), and are active as a single chain. Non-limiting examples of single-chain Factor VIII polypeptides are described in Zollner et al. (Thromb Res, 134(1):125-31 (2014)) and Donath et al. (Biochem J., 312 (1):49-55 (1995)), the disclosures of which are hereby incorporated by reference in their entireties for all purposes.

As used herein, the terms "Factor VIII heavy chain," or simply "heavy chain," refers to the aggregate of the A1 and A2 domains of a Factor VIII polypeptide. In an exemplary embodiment, amino acids 20-759 of CS04-FL-AA (SEQ ID NO: 2) constitute a Factor VIII heavy chain.

As used herein, the term "Factor VIII light chain," or simply "light chain," refers to the aggregate of the A3, C1, and C2 domains of a Factor VIII polypeptide. In an exemplary embodiment, amino acids 774-1457 CS04-FL-AA (SEQ ID NO: 2) constitute a Factor VIII light chain. In some embodiments, a Factor VIII light chain excludes the acidic a3 peptide, which is released during maturation in vivo.

Generally, Factor VIII heavy and light chains are expressed as a single polypeptide chain, e.g., along with an optional B-domain or B-domain substituted linker. However, in some embodiments, a Factor VIII heavy chain and Factor VIII light chain are expressed as separate polypeptide chains (e.g., co-expressed), and reconstituted to form a Factor VIII protein (e.g., in vivo or in vitro).

As used herein, the terms "B-domain substituted linker" and "Factor VIII linker" are used interchangeably, and refer to truncated versions of a wild type Factor VIII B-domain (e.g., amino acids 760-1667 of FVIII-FL-AA (SEQ ID NO: 19)) or peptides engineered to replace the B-domain of a Factor VIII polypeptide. As used herein, a Factor VIII linker is positioned between the C-terminus of a Factor VIII heavy chain and the N-terminus of a Factor VIII light chain in a Factor VIII variant polypeptide in accordance with some embodiments. Non-limiting examples of B-domain substituted linkers are disclosed in U.S. Pat. Nos. 4,868,112, 5,112,950, 5,171,844, 5,543,502, 5,595,886, 5,610,278, 5,789,203, 5,972,885, 6,048,720, 6,060,447, 6,114,148, 6,228,620, 6,316,226, 6,346,513, 6,458,563, 6,924,365, 7,041,635, and 7,943,374; U.S. Patent Application Publication Nos. 2013/024960, 2015/0071883, and 2015/0158930; and PCT Publication Nos. WO 2014/064277 and WO 2014/127215, the disclosures of which are hereby incorporated by reference, in their entireties, for all purposes.

Unless otherwise specified herein, the numbering of Factor VIII amino acids refers to the corresponding amino acid in the full-length, wild-type human Factor VIII sequence (FVIII-FL-AA), presented as SEQ ID NO: 19 in FIG. 22. As such, when referring to an amino acid substitution in a Factor VIII variant protein disclosed herein, the recited amino acid number refers to the analogous (e.g., structurally or functionally equivalent) and/or homologous (e.g., evolutionarily conserved in the primary amino acid sequence) amino acid in the full-length, wild-type Factor VIII sequence. For example, a T2105N amino acid substitution refers to a T to N substitution at position 2105 of the full-length, wild-type human Factor VIII sequence (FVIII-FL-AA; SEQ ID NO: 19), a T to N substitution at position 1211 of the Factor VIII variant protein encoded by CS04 (CS04-FL-AA; SEQ ID NO: 2), and a T to N substitution at position 1212 of the Factor VIII variant encoded by CS04m3 (CS04m3-FL-AA; SEQ ID NO: 105).

As described herein, the Factor VIII amino acid numbering system is dependent on whether the Factor VIII signal peptide (e.g., amino acids 1-19 of the full-length, wild-type human Factor VIII sequence) is included. Where the signal peptide is included, the numbering is referred to as "signal peptide inclusive" or "SPI". Where the signal peptide is not included, the numbering is referred to as "signal peptide exclusive" or "SPE." For example, F328S is SPI numbering for the same amino acid as F309S, in SPE numbering. Unless otherwise indicated, all amino acid numbering refers to the corresponding amino acid in the full-length, wild-type human Factor VIII sequence (FVIII-FL-AA), presented as SEQ ID NO: 19 in FIG. 22.

As described herein, the codon-altered polynucleotides provide increased expression of transgenic Factor VIII in vivo (e.g., when administered as part of a gene therapy vector), as compared to the level of Factor VIII expression provided by a natively-coded Factor VIII construct (e.g., a polynucleotide encoding the same Factor VIII construct using the wild-type human codons). As used herein, the term "increased expression" refers to an increased level of transgenic Factor VIII activity in the blood of an animal administered the codon-altered polynucleotide encoding Factor VIII, as compared to the level of transgenic Factor VIII activity in the blood of an animal administered a natively-coded Factor VIII construct. The activity levels can be measured using any Factor VIII activity known in the art. An exemplary assay for determining Factor VIII activity is the Technochrome FVIII assay (Technoclone, Vienna, Austria).

In some embodiments, increased expression refers to at least 25% greater transgenic Factor VIII activity in the blood of an animal administered the codon-altered Factor VIII polynucleotide, as compared to the level of transgenic Factor VIII activity in the blood of an animal administered a natively coded Factor VIII polynucleotide. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor VIII activity in the blood of an animal administered the codon-altered Factor VIII polynucleotide, as compared to the level of transgenic Factor VIII activity in the blood of an animal administered a natively coded Factor VIII polynucleotide.

As described herein, the codon-altered polynucleotides provide increased vector production, as compared to the level of vector production provided by a natively-coded Factor VIII construct (e.g., a polynucleotide encoding the same Factor VIII construct using the wild-type human codons). As used herein, the term "increased virus production" refers to an increased vector yield in cell culture (e.g., titer per liter culture) inoculated with the codon-altered polynucleotide encoding Factor VIII, as compared to the vector yield in cell culture inoculated with a natively-coded Factor VIII construct. The vector yields can be measured using any vector titer assay known in the art. An exemplary assay for determining vector yield (e.g., of an AAV vector) is qPCR targeting the AAV2 inverted terminal repeats (Aurnhammer, Human Gene Therapy Methods: Part B 23:18-28 (2012)).

In some embodiments, increased virus production refers to at least 25% greater codon-altered vector yield, as compared to the yield of a natively-coded Factor VIII construct in the same type of culture. In some embodiments, increased vector production refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, or at least 20-fold greater codon-altered vector yield, as compared to the yield of a natively-coded Factor VIII construct in the same type of culture.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®—VH, and FXI, as well as FEIBA-VH, desmopressin, and plasma infusions.

As used herein, the term "FVIII gene therapy" includes any therapeutic approach of providing a nucleic acid encoding Factor VIII to a patient to relieve, diminish, or prevent the reoccurrence of one or more symptoms (e.g., clinical factors) associated with hemophilia. The term encompasses administering any compound, drug, procedure, or regimen comprising a nucleic acid encoding a Factor VIII molecule, including any modified form of Factor VIII (e.g., Factor VIII variant), for maintaining or improving the health of an individual with hemophilia. One skilled in the art will appreciate that either the course of FVIII therapy or the dose of a FVIII therapeutic agent can be changed, e.g., based upon the results obtained in accordance with the present disclosure.

As used herein, the term "bypass therapy" includes any therapeutic approach of providing non-Factor VIII hemostatic agents, compounds or coagulation factors to a patient to relieve, diminish, or prevent the reoccurrence of one or more symptoms (e.g., clinical factors) associated with hemophilia. Non-Factor VIII compounds and coagulation factors include, but are not limited to, Factor VIII Inhibitor Bypass Activity (FEIBA), recombinant activated factor VII (FVIIa), prothrombin complex concentrates, and activated prothrombin complex concentrates. These non-Factor VIII compounds and coagulation factors may be recombinant or plasma-derived. One skilled in the art will appreciate that either the course of bypass therapy or the dose of bypass therapy can be changed, e.g., based upon the results obtained in accordance with the present disclosure.

As used herein, a "combination therapy" including administration of a nucleic acid encoding a Factor VIII molecule and a conventional hemophilia A therapeutic agent includes any therapeutic approach of providing both a nucleic acid encoding a Factor VIII molecule and a Factor VIII molecule and/or non-Factor VIII hemostatic agent (e.g., bypass therapeutic agent) to a patient to relieve, diminish, or prevent the reoccurrence of one or more symptoms (e.g., clinical factors) associated with hemophilia. The term encompasses administering any compound, drug, procedure, or regimen including a nucleic acid encoding a Factor VIII molecule, including any modified form of factor VIII, which is useful for maintaining or improving the health of an individual with hemophilia and includes any of the therapeutic agents described herein.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleotide sequences, such as promoters, enhancers, terminators, polyadenylation sequences, introns, etc, that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the β-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, the term "vector" refers to any vehicle used to transfer a nucleic acid (e.g., encoding a Factor VIII gene therapy construct) into a host cell. In some embodiments, a vector includes a replicon, which functions to replicate the vehicle, along with the target nucleic acid. Non-limiting examples of vectors useful for gene therapy include plasmids, phages, cosmids, artificial chromosomes, and viruses, which function as autonomous units of replication in vivo. In some embodiments, a vector is a viral vehicle for introducing a target nucleic acid (e.g., a codon-altered polynucleotide encoding a Factor VIII variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "CpG island" refers to a region within a polynucleotide having a statistically elevated density of CpG dinucleotides. As used herein, a region of a polynucleotide (e.g., a polynucleotide encoding a codon-altered Factor VIII protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG] * N[\text{length of window}]}{N[C] * N[G]} \geq 0.6.$$

For additional information on methods for identifying CpG islands, see Gardiner-Garden M. et al., J Mol Biol., 196(2): 261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The nucleotide sequences that encode the mutant Factor VIII constructs herein may be identical to the coding sequence provided herein or may be a different coding sequence, which sequence, as a result of the redundancy or degeneracy of the genetic code, encodes the same polypeptides as the coding sequences provided herein. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each variation of a nucleic acid which encodes a same polypeptide is implicit in each described sequence with respect to the expression product, but not with respect to actual gene therapy constructs.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 2 (SEQ ID NO:1), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 2 (SEQ ID NO:1), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor VIII variant protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS04", "CS01", "C523", etc.) refer to codon altered polynucleotides encoding FVIII polypeptides and/or the encoded polypeptides, including variants. For example, CS01-FL refers to the Full Length codon altered CS01 polynucleotide sequence or amino acid sequence (sometimes referred to herein as "CS01-FL-AA" for the Amino Acid sequence and "CS01-FL-NA" for the Nucleic Acid sequence) encoded by the CS01 polynucleotide sequence. Similarly, "CS01-LC" refers to either the codon altered nucleic acid sequence ("CS01-LC-NA") encoding the light chain of a FVIII polypeptide or the amino acid sequence (also sometimes referred to herein as "CS01-LC-AA") of the FVIII light chain encoded by the CS01 polynucleotide sequence. Likewise, CS01-HC, CS01-HC-AA and CS01-HC-NA are the same for the FVIII heavy chain. As will be appreciated by those in the art, for constructs such as CS01, CS04, CS23, etc., that are only codon-altered (e.g. they do not contain additional amino acid substitutions as compared to Refacto), the amino acid sequences will be identical, as the amino acid sequences are not altered by the codon optimization. Thus, sequence constructs of the disclosure include, but are not limited to, CS01-FL-NA, CS01-FL-AA, CS01-LC-NA, CS01-LC-AA, CS01-HC-AA, CS01-HC-NA, CS04-FL-NA, CS04-FL-AA, CS04-LC-NA, CS04-LC-AA, CS04-HC-AA, CS04-HC-NA, CS23-FL-NA, CS23-FL-AA, CS23-LC-NA, CS23-LC-AA, CS23-HC-AA and CS23-HC-NA.

This nomenclature also applies to glycosylation peptides as shown in FIG. 13, such that "NGA1-AA" refers to the amino acid sequence and NGA1-NA refers to the nucleic acid sequence.

The disclosure also includes additional new Factor VIII variants, as described below, with the appropriate nomenclature.

III. Codon-Altered Factor VIII Variants

In some embodiments, the present disclosure provides codon-altered polynucleotides encoding Factor VIII variants. These codon-altered polynucleotides provide markedly improved expression of Factor VIII when administered in an AAV-based gene therapy construct. The codon-altered polynucleotides also demonstrate improved AAV-virion packaging, as compared to conventionally codon-optimized constructs. As demonstrated in Example 2 and Example 4, Applicants have achieve these advantages through the discovery of three codon-altered polynucleotides (CS01-FL-NA, CS04-FL-NA, and CS23-FL-NA) encoding a Factor VIII polypeptide with human wild-type Factor VIII heavy and light chains, and a short, 14 amino acid, B-domain substituted linker (the "SQ" linker) containing a furin cleavage site to facilitate maturation of an active FVIIIa protein in vivo. As further demonstrated in Example 4, incorporation of various combinations of the F328S, X5, and X1 amino acid mutations into the encoded Factor VIII molecule further increased the in vivo expression of Factor VIII activity.

In one embodiment, a codon-altered polynucleotide provided herein has nucleotide sequences with high sequence identity to at least the sequences within CS01, CS04, or CS23 (SEQ ID NOS 13, 1, and 20, respectively) encoding the Factor VIII heavy chain and Factor VIII light chains. As known in the art, the B-domain of Factor VIII is dispensable for activity in vivo. Thus, in some embodiments, the codon-altered polynucleotides provided herein completely lack a Factor VIII B-domain. In some embodiments, the native Factor VIII B-domain is replaced with a short amino acid linker containing a furin cleavage site, e.g., the "SQ" linker consisting of amino acids 760-773 of the CS01, CS04, or CS23 (SEQ ID NOS 2, 2, and 21, respectively) constructs. The "SQ" linker is also referred to as BDLO04, (–AA for the amino acid sequence and -NA for the nucleotide sequence shown in FIG. 6).

In one embodiment, the Factor VIII heavy and light chains encoded by the codon-altered polynucleotide are human Factor VIII heavy and light chains, respectively. In other embodiments, the Factor VIII heavy and light chains encoded by the codon-altered polynucleotide are heavy and light chain sequences from another mammal (e.g., porcine Factor VIII). In yet other embodiments, the Factor VIII heavy and light chains are chimeric heavy and light chains (e.g., a combination of human and a second mammalian sequence). In yet other embodiments, the Factor VIII heavy and light chains are humanized version of the heavy and light chains from another mammal, e.g., heavy and light chain sequences from another mammal in which human residues are substituted at select positions to reduce the immunogenicity of the resulting peptide when administered to a human.

The GC content of human genes varies widely, from less than 25% to greater than 90%. However, in general, human genes with higher GC contents are expressed at higher levels. For example, Kudla et al. (PLoS Biol., 4(6):80 (2006)) demonstrate that increasing a gene's GC content increases expression of the encoded polypeptide, primarily by increasing transcription and effecting a higher steady state level of the mRNA transcript. Generally, the desired GC content of a codon-optimized gene construct is equal or greater than 60%. However, native AAV genomes have GC contents of around 56%.

Accordingly, in some embodiments, the codon-altered polynucleotides provided herein have a CG content that more closely matches the GC content of native AAV virions (e.g., around 56% GC), which is lower than the preferred CG contents of polynucleotides that are conventionally codon-optimized for expression in mammalian cells (e.g., at or above 60% GC). As outlined in Example 1, CS04-FL-NA (SEQ ID NO: 1), which has a GC content of about 56%, has improved virion packaging as compared to similarly codon-altered coding sequences with higher GC content.

Thus, in some embodiments, the overall GC content of a codon-altered polynucleotide encoding a Factor VIII polypeptide is less than 60%. In some embodiments, the overall GC content of a codon-altered polynucleotide encoding a Factor VIII polypeptide is less than 59%. In some embodiments, the overall GC content of a codon-altered polynucleotide encoding a Factor VIII polypeptide is less than 58%. In some embodiments, the overall GC content of a codon-altered polynucleotide encoding a Factor VIII polypeptide is less than 57%. In some embodiments, the overall GC content of a codon-altered polynucleotide encoding a Factor VIII polypeptide is no more than 56%.

In some embodiments, the overall GC content of a codon-altered polynucleotide encoding a Factor VIII polypeptide is from 54% to 59%. In some embodiments, the overall GC content of a codon-altered polynucleotide encoding a Factor VIII polypeptide is from 55% to 59%. In some embodiments, the overall GC content of a codon-altered polynucleotide encoding a Factor VIII polypeptide is from 56% to 59%. In some embodiments, the overall GC content of a codon-altered polynucleotide encoding a Factor VIII polypeptide is from 54% to 58%. In some embodiments, the overall GC content of a codon-altered polynucleotide encoding a Factor VIII polypeptide is from 55% to 58%. In some embodiments, the overall GC content of a codon-altered polynucleotide encoding a Factor VIII polypeptide is from 56% to 58%. In some embodiments, the overall GC content of a codon-altered polynucleotide encoding a Factor VIII polypeptide is from 54% to 57%. In some embodiments, the overall GC content of a codon-altered polynucleotide encoding a Factor VIII polypeptide is from 55% to 57%. In some embodiments, the overall GC content of a codon-altered polynucleotide encoding a Factor VIII polypeptide is from 56% to 57%. In some embodiments, the overall GC content of a codon-altered polynucleotide encoding a Factor VIII polypeptide is from 54% to 56%. In some embodiments, the overall GC content of a codon-altered polynucleotide encoding a Factor VIII polypeptide is from 55% to 56%.

In some embodiments, the overall GC content of a codon-altered polynucleotide encoding a Factor VIII polypeptide is 56±0.5%. In some embodiments, the overall GC content of a codon-altered polynucleotide encoding a Factor VIII polypeptide is 56±0.4%. In some embodiments, the overall GC content of a codon-altered polynucleotide encoding a Factor VIII polypeptide is 56±0.3%. In some embodiments, the overall GC content of a codon-altered polynucleotide encoding a Factor VIII polypeptide is 56±0.2%. In some embodiments, the overall GC content of a codon-altered polynucleotide encoding a Factor VIII polypeptide is 56±0.1%. In some embodiments, the overall GC content of a codon-altered polynucleotide encoding a Factor VIII polypeptide is 56%.

A. Factor VIII Amino Acid Substitutions

To further increase the efficiency of AAV-vector based expression of the Factor VIII constructs described herein, amino acid substitutions know to improve secretion, increase specific activity, and/or enhanced the stability of Factor VIII are further incorporated, in some implementations. A number of potential variants were identified that increase the plasma levels of FVIII activity at a given vector dose. These variants include those with a more efficient signal peptide, amino acid substitutions that prevent BiP interactions, amino acid substitutions resembling more efficiently secreted Factor VIII orthologs (e.g., porcine Factor VIII), single-chain Factor VIII variants, and amino acid substitutions that stabilize Factor VIII and/or reduce subunit dissociation.

Mutation of residues A108, R121, and L2302 (SPE), located at the interface between the A1 and C2 domains, increases the stability of Factor VIII. For example, the A108I amino acid substitution introduces a hydrophobic residue that better fills the inter-domain space, stabilizing the interaction. Likewise, an R121C/L2302C (SPE) double amino acid substitution introduces a disulfide bond spanning the A1-C2 domains, further stabilizing the interaction. Taken together, all three amino acid substitutions increase the thermal stability of Factor VIII by 3 to 4-fold. For review, see Wakabayashi et al., J Biol Chem. 286(29):25748-55 (2011) and Wakabayashi et al., Thromb Haemost. 10(3): 492-95 (2012). Accordingly, in some embodiments, the encoded Factor VIII polypeptide includes A108I and/or R121C/L2302C amino acid substitutions.

Mutation of E113 (SPE), located within the calcium binding domain of Factor VIII, increases the specific FVIII clotting activity. For example, E113A appears to increase FXase formation through increased FVIII affinity for Factor IXa. Specifically, the E113A amino acid substitution increases specific FVIII clotting activity two-fold and increases affinity for Factor IXa by four-fold (Biochemistry, 41:8485 (2002); J. Biol. Chem., 279:12677 (2004); and Biochemistry, 44:10298 (2005)). Accordingly, in some embodiments, the encoded Factor VIII polypeptides include an E113A amino acid substitution.

Substitution of one or more amino acid residues surrounding the Factor VIII APC cleavage site (residues 331-341 (SPE)) reduce Factor VIIIa inactivation by activated protein C, without affecting FVIII activity. For example PQL333-335VDQ (SPE) amino acid substitutions reduce Factor VIII inactivation by 16-fold. Likewise, MKN336-339GNQ amino acid substitutions reduce Factor VIII inactivation by 9-fold. When combined, the two triple amino acid substitutions (e.g., PQLRMKN333-339VDQRGNQ) (SEQ ID NOS 34 and 35, respectively) reduce Factor VIII inactivation by 100-fold (J. Biol. Chem., 282:20264 (2007). Accordingly, in some embodiments, the encoded Factor VIII polypeptide include PQL333-335VDQ and/or MKN337-339GNQ (SPE) amino acid substitutions.

Mutations within the A2 domain interface also increase Factor VIII stability. Specifically, mutating charged residues in the A1-A2 and A2-A3 domain interfaces increases stability and retention of the A2 subunit in Factor VIIIa. For example, mutation of D519, E665, and E1984 to V or A yields up to 2-fold increased stability in Factor VIII and up to 5-fold stability in Factor VIIIa. Specifically, D519A/E665V amino acid substitutions provide a 3-fold increase in stability; D519V/E665V amino acid substitutions provide a 2-fold increase in stability, an 8-fold decrease in A2 dissociation, and a 2-4-fold increase in thrombin generation potential; D519V/E1984A amino acid substitutions provide a 2-fold increase in stability; and D519V/E665V/E1984A amino acid substitution provide a 2-fold increase in stability (Blood 112:2761-69 (2008); J. Thromb. Haemost., 7:438-44 (2009)). Accordingly, in some embodiments, the encoded Factor VIII polypeptides include one or more of D519A/V, E665A/V, and E1984A/V amino acid substitutions.

Of particular relevance to the present disclosure are a number of specific mutations that can be included separately or in combinations with other variants described herein. These variants are coded as sets herein as follows: "m1" refers to a single amino acid change, "m2" is a set of 5 amino acid variants, "m3" is a combination of a deletion of 7 amino acids and an insertion of six amino acids that span the junction between the polypeptide linker and the heavy chain, "m4" is a combination of the m1 single mutation and the m5 double mutation, and "m5" is a set of two cysteine ablations. These mutations are described below. These can be included in any particular construct alone or in combination with other variants, and they are coded accordingly. For example, "m23" is a combination of the m2 and m3 variants onto a particular scaffold, as outlined herein; thus "CS01m23-FL-NA" or "CS01-FL-NAm23" refers to the CS01 codon-altered polynucleotide sequence with the nucleotides encoding the m2 and m3 mutations included, and "CS01m23-FL-AA" or "CS01-FL-AAm23" refers to the amino acid sequence. As CS01 is codon-altered but does not change the amino acid sequence of Refacto, these can be thought of on the amino acid level as mutations as compared to the Refacto amino acid sequence of CS01-FL-AA (SEQ ID NO: 2).

In many embodiments, the polypeptides of the disclosure are made with the "m1" variant included. Mutations within an 11 amino acid hydrophobic β-sheet in the A1 domain, which interacts with BiP, increase secretion of Factor VIII. For example, an F328S (SPI, F309S SPE) amino acid substitution within the pocket increased Factor VIII secretion 3-fold. The F328S variant is referred to herein as the "m1" mutation and is within the heavy chain. Again, as described herein, the number of the variants can be done inclusive of the signal peptide, "Signal Peptide Inclusive", or "SPI", or starting from the processed final protein sequence, "Signal Peptide Exclusive", or "SPE". Thus, using SPI numbering, the mutation F328S is the same as the F309 SPE mutant. Generally the specification uses the SPI numbering, but as will be appreciated by those in the art, either numbering system results in the same mutation(s).

Accordingly, included in the present disclosure are polypeptides that include the m1 mutation, including CS01-FL-AAm1, CS01-HC-AAm1, CS04-FL-AAm1, CS04-HC-AAm1 CS23-FL-AAm1, CS23-HC-AAm1, CS40-FL-AAm1 and CS40-HC-AAm1 (all of which encode the same corresponding protein sequences).

In addition, included in the present disclosure are not only polypeptide sequences that include the m1 mutation, but also those codon-altered polynucleotide sequences that encode proteins with the m1 mutation, such as CS01-FL-NAM1, CS01-HC-NAM1, CS04-FL-NAm1, CS04-HC-NAM1, CS23-FL-NAM1, CS23-HC-NA-m1, CS40-FL-NAm1 and CS40-HC-NAm1.

In many embodiments, the polypeptides of the disclosure are made with the "m2" variant set included, which is the I105V/A127S/G151K/M166T/L171P mutations (SPI numbering; (SPE numbering is V86I/S108A/K132G/T147M/P152L, respectively). The m2 mutation set is based on the fact that substitution of porcine amino acids 82-176 for the corresponding human amino acids in a B-domain deleted gene therapy construct increased Factor VIII activity when expressed in HEK293 cells (W. Xiao, communication). Id. Back-mutation of single porcine amino acids into the human BDD-FVIII construct identified five amino acids within the A1 domain that contribute to this phenomenon: I105V, A127S, G151K, M166T, and L171P (SPI). Introduction of the combination of these mutations into the human construct recapitulated the improved activity of the larger porcine substitution. Id. Accordingly, in some embodiments, the encoded Factor VIII polypeptides include one or more amino acid substitutions selected from I105V, A127S, G151K, M166T, and L171P, with the entire 5 amino acid set, m2, finding particular use in many embodiments. As for the m1 mutation, the m2 variants are in the heavy chain, and thus the present disclosure includes polypeptides that include the m2 mutation, including CS01-FL-AAm2, CS01-HC-AAm2, CS04-FL-AAm2, CS04-HC-AAm2, CS23-FL-AAm2, CS23-HC-AAm2, CS40-FL-AAm2 and CS40-HC-AAm2 (all of which encode the same corresponding protein sequences).

In addition, included in the present disclosure are not only polypeptide sequences that include the m2 mutation, but also those codon-altered polynucleotide sequences that encode proteins with the m2 mutation, such as CS01-FL-NAm2, CS01-HC-NAm2, CS04-FL-NAm2, CS04-HC-NAm2, CS23-FL-NAm2, CS23-HC-NA-m2, CS40-FL-NAm2 and CS40-HC-NAm2.

In additional embodiments, the polypeptides and polynucleotides of the disclosure include m3 mutations. m3 is the substitution of seven amino acids for six across the HC-B domain interface that introduces an additional glycosylation site introduced close to the interface. Accordingly, in some embodiments, m3 is the deletion of amino acids AIEPRSF755-761 and the insertion of amino acids TTYVNRSL (SEQ ID NO: 33) after N754, relative to FVIII-FL-AA (SEQ ID NO: 19) (e.g., AIEPRSF755-761TTYVNRSL) ("TTYVNRSL" disclosed as SEQ ID NO: 33). Residues AIEPR755-759, relative to SEQ ID NO: 19, fall within the end of the heavy chain, while residues S760 and F761 fall within the B-domain. In some embodiments, where the FVIII B-domain is deleted, truncated, or replaced, residues 5760 and F761 may not be present in the underlying amino acid sequence being mutated. Accordingly, in some embodiments, m3 is the deletion of amino acids AIEPR755-759 and the insertion of amino acids TTYVNRSL (SEQ ID NO: 33) after N754, relative to FVIII-FL-AA (SEQ ID NO: 19) (e.g., AIEPR755-759TTYVNRSL ("TTYVNRSL" disclosed as SEQ ID NO: 33)

The m3 variants are in the junction between the heavy chain and the B domain, and thus the present disclosure includes polypeptides that include the m3 mutation, including CS01-FL-AAm3, CS01-HC-AAm3, CS04-FL-AAm3, CS04-HC-AAm3, CS23-FL-AAm3, CS23-HC-AAm3, CS40-FL-AAm3 and CS40-HC-AAm3 (all of which encode the same corresponding protein sequences).

In addition, included in the present disclosure are not only polypeptide sequences that include the m3 mutation, but also those codon-altered polynucleotide sequences that encode proteins with the m3 mutations, such as CS01-FL-NAm3, CS01-HC-NAm3, CS04-FL-NAm3, CS04-HC-NAm3, CS23-FL-NAm3, C523-HC-NA-m3, CS40-FL-NAm3 and CS40-HC-NAm3.

In additional embodiments, the polypeptides and polynucleotides of the disclosure include m4 mutations. Elimination of the C1899-C1903 disulfide bond in Factor VIII also increased secretion. Moreover, the increases in Factor VIII secretion are additive for the combination of F328S (SPI, F309S SPE) and C1918G/C1922G amino acid substitutions (Miao et al., Blood, 103:3412-19 (2004); Selvaraj et al., J. Thromb. Haemost., 10:107-15 (2012)). Accordingly, in some embodiments, the encoded Factor VIII polypeptides include m4 mutations, which is the F328S (SPI, F309S SPE) and C1918G/C1922G (SPI) amino acid substitutions. As the F328S variant is in the heavy chain and the two cysteine variants are in the light chain, polypeptide sequences that include m4 mutations are CS01-FL-AAm4, CS01-HC-AAm4, CS01-LCAAm4, CS04-FL-AAm4, CS04-HC-AAm4, CS04-LC-AAm4, CS23-FL-AAm4, CS23-HC-LCAAm4 and CS23-LC-AAm4.

In addition, included in the present disclosure are not only polypeptide sequences that include the m4 mutation, but also those codon-altered polynucleotide sequences that encode proteins with the m4 mutations, such as CS01-FL-NAm4, CS01-HC-NAm4, CS01-LC-NAm4, CS04-FL-NAm4, CS04-HC-NAm4, CS04-LC-NAm4, CS23-FL-NAm4, CS23-HC-NAm4, CS23-LC-NAm4, CS40-FL-NA-m4, CS40-HC-NA-m4 and CS40-LC-NA-m4.

In additional embodiments, the polypeptides and polynucleotides of the disclosure include m5 mutations. As above, elimination of the C1899-C1903 disulfide bond in Factor VIII also increased secretion. C1918G/C1922G (SPI) amino acid substitutions, contained within the light chain, referred to herein as the m5 mutation set.

The m5 variants are in the light chain, and thus the present disclosure includes polypeptides that include the m5 mutation, including CS01-FL-AAm5, CS01-LC-AAm5, CS04-FL-AAm5, CS04-LC-AAm5, CS23-FL-AAm5, CS23-LC-AAm5, CS40-FL-AAm5 and CS40-LC-AAm5 (all of which encode the same corresponding protein sequences).

In addition, included in the present disclosure are not only polypeptide sequences that include the m5 mutation, but also those codon-altered polynucleotide sequences that encode proteins with the m5 mutations, such as CS01-FL-NAm5, CS01-LC-NAm5, CS04-FL-NAm5, CS04-LC-NAm5, CS23-FL-NA-m5, CS23-LC-NA-m5, CS40-FL-NA-m5 and CS40-LC-NA-m5.

In addition to specific constructs (both amino acid and nucleic acid) that include m1, m2, m3, m4 and m5 individually, combinations of mutation sets can be made as outlined herein. As noted herein, these are noted as "m12", which is the combination of m1 and m2 sets, or "m123" which is the combination of m1, m2 and m3 sets. Thus, included in the disclosure are dual combinations including m12, m13, m14, m15, m23, m24, m25, m34, m35 and m45. Also included are triple combinations, m123, m124, m125, m234, m235 and m345. Further included are quad combinations, m1234, m1235, m1345 and the m12345 combination. Of particular interest in some embodiments are the following mutation sets: m1, m2, m3 and m4, m23, m123, and m234.

B. Factor VIII B-Domain Substituted Linkers

In some embodiments, the linkage between the FVIII heavy chain and the light chain (e.g., the B-domain in wild-type Factor VIII) is further altered. Due to size constraints of AAV packaging capacity, B-domain deleted, truncated, and or linker substituted variants should improve the efficacy of the FVIII gene therapy construct. The most conventionally used B-domain substituted linker is that of SQ FVIII, which retains only 14 amino acids of the B domain as linker sequence. Another variant of porcine VIII ("OBI-1," described in U.S. Pat. No. 6,458,563) is well expressed in CHO cells, and has a slightly longer linker of 24 amino acids. In some embodiments, the Factor VIII constructs encoded by the codon-altered polynucleotides described herein include an SQ-type B-domain linker sequence. In other embodiments, the Factor VIII constructs encoded by the codon-altered polynucleotides described herein include an OBI-1-type B-domain linker sequence.

In some embodiments, the encoded Factor VIII polypeptides described herein include an SQ-type B-domain linker, including amino acids 760-762/1657-1667 of the wild-type human Factor VIII B-domain (FVIII-FL-AA; SEQ ID NO: 19) (Sandberg et al. Thromb. Haemost. 85:93 (2001)). In some embodiments, the SQ-type B-domain linker has one amino acid substitution relative to the corresponding wild-type sequence. In some embodiments, the SQ-type B-domain linker has two amino acid substitutions relative to the corresponding wild-type sequence. In some embodiments, a glycosylation peptide is inserted into the SQ-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a Greengene-type B-domain linker, including amino acids 760/1582-1667 of the wild-type human Factor VIII B-domain (FVIII-FL-AA; SEQ ID NO: 19) (Oh et al., Biotechnol. Prog., 17:1999 (2001)). In some embodiments, the Greengene-type B-domain linker has one amino acid substitution relative to the corresponding wild-type sequence. In some embodiments, the Greengene-type B-domain linker has two amino acid substitutions relative to the corresponding wild-type sequence. In some embodiments, a glycosylation peptide is inserted into the Greengene-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include an extended SQ-type B-domain linker (SFSQNPPVLKRHQR; BDL-SQ-AA; SEQ ID NO: 30), including amino acids 760-769/1657-1667 of the wild-type human Factor VIII B-domain (FVIII-FL-AA; SEQ ID NO: 19) (Thim et al., Haemophilia, 16:349 (2010)). In some embodiments, the extended SQ-type B-domain linker has one amino acid substitution relative to the corresponding wild-type sequence. In some embodiments, the extended SQ-type B-domain linker has two amino acid substitutions relative to the corresponding wild-type sequence. In some embodiments, a glycosylation peptide is inserted into the extended SQ-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a porcine OBI-1-type B-domain linker, including the amino acids SFAQNSR-PPSASAPKPPVLRRHQR (SEQ ID NO: 31) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence. In some embodiments, a glycosylation peptide is inserted into the porcine OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include a human OBI-1-type B-domain linker, including amino acids 760-772/1655-1667 of the wild-type human Factor VIII B-domain (FVIII-FL-AA; SEQ ID NO: 19). In some embodiments, the human OBI-1-type B-domain linker has one amino acid substitution relative to the corresponding wild-type sequence. In some embodiments, the human OBI-1-type B-domain linker has two amino acid substitutions relative to the corresponding wild-type sequence. In some embodiments, a glycosylation peptide is inserted into the human OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

In some embodiments, the encoded Factor VIII polypeptides described herein include an 08-type B-domain linker, including the amino acids SFSQNSRHQAYRYRRG (SEQ ID NO: 32) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence. In some embodiments, a glycosylation peptide is inserted into the porcine OBI-1-type B-domain linker. In some embodiments, the glycosylation peptide is selected from those shown in FIG. 13 (SEQ ID NOS 51, 53, 55, 57, 59, 61, 63, 65, 67, 69, 71, 73, and 75, respectively, in order of appearance).

Figures 14, 15:
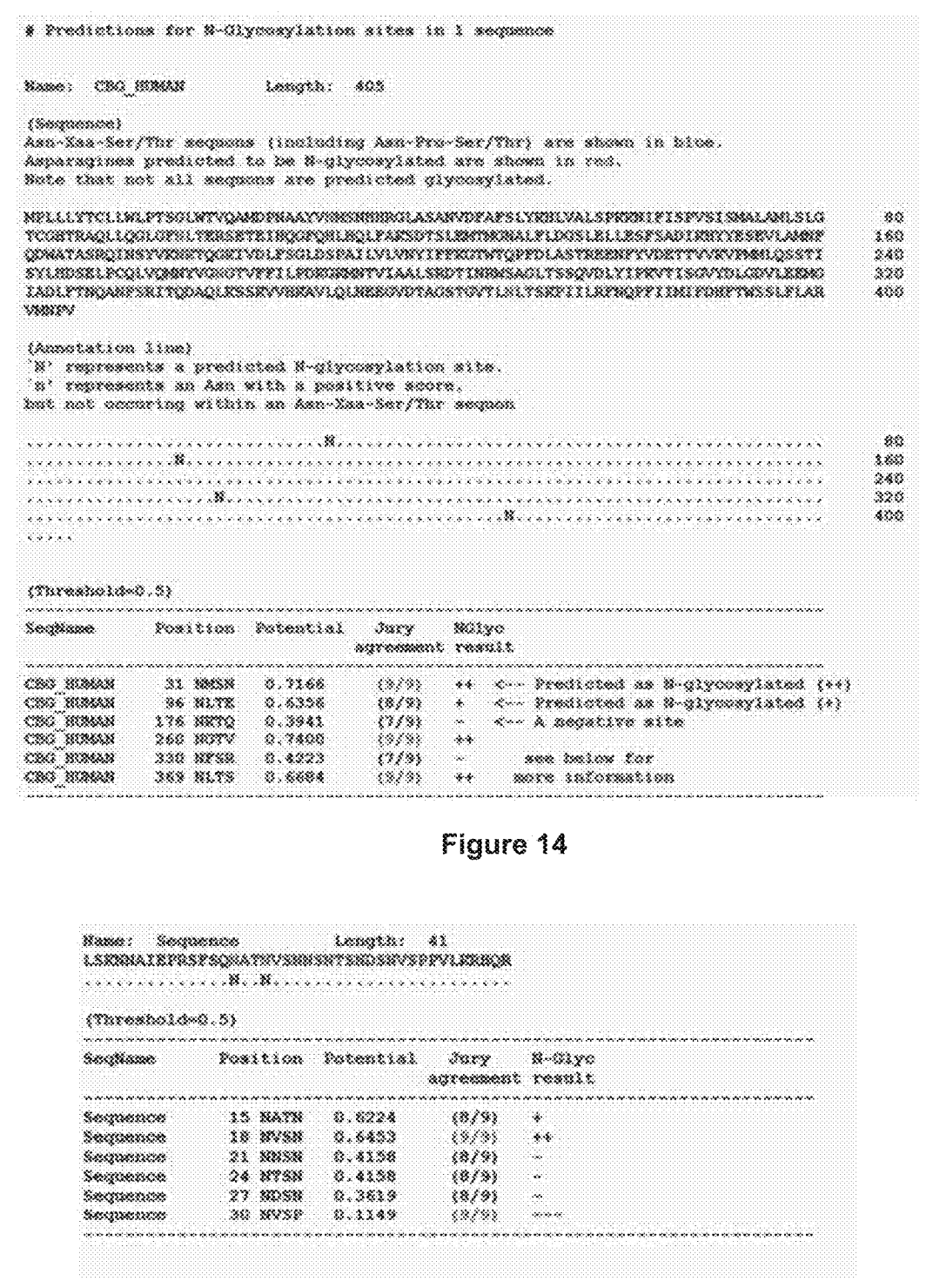

Removal of the B-domain from Factor VIII constructs does not appear to affect the activity of the activated enzyme (e.g., FVIIIa), presumably because the B-domain is removed during activation. However, the B-domain of Factor VIII contains several residues that are post-translationally modified, e.g., by N- or O-linked glycosylation. In silico analysis (Prediction of N-glycosylation sites in human proteins, R. Gupta, E. Jung and S. Brunak, in preparation (2004)) of the wild-type Factor VIII B-domain predicts that at least four of these sites are glycosylated in vivo (FIG. 14). It is thought that these modifications within the B-domain contribute to the post-translational regulation and/or half-life of Factor VIII in vivo.

While the Factor VIII B-domain is absent in mature Factor VIIIa protein, glycosylation within the B-domain of the precursor Factor VIII molecule may increase the circulating half-life of the protein prior to activation. Thus, in some embodiments, the polypeptide linker of the encoded Factor VIII constructs described herein includes one or more glycosylation sequences, to allow for glycosylation in vivo. In some embodiments, the polypeptide linker includes at least one consensus glycosylation sequence (e.g., an N- or O-linked glycosylation consensus sequence). In some embodiments, the polypeptide linker includes at least two consensus glycosylation sequences. In some embodiments, the polypeptide linker includes at least three consensus glycosylation sequences. In some embodiments, the polypeptide linker includes at least four consensus glycosylation sequences. In some embodiments, the polypeptide linker includes at least five consensus glycosylation sequences. In some embodiments, the polypeptide linker includes at least 6, 7, 8, 9, 10, or more consensus glycosylation sequences.

In some embodiments, the polypeptide linker contains at least one N-linked glycosylation sequence N-X-S/T, where X is any amino acid other than P, S, or T. In some embodiments, the polypeptide linker contains at least two N-linked glycosylation sequences N-X-S/T, where X is any amino acid other than P, S, or T. In some embodiments, the polypeptide linker contains at least three N-linked glycosylation sequences N-X-S/T, where X is any amino acid other than P, S, or T. In some embodiments, the polypeptide linker contains at least four N-linked glycosylation sequences N-X-S/T, where X is any amino acid other than P, S, or T. In some embodiments, the polypeptide linker contains at least five N-linked glycosylation sequences N-X-S/T, where X is any amino acid other than P, S, or T. In some embodiments, the polypeptide linker contains at least 6, 7, 8, 9, 10, or more N-linked glycosylation sequences N-X-S/T, where X is any amino acid other than P, S, or T.

In some embodiments, the polypeptide linker includes a glycosylation peptide with high sequence identity to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation polypeptide has at least 92% identity to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has no more than one amino acid substitution relative to any of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide has an amino acid sequence selected from any of SEQ ID NOS 51, 53, 55, 57, 59, 61, 63, 65, 67, 69, 71, 73, and 75, respectively, in order of appearance, as shown in FIGS. 13A-13B.

In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, as shown in FIGS. 13A-13B. In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has at least 92% identity to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 90% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 95% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B. In some embodiments, the glycosylation peptide has a sequence selected from any one of SEQ ID NOS 51, 53, 55, 57, 59, 61, 63, 65, 67, 69, 71, 73, and 75, respectively, in order of appearance, as shown in FIGS. 13A-13B and is encoded by a polynucleotide sequence having at least 98% identity to a corresponding nucleotide sequence selected from SEQ ID NOS 50, 52, 54, 56, 58, 60, 62, 64, 66, 68, 70, 72, and 74, respectively, in order of appearance, as shown in FIGS. 13A-13B.

In some embodiments, the Factor VIII polypeptide encoded by a codon-altered polynucleotide described herein has a B-domain substituted linker in which a glycosylation peptide is inserted into the SQ linker sequence (amino acids 760-773 of CS04-FL-AA; SEQ ID NO: 2). In a specific embodiment, the glycosylation peptide is selected from selected from any one of SEQ ID NOS 51, 53, 55, 57, 59, 61, 63, 65, 67, 69, 71, 73, and 75, respectively, in order of appearance, as shown in FIGS. 13A-13B, a glycosylation peptide having at least 92% identity to any one of SEQ ID NOS 51, 53, 55, 57, 59, 61, 63, 65, 67, 69, 71, 73, and 75, respectively, in order of appearance, as shown in FIGS. 13A-13B, a glycosylation peptide having no more than two amino acid substitutions relative to any one of SEQ ID NOS 51, 53, 55, 57, 59, 61, 63, 65, 67, 69, 71, 73, and 75, respectively, in order of appearance, as shown in FIGS. 13A-13B, and a glycosylation peptide having no more than one amino acid substitution relative to any one of SEQ ID NOS 51, 53, 55, 57, 59, 61, 63, 65, 67, 69, 71, 73, and 75, respectively, in order of appearance, as shown in FIGS. 13A-13B. In some embodiments, the glycosylation peptide is inserted in the SQ peptide between residues N768 and P769 (relative to CS04-FL-AA; SEQ ID NO: 2).

In some embodiments, the polypeptide linker of the Factor VIII construct is encoded by a third nucleotide sequence having high sequence identity to any one of those shown in FIG. 6 (SEQ ID NOS 5-7 and 36-48, respectively, in order of appearance). In some embodiments, the third nucleotide sequence has at least 95% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 96% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 97% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 98% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99.5% identity to any one of those shown in FIG. 13 (SEQ ID NOS 50, 52, 54, 56, 58, 60, 62, 64, 66, 68, 70, 72, and 74, respectively, in order of appearance). In some embodiments, the third nucleotide sequence has at least 99.9% identity to any one of those shown in FIG.

13 (SEQ ID NOS 50, 52, 54, 56, 58, 60, 62, 64, 66, 68, 70, 72, and 74, respectively, in order of appearance). In some embodiments, the third nucleotide sequence is identical to any one of those shown in FIG. 13 (SEQ ID NOS 50, 52, 54, 56, 58, 60, 62, 64, 66, 68, 70, 72, and 74, respectively, in order of appearance).

C. Codon-Altered Polynucleotides Encoding a Factor VIII Variant with a Cleavable Linker CS04 Codon Altered Polynucleotides In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1).

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

In some embodiments, the Factor VIII variant encoded by the CS04 polynucleotide, having high sequence homology to CS04-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS04 polynucleotide comprises an m1 amino acid substitution. In one embodiment, the Factor VIII variant encoded by the CS04 polynucleotide comprises an m2 amino acid substitution. In one embodiment, the Factor VIII variant encoded by the CS04 polynucleotide comprises an m3 amino acid substitution. In one embodiment, the Factor VIII variant encoded by the CS04 polynucleotide comprises an m4 amino acid substitution. In one embodiment, the Factor VIII variant encoded by the CS04 polynucleotide comprises an m5 amino acid substitution.

In one embodiment, the Factor VIII variant encoded by the CS04 polynucleotide comprises m12 amino acid substitutions. In one embodiment, the Factor VIII variant encoded by the CS04 polynucleotide comprises m13 amino acid substitutions. In one embodiment, the Factor VIII variant encoded by the CS04 polynucleotide comprises m23 amino acid substitutions. In one embodiment, the Factor VIII variant encoded by the CS04 polynucleotide comprises m24 amino acid substitutions. In one embodiment, the Factor VIII variant encoded by the CS04 polynucleotide comprises m25 amino acid substitutions. In one embodiment, the Factor VIII variant encoded by the CS04 polynucleotide comprises m34 amino acid substitutions. In one embodiment, the Factor VIII variant encoded by the CS04 polynucleotide comprises m35 amino acid substitutions.

In one embodiment, the Factor VIII variant encoded by the CS04 polynucleotide comprises m123 amino acid substitutions. In one embodiment, the Factor VIII variant encoded by the CS04 polynucleotide comprises m234 amino acid substitutions. In one embodiment, the Factor VIII variant encoded by the CS04 polynucleotide comprises m125 amino acid substitutions.

CS01 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS01-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS01-FL-NA (SEQ ID NO: 13). In some embodiments, the nucleotide sequence has at least 95% identity to CS01-FL-NA (SEQ ID NO: 13). In some embodiments, the nucleotide sequence has at least 96% identity to CS01-FL-NA (SEQ ID NO: 13). In some embodiments, the nucleotide sequence has at least 97% identity to CS01-FL-NA (SEQ ID NO: 13). In some embodiments, the nucleotide sequence has at least 98% identity to CS01-FL-NA (SEQ ID NO: 13). In some embodiments, the nucleotide sequence has at least 99% identity to CS01-FL-NA (SEQ ID NO: 13). In some embodiments, the nucleotide sequence has at least 99.5% identity to CS01-FL-NA (SEQ ID NO: 13). In some embodiments, the nucleotide sequence has at least 99.9% identity to CS01-FL-NA (SEQ ID NO: 13). In some embodiments, the nucleotide sequence is identical to CS01-FL-NA (SEQ ID NO: 13).

In some embodiments, the Factor VIII variant encoded by the codon-altered polynucleotide has an amino acid sequence with high sequence identity to CS01-FL-AA (SEQ ID NO: 2). In some embodiments, the amino acid sequence has at least 97% identity to CS01-FL-AA (SEQ ID NO: 2). In some embodiments, the amino acid sequence has at least 98% identity to CS01-FL-AA (SEQ ID NO: 2). In some embodiments, the amino acid sequence has at least 99% identity to CS01-FL-AA (SEQ ID NO: 2). In some embodiments, the amino acid sequence has at least 99.5% identity to CS01-FL-AA (SEQ ID NO: 2). In some embodiments, the amino acid sequence has at least 99.9% identity to CS01-FL-AA (SEQ ID NO: 2). In some embodiments, the amino acid sequence is identical to CS01-FL-AA (SEQ ID NO: 2).

In some embodiments, the Factor VIII variant encoded by the CS01 polynucleotide, having high sequence homology to CS01-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS01 polynucleotide comprises an m1 amino acid substitution. In one embodiment, the Factor VIII variant encoded by the CS01 polynucleotide comprises an m2 amino acid substitution. In one embodiment, the Factor VIII variant encoded by the CS01 polynucleotide comprises an m3 amino acid substitution. In one embodiment, the Factor VIII variant encoded by the CS01 polynucleotide comprises an m4 amino acid substitution. In one embodiment, the Factor VIII variant encoded by the CS01 polynucleotide comprises an m5 amino acid substitution.

In one embodiment, the Factor VIII variant encoded by the CS01 polynucleotide comprises m12 amino acid substitutions. In one embodiment, the Factor VIII variant encoded by the CS01 polynucleotide comprises m13 amino acid substitutions. In one embodiment, the Factor VIII variant encoded by the CS01 polynucleotide comprises m23 amino acid substitutions. In one embodiment, the Factor VIII variant encoded by the CS01 polynucleotide comprises m24 amino acid substitutions. In one embodiment, the Factor VIII variant encoded by the CS01 polynucleotide comprises m25 amino acid substitutions. In one embodiment, the Factor VIII variant encoded by the CS01 polynucleotide comprises m34 amino acid substitutions. In one embodiment, the Factor VIII variant encoded by the CS01 polynucleotide comprises m35 amino acid substitutions.

In one embodiment, the Factor VIII variant encoded by the CS01 polynucleotide comprises m123 amino acid substitutions. In one embodiment, the Factor VIII variant encoded by the CS01 polynucleotide comprises m234 amino acid substitutions. In one embodiment, the Factor VIII variant encoded by the CS01 polynucleotide comprises m125 amino acid substitutions.

CS23 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS23-FL-AA (SEQ ID NO: 21). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS23-FL-NA (SEQ ID NO: 20). In some embodiments, the nucleotide sequence has at least 95% identity to CS23-FL-NA (SEQ ID NO: 20). In some embodiments, the nucleotide sequence has at least 96% identity to CS23-FL-NA (SEQ ID NO: 20). In some embodiments, the nucleotide sequence has at least 97% identity to CS23-FL-NA (SEQ ID NO: 20). In some embodiments, the nucleotide sequence has at least 98% identity to CS23-FL-NA (SEQ ID NO: 20). In some embodiments, the nucleotide sequence has at least 99% identity to CS23-FL-NA (SEQ ID NO: 20). In some embodiments, the nucleotide sequence has at least 99.5% identity to CS23-FL-NA (SEQ ID NO: 20). In some embodiments, the nucleotide sequence has at least 99.9% identity to CS23-FL-NA (SEQ ID NO: 20). In some embodiments, the nucleotide sequence is identical to CS23-FL-NA (SEQ ID NO: 20).

In some embodiments, the Factor VIII variant encoded by the codon-altered polynucleotide has an amino acid sequence with high sequence identity to CS23-FL-AA (SEQ ID NO: 21). In some embodiments, the amino acid sequence has at least 97% identity to CS23-FL-AA (SEQ ID NO: 21). In some embodiments, the amino acid sequence has at least 98% identity to CS23-FL-AA (SEQ ID NO: 21). In some embodiments, the amino acid sequence has at least 99% identity to CS23-FL-AA (SEQ ID NO: 21). In some embodiments, the amino acid sequence has at least 99.5% identity to CS23-FL-AA (SEQ ID NO: 21). In some embodiments, the amino acid sequence has at least 99.9% identity to CS23-FL-AA (SEQ ID NO: 21). In some embodiments, the amino acid sequence is identical to CS23-FL-AA (SEQ ID NO: 21).

In some embodiments, the Factor VIII variant encoded by the CS23 polynucleotide, having high sequence homology to CS23-FL-AA (e.g., at least 95%, 96%, 97%, 98%, 99%, 99.5%, or 99.9% identity), comprises one or more amino acid substitutions selected from m1, m2, m3, m4, and m5.

In one embodiment, the Factor VIII variant encoded by the CS23 polynucleotide comprises an m1 amino acid substitution. In one embodiment, the Factor VIII variant encoded by the CS23 polynucleotide comprises an m2 amino acid substitution. In one embodiment, the Factor VIII variant encoded by the CS23 polynucleotide comprises an m3 amino acid substitution. In one embodiment, the Factor VIII variant encoded by the CS23 polynucleotide comprises an m4 amino acid substitution. In one embodiment, the Factor VIII variant encoded by the CS23 polynucleotide comprises an m5 amino acid substitution.

In one embodiment, the Factor VIII variant encoded by the CS23 polynucleotide comprises m12 amino acid substitutions. In one embodiment, the Factor VIII variant encoded by the CS23 polynucleotide comprises m13 amino acid substitutions. In one embodiment, the Factor VIII variant encoded by the CS23 polynucleotide comprises m23 amino acid substitutions. In one embodiment, the Factor VIII variant encoded by the CS23 polynucleotide comprises m24 amino acid substitutions. In one embodiment, the Factor VIII variant encoded by the CS23 polynucleotide comprises m25 amino acid substitutions. In one embodiment, the Factor VIII variant encoded by the CS23 polynucleotide comprises m34 amino acid substitutions. In one embodiment, the Factor VIII variant encoded by the CS23 polynucleotide comprises m35 amino acid substitutions.

In one embodiment, the Factor VIII variant encoded by the CS23 polynucleotide comprises m123 amino acid substitutions. In one embodiment, the Factor VIII variant encoded by the CS23 polynucleotide comprises m234 amino acid substitutions. In one embodiment, the Factor VIII variant encoded by the CS23 polynucleotide comprises m125 amino acid substitutions.

D. Codon-Altered Polynucleotides Encoding a Single-Chain Factor VIII Protein

Factor VIII constructs in which the furin cleavage site located at the C-terminal end of the B-domain is removed retain activity as a single chain polypeptide, despite that normal maturation of the Factor VIII molecule cannot occur (Leyte et al. (1991)). Similarly, a B-domain deleted Factor VIII construct with an attenuated furin site (containing an R1664H amino acid substitution) is more biologically active than the corresponding Factor VIII construct with a wild-type furin cleavage site (Siner et al. (2013)). Accordingly, in some embodiments, the codon-altered polynucleotides provided herein include a nucleotide sequence encoding a single-chain Factor VIII variant polypeptide. The single-chain Factor VIII polypeptide includes a Factor VIII light chain, a Factor VIII heavy chain, and a polypeptide linker joining the C-terminus of the heavy chain to the N-terminus of the light chain. The polypeptide linker does not include a furin cleavage site.

Single-Chain CS04 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The optional polypeptide linker does not include a furin cleavage site.

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the codon-altered polynucleotide has a nucleotide sequence with high sequence identity to CS04-SC1-NA (SEQ ID NO: 9). In some embodiments, the nucleotide sequence has at least 95% identity to CS04-SC1-NA (SEQ ID NO: 9). In some embodiments, the nucleotide sequence has at least 96% identity to CS04-SC1-NA (SEQ ID NO: 9). In some embodiments, the nucleotide sequence has at least 97% identity to CS04-SC1-NA (SEQ ID NO: 9). In some embodiments, the nucleotide sequence has at least 98% identity to CS04-SC1-NA (SEQ ID NO: 9). In some embodiments, the nucleotide sequence has at least 99% identity to CS04-SC1-NA (SEQ ID NO: 9). In some embodiments, the nucleotide sequence has at least 99.5% identity to CS04-SC1-NA (SEQ ID NO: 9). In some embodiments, the nucleotide sequence has at least 99.9% identity to CS04-SC1-NA (SEQ ID NO: 9). In some embodiments, the nucleotide sequence is identical to CS04-SC1-NA (SEQ ID NO: 9).

In some embodiments, the codon-altered polynucleotide has a nucleotide sequence with high sequence identity to CS04-SC2-NA (SEQ ID NO: 11). In some embodiments, the nucleotide sequence has at least 95% identity to CS04-SC2-NA (SEQ ID NO: 11). In some embodiments, the nucleotide sequence has at least 96% identity to CS04-SC2-NA (SEQ ID NO: 11). In some embodiments, the nucleotide sequence has at least 97% identity to CS04-SC2-NA (SEQ ID NO: 11). In some embodiments, the nucleotide sequence has at least 98% identity to CS04-SC2-NA (SEQ ID NO: 11). In some embodiments, the nucleotide sequence has at least 99% identity to CS04-SC2-NA (SEQ ID NO: 11). In some embodiments, the nucleotide sequence has at least 99.5% identity to CS04-SC2-NA (SEQ ID NO: 11). In some embodiments, the nucleotide sequence has at least 99.9% identity to CS04-SC2-NA (SEQ ID NO: 11). In some embodiments, the nucleotide sequence is identical to CS04-SC2-NA (SEQ ID NO: 11).

In some embodiments, the single-chain Factor VIII variant encoded by the codon-altered polynucleotide has an amino acid sequence with high sequence identity to CS04-SC1-AA (SEQ ID NO: 10; human Factor VIIIΔ(760-1667) (SPI; HsFVIIIΔ(741-1648), SPE)). In some embodiments, the Factor VIII variant encoded by the codon-altered polynucleotide has an amino acid sequence with high sequence identity to CS04-SC1-AA (SEQ ID NO: 10). In some embodiments, the amino acid sequence has at least 97% identity to CS04-SC1-AA (SEQ ID NO: 10). In some embodiments, the amino acid sequence has at least 98% identity to CS04-SC1-AA (SEQ ID NO: 10). In some embodiments, the amino acid sequence has at least 99% identity to CS04-SC1-AA (SEQ ID NO: 10). In some embodiments, the amino acid sequence has at least 99.5% identity to CS04-SC1-AA (SEQ ID NO: 10). In some embodiments, the amino acid sequence has at least 99.9% identity to CS04-SC1-AA (SEQ ID NO: 10). In some embodiments, the amino acid sequence is identical to CS04-SC1-AA (SEQ ID NO: 10).

In some embodiments, the Factor VIII variant encoded by the CS04-SC1 polynucleotide, having high sequence homology to CS04-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS04-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS04-SC2-AA (SEQ ID NO: 12). In some embodiments, the amino acid sequence has at least 97% identity to CS04-SC2-AA (SEQ ID NO: 12). In some embodiments, the amino acid sequence has at least 98% identity to CS04-SC2-AA (SEQ ID NO: 12). In some embodiments, the amino acid sequence has at least 99% identity to CS04-SC2-AA (SEQ ID NO: 12). In some embodiments, the amino acid sequence has at least 99.5% identity to CS04-SC2-AA (SEQ ID NO: 12). In some embodiments, the amino acid sequence has at least 99.9% identity to CS04-SC2-AA (SEQ ID NO: 12). In some embodiments, the amino acid sequence is identical to CS04-SC2-AA (SEQ ID NO: 12).

In some embodiments, the single-chain Factor VIII variant encoded by the CS04-SC2 polynucleotide, having high sequence homology to CS04-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS04 polynucleotide comprises an m1 amino acid substitution. In one embodiment, the Factor VIII variant encoded by the CS04 polynucleotide comprises an m2 amino acid substitution. In one embodiment, the Factor VIII variant encoded by the CS04 polynucleotide comprises an m3 amino acid substitution. In one embodiment, the Factor VIII variant encoded by the CS04 polynucleotide comprises an m4 amino acid substitution. In one embodiment, the Factor VIII variant encoded by the CS04 polynucleotide comprises an m5 amino acid substitution.

In one embodiment, the single-chain Factor VIII variant encoded by the CS04 polynucleotide comprises m12 amino acid substitutions. In one embodiment, the Factor VIII variant encoded by the CS04 polynucleotide comprises m13 amino acid substitutions. In one embodiment, the Factor VIII variant encoded by the CS04 polynucleotide comprises m23 amino acid substitutions. In one embodiment, the Factor VIII variant encoded by the CS04 polynucleotide comprises m24 amino acid substitutions. In one embodiment, the Factor VIII variant encoded by the CS04 polynucleotide comprises m25 amino acid substitutions. In one embodiment, the Factor VIII variant encoded by the CS04 polynucleotide comprises m34 amino acid substitutions. In one embodiment, the Factor VIII variant encoded by the CS04 polynucleotide comprises m35 amino acid substitutions.

In one embodiment, the single-chain Factor VIII variant encoded by the CS04 polynucleotide comprises m123 amino acid substitutions. In one embodiment, the Factor VIII variant encoded by the CS04 polynucleotide comprises m234 amino acid substitutions. In one embodiment, the Factor VIII variant encoded by the CS04 polynucleotide comprises m125 amino acid substitutions.

Single-Chain CS01 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The optional polypeptide linker does not include a furin cleavage site.

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the codon-altered polynucleotide has a nucleotide sequence with high sequence identity to CS01-SC1-NA (SEQ ID NO: 26). In some embodiments, the nucleotide sequence has at least 95% identity to CS01-SC1-NA (SEQ ID NO: 26). In some embodiments, the nucleotide sequence has at least 96% identity to CS01-SC1-NA (SEQ ID NO: 26). In some embodiments, the nucleotide sequence has at least 97% identity to CS01-SC1-NA (SEQ ID NO: 26). In some embodiments, the nucleotide sequence has at least 98% identity to CS01-SC1-NA (SEQ ID NO: 26). In some embodiments, the nucleotide sequence has at least 99% identity to CS01-SC1-NA (SEQ ID NO: 26). In some embodiments, the nucleotide sequence has at least 99.5% identity to CS01-SC1-NA (SEQ ID NO: 26). In some embodiments, the nucleotide sequence has at least 99.9% identity to CS01-SC1-NA (SEQ ID NO: 26). In some embodiments, the nucleotide sequence is identical to CS01-SC1-NA (SEQ ID NO: 26).

In some embodiments, the codon-altered polynucleotide has a nucleotide sequence with high sequence identity to CS01-SC2-NA (SEQ ID NO: 27). In some embodiments, the nucleotide sequence has at least 95% identity to CS01-SC2-NA (SEQ ID NO: 27). In some embodiments, the nucleotide sequence has at least 96% identity to CS01-SC2-NA (SEQ ID NO: 27). In some embodiments, the nucleotide sequence has at least 97% identity to CS01-SC2-NA (SEQ ID NO: 27). In some embodiments, the nucleotide sequence has at least 98% identity to CS01-SC2-NA (SEQ ID NO: 27). In some embodiments, the nucleotide sequence has at least 99% identity to CS01-SC2-NA (SEQ ID NO: 27). In some embodiments, the nucleotide sequence has at least 99.5% identity to CS01-SC2-NA (SEQ ID NO: 27). In some embodiments, the nucleotide sequence has at least 99.9% identity to CS01-SC2-NA (SEQ ID NO: 27). In some embodiments, the nucleotide sequence is identical to CS01-SC2-NA (SEQ ID NO: 27).

In some embodiments, the single-chain Factor VIII variant encoded by the codon-altered polynucleotide has an amino acid sequence with high sequence identity to CS01-SC1-AA (SEQ ID NO: 10; human Factor VIIIΔ(760-1667) (SPI; HsFVIIIΔ(741-1648), SPE)). In some embodiments, the Factor VIII variant encoded by the codon-altered polynucleotide has an amino acid sequence with high sequence identity to CS01-SC1-AA (SEQ ID NO: 10). In some embodiments, the amino acid sequence has at least 97% identity to CS01-SC1-AA (SEQ ID NO: 10). In some embodiments, the amino acid sequence has at least 98% identity to CS01-SC1-AA (SEQ ID NO: 10). In some embodiments, the amino acid sequence has at least 99% identity to CS01-SC1-AA (SEQ ID NO: 10). In some embodiments, the amino acid sequence has at least 99.5% identity to CS01-SC1-AA (SEQ ID NO: 10). In some embodiments, the amino acid sequence has at least 99.9% identity to CS01-SC1-AA (SEQ ID NO: 10). In some embodiments, the amino acid sequence is identical to CS01-SC1-AA (SEQ ID NO: 10).

In some embodiments, the Factor VIII variant encoded by the CS01-SC1 polynucleotide, having high sequence homology to CS01-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS01-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS01-SC2-AA (SEQ ID NO: 12). In some embodiments, the amino acid sequence has at least 97% identity to CS01-SC2-AA (SEQ ID NO: 12). In some embodiments, the amino acid sequence has at least 98% identity to CS01-SC2-AA (SEQ ID NO: 12). In some embodiments, the amino acid sequence has at least 99% identity to CS01-SC2-AA (SEQ ID NO: 12). In some embodiments, the amino acid sequence has at least 99.5% identity to CS01-SC2-AA (SEQ ID NO: 12). In some embodiments, the amino acid sequence has at least 99.9% identity to CS01-SC2-AA (SEQ ID NO: 12). In some embodiments, the amino acid sequence is identical to CS01-SC2-AA (SEQ ID NO: 12).

In some embodiments, the single-chain Factor VIII variant encoded by the CS01-SC 2 polynucleotide, having high sequence homology to CS01-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS01 polynucleotide comprises an m1 amino acid substitution. In one embodiment, the Factor VIII variant encoded by the CS01 polynucleotide comprises an m2 amino acid substitution. In one embodiment, the Factor VIII variant encoded by the CS01 polynucleotide comprises an m3 amino acid substitution. In one embodiment, the Factor VIII variant encoded by the CS01 polynucleotide comprises an m4 amino acid substitution. In one embodiment, the Factor VIII variant encoded by the CS01 polynucleotide comprises an m5 amino acid substitution.

In one embodiment, the single-chain Factor VIII variant encoded by the CS01 polynucleotide comprises m12 amino acid substitutions. In one embodiment, the Factor VIII variant encoded by the CS01 polynucleotide comprises m13 amino acid substitutions. In one embodiment, the Factor VIII variant encoded by the CS01 polynucleotide comprises m23 amino acid substitutions. In one embodiment, the Factor VIII variant encoded by the CS01 polynucleotide comprises m24 amino acid substitutions. In one embodiment, the Factor VIII variant encoded by the CS01 polynucleotide comprises m25 amino acid substitutions. In one embodiment, the Factor VIII variant encoded by the CS01 polynucleotide comprises m34 amino acid substitutions. In one embodiment, the Factor VIII variant encoded by the CS01 polynucleotide comprises m35 amino acid substitutions.

In one embodiment, the single-chain Factor VIII variant encoded by the CS01 polynucleotide comprises m123 amino acid substitutions. In one embodiment, the Factor VIII variant encoded by the CS01 polynucleotide comprises m234 amino acid substitutions. In one embodiment, the Factor VIII variant encoded by the CS01 polynucleotide comprises m125 amino acid substitutions.

Single-Chain CS23 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The optional polypeptide linker does not include a furin cleavage site.

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the codon-altered polynucleotide has a nucleotide sequence with high sequence identity to CS23-SC1-NA (SEQ ID NO: 28). In some embodiments, the nucleotide sequence has at least 95% identity to CS23-SC1-NA (SEQ ID NO: 28). In some embodiments, the nucleotide sequence has at least 96% identity to CS23-SC1-NA (SEQ ID NO: 28). In some embodiments, the nucleotide sequence has at least 97% identity to CS23-SC1-NA (SEQ ID NO: 28). In some embodiments, the nucleotide sequence has at least 98% identity to CS23-SC1-NA (SEQ ID NO: 28). In some embodiments, the nucleotide sequence has at least 99% identity to CS23-SC1-NA (SEQ ID NO: 28). In some embodiments, the nucleotide sequence has at least 99.5% identity to CS23-SC1-NA (SEQ ID NO: 28). In some embodiments, the nucleotide sequence has at least 99.9% identity to CS23-SC1-NA (SEQ ID NO: 28). In some embodiments, the nucleotide sequence is identical to CS23-SC1-NA (SEQ ID NO: 28).

In some embodiments, the codon-altered polynucleotide has a nucleotide sequence with high sequence identity to CS23-SC2-NA (SEQ ID NO: 29). In some embodiments, the nucleotide sequence has at least 95% identity to CS23-SC2-NA (SEQ ID NO: 29). In some embodiments, the nucleotide sequence has at least 96% identity to CS23-SC2-NA (SEQ ID NO: 29). In some embodiments, the nucleotide sequence has at least 97% identity to CS23-SC2-NA (SEQ ID NO: 29). In some embodiments, the nucleotide sequence has at least 98% identity to CS23-SC2-NA (SEQ ID NO: 29). In some embodiments, the nucleotide sequence has at least 99% identity to CS23-SC2-NA (SEQ ID NO: 29). In some embodiments, the nucleotide sequence has at least 99.5% identity to CS23-SC2-NA (SEQ ID NO: 29). In some embodiments, the nucleotide sequence has at least 99.9% identity to CS23-SC2-NA (SEQ ID NO: 29). In some embodiments, the nucleotide sequence is identical to CS23-SC2-NA (SEQ ID NO: 29).

In some embodiments, the single-chain Factor VIII variant encoded by the codon-altered polynucleotide has an amino acid sequence with high sequence identity to CS23-SC1-AA (SEQ ID NO: 10; human Factor VIIIΔ(760-1667) (SPI; CS04Δ(741-1648), SPE)). In some embodiments, the Factor VIII variant encoded by the codon-altered polynucleotide has an amino acid sequence with high sequence identity to CS23-SC1-AA (SEQ ID NO: 10). In some embodiments, the amino acid sequence has at least 97% identity to CS23-SC1-AA (SEQ ID NO: 10). In some embodiments, the amino acid sequence has at least 98% identity to CS23-SC1-AA (SEQ ID NO: 10). In some embodiments, the amino acid sequence has at least 99% identity to CS23-SC1-AA (SEQ ID NO: 10). In some embodiments, the amino acid sequence has at least 99.5% identity to CS23-SC1-AA (SEQ ID NO: 10). In some embodiments, the amino acid sequence has at least 99.9% identity to CS23-SC1-AA (SEQ ID NO: 10). In some embodiments, the amino acid sequence is identical to CS23-SC1-AA (SEQ ID NO: 10).

In some embodiments, the Factor VIII variant encoded by the CS23-SC1 polynucleotide, having high sequence homology to CS23-SC1-AA (e.g., at least 95%, 96%, 97%, 98%, 99%, 99.5%, or 99.9% identity), comprises one or more amino acid substitutions selected from m1, m2, m3, m4, and m5.

In some embodiments, the single-chain Factor VIII variant encoded by the codon-altered polynucleotide has an amino acid sequence with high sequence identity to CS23-SC2-AA (SEQ ID NO: 12; human Factor VIIIΔ(772-1667) (SPI; HsFVIIIΔ(753-1648), SPE)). In some embodiments, the Factor VIII variant encoded by the codon-altered polynucleotide has an amino acid sequence with high sequence identity to CS23-SC2-AA (SEQ ID NO: 12). In some embodiments, the amino acid sequence has at least 97% identity to CS23-SC2-AA (SEQ ID NO: 12). In some embodiments, the amino acid sequence has at least 98% identity to CS23-SC2-AA (SEQ ID NO: 12). In some embodiments, the amino acid sequence has at least 99% identity to CS23-SC2-AA (SEQ ID NO: 12). In some embodiments, the amino acid sequence has at least 99.5% identity to CS23-SC2-AA (SEQ ID NO: 12). In some embodiments, the amino acid sequence has at least 99.9% identity to CS23-SC2-AA (SEQ ID NO: 12). In some embodiments, the amino acid sequence is identical to CS23-SC2-AA (SEQ ID NO: 12).

In some embodiments, the single-chain Factor VIII variant encoded by the CS23-SC2 polynucleotide, having high sequence homology to CS23-SC2-AA (e.g., at least 95%, 96%, 97%, 98%, 99%, 99.5%, or 99.9% identity), comprises one or more amino acid substitutions selected from m1, m2, m3, m4, and m5.

In one embodiment, the single-chain Factor VIII variant encoded by the CS23 polynucleotide comprises an m1 amino acid substitution. In one embodiment, the Factor VIII variant encoded by the CS23 polynucleotide comprises an m2 amino acid substitution. In one embodiment, the Factor VIII variant encoded by the CS23 polynucleotide comprises an m3 amino acid substitution. In one embodiment, the Factor VIII variant encoded by the CS23 polynucleotide comprises an m4 amino acid substitution. In one embodiment, the Factor VIII variant encoded by the CS23 polynucleotide comprises an m5 amino acid substitution.

In one embodiment, the single-chain Factor VIII variant encoded by the CS23 polynucleotide comprises m12 amino acid substitutions. In one embodiment, the Factor VIII variant encoded by the CS23 polynucleotide comprises m13 amino acid substitutions. In one embodiment, the Factor VIII variant encoded by the CS23 polynucleotide comprises m23 amino acid substitutions. In one embodiment, the Factor VIII variant encoded by the CS23 polynucleotide comprises m24 amino acid substitutions. In one embodiment, the Factor VIII variant encoded by the CS23 polynucleotide comprises m25 amino acid substitutions. In one embodiment, the Factor VIII variant encoded by the CS23 polynucleotide comprises m34 amino acid substitutions. In one embodiment, the Factor VIII variant encoded by the CS23 polynucleotide comprises m35 amino acid substitutions.

In one embodiment, the single-chain Factor VIII variant encoded by the CS23 polynucleotide comprises m123 amino acid substitutions. In one embodiment, the Factor VIII variant encoded by the CS23 polynucleotide comprises m234 amino acid substitutions. In one embodiment, the Factor VIII variant encoded by the CS23 polynucleotide comprises m125 amino acid substitutions.

E. Factor VIII Expression Vectors

In some embodiments, the codon-altered polynucleotides described herein are integrated into expression vectors. Non-limiting examples of expression vectors include viral vectors (e.g., vectors suitable for gene therapy), plasmid vectors, bacteriophage vectors, cosmids, phagemids, artificial chromosomes, and the like.

Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In some embodiments, the codon-altered polynucleotides described herein are integrated into a gene therapy vector. In some embodiments, the gene therapy vector is a retrovirus, and particularly a replication-deficient retrovirus. Protocols for the production of replication-deficient retroviruses are known in the art. For review, see Kriegler, M., Gene Transfer and Expression, A Laboratory Manual, W. H. Freeman Co., New York (1990) and Murry, E. J., Methods in Molecular Biology, Vol. 7, Humana Press, Inc., Cliffton, N.J. (1991).

In one embodiment, the gene therapy vector is an adeno-associated virus (AAV) based gene therapy vector. AAV systems have been described previously and are generally well known in the art (Kelleher and Vos, *Biotechniques*, 17(6):1110-17 (1994); Cotten et al., *Proc Natl Acad Sci USA*, 89(13):6094-98 (1992); Curiel, *Nat Immun*, 13(2-3): 141-64 (1994); Muzyczka, *Curr Top Microbiol Immunol*, 158:97-129 (1992); and Asokan A, et al., Mol. Ther., 20(4): 699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes. In a particular embodiment, the AAV vector is an AAV-8 vector.

In some embodiments, the codon-altered polynucleotides described herein are integrated into a retroviral expression vector. These systems have been described previously, and are generally well known in the art (Mann et al., *Cell*, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science*, 272(5259):263-267, 1996; Zufferey et al., *Nat Biotechnol*, 15(9):871-875, 1997; Blomer et al., *J Virol.*, 71(9):6641-6649, 1997; U.S. Pat. Nos. 6,013,516 and 5,994,136).

A wide variety of vectors can be used for the expression of a Factor VIII polypeptide from a codon-altered polypeptide in cell culture, including eukaryotic and prokaryotic expression vectors. In certain embodiments, a plasmid vector is contemplated for use in expressing a Factor VIII polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor VIII polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

IV. EXAMPLES

Example 1—Construction of a Codon Altered Factor VIII Variant Expression Sequence Two hurdles had to be overcome in order to create a Factor VIII coding sequence that is effective for gene therapy of hemophilia A. First, because of the genomic size limitations of conventional gene therapy delivery vectors (e.g., AAV virions), the encoded Factor VIII polypeptide had to be shortened considerably. Second, the coding sequence had to be altered to: (i) stabilize packaging interactions within the delivery vector, (ii) stabilize the mRNA intermediary, and (iii) improve the robustness of transcription/translation of the mRNA.

To achieve the first objective, Applicants started with a B-domain deleted Factor VIII variant construct, referred to herein as "FVIII-BDD-SQ." In this construct, the B-domain is replaced with a fourteen amino acid sequence referred to as the "SQ" sequence. Recombinant FVIII-BDD-SQ is sold under the trade name REFACTO®, and has been shown to be effective for the management of hemophilia A. However, the native coding sequence for FVIII-BDD-SQ, which includes human wild-type nucleic acid sequences for the Factor VIII heavy and light chains, is ineffectively expressed in gene therapy vectors.

To address the poor expression of the native FVIII-BDD-SQ, the codon optimization algorithm described in Fath et al. (PLoS ONE, 6:e17596 (2011)), modified as described in Ward et al. (Blood, 117:798 (2011)) and in McIntosh et al. (Blood, 121, 3335-3344 (2013)), was applied to the FVIII-BDD-SQ sequence to create first intermediate coding sequence CS04a. However, Applicants recognized that the CS04a sequence created using the modified algorithm could be improved by further modifying the sequence. Accordingly, Applicants re-introduced CpG dinucleotides, re-introduced the CGC codon for arginine, changed the leucine and serine codon distributions, re-introduced highly conserved codon pairs, and removed cryptic TATA box, CCAAT box, and splice site elements, while avoiding CpG islands and local overrepresentation of AT-rich and GC-rich stretches.

First, the modified algorithm systematically replaces codons containing CpG-dinucleotides (e.g., arginine codons) with non-CpG-dinucleotide codons, and eliminates/avoids CpG-dinucleotides created by neighboring codons. This strict avoidance of CpG dinucleotides is usually done to prevent TLR-induced immunity after intramuscular injection of DNA vaccines. However, doing so limits the codon optimization possibilities. For example, the modified algorithm excludes use of the complete set of CGX arginine codons. This is particularly disruptive in the coding of genes for expression in human cells, because CGC is the most frequently used arginine codon in highly expressed human genes. Additionally, avoiding the creation of CpGs by neighboring codons further limits the optimization possibilities (e.g., limits the number of codon pairs that may be used together).

Because TLR-induced immunity is not expected to be a problem associated with liver-directed, AAV-based gene therapy, codons including CpGs, and neighboring codons creating CpGs, were re-introduced into intermediate coding sequence CS04a, preferentially in the sequence coding for the Factor VIII light chain (e.g., at the 3' end of the FVIII-BDD-SQ coding sequence). This allowed for more frequent use of preferred human codons, particularly those for arginine. Care was taken, however, to avoid creation of CpG islands, which are regions of coding sequence having a high frequency of CpG sites. This is contrary to the teachings of Krinner et al. (Nucleic Acids Res., 42(6):3551-64 (201Δ)), which suggests that CpG domains downstream of transcriptional start sites promote high levels of gene expression.

Second, the modified algorithm applies certain codons exclusively, such as CTG for leucine, GTG for valine, and CAG for glutamine. However, this offends the principles of balanced codon use, for example, as proposed in Haas et al. (Current Biology, 6(3):315-24 (1996)). To account for the overuse of preferred codons by the modified algorithm, alternate leucine codons were re-introduced where allowed by the other rules applied to the codon alteration (e.g., CpG frequency and GC content).

Third, the modified algorithm replaces codon pairs without regard to how conserved they are in nature, when certain criteria (e.g., the presence of CG-dinucleotides) are met. To account for beneficial properties which may have been conserved by evolution, the most conserved codon pairs that were replaced by the algorithm and the most conserved preferred codon pairs, e.g., as described in Tats et al. (BMC Genomics 9:463 (2008)), were analyzed and adjusted where allowed by the other rules applied to the codon alteration (e.g., CpG frequency and GC content).

Fourth, serine codons used in the intermediate coding sequence were also re-engineered. Specifically, AGC, TCC, and TCT serine codons were introduced into the modified coding sequence with higher frequency, to better match overall for human codon usage (Haas et al., supra).

Fifth, TATA box, CCAAT box elements, and intron/exon splice sites were screened and removed from the modified coding sequence. When modifying the coding sequence, care was taken to avoid local overrepresentation of AT-rich or GC rich stretches.

Finally, in addition to optimizing the codon usage within the coding sequence, the structural requirements of the underlying AAV virion were considered when further refining the intermediate coding sequence CS04a. AAV vectors (e.g., the nucleic acid portion of an AAV virion) are packaged as single stranded DNA molecules into their capsids (for review, see, Daya and Berns, Clin. Microbiol Rev., 21(4):583-93 (2008)). The GC content of the vector is therefore likely to influence packaging of the genome and, thus, vector yields during production. Like many algorithms, the modified algorithm used here creates an optimized gene sequence with a GC content of at least 60% (see, Fath et al., PLoS One, 6(3):e17596 (2011) (erratum in: PLoS One, (6)3 (2011)). However, the AAV8 capsid protein is encoded by a nucleotide sequence having a lower GC content of about 56%. Thus, to better mimic the native AAV8 capsid protein coding sequence, the GC content of the intermediate coding sequence CS04a was reduced to 56%.

The resulting CS04 coding sequence, shown in FIG. 2, has an overall GC content of 56%. The CpG-dinucleotide content of the sequence is moderate. However, CpG dinucleotides are predominantly present in the downstream portion of the coding sequence, e.g., the portion coding for the Factor VIII light chain. The CS04 sequence has 79.77% nucleotide sequence identity to the corresponding coding sequences in wild-type Factor VIII (Genbank accession M14113).

For comparison purposes, several other codon-optimized, ReFacto constructs were prepared. CS01 was constructed by applying the codon-optimization algorithm of Fath et al., as modified by Ward et al., as done for CS04. However, unlike CS04, the CS01 construct does not contain any CpG islands. The CS08 ReFacto construct was codon-optimized as described in Radcliff P. M. et al., Gene Therapy, 15:289-97 (2008), the content of which is hereby expressly incorporated by reference herein, in its entirety, for all purposes. The CS10 codon-optimized ReFacto construct was obtained from Eurofins Genomics (Ebersberg, Germany). The CS11 codon-optimized ReFacto construct was obtained from Integrated DNA Technologies, Inc. (Coralville, USA). The CH25 codon-optimized ReFacto construct was obtained from ThermoFischer Scientific's GeneArt services (Regensburg, Germany). The CS40 ReFacto construct consists of the wild type Factor VIII coding sequence. The algorithm used to construct CS23 is based on the JCAT tool (www.jcat.de), an on-line tool for codon-optimizations (Grote et al., 2005; Nucl. Acids Res. W526-31). The sequence was further modified to more reflect the codon usage of the albumin superfamily (Mirsafian et al. 2014: Sc. Word Journal 2014, ID 639682). The sequence identities shared between each of the ReFacto coding sequences is shown in Table 2, below.

Figure 23:
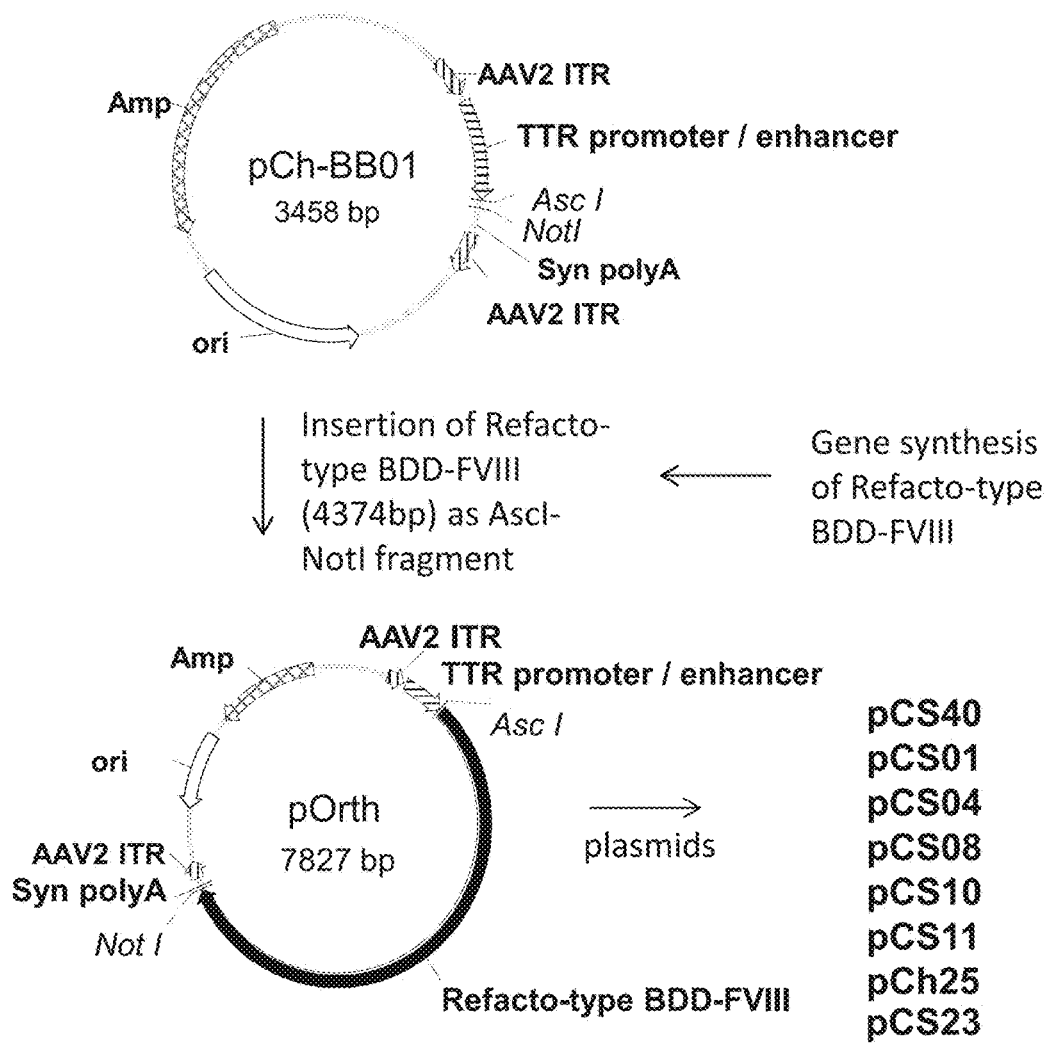
FIG. 23 illustrates the scheme for cloning the pCS40, pCS01, pCS04, pCS08, pCS10, pCS11, and pCh25 constructs, by inserting synthetic Refacto-type BDD-FVIII DNA sequences into the vector backbone pCh-BB01 via AscI and NotI restriction sites.

Plasmids of each construct were constructed by cloning different synthetic DNA fragments into the same vector backbone plasmid (pCh-BB01). DNA synthesis of the Refacto-type BDD-FVIII fragments with flanking Ascl and Notl enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, Ascl and Notl enzyme restriction sites for insertion of the respective Refacto-type BDD-FVIII and a synthetic polyA site. After ligation of the prepared vector backbone and inserts via the Ascl and Notl sites, the resulting plasmids were amplified in milligram scale. The Refacto-type BDD-FVIII sequences of the constructs were verified by direct sequencing (Microsynth, Balgach, Switzerland). The cloning resulted in seven different plasmid constructs named pCS40, pCS01, pCS04, pCS08, pCS10, pCS11, and pCh25 (FIG. 23). The constructs have the same vector backbone and encode the same B-domain deleted FVIII protein (Refacto-type BDD-FVIII), but differ in their FVIII coding sequence.

AAV8-based vectors were prepared by the three plasmid transfection method, as described in Grieger J C, et al. (Virus Vectors Using Suspension HEK293 Cells and Continuous Harvest of Vector From the Culture Media for GMP FIX and FLT1 Clinical Vector, Mol Ther., October 6. (2015) doi: 10.1038/mt.2015.187. [Epub ahead of print]), the content of which is hereby expressly incorporated by reference herein, in its entirety, for all purposes. HEK293 suspensions cells were used for plasmid transfections using the corresponding FVIII vector plasmid, the helper plasmid pXX6-80 (carrying adenoviral helper genes), and the packaging plasmid pGSK2/8 (contributing the rep2 and cap8 genes). To isolate the AAV8 constructs, the cell pellets of one liter cultures were processed using iodixanol gradients, as described in Grieger et al. (2015, Supra). The procedure resulted in vector preparations called vCS01, vCS04, vCS08, vCS10, vCS11, and vCH25. Vectors were quantified by qPCR using the universal qPCR procedure targeting the AAV2 inverted terminal repeats (Aurnhammer, Human Gene Therapy Methods: Part B 23:18-28 (2012)). A control vector plasmid carrying AAV2 inverted terminal repeats served for preparing the standard curve. The resulting vCS04 construct is presented as SEQ ID NO: 8 in FIGS. 7A-7C.

The integrity of the vector genomes was analyzed by AAV agarose gel electrophoresis. The electrophoresis was performed as described in Fagone et al., Human Gene Therapy Methods 23:1-7 (2012). Briefly, AAV vector preparations were incubated at 75° C. for 10 minutes in the presence of 0.5% SDS and then cooled down to room temperature. Approximately 1.5E10 vector genomes (vg) were loaded per

TABLE 2

Percent identity matrix for codon-altered Factor VIII constructs.

Figure 24:
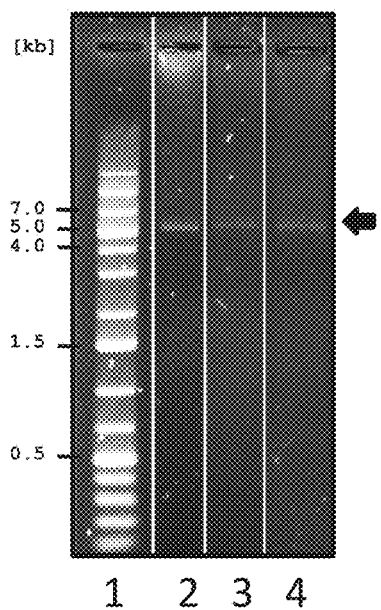
FIG. 24 shows the integrity of AAV vector genome preparations, as analyzed by agarose gel electrophoresis. Lane 1, DNA marker; lane 2, vCS40; lane 3, vCS01; lane 4, vCS04. The AAV vectors have all the same-sized genomes, migrating at approximately 5 kb (arrow, right side). The scale on the left side indicates size of the DNA fragments in kilobases (kb).

|  | CS01 | CS04 | CS08 | CS10 | CS11 | CS40 | CH25 | CS23 |
| --- | --- | --- | --- | --- | --- | --- | --- | --- |
| CS01 | 100% | | | | | | | |
| CS04 | 93.0% | 100% | | | | | | |
| CS08 | 80.7% | 82.2.% | 100% | | | | | |
| CS10 | 79.1% | 79.4% | 78.4% | 100% | | | | |
| CS11 | 78.3% | 78.3% | 78.1% | 77.5% | 100% | | | |
| CS40 | 79.6% | 79.8% | 76.7% | 77.6% | 75.4% | 100% | | |
| CH25 | 81.3% | 85.1% | 85.0% | 79.9% | 79.4% | 75.8% | 100% | |
| CS23 | 84.3% | 89.2% | 85.1% | 80.3% | 79.9 | 76.5% | 93.2% | 100% | lane on a 1% 1×TAE agarose gel and electrophoresed for 60 min at 7 V/cm of gel length. The gel was then stained in 2x GelRed (Biotium Cat#41003) solution and imaged by ChemiDocTMMP (Biorad). The results shown in FIG. 24 demonstrate that the vCS01, vCS04, and vCS40 viral vectors have the same-sized genome, indicated by a distinct band in the 5 kb range (FIG. 24, lanes 2-4). Despite a vector size of approx. 5.2 kb, the genome is a homogenous band confirming correct packaging of the somewhat oversized genome (relative to an AAV wild-type genome of 4.7 kb). All other vCS vector preparations show the same genomic size (data not shown).

Figure 25:
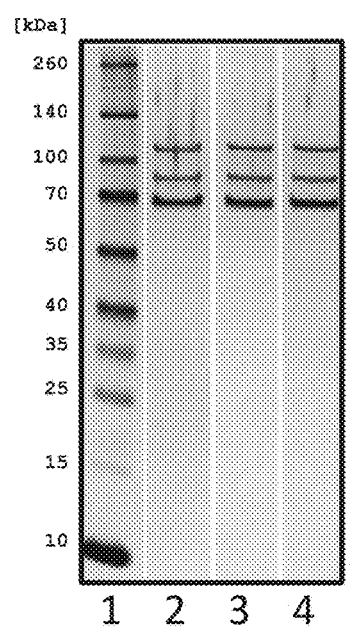
FIG. 25 shows the protein analysis of AAV vector preparations by PAGE and silver staining. Lane 1, protein marker (M); lane 2, vCS40, lane 3, vCS01; and lane 4, vCS04. The constructs all have the same AAV8 capsids consisting of VP1, VP2, and VP3 (arrows right side). The scale on the left side indicates size of the protein marker in kilodaltons (kDa).

In order to confirm the expected pattern of capsid proteins, SDS PAGE followed by silver staining was performed with the vectors vCS01, vCS04, and vCS40 (FIG. 25). As shown in the figure, the downstream purification procedure resulted in highly purified material displaying the expected protein pattern of VP1, VP2 and VP3 (FIG. 25, lanes 2-4). The same pattern was seen with all other viral preparations (not shown). The SDS-PAGE procedure of AAV preparations was done according to standard procedures. Each lane contained 1E10 vg of the respective viral construct, and were separated on a 4-12% Bis-Tris (NuPAGE® Novex, Life Technologies) gel as per manufacturer's instructions. Silver staining was performed with a SilverQuest™ (Novex, Life Technologies) according to the manufacturer's instructions.

Surprisingly, AAV vectors vCS01 and vCS04 had higher virion packaging, measured by higher yields in AAV virus production, as compared to the vCS40 wild-type coding construct and the other codon-optimized constructs. As shown in Table 3, the vCS01 and vCS04 vectors replicated substantially better than vCS40, providing a 5-7 fold yield increase in AAV titer.

TABLE 3

Yields per liter cell culture obtained with AAV vector constructs vCS01, vCS04, and vCD40, as purified from cell pellets.

| Construct | Vector concentration [vg/ml] ×10E12 | Yields [vg/liter] ×10E12 | Fold increase vs wt |
|---|---|---|---|
| vCS40 | 2.0 | 11.0 | — |
| vCS01 | 9.2 | 51.4 | 4.7 |
| vCS04 - Sample 1 | 17.6 | 79.2 | 7.2 |
| vCS04 - Sample 2 | 15.9 | 58.8 | 5.4 |

Example 2—In Vivo Expression of Codon Altered Factor VIII Variant Expression Sequences To test the biological potency of the codon-altered Factor VIII variant sequences, the ReFacto-type FVIII constructs described in Example 1 were administered to mice lacking Factor VIII. Briefly, the assays were performed in C57B1/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. Expression levels at day 14 were chosen because there is minimal influence of inhibitory antibodies at this time, which are seen in some animals of this mouse model at later times. FVIII activity in the mouse plasma was determined using the Technochrome FVIII assay performed, with only minor modifications, as suggested by the manufacture (Technoclone, Vienna, Austria). For the assay, the plasma samples were appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results, presented in Table 4 below, demonstrate that the codon-altered sequences designed using commercial algorithms (CS10, CS11, and CH25) provided only a modest increase in BDD-Factor VIII (3-4 fold) as compared to the wild-type BDD-Factor VIII construct (CS40). Similarly, the codon-altered BDD-Factor VIII construct prepared as described in Radcliffe et al. (C508), only provided a 3-4 fold increase in BDD-FVIII expression. This result is consistent with the results reported in Radcliff et al. Surprisingly, the CS01, CS04, and CS23 constructs provided much higher BDD-FVIII expression in the in-vivo biopotency assays (18-, 74-, and -30-fold increases, respectively).

TABLE 4

Expression of FVIII in the plasma of FVIII-knock-out mice induced by the different AAV vector constructs.

| Construct | Codon Algorithm | Average FVIII Expression at Day 14 [IU/ml] | Standard deviation | Number of mice | Fold increase vs wt |
|---|---|---|---|---|---|
| vCS40 | Human wild-type | 0.03 | 0.03 | 12 | — |
| vCS01 | Applicants' | 0.55 | 0.28 | 22 | 18.3 |
| vCS04 | Applicants' | 2.21 | 1.20 | 55 | 73.7 |
| vCS08 | Radcliffe et al. | 0.11 | 0.01 | 6 | 3.6 |
| vCS10 | Eurofins | 0.09 | 0.01 | 7 | 3.0 |
| vCS11 | IDT | 0.08 | 0.02 | 8 | 2.7 |
| vCH25 | GeneArt | 0.13 | 0.12 | 18 | 4.3 |
| vCS23 | Applicants' | 0.91 | 0.32 | 5 | 30.3 |

Example 3—Design of Glycosylation Peptides for the B-domain Substituted Linker

Others have shown that inclusion of a small peptide (the "V3 peptide") containing six putative N-linked glycosylation sites from the wild-type Factor VIII B-domain, into a B-domain deleted gene therapy construct, increased Factor VIII levels in the plasma of mice (McIntosh et al., Blood 121(17):3335-44 (2013)). However, in order to maintain the small size of the B-domain substituted linker, the glycosylation sites were taken out of the context of the wild-type B-domain. In silico prediction (Gupta et al., Supra) of the linker containing the V3 peptide suggests that only two of these glycosylation sites in the V3 peptide will be modified in vivo (FIG. 15).

Thus, Applicants attempted to identify alternative glycosylation peptides that would support higher levels of glycosylation in vivo, which matched wild type glycosylation more closely than the V3 peptide. Applicants designed and tested several alternative glycosylation peptides, in silico. Several of these peptides, shown in FIGS. 13A-13B, were predicted to have equal or greater glycosylation in vivo than the V3 peptide, when placed between amino acids N768 and P769 of the B-domain substituted linker in SEQ ID NO:2. The results of the in silico predictions are shown in Table 5, below. Table 5 also reports the results of expression experiments performed for several constructs encoding a ReFacto-type Factor VIII protein with a glycosylation peptide incorporated into the B-domain substituted linker, in a CS01 codon-optimized background.

TABLE 5

Prediction of N-glycosylation in B-domain substituted linker peptides and performance of AAV vector constructs in vivo.

| Sequence | Number of Predicted N-glycosylation sites | Day 28 expression [IU/ml] | SD | Number of mice [n] | Fold expression |
|---|---|---|---|---|---|
| vCS01 | 0 | 0.74 | 0.52 | 5 | 21 |
| vNG1/CS01 | 4 | n.d. | — | — | — |
| vNG4/CS01 | 3 | 1.93 | 0.57 | 6 | 55 |
| vNG5/CS01 | 2 | n.d. | — | — | — |
| vNG6/CS01 | 1 | 0.80 | 0.67 | 5 | 23 |
| vNG9/CS01 | 1 | n.d. | — | — | — |
| vNG10/CS01 | 2 | 2.66 | 0.52 | 6 | 76 |
| vNG16/CS01 | 2 | 1.59 | 0.57 | 6 | 45 |
| vNG17/CS01 | 2 | n.d. | — | — | — |
| vNG18/CS01 | 2 | n.d. | — | — | — |
| vNG19/CS01 | 2 | 0.88 | 0.25 | 5 | 25 |
| vNG20/CS01 | 2 | n.d. | — | — | — |
| vNG21/CS01 | 2 | n.d. | — | — | — |
| vCS40 | 0 | 0.035 | 0.030 | 12 | 1 |

AAV vectors containing the NG variants were constructed as described in Example 1 and tested in FVIII knock-out mice as described in Example 2. All virus vectors (except the control vector vCS40) shown in Table 5 are based on the algorithm as used in vCS01. A parallel set of constructs using the algorithm of vCS04 was also prepared (vNG/CS04 series) and is tested in the mouse model. Results were compared to the expression levels achieved with the wild-type vCS40 construct. The day 28 expression levels were chosen in this example, because expression levels of the majority of construct reached the highest levels at this time point. Three AAV vectors achieved greater than 40-fold FVIII expression levels including vNG4/CS01, vNG10/CS01 and vNG16/CS01 (Table 5). The corrresponding constructs vNG4/CS04, vNG10/CS04 and vNG16/CS04 are expected to show even higher expression because they are based on the superior vCS04 algorithm.

Surprisingly, the AAV vectors of the vNG/CS01 series had higher virion packaging, measured by higher yields in AAV virus production, as compared to the vCS40 wild-type coding construct. As shown in Table 6, the vNG/CS01-based vectors replicated substantially better than vCS40, providing an approximately 3-fold yield increase in AAV titer.

TABLE 6

Yields per liter cell culture obtained with AAV vector constructs as purified from cell pellets.

| Sequence | Vector conc. [vg/ml] ×10$^{12}$ | Yields [vg/liter] ×10$^{12}$ | Fold increase vs wild-type |
|---|---|---|---|
| vCS01 | 9.17 | 51.35 | 4.7 |
| vNG1/CS01 | 2.13 | 17.04 | 1.5 |
| vNG4/CS01 | 5.74 | 33.01 | 3.0 |
| vNG5/CS01 | 6.91 | 27.29 | 2.5 |
| vNG6/CS01 | 7.01 | 40.66 | 3.7 |
| vNG9/CS01 | 6.39 | 29.39 | 2.7 |
| vNG10/CS01 | 8.57 | 37.71 | 3.4 |
| vNG16/CS01 | 5.3 | 28.36 | 2.6 |

TABLE 6-continued

Yields per liter cell culture obtained with AAV vector constructs as purified from cell pellets.

| Sequence | Vector conc. [vg/ml] ×10$^{12}$ | Yields [vg/liter] ×10$^{12}$ | Fold increase vs wild-type |
|---|---|---|---|
| vNG17/CS01 | 4.24 | 32.22 | 2.9 |
| vNG18/CS01 | 6.11 | 37.88 | 3.4 |
| vNG19/CS01 | 9.42 | 39.56 | 3.6 |
| vNG20/CS01 | 4.09 | 30.27 | 2.8 |
| vNG21/CS01 | n.d | — | — |
| vCS40 | 2.03 | 11 | 1.0 |

Example 4—Construction of Mutant BDD-FVIII Constructs

Numerous different mutated Refacto-type BDD-FVIII constructs, carrying amino acid mutations within the Factor VIII heavy chain and/or B-domain substituted linker, were cloned and screened. The corresponding vectors, as referred to herein as the "vCS" series of vectors, encode BDD-FVIII variants in the CS01, CS04, and CS23 codon-altered backgrounds. The method used to construct the CS01 and CS04 backgrounds is described in Example 1. The method used to construct CS23 was based on the JCAT tool (www.jcat.de), an on-line tool for codon-optimizations (Grote et al., 2005; Nucl. Acids Res. W526-31). The sequence was further modified to better reflect the codon usage of the albumin superfamily (Mirsafian et al., Sc. Word Journal, ID 639682 (201Δ)), the content of which is hereby expressly incorporated by reference, in its entirety, for all purposes.

Combinations of three types of mutations were included in the FVIII sequences of the vCS series of constructs. The first amino acid change introduced into the FVIII sequence is the X1 mutation (TTYVNRSL (SEQ ID NO: 33); X. Xiao), which introduces an additional glycosylation site near the B-domain substituted linker. The X1 mutation is also referred to herein as the "m3" mutation. The second amino acid change made in the FVIII sequence includes the F328S (SPI, F309S SPE) mutation, an amino acid change known to improve secretion of FVIII (Swaaroop, J. Biol. Chem., 272:24121-24 (1997)). This mutation is also referred to herein as the "m1" mutation. The third change is the so-called X5 mutation, which is a combination of five amino acid changes in the A1 domain of the heavy chain that improves specific activity and secretion of BDD-FVIII (Cao et al., 2014; ASGCT abstract #460; details of mutations disclosed in oral presentation). The X5 mutation is also referred to herein as the "m2" mutation. Next, combinations of X1 and F328S (SPI, F309S SPE) were made, followed by combinations of X1 and X5, also referred to as "X6," and yet other combinations of X5 and F328S (SPI, F309S SPE) were made (Table 7).

Gene Synthesis and Cloning of the Vector Plasmids.

The plasmids were constructed by cloning different synthetic DNA fragments into the same vector backbone plasmid (pCh-BB01). DNA synthesis of the Refacto-type BDD-FVIII fragments with flanking AscI and NotI enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, AscI and NotI enzyme restriction sites for insertion of the respective Refacto-type BDD-FVIII, and a synthetic polyA site. After ligation of the prepared vector backbone and insertions via the AscI and NotI sites, the resulting plasmids were amplified in milligram scale. The Refacto-type BDD-FVIII sequences of the constructs were verified by direct sequencing (Microsynth, Balgach, Switzerland). The cloning resulted in different plasmid constructs, as shown in FIG. 44.

Small Scale Vector Preparations and Quantification by Quantitative PCR (qPCR).

AAV8-based vectors were prepared by the three plasmid transfection method essentially as described in Grieger et al. (2015, Supra). HEK293 suspensions cells were used for plasmid transfections using the corresponding FVIII vector plasmid, the helper plasmid pXX6X80 (carrying adenoviral helper genes) and the packaging plasmid pGSK2/8 (contributing the rep2 and cap8 genes). In the downstream process the cell pellet of a one liter culture was processed using iodixanol gradients as described above. The procedure resulted in vector preparations as outlined in Table 8. Vectors were quantified by qPCR using the universal qPCR procedure targeting the AAV2 inverted terminal repeats (Aurnhammer, HUMAN GENE THERAPY METHODS: Part B 23:18-28 (2012)). An accurately quantified vector plasmid carrying AAV2 Inverted terminal repeats served for preparing the standard curve.

AAV Vector Characterizations.

The integrity of the vector genome was analyzed by AAV agarose gel electrophoresis. The electrophoresis was done similar as described in Fagone et al. (Human Gene Therapy Methods, 23:1-7 (2012)). AAV vector preparations were incubated at 75° C. for 10 minutes in the presence of 0.5% SDS and then cooled down to room temperature. Approximately 1.5E10 vector genomes (vg) were loaded per lane on a 1% 1×TAE agarose gel and electrophoresed for 60 min at 7 V/cm of gel length. The gel was then stained in 2× GelRed (Biotium Cat#41003) solution and imaged by ChemiDoc™ MP (Biorad). The results of a selection of vectors are shown in FIG. 45. The viral vectors vCS04 (control), vCS17, vCS20, vCS24, vCS16 and vCS40 (control) show all the same-sized genome as a distinct band in the 5 kb range (FIG. 45, lanes 2-7; arrow right side). Despite a vector size of approx. 5.2 kb, the genome is a homogenous band confirming correct packaging of the somewhat oversized genome (relative to an AAV wild-type genome of 4.7 kb).

In order to confirm purity of the vector and the expected pattern of capsid proteins, SDS PAGE followed by silver staining was performed with the vectors, as shown in FIG. 46. As shown in the figure, the downstream purification procedure resulted in highly purified material displaying the expected protein pattern of VP1, VP2 and VP3 (FIG. 46 lanes 2-9; arrows right hand side). The SDS-PAGE procedure of AAV preparations was done according to standard procedures. The amounts of 1E10 vg per lane were separated on a 4-12% Bis-Tris (NuPAGE® Novex, Life Technologies) gel as per manufacturer's instructions. Silver staining was performed with a SilverQuest™ kit (Novex, Life Technologies) according to the instructions of the manufacturer.

In-Vivo Biopotency Screening of Vectors.

The different Refacto-type BDD-FVIII constructs were screened in mice. The assay was performed in C57Bl/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. FVIII activity in mouse plasma was determined with a chromogenic assay from Technoclone with minor modifications (Technochrome FVIII, Technoclone, Vienna, Austria). In brief, the plasma sample was appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results of the mouse biopotency assay (day 14 expression data of FVIII in international units per milliliter [IU/ml] in mouse plasma and fold expression compared to the wild-type vCS40 control) are shown in Table 7. AAV vectors vCS19, vCS26 and vCS32 all contain the X1 glycosylation site in the CS01, CS04, and CS23 codon-altered backgrounds, respectively. As seen in Table 7, surprisingly high expression levels were obtained, as compared to the wild-type construct vCS40 (level defined as 1). vCS26, for instance, expressed 202-fold higher levels compared to the wild-type vCS40 vector. Another control construct for the X1-series of vectors, vCH111, that contains the X1 mutation in the Geneart codon context, showed a more modest increase in expression (12-fold).

Vectors vCS16, vCS28, and vCS34 all contain the F328S (SPI, F309S SPE) mutation enhancing secretion in the CS01, CS04, and CS23 codon-altered backgrounds, respectively. As seen in Table 7, high expression levels (45-93-fold higher than the wt vCS40 control) were obtained with vCS16 and vCS28.

Vectors vCS20, vCS24, and vCS33 contain the X5 mutation in the CS01, CS04, and CS23 codon-altered backgrounds, respectively. The best performing variant in the X5 series was vCS20, achieving levels of >3 units/ml after day 14 and a 121-fold increase over the wt vCS40 control.

Vectors vCS17, vCS29, and vCS31 contain the combination of the X1 and F328S (SPI, F309S SPE) mutations in the CS01, CS04, and CS23 codon-altered backgrounds, respectively (Table 6). The vCS17 and vCS29 constructs achieved very high expression levels in the mouse studies (115 to 246-fold increase over the vCS40 control). Remarkably, in the FVIII KO mouse model used, the majority of mice treated with the vCS17 construct did not develop neutralizing antibodies over time, evidenced by increasing levels of FVIII at later time points (e.g., day 28 and day 42; data not shown). This is an unexpected finding, because in some other constructs the expression levels began to decrease with time due to the formation of neutralizing antibodies. The CS01 background combined with the secretion-enhancing mutations F328S (SPI, F309S SPE) and X1 resulted in low immunogenicity induction.

Vectors vCS18, vCS27, and vCS35 contain the combination of the X1 and X5 mutations in the CS01, CS04, and CS23 codon-altered backgrounds, respectively. The combination of these two mutations was also very efficient. A 145-fold increase over the vCS40 control could be achieved with vCS18, for example (Table 7).

Vectors vCS48 and vCS49 contain the combination of the X5 and F328S (SPI, F309S SPE) mutations in the CS01 and CS04 codon-altered backgrounds, respectively. The combination of these two mutations was also very efficient. One of the largest increases of all mutants, a 239-fold increase over the vCS40 control, could be achieved with vCS49 confirming the special value of the combinations including the F328S (SPI, F309S SPE) mutation.

A further surprising observation was that the mutant AAV vectors grew substantially better than the vCS40 construct harboring the wild-type BDD-FVIII codons. Sequence optimization resulted in a several-fold yield increase in vector production. In some of the best expressing constructs (e.g., vCS29, vCS17, vCS20, and vCS26) the increase in yields due to codon-alteration and/or mutant sequence was approximately 3-5-fold higher, as compared to the wild-type vector (Table 8).

Expression of BDD-FVIII in the plasma of FVIII-knockout mice induced by the different AAV vector constructs is shown in Table 7. The constructs have the same vector backbone, however, encode different types of mutated FVIII, including different codon optimization backgrounds. Expression levels at day 14 were chosen because at this time point there is minimal influence of inhibitory antibodies usually seen in some animals in the mouse model at later times. N.d., not determined.

TABLE 7

In vivo biopotency data of vCS constructs.

| # | Vector | Algorithm, mutations | Day 14 expression [IU/ml] | SD | Number of mice [n] | Fold expression |
|---|---|---|---|---|---|---|
| 1 | vCS19 | CS01, X1 | 2.34 | 1.10 | 13 | 78 |
| 2 | vCS26 | CS04, X1 | 6.07 | 2.72 | 12 | 202 |
| 3 | vCS32 | CS23, X1 | n.d. | — | — | — |
| 4 | vCS16 | CS01, F328S | 1.35 | 0.88 | 6 | 45 |
| 5 | vCS28 | CS04, F328S | 2.78 | 0.92 | 7 | 93 |
| 6 | vCS34 | CS23, F328S | n.d. | — | — | — |
| 7 | vCS20 | CS01, X5 | 3.62 | 1.96 | 21 | 121 |
| 8 | vCS24 | CS04, X5 | 0.79 | 0.89 | 18 | 26 |
| 9 | vCS33 | CS23, X5 | n.d. | — | — | n.d. |
| 10 | vCS17 | CS01, X1, F328S | 3.44 | 1.92 | 20 | 115 |
| 11 | vCS29 | CS04, X1, F328S | 7.39 | 2.64 | 9 | 246 |
| 12 | vCS31 | CS23, X1, F328S | n.d. | — | — | n.d. |
| 13 | vCS18 | CS01, X1 + X5(X6) | 4.34 | 2.50 | 6 | 145 |
| 14 | vCS27 | CS04, X1 + X5(X6) | 8.03 | 3.97- | 6- | 268- |
| 15 | vCS35 | CS23, X1 + X5(X6) | n.d. | — | — | — |
| 19 | vCS48 | CS01, X5, F328S | 2.54 | 0.72 | 8 | 85 |
| 20 | vCS49 | CS04, X5, F328S | 7.17 | 1.30 | 7 | 239 |
| controls | | | | | | |
| 16 | vCS40 | Human wild-type | 0.03 | 0.03 | 12 | 1 |
| 17 | vCh25 | Geneart | 0.13 | 0.12 | 18 | 4 |
| 18 | vCh111 | Geneart + X1 | 0.37 | 0.21 | 17 | 12 |

TABLE 8

Yields per liter cell culture (packaging efficiency) obtained with the different AAV vector constructs. The vectors were purified out of the cell pellets;

| | construct | Algorithm, mutations | Vector conc. [vg/ml] ×$10^{12}$ | Yields [vg/liter] ×$10^{12}$ | Fold increase vs wt |
|---|---|---|---|---|---|
| 1 | vCS19 | CS01, X1 | 9.71 | 36 | 3.22 |
| 2 | vCS26 | CS04, X1 | 5.93 | 32 | 2.87 |
| 3 | vCS32 | CS23, X1 | n.d. | n.d. | n.d. |
| 4 | vCS16 | CS01, F328S | 6.51 | 29 | 2.56 |
| 5 | vCS28 | CS04, F328S | 5.85 | 32 | 2.88 |
| 6 | vCS34 | CS23, F328S | n.d. | n.d. | n.d. |
| 7 | vCS20 | CS01, X5 | 9.90 | 50 | 4.48 |
| 8 | vCS24 | CS04, X5 | 3.00 | 16 | 1.46 |
| 9 | vCS33 | CS23, X5 | n.d. | n.d. | n.d. |
| 10 | vCS17 | CS01, X1, F328S | 8.94 | 37 | 3.34 |
| 11 | vCS29 | CS04, X1, F328S | 7.42 | 53 | 4.72 |
| 12 | vCS31 | CS23, X1, F328S | n.d. | n.d. | n.d. |
| 13 | vCS18 | CS01, X1 + X5 (X6) | 21.20 | 53 | 4.75 |
| 14 | vCS27 | CS04, X1 + X5 (X6) | 4.15 | 19 | 1.67 |
| 15 | vCS35 | CS23, X1 + X5 (X6) | n.d. | n.d. | n.d. |
| 16 | vCS48 | CS01, X5, F328S | 7.14 | 42.1 | 3.77 |
| 17 | vCS49 | CS04, X5, F328S | 8.27 | 37.2 | 3.33 |
| 18 | vCS40 | Human wild-type | 2.03 | 11 | 1.00 | n.d., not determined.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide comprising a nucleotide sequence encoding a Factor VIII polypeptide, the Factor VIII polypeptide comprising a light chain, a heavy chain, and a polypeptide linker joining the C-terminus of the heavy chain to the N-terminus of the light chain,
   wherein the heavy chain of the Factor VIII polypeptide is encoded by a first nucleotide sequence having at least 99% identity over the entire length of SEQ ID NO: 3;
   wherein the light chain of the Factor FVIII polypeptide is encoded by a second nucleotide sequence having at least 99% identity over the entire length of SEQ ID NO: 4; and
   wherein the polypeptide linker comprises a furin cleavage site and a glycosylation peptide having an amino acid sequence of SEQ ID NO:55.

2. The polynucleotide of claim 1, wherein the polypeptide linker is encoded by a third nucleotide sequence having at least 95% identity over the entire length of SEQ ID NO:38.

3. The polynucleotide of claim 1, wherein the polypeptide linker is encoded by a third nucleotide sequence of SEQ ID NO:38.

4. The polynucleotide of claim 1, wherein:
   the first nucleotide sequence is SEQ ID NO: 3; and
   the second nucleotide sequence is SEQ ID NO: 4.

5. The polynucleotide of claim 4, wherein the polypeptide linker is encoded by a third nucleotide sequence of SEQ ID NO:38.

6. The polynucleotide of claim 1, further comprising a promoter element operably linked to the polynucleotide encoding the Factor VIII polypeptide.

7. The polynucleotide of claim 6, wherein the promoter element is a liver-specific promoter sequence upstream of the nucleotide sequence encoding the Factor VIII polypeptide.

8. The polynucleotide of claim 7, further comprising an intron sequence positioned between the liver-specific promoter sequence and the nucleotide sequence encoding the Factor VIII polypeptide.

9. An adeno-associated virus (AAV) vector comprising a polynucleotide according to claim 1.

10. An adeno-associated virus (AAV) particle comprising a polynucleotide according to claim 1.

11. A host cell infected with an adeno-associated virus (AAV) particle comprising a polynucleotide according to claim 1.

12. A method for producing an adeno-associated virus (AAV) particle comprising introducing a polynucleotide according to claim 1 into a mammalian host cell, wherein the polynucleotide is competent for replication in the mammalian host cell.

13. A method for treating hemophilia A comprising administering, to a patient in need thereof, an adeno-associated virus (AAV) particle according to claim 10.

14. A method for transducing a host cell comprising contacting the host cell with an adeno-associated virus (AAV) particle according to claim 10.

15. A polynucleotide comprising a nucleotide sequence having at least 99% identity over the entire length of SEQ ID NO:1, wherein the polynucleotide encodes a Factor VIII polypeptide having I105V, A127S, G151K, M166T, and L171P amino acid substitutions, relative to SEQ ID NO: 19.

16. The polynucleotide of claim 15, wherein:
   the Factor VIII polypeptide comprises a light chain, a heavy chain, and a polypeptide linker joining the C-terminus of the heavy chain to the N-terminus of the light chain; and
   the polypeptide linker includes a glycosylation peptide having an amino acid sequence of SEQ ID NO:55 inserted between the heavy chain and the light chain.

17. The polynucleotide of claim 15, comprising the sequence of SEQ ID NO:94.

18. The polynucleotide of claim 15, further comprising a promoter element operably linked to the polynucleotide encoding the Factor VIII polypeptide.

19. The polynucleotide of claim 18, wherein the promoter element is a liver-specific promoter sequence upstream of the nucleotide sequence encoding the Factor VIII polypeptide.

20. The polynucleotide of claim 19, further comprising an intron sequence positioned between the liver-specific promoter sequence and the nucleotide sequence encoding the Factor VIII polypeptide.

21. An adeno-associated virus (AAV) vector comprising a polynucleotide according to claim 15.

22. An adeno-associated virus (AAV) particle comprising a polynucleotide according to claim 15.

23. A host cell infected with an adeno-associated virus (AAV) particle comprising a polynucleotide according to claim 15.

24. A method for producing an adeno-associated virus (AAV) particle comprising introducing a polynucleotide according to claim 15 into a mammalian host cell, wherein the polynucleotide is competent for replication in the mammalian host cell.

25. A method for treating hemophilia A comprising administering, to a patient in need thereof, an adeno-associated virus (AAV) particle according to claim 22.

26. A method for transducing a host cell comprising contacting the host cell with an adeno-associated virus (AAV) particle according to claim 22.

27. A polynucleotide comprising a nucleotide sequence encoding a Factor VIII polypeptide, the Factor VIII polypeptide comprising a light chain, a heavy chain, and a polypeptide linker joining the C-terminus of the heavy chain to the N-terminus of the light chain, the Factor VIII polypeptide having I105V, A127S, G151K, M166T, and L171P amino acid substitutions, relative to SEQ ID NO: 19,
   wherein the heavy chain of the Factor VIII polypeptide is encoded by a first nucleotide sequence having at least 99% identity over the entire length of SEQ ID NO: 3;
   wherein the light chain of the Factor FVIII polypeptide is encoded by a second nucleotide sequence having at least 99% identity over the entire length of SEQ ID NO: 4; and
   wherein the polypeptide linker comprises a furin cleavage site and a glycosylation peptide having an amino acid sequence of SEQ ID NO:55.

28. The polynucleotide of claim 27, wherein the polypeptide linker is encoded by a third nucleotide sequence having at least 95% identity over the entire length of SEQ ID NO:38.

29. The polynucleotide of claim 27, wherein the polypeptide linker is encoded by a third nucleotide sequence of SEQ ID NO:38.

30. The polynucleotide of claim 27, further comprising a promoter element operably linked to the polynucleotide encoding the Factor VIII polypeptide.

31. The polynucleotide of claim 30, wherein the promoter element is a liver-specific promoter sequence upstream of the nucleotide sequence encoding the Factor VIII polypeptide.

32. The polynucleotide of claim 31, further comprising an intron sequence positioned between the liver-specific promoter sequence and the nucleotide sequence encoding the Factor VIII polypeptide.

33. An adeno-associated virus (AAV) vector comprising a polynucleotide according to claim 27.

34. An adeno-associated virus (AAV) particle comprising a polynucleotide according to claim 27.

35. A host cell infected with an adeno-associated virus (AAV) particle comprising a polynucleotide according to claim 27.

36. A method for producing an adeno-associated virus (AAV) particle comprising introducing a polynucleotide according to claim 27 into a mammalian host cell, wherein the polynucleotide is competent for replication in the mammalian host cell.

37. A method for treating hemophilia A comprising administering, to a patient in need thereof, an adeno-associated virus (AAV) particle according to claim 34.

38. A method for transducing a host cell comprising contacting the host cell with an adeno-associated virus (AAV) particle according to claim 34.

* * * * *